United States Patent
Xu et al.

(10) Patent No.: US 11,845,806 B2
(45) Date of Patent: Dec. 19, 2023

(54) PROTEINACEOUS HETERODIMER AND USE THEREOF

(71) Applicant: DINGFU BIOTARGET CO., LTD., Jiangsu (CN)

(72) Inventors: Ting Xu, Jiangsu (CN); Yan Luan, Jiangsu (CN); Jianjian Peng, Jiangsu (CN); Kai Fu, Jiangsu (CN); Meng Zhao, Jiangsu (CN); Xiaoxiao Wang, Jiangsu (CN)

(73) Assignee: DINGFU BIOTARGET CO., LTD., Jiangsu (CN)

( * ) Notice: Subject to any disclaimer, the term of this patent is extended or adjusted under 35 U.S.C. 154(b) by 429 days.

(21) Appl. No.: 16/621,925

(22) PCT Filed: Jun. 13, 2018

(86) PCT No.: PCT/CN2018/091107
§ 371 (c)(1),
(2) Date: Dec. 12, 2019

(87) PCT Pub. No.: WO2018/228442
PCT Pub. Date: Dec. 20, 2018

(65) Prior Publication Data
US 2020/0354478 A1    Nov. 12, 2020

(30) Foreign Application Priority Data
Jun. 14, 2017  (WO) ................ PCT/CN2017/088344

(51) Int. Cl.
| C07K 19/00 | (2006.01) |
| C07K 16/22 | (2006.01) |
| C07K 16/30 | (2006.01) |
| C07K 16/46 | (2006.01) |

(52) U.S. Cl.
CPC .............. *C07K 16/46* (2013.01); *C07K 16/22* (2013.01); *C07K 16/30* (2013.01); *C07K 2317/52* (2013.01); *C07K 2319/30* (2013.01)

(58) Field of Classification Search
None
See application file for complete search history.

(56) References Cited

U.S. PATENT DOCUMENTS

| 9,248,181 | B2 | 2/2016 | De Kruif et al. |
| 9,248,182 | B2 | 2/2016 | De Kruif et al. |
| 9,358,286 | B2 | 6/2016 | De Kruif et al. |
| 9,758,805 | B2 | 9/2017 | De Kruif et al. |
| 2013/0336973 | A1 | 12/2013 | Von Kreudenstein et al. |
| 2013/0336981 | A1 | 12/2013 | Von Kreudenstein et al. |
| 2014/0072579 | A1 | 3/2014 | De Kruif et al. |
| 2014/0140999 | A1 | 5/2014 | De Kruif et al. |
| 2014/0154253 | A1 | 6/2014 | Ng et al. |
| 2015/0094451 | A1 | 4/2015 | Fischer et al. |
| 2015/0139996 | A1 | 5/2015 | De Kruif et al. |
| 2015/0196637 | A1 | 7/2015 | De Kruif et al. |
| 2016/0177364 | A1 | 6/2016 | De Kruif et al. |
| 2016/0257763 | A1 | 9/2016 | Von Kreudenstein et al. |
| 2017/0327860 | A1 | 11/2017 | De Kruif et al. |
| 2017/0340708 | A1 | 11/2017 | Xu et al. |
| 2017/0369923 | A1 | 12/2017 | De Kruif et al. |

FOREIGN PATENT DOCUMENTS

| CN | 102558355 A | 7/2012 |
| JP | 2016-513106 A | 5/2016 |
| WO | WO 2012/058768 A1 | 5/2012 |
| WO | WO 2013/157953 A1 | 10/2013 |
| WO | WO 2013/157954 A1 | 10/2013 |
| WO | WO 2013/166594 A1 | 11/2013 |
| WO | WO 2014/012085 A2 | 1/2014 |
| WO | WO 2015/033223 A2 | 3/2015 |
| WO | WO 2016/082677 A1 | 6/2016 |
| WO | WO 2017/101828 A1 | 6/2017 |

OTHER PUBLICATIONS

International Search Report dated Aug. 29, 2018 in PCT/CN2018/091107 filed on Jun. 13, 2018.
Liu, H., et al., "Fc Engineering for Developing Therapeutic Bispecific Antibodies and Novel Scaffolds", Frontiers in Immunology, Jan. 26, 2017, vol. 8, article 38, pp. 1-15.
Japanese Office Action dated Jun. 7, 2022 in Japanese Patent Application No. 2019-568667, 7 pages.

*Primary Examiner* — Christine J Saoud
*Assistant Examiner* — Jon M Lockard
(74) *Attorney, Agent, or Firm* — Oblon, McClelland, Maier & Neustadt, L.L.P.

(57) ABSTRACT

Provided are proteinaceous heterodimers, pharmaceutical compositions, medicaments and/or kits comprising the proteinaceous heterodimers, methods for producing the proteinaceous heterodimers, and uses thereof.

6 Claims, 18 Drawing Sheets

Specification includes a Sequence Listing.

MC38-GPC3 cell line

1 Isotype control
2 C-mab
3 C-mab-(huIL10)2-6-9
4 C-mab-huIFNa2-6-9

MC38-FAP cell line

1 Isotype control
2 28H1
3 28H1-(huIL10)2-6-9
4 28H1-huIFNa2-6-9

SEQUENCE LISTING

<160> NUMBER OF SEQ ID NOS: 180

<210> SEQ ID NO 1
<211> LENGTH: 227
<212> TYPE: PRT
<213> ORGANISM: Artificial Sequence
<220> FEATURE:
<223> OTHER INFORMATION: A Y349C+T366W

<400> SEQUENCE: 1

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 2
<211> LENGTH: 227
<212> TYPE: PRT
<213> ORGANISM: Artificial Sequence
<220> FEATURE:
<223> OTHER INFORMATION: B D356C+T366S+L368A+Y407V

<400> SEQUENCE: 2

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60
```

```
His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Cys Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 3
<211> LENGTH: 227
<212> TYPE: PRT
<213> ORGANISM: Artificial Sequence
<220> FEATURE:
<223> OTHER INFORMATION: B D356C+T366S+L368A+Y407V+F405K

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Cys Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Val Ser Lys Leu Thr Val
            180                 185                 190
```

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys
225

<210> SEQ ID NO 4
<211> LENGTH: 227
<212> TYPE: PRT
<213> ORGANISM: Artificial Sequence
<220> FEATURE:
<223> OTHER INFORMATION: A Y349C+T366W+F405K

<400> SEQUENCE: 4

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 5
<211> LENGTH: 227
<212> TYPE: PRT
<213> ORGANISM: Artificial Sequence
<220> FEATURE:
<223> OTHER INFORMATION: A Y349C+T366W+K409E

<400> SEQUENCE: 5

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

```
Ile Ser Arg Thr Pro Glu Val Thr Cys Val Val Asp Val Ser His
            35                  40                  45

Glu Asn Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
            130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Glu Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 6
<211> LENGTH: 227
<212> TYPE: PRT
<213> ORGANISM: Artificial Sequence
<220> FEATURE:
<223> OTHER INFORMATION: A Y349C+T366W+K409A

<400> SEQUENCE: 6

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asn Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
            130                 135                 140

Leu Trp Cys Leu Val Lys Gly Phe Tyr Pro Ser Asp Ile Ala Val Glu
145                 150                 155                 160
```

```
Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 7
<211> LENGTH: 227
<212> TYPE: PRT
<213> ORGANISM: Artificial Sequence
<220> FEATURE:
<223> OTHER INFORMATION: A Y349C+T366W+F405K+K360E+Q347E

<400> SEQUENCE: 7

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
        115                 120                 125

Cys Thr Leu Pro Pro Ser Arg Asp Glu Leu Thr Glu Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 8
<211> LENGTH: 227
<212> TYPE: PRT
<213> ORGANISM: Artificial Sequence
<220> FEATURE:
<223> OTHER INFORMATION: B D356C+T366S+L368A+Y407V+Q347R
```

```
<400> SEQUENCE: 8

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Arg Val
            115                 120                 125

Tyr Thr Leu Pro Pro Ser Arg Cys Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Lys
225

<210> SEQ ID NO 9
<211> LENGTH: 227
<212> TYPE: PRT
<213> ORGANISM: Artificial Sequence
<220> FEATURE:
<223> OTHER INFORMATION: A Y349C+T366W+F405K+Q347R

<400> SEQUENCE: 9

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asn Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Arg Val
```

```
            115                 120                 125
Cys Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 10
<211> LENGTH: 227
<212> TYPE: PRT
<213> ORGANISM: Artificial Sequence
<220> FEATURE:
<223> OTHER INFORMATION: B D356C+T366S+L368A+Y407V+K360E+Q347E

<400> SEQUENCE: 10

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
        115                 120                 125

Tyr Thr Leu Pro Pro Ser Arg Cys Glu Leu Thr Glu Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225
```

<210> SEQ ID NO 11
<211> LENGTH: 227
<212> TYPE: PRT
<213> ORGANISM: Artificial Sequence
<220> FEATURE:
<223> OTHER INFORMATION: A Y349C+T366W+K409A+K360E+Q347E

<400> SEQUENCE: 11

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
        115                 120                 125

Cys Thr Leu Pro Pro Ser Arg Asp Glu Leu Thr Glu Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 12
<211> LENGTH: 227
<212> TYPE: PRT
<213> ORGANISM: Artificial Sequence
<220> FEATURE:
<223> OTHER INFORMATION: B D356C+T366S+L368A+Y407V+F405K+Q347R

<400> SEQUENCE: 12

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80
```

```
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Arg Val
            115                 120                 125
Tyr Thr Leu Pro Pro Ser Arg Cys Glu Leu Thr Lys Asn Gln Val Ser
130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Lys Leu Val Ser Lys Leu Thr Val
            180                 185                 190
Asp Lys Ser Arg Trp Gln Gln Gly Asn Val Phe Ser Cys Ser Val Met
            195                 200                 205
His Glu Ala Leu His Asn His Tyr Thr Gln Lys Ser Leu Ser Leu Ser
            210                 215                 220
Pro Gly Lys
225

<210> SEQ ID NO 13
<211> LENGTH: 227
<212> TYPE: PRT
<213> ORGANISM: Artificial Sequence
<220> FEATURE:
<223> OTHER INFORMATION: A Y349C+T366W+K409A+Q347R

<400> SEQUENCE: 13

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asn Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Arg Val
            115                 120                 125
Cys Thr Leu Pro Pro Ser Arg Asp Glu Leu Thr Lys Asn Gln Val Ser
130                 135                 140
Leu Trp Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Ala Leu Thr Val
            180                 185                 190
Asp Lys Ser Arg Trp Gln Gln Gly Asn Val Phe Ser Cys Ser Val Met
            195                 200                 205
```

```
His Glu Ala Leu His Asn His Tyr Thr Gln Lys Ser Leu Ser Leu Ser
        210                 215                 220

Pro Gly Lys
225

<210> SEQ ID NO 14
<211> LENGTH: 227
<212> TYPE: PRT
<213> ORGANISM: Artificial Sequence
<220> FEATURE:
<223> OTHER INFORMATION: B D356C+T366S+L368A+Y407V+F405K+K360E+Q347E

<400> SEQUENCE: 14

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Glu Val
        115                 120                 125

Tyr Thr Leu Pro Pro Ser Arg Cys Glu Leu Thr Glu Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 15
<211> LENGTH: 227
<212> TYPE: PRT
<213> ORGANISM: Artificial Sequence
<220> FEATURE:
<223> OTHER INFORMATION: A T366W+K409A+K392D

<400> SEQUENCE: 15

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45
```

```
Glu Asn Pro Glu Val Lys Phe Asn Trp Tyr Val Asp Gly Val Glu Val
         50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Asp Thr Thr Pro Pro
                165                 170                 175

Val Leu Asp Ser Asp Gly Ser Phe Phe Leu Tyr Ser Ala Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys
225

<210> SEQ ID NO 16
<211> LENGTH: 227
<212> TYPE: PRT
<213> ORGANISM: Artificial Sequence
<220> FEATURE:
<223> OTHER INFORMATION: B T366S+L368A+Y407V+D399S+F405K

<400> SEQUENCE: 16

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
                 20                  25                  30

Ile Ser Arg Thr Pro Glu Val Thr Cys Val Val Val Asp Val Ser His
             35                  40                  45

Glu Asp Pro Glu Val Lys Phe Asn Trp Tyr Val Asp Gly Val Glu Val
         50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175
```

```
Val Leu Ser Ser Asp Gly Ser Phe Lys Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 17
<211> LENGTH: 227
<212> TYPE: PRT
<213> ORGANISM: Artificial Sequence
<220> FEATURE:
<223> OTHER INFORMATION: A T366W+K409A

<400> SEQUENCE: 17

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 18
<211> LENGTH: 227
<212> TYPE: PRT
<213> ORGANISM: Artificial Sequence
<220> FEATURE:
<223> OTHER INFORMATION: B T366S+L368G+Y407A+F405K

<400> SEQUENCE: 18

Asp Lys Thr His Thr Cys Pro Pro Cys Pro Ala Pro Glu Leu Leu Gly
```

```
            1               5                  10                 15
Gly Pro Ser Val Phe Leu Phe Pro Pro Lys Pro Lys Asp Thr Leu Met
            20                 25                 30

Ile Ser Arg Thr Pro Glu Val Thr Cys Val Val Val Asp Val Ser His
            35                 40                 45

Glu Asp Pro Glu Val Lys Phe Asn Trp Tyr Val Asp Gly Val Glu Val
    50                 55                 60

His Asn Ala Lys Thr Lys Pro Arg Glu Glu Gln Tyr Asn Ser Thr Tyr
65                 70                 75                 80

Arg Val Val Ser Val Leu Thr Val Leu His Gln Asp Trp Leu Asn Gly
                85                 90                 95

Lys Glu Tyr Lys Cys Lys Val Ser Asn Lys Ala Leu Pro Ala Pro Ile
            100                105                110

Glu Lys Thr Ile Ser Lys Ala Lys Gly Gln Pro Arg Glu Pro Gln Val
            115                120                125

Tyr Thr Leu Pro Pro Ser Arg Asp Glu Leu Thr Lys Asn Gln Val Ser
130                135                140

Leu Ser Cys Gly Val Lys Gly Phe Tyr Pro Ser Asp Ile Ala Val Glu
145                150                155                160

Trp Glu Ser Asn Gly Gln Pro Glu Asn Asn Tyr Lys Thr Thr Pro Pro
                165                170                175

Val Leu Asp Ser Asp Gly Ser Phe Lys Leu Ala Ser Lys Leu Thr Val
            180                185                190

Asp Lys Ser Arg Trp Gln Gln Gly Asn Val Phe Ser Cys Ser Val Met
            195                200                205

His Glu Ala Leu His Asn His Tyr Thr Gln Lys Ser Leu Ser Leu Ser
        210                215                220

Pro Gly Lys
225

<210> SEQ ID NO 19
<211> LENGTH: 227
<212> TYPE: PRT
<213> ORGANISM: Artificial Sequence
<220> FEATURE:
<223> OTHER INFORMATION: A T366W+K409A+Y349D

<400> SEQUENCE: 19

Asp Lys Thr His Thr Cys Pro Pro Cys Pro Ala Pro Glu Leu Leu Gly
1               5                  10                 15

Gly Pro Ser Val Phe Leu Phe Pro Pro Lys Pro Lys Asp Thr Leu Met
            20                 25                 30

Ile Ser Arg Thr Pro Glu Val Thr Cys Val Val Val Asp Val Ser His
            35                 40                 45

Glu Asn Pro Glu Val Lys Phe Asn Trp Tyr Val Asp Gly Val Glu Val
    50                 55                 60

His Asn Ala Lys Thr Lys Pro Arg Glu Glu Gln Tyr Asn Ser Thr Tyr
65                 70                 75                 80

Arg Val Val Ser Val Leu Thr Val Leu His Gln Asp Trp Leu Asn Gly
                85                 90                 95

Lys Glu Tyr Lys Cys Lys Val Ser Asn Lys Ala Leu Pro Ala Pro Ile
            100                105                110

Glu Lys Thr Ile Ser Lys Ala Lys Gly Gln Pro Arg Glu Pro Gln Val
            115                120                125

Asp Thr Leu Pro Pro Ser Arg Asp Glu Leu Thr Lys Asn Gln Val Ser
```

-continued

```
                130                 135                 140
Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
                210                 215                 220

Pro Gly Lys
225

<210> SEQ ID NO 20
<211> LENGTH: 227
<212> TYPE: PRT
<213> ORGANISM: Artificial Sequence
<220> FEATURE:
<223> OTHER INFORMATION: B T366S+L368A+Y407V+F405K+E357A

<400> SEQUENCE: 20

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
            50                  55                  60

His Asn Ala Lys Thr Lys Pro Arg Glu Glu Gln Tyr Asn Ser Thr Tyr
65              70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Ser Arg Asp Ala Leu Thr Lys Asn Gln Val Ser
                130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Val Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
                210                 215                 220

Pro Gly Lys
225

<210> SEQ ID NO 21
<211> LENGTH: 227
<212> TYPE: PRT
```

<213> ORGANISM: Artificial Sequence
<220> FEATURE:
<223> OTHER INFORMATION: A T366W+K409A+Y349D+S354D

<400> SEQUENCE: 21

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Asp Thr Leu Pro Pro Asp Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 22
<211> LENGTH: 227
<212> TYPE: PRT
<213> ORGANISM: Artificial Sequence
<220> FEATURE:
<223> OTHER INFORMATION: A T366W+F405K

<400> SEQUENCE: 22

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 23
<211> LENGTH: 227
<212> TYPE: PRT
<213> ORGANISM: Artificial Sequence
<220> FEATURE:
<223> OTHER INFORMATION: B T366S+L368A+Y407V+K409A

<400> SEQUENCE: 23

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Ala Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 24
<211> LENGTH: 227
<212> TYPE: PRT
<213> ORGANISM: Artificial Sequence
<220> FEATURE:
<223> OTHER INFORMATION: A T366W+F405K+D399S

<400> SEQUENCE: 24

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Ser Ser Asp Gly Ser Phe Lys Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 25
<211> LENGTH: 227
<212> TYPE: PRT
<213> ORGANISM: Artificial Sequence
<220> FEATURE:
<223> OTHER INFORMATION: B T366S+L368A+Y407V+K409A+K392D

<400> SEQUENCE: 25

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
        100                 105                 110

Glu Lys Thr Ile Ser Lys Ala Lys Gly Gln Pro Arg Glu Pro Gln Val
    115                 120                 125

Tyr Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Asp Thr Thr Pro Pro
                165                 170                 175

Val Leu Asp Ser Asp Gly Ser Phe Phe Leu Val Ser Ala Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys
225

<210> SEQ ID NO 26
<211> LENGTH: 227
<212> TYPE: PRT
<213> ORGANISM: Artificial Sequence
<220> FEATURE:
<223> OTHER INFORMATION: A T366S+L368G+Y407A+K409A

<400> SEQUENCE: 26

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
        100                 105                 110

Glu Lys Thr Ile Ser Lys Ala Lys Gly Gln Pro Arg Glu Pro Gln Val
    115                 120                 125

Tyr Thr Leu Pro Pro Ser Arg Asp Glu Leu Thr Lys Asn Gln Val Ser
130                 135                 140

Leu Ser Cys Gly Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Ala Ser Ala Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Lys
225

<210> SEQ ID NO 27
<211> LENGTH: 227
<212> TYPE: PRT
<213> ORGANISM: Artificial Sequence
<220> FEATURE:
<223> OTHER INFORMATION: A T366W +F405K +Y349D

<400> SEQUENCE: 27

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asn Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Asp Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Lys Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 28
<211> LENGTH: 227
<212> TYPE: PRT
<213> ORGANISM: Artificial Sequence
<220> FEATURE:
<223> OTHER INFORMATION: B T366S+L368A+Y407V +K409A +E357A

<400> SEQUENCE: 28

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met

```
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Ala Leu Thr Lys Asn Gln Val Ser
    130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Val Ser Ala Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys
225

<210> SEQ ID NO 29
<211> LENGTH: 227
<212> TYPE: PRT
<213> ORGANISM: Artificial Sequence
<220> FEATURE:
<223> OTHER INFORMATION: A T366W+F405K+Y349D+S354D

<400> SEQUENCE: 29

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asn Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Asp Thr Leu Pro Pro Asp Arg Asp Glu Leu Thr Lys Asn Gln Val Ser
    130                 135                 140
Leu Trp Cys Leu Val Lys Gly Phe Tyr Pro Ser Asp Ile Ala Val Glu
```

```
                145                 150                 155                 160
Trp Glu Ser Asn Gly Gln Pro Glu Asn Asn Tyr Lys Thr Thr Pro Pro
                    165                 170                 175

Val Leu Asp Ser Asp Gly Ser Phe Lys Leu Tyr Ser Lys Leu Thr Val
                    180                 185                 190

Asp Lys Ser Arg Trp Gln Gln Gly Asn Val Phe Ser Cys Ser Val Met
                    195                 200                 205

His Glu Ala Leu His Asn His Tyr Thr Gln Lys Ser Leu Ser Leu Ser
                    210                 215                 220

Pro Gly Lys
225

<210> SEQ ID NO 30
<211> LENGTH: 227
<212> TYPE: PRT
<213> ORGANISM: Homo sapiens

<400> SEQUENCE: 30

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
            50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Ser Arg Asp Glu Leu Thr Lys Asn Gln Val Ser
                130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                    165                 170                 175

Val Leu Asp Ser Asp Gly Ser Phe Phe Leu Tyr Ser Lys Leu Thr Val
                    180                 185                 190

Asp Lys Ser Arg Trp Gln Gln Gly Asn Val Phe Ser Cys Ser Val Met
                    195                 200                 205

His Glu Ala Leu His Asn His Tyr Thr Gln Lys Ser Leu Ser Leu Ser
                    210                 215                 220

Pro Gly Lys
225

<210> SEQ ID NO 31
<211> LENGTH: 681
<212> TYPE: DNA
<213> ORGANISM: Homo sapiens

<400> SEQUENCE: 31
gacaagaccc acacctgccc ccctgccccc gcccccgagc tgctgggcgg ccccagcgtg    60
```

```
ttcctgttcc cccccaagcc caaggacacc ctgatgatca gccgcacccc cgaggtgacc    120
tgcgtggtgg tggacgtgag ccacgagaac cccgaggtga agttcaactg gtacgtggac    180
ggcgtggagg tgcacaacgc caagaccaag ccccgcgagg agcagtacaa cagcacctac    240
cgcgtggtga gcgtgctgac cgtgctgcac caggactggc tgaacggcaa ggagtacaag    300
tgcaaggtga gcaacaaggc cctgcccgcc cccatcgaga agaccatcag caaggccaag    360
ggccagcccc gcgagcccca ggtgtacacc ctgccccca gccgcgacga gctgaccaag    420
aaccaggtga gcctgacctg cctggtgaag ggcttctacc ccagcgacat cgccgtggag    480
tgggagagca acggccagcc cgagaacaac tacaagacca cccccccgt gctggacagc    540 gacggcagct tcttcctgta cagcaagctg accgtggaca agagccgctg gcagcagggc    600
aacgtgttca gctgcagcgt gatgcacgag gccctgcaca ccactacac ccagaagagc    660 ctgagcctga gccccggcaa g                                              681

<210> SEQ ID NO 32
<211> LENGTH: 741
<212> TYPE: DNA
<213> ORGANISM: Mus musculus

<400> SEQUENCE: 32
atggagaccg acaccctgct gctgtgggtg ctgctgctgt gggtgcccgg cagcaccggc     60
gacaagaccc acacctgccc ccctgcccc gccccgagc tgctgggcgg ccccagcgtg    120
ttcctgttcc cccccaagcc caaggacacc ctgatgatca gccgcacccc cgaggtgacc    180
tgcgtggtgg tggacgtgag ccacgagaac cccgaggtga agttcaactg gtacgtggac    240
ggcgtggagg tgcacaacgc caagaccaag ccccgcgagg agcagtacaa cagcacctac    300
cgcgtggtga gcgtgctgac cgtgctgcac caggactggc tgaacggcaa ggagtacaag    360
tgcaaggtga gcaacaaggc cctgcccgcc cccatcgaga agaccatcag caaggccaag    420
ggccagcccc gcgagcccca ggtgtacacc ctgccccca gccgcgacga gctgaccaag    480
aaccaggtga gcctgacctg cctggtgaag ggcttctacc ccagcgacat cgccgtggag    540
tgggagagca acggccagcc cgagaacaac tacaagacca cccccccgt gctggacagc    600 gacggcagct tcttcctgta cagcaagctg accgtggaca agagccgctg gcagcagggc    660
aacgtgttca gctgcagcgt gatgcacgag gccctgcaca ccactacac ccagaagagc    720 ctgagcctga gccccggcaa g                                              741

<210> SEQ ID NO 33
<211> LENGTH: 1121
<212> TYPE: DNA
<213> ORGANISM: Artificial Sequence
<220> FEATURE:
<223> OTHER INFORMATION: fusion gene fragment

<400> SEQUENCE: 33
atggagaccg acaccctgct gctgtgggtg ctgctgctgt gggtgcccgg cagcaccggc     60
caggtgcagc tgcaggagtc tggggggaggc tcggtgcagg ctggagggtc tctgagactc    120
tcctgtgcag cctctgaata catctacagt agctactgca tggcctggtt ccgccaggct    180
ccagggaagg agcgcgaggg ggtcgcagtt attgggagtg atggtagcac aagctacgca    240
gactccgtga aggccgatt caccatctcc aaagacaacg ccaagaacac tctgtatctg    300
caaatgaaca gcctgaaacc tgaggacact gccatgtact actgtgcggc catcggtggt    360
```

```
tactgctacc aaccacccta tgagtaccag tactggggcc aggggaccca ggtcaccgtc    420
tcccagaacc gaaaagcagc gacaagaccc acacctgccc ccctgcccc gcccccgagc    480 tgctgggcgg ccccagcgtg ttcctgttcc ccccaagcc aaggacacc ctgatgatca    540 gccgcacccc cgaggtgacc tgcgtggtgg tggacgtgag ccacgagaac ccgaggtga    600 agttcaactg gtacgtggac ggcgtggagg tgcacaacgc caagaccaag cccgcgagg    660 agcagtacaa cagcacctac cgcgtggtga gcgtgctgac cgtgctgcac caggactggc    720
tgaacggcaa ggagtacaag tgcaaggtga gcaacaaggc cctgcccgcc ccatcgaga    780 agaccatcag caaggccaag ggccagcccc gcgagcccca ggtgtacacc ctgcccccca    840
gccgcgacga gctgaccaag aaccaggtga gcctgacctg cctggtgaag ggcttctacc    900
ccagcgacat cgccgtggag tgggagagca acggccagcc cgagaacaac tacaagacca    960 cccccccgt gctggacagc gacggcagct tcttcctgta cagcaagctg accgtggaca    1020
agagccgctg gcagcagggc aacgtgttca gctgcagcgt gatgcacgag gccctgcaca    1080
accactacac ccagaagagc ctgagcctga gccccggcaa g                      1121
```

<210> SEQ ID NO 34
<211> LENGTH: 354
<212> TYPE: PRT
<213> ORGANISM: Artificial Sequence
<220> FEATURE:
<223> OTHER INFORMATION: fusion protein VhH-Fc

<400> SEQUENCE: 34

```
Gln Val Gln Leu Gln Glu Ser Gly Gly Gly Ser Val Gln Ala Gly Gly
1               5                   10                  15

Ser Leu Arg Leu Ser Cys Ala Ala Ser Glu Tyr Ile Tyr Ser Ser Tyr
                20                  25                  30

Cys Met Ala Trp Phe Arg Gln Ala Pro Gly Lys Glu Arg Glu Gly Val
            35                  40                  45

Ala Val Ile Gly Ser Asp Gly Ser Thr Ser Tyr Ala Asp Ser Val Lys
        50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Ala Ile Gly Gly Tyr Cys Tyr Gln Pro Pro Tyr Glu Tyr Gln Tyr Trp
            100                 105                 110

Gly Gln Gly Thr Gln Val Thr Val Ser Ser Glu Pro Lys Ser Ser Asp
        115                 120                 125

Lys Thr His Thr Cys Pro Pro Cys Pro Ala Pro Glu Leu Leu Gly Gly
130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
    210                 215                 220

Glu Tyr Lys Cys Lys Val Ser Asn Lys Ala Leu Pro Ala Pro Ile Glu
```

```
                225                 230                 235                 240
Lys Thr Ile Ser Lys Ala Lys Gly Gln Pro Arg Glu Pro Gln Val Tyr
                245                 250                 255

Thr Leu Pro Pro Ser Arg Asp Glu Leu Thr Lys Asn Gln Val Ser Leu
                260                 265                 270

Thr Cys Leu Val Lys Gly Phe Tyr Pro Ser Asp Ile Ala Val Glu Trp
                275                 280                 285

Glu Ser Asn Gly Gln Pro Glu Asn Asn Tyr Lys Thr Thr Pro Pro Val
                290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
                340                 345                 350

Gly Lys

<210> SEQ ID NO 35
<211> LENGTH: 1473
<212> TYPE: DNA
<213> ORGANISM: Artificial Sequence
<220> FEATURE:
<223> OTHER INFORMATION: gene for anti-Her2 single chain ScFv-Fc fusion
      protein

<400> SEQUENCE: 35
atggagaccg acaccctgct gctgtgggtg ctgctgctgt gggtgcccgg cagcaccggc      60
gaggtgcagc tgctggagag cggcggcggc gtggtgcagc ccggccgcag cctgcgcctg     120
agctgcatcg ccagcggctt caccttcagc agctacccca tgacctgggt cgcgcaggcc     180
cccggcaagg gcctggagtg ggtggccagc atcagctacg acggcagcta caagtacaag     240
gccgacagca tgaagggccg cctgaccatc agccgcgaca cagcaagaa cacccctgtac     300 ctggagatga acagcctgac cgccgaggac accgcgtgt actactgcgc ccgcaccgcc     360
ttcttcaacg cctacgactt ctggggccag ggcaccctgg tgaccgtgag cagcgccagc     420
accaagggcc ccagcgtggg cggcggcggc agcggcggcg cggcagcga gatcgtgatg     480 acccagagcc ccgccaccct gagcgtgagc ccgggcgagc gcgccaccct gagctgccgc     540
gccagccaga gcgtgcgcag caacctggcc tggtaccagc agaagcccgg ccaggccccc     600
cgcctgctga tctacgccgc cagcacccgc gccaccggca tccccgcccg cttcagcggc     660
agcggcagcg gcaccgagtt caccctgacc atcagcagcc tgcagagcga ggacttcgcc     720
gtgtactact gccagcagta caacgagtgg ttccgcacca cggccagggg caccaaggtg     780
gagatcaagc gcgacaagac ccacacctgc ccccctgcc cgcccccga gctgctgggc     840 ggccccagcg tgttcctgtt ccccccaag cccaaggaca ccctgatgat cagccgcacc     900
cccgaggtga cctgcgtggt ggtggacgtg agccacgaga accccgaggt gaagttcaac     960
tggtacgtgg acggcgtgga ggtgcacaac gccaagacca gccccgcga ggagcagtac    1020 aacagcacct accgcgtggt gagcgtgctg accgtgctgc accaggactg gctgaacggc    1080
aaggagtaca agtgcaaggt gagcaacaag gccctgcccg cccccatcga aagaccatc    1140 agcaaggcca aggccagcc cgcgagccc aggtgtaca ccctgccccc cagccgcgac    1200
gagctgacca gaaccaggt gagcctgacc tgcctggtga agggcttcta ccccagcgac    1260
atcgccgtgg agtgggagag caacggccag cccgagaaca actacaagac cacccccccc    1320
```

```
gtgctggaca cgacggcag cttcttcctg tacagcaagc tgaccgtgga caagagccgc    1380
tggcagcagg gcaacgtgtt cagctgcagc gtgatgcacg aggccctgca caaccactac    1440
acccagaaga gcctgagcct gagccccggc aag                                 1473
```

<210> SEQ ID NO 36
<211> LENGTH: 471
<212> TYPE: PRT
<213> ORGANISM: Artificial Sequence
<220> FEATURE:
<223> OTHER INFORMATION: anti-Her2 single chain ScFv -Fc fusion protein

<400> SEQUENCE: 36

```
Glu Val Gln Leu Leu Glu Ser Gly Gly Gly Val Val Gln Pro Gly Arg
1               5                   10                  15

Ser Leu Arg Leu Ser Cys Ile Ala Ser Gly Phe Thr Phe Ser Ser Tyr
            20                  25                  30

Pro Met Thr Trp Val Arg Gln Ala Pro Gly Lys Gly Leu Glu Trp Val
        35                  40                  45

Ala Ser Ile Ser Tyr Asp Gly Ser Tyr Lys Tyr Lys Ala Asp Ser Met
    50                  55                  60

Lys Gly Arg Leu Thr Ile Ser Arg Asp Asn Ser Lys Asn Thr Leu Tyr
65                  70                  75                  80

Leu Glu Met Asn Ser Leu Thr Ala Glu Asp Thr Ala Val Tyr Tyr Cys
                85                  90                  95

Ala Arg Thr Ala Phe Phe Asn Ala Tyr Asp Phe Trp Gly Gln Gly Thr
            100                 105                 110

Leu Val Thr Val Ser Ser Ala Ser Thr Lys Gly Pro Ser Val Gly Gly
        115                 120                 125

Gly Gly Ser Gly Gly Gly Ser Glu Ile Val Met Thr Gln Ser Pro
    130                 135                 140

Ala Thr Leu Ser Val Ser Pro Gly Glu Arg Ala Thr Leu Ser Cys Arg
145                 150                 155                 160

Ala Ser Gln Ser Val Arg Ser Asn Leu Ala Trp Tyr Gln Gln Lys Pro
                165                 170                 175

Gly Gln Ala Pro Arg Leu Leu Ile Tyr Ala Ala Ser Thr Arg Ala Thr
            180                 185                 190

Gly Ile Pro Ala Arg Phe Ser Gly Ser Gly Ser Gly Thr Glu Phe Thr
        195                 200                 205

Leu Thr Ile Ser Ser Leu Gln Ser Glu Asp Phe Ala Val Tyr Tyr Cys
    210                 215                 220

Gln Gln Tyr Asn Glu Trp Phe Arg Thr Ser Gly Gln Gly Thr Lys Val
225                 230                 235                 240

Glu Ile Lys Arg Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asn Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335
```

```
Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
        370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys
465                 470

<210> SEQ ID NO 37
<211> LENGTH: 214
<212> TYPE: PRT
<213> ORGANISM: Artificial Sequence
<220> FEATURE:
<223> OTHER INFORMATION: Erb-LC

<400> SEQUENCE: 37

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 38
<211> LENGTH: 642
<212> TYPE: DNA
<213> ORGANISM: Artificial Sequence
<220> FEATURE:
<223> OTHER INFORMATION: nucleic acid molecules encoding Erb-LC

<400> SEQUENCE: 38

```
gacatcctgc tgacccagag ccccgtgatc ctgagcgtga gccccggcga gcgcgtgagc      60
ttcagctgcc gcgccagcca gagcatcggc accaacatcc actggtacca gcagcgcacc     120
aacggcagcc cccgcctgct gatcaagtac gccagcgaga gcatcagcgg catccccagc     180
cgcttcagcg gcagcggcag cggcaccgac ttcaccctga gcatcaacag cgtggagagc     240
gaggacatcg ccgactacta ctgccagcag aacaacaact ggcccaccac cttcggcgcc     300
ggcaccaagc tggagctgaa gcgcaccgtg gccgccccca gcgtgttcat cttccccccc     360
agcgacgagc agctgaagag cggcaccgcc agcgtggtgt gcctgctgaa caacttctac     420
ccccgcgagg ccaaggtgca gtggaaggtg gacaacgccc tgcagagcgg caacagccag     480
gagagcgtga ccgagcagga cagcaaggac agcacctaca gcctgagcag caccctgacc     540
ctgagcaagg ccgactacga aagcacaag gtgtacgcct gcgaggtgac ccaccagggc     600
ctgagcagcc ccgtgaccaa gagcttcaac cgcggcgagt gc                        642
```

<210> SEQ ID NO 39
<211> LENGTH: 449
<212> TYPE: PRT
<213> ORGANISM: Artificial Sequence
<220> FEATURE:
<223> OTHER INFORMATION: erb-Fc9

<400> SEQUENCE: 39

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

| | | | | | | | | | | | |
|---|---|---|---|---|---|---|---|---|---|---|---|
|Ser|Ser|Leu|Gly|Thr|Gln|Thr|Tyr|Ile|Cys|Asn|Val|Asn|His|Lys|Pro|
| |195| | | |200| | | |205| | | | | | |

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Trp
355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Ala Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 40
<211> LENGTH: 1347
<212> TYPE: DNA
<213> ORGANISM: Artificial Sequence
<220> FEATURE:
<223> OTHER INFORMATION: nucleic acid molecules encoding erb-Fc9

<400> SEQUENCE: 40

```
caggtgcagc tgaagcagag cggccccggc ctggtgcagc ccagccagag cctgagcatc      60
acctgcaccg tgagcggctt cagcctgacc aactacggcg tgcactgggt gcgccagagc     120
cccggcaagg gcctggagtg gctgggcgtg atctggagcg gcggcaacac cgactacaac     180 accccccttca ccagccgcct gagcatcaac aaggacaaca gcaagagcca ggtgttcttc     240
aagatgaaca gcctgcagag caacgacacc gccatctact actgcgcccg cgccctgacc     300
tactacgact acgagttcgc ctactggggc cagggcaccc tggtgaccgt gagcgccgcc     360
agcactaagg ggccctctgt gtttccactc gcccccttcta gcaaaagcac ttccggagga     420
actgccgctc tgggctgtct ggtgaaagat tacttccccg aaccagtcac tgtgtcatgg     480
aactctggag cactgacatc tggagttcac acctttcctg ctgtgctgca gagttctgga     540
ctgtactccc tgtcatctgt ggtcaccgtg ccatcttcat ctctggggac ccagacctac     600
```

```
atctgtaacg tgaaccacaa accctccaac acaaaagtgg acaaacgagt cgaaccaaaa      660
tcttgtgaca aacccacac atgcccaccg tgcccagctc cggaactcct gggcggaccg       720
tcagtcttcc tcttcccccc aaaacccaag acaccctca tgatctcccg gacccctgag      780
gtcacatgcg tggtggtgga cgtgagccac gaagacctg aggtcaagtt caactggtac       840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa   1020
gccaagggc agccccgaga accacaggtg tacaccctgc ccccaagtcg ggatgagctg     1080
accaagaacc aggtcagcct gtggtgcctg gtcaaaggct tctatcccag cgacatcgcc    1140
gtggagtggg agagcaatgg gcagccggag aacaactaca agaccacgcc tcccgtgttg    1200
gactccgacg gctccttctt cctctacagc gcgctcaccg tggacaagag caggtggcag    1260
caggggaacg tcttctcatg ctccgtgatg catgaggctc tgcacaacca ctacacgcag    1320
aagagcctct ccctgtctcc gggtaaa                                                            1347
```

<210> SEQ ID NO 41
<211> LENGTH: 346
<212> TYPE: PRT
<213> ORGANISM: Artificial Sequence
<220> FEATURE:
<223> OTHER INFORMATION: Erb-Fc6

<400> SEQUENCE: 41

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Asp Lys Thr His Thr Cys Pro Pro Cys
        115                 120                 125

Pro Ala Pro Glu Leu Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220
```

```
Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Asp Glu
            245                 250                 255

Leu Thr Lys Asn Gln Val Ser Leu Ser Cys Gly Val Lys Gly Phe Tyr
        260                 265                 270

Pro Ser Asp Ile Ala Val Glu Trp Glu Ser Asn Gly Gln Pro Glu Asn
    275                 280                 285

Asn Tyr Lys Thr Thr Pro Pro Val Leu Asp Ser Asp Gly Ser Phe Lys
290                 295                 300

Leu Ala Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 42
<211> LENGTH: 1038
<212> TYPE: DNA
<213> ORGANISM: Artificial Sequence
<220> FEATURE:
<223> OTHER INFORMATION: nucleic acid molecules encoding Erb-Fc6

<400> SEQUENCE: 42
caggtgcagc tgaagcagag cggccccggc ctggtgcagc ccagccagag cctgagcatc      60
acctgcaccg tgagcggctt cagcctgacc aactacggcg tgcactgggt gcgccagagc     120
cccggcaagg gcctggagtg gctgggcgtg atctggagcg gcggcaacac cgactacaac     180
acccccttca ccagccgcct gagcatcaac aaggacaaca gcaagagcca ggtgttcttc     240
aagatgaaca gcctgcagag caacgacacc gccatctact actgcgcccg cgccctgacc     300
tactacgact acgagttcgc ctactggggc cagggcaccc tggtgaccgt gagcgccgac     360
aagacccaca cttgcccccc ttgtcccgct ccggaactcc tgggcggacc gtcagtcttc     420
ctcttccccc caaaacccaa ggacaccctc atgatctccc ggacccctga ggtcacatgc     480
gtggtggtgg acgtgagcca cgaagaccct gaggtcaagt tcaactggta cgtggacggc     540
gtggaggtgc ataatgccaa gacaaagccg cgggaggagc agtacaacag cacgtaccgt     600
gtggtcagcg tcctcaccgt cctgcaccag gactggctga atggcaagga gtacaagtgc     660
aaggtctcca acaaagccct cccagccccc atcgagaaaa ccatctccaa agccaaaggg     720
cagccccgag aaccacaggt gtataccctg cccccatccc gggatgagct gaccaagaac     780
caggtcagcc tgagttgcgg ggtcaaaggc ttctatccca gcgacatcgc cgtggagtgg     840
gagagcaatg ggcagccgga gaacaactac aagaccacgc tcccgtgtt ggactccgac     900
ggctccttca gctcgccag caagctcacc gtggacaaga gcaggtggca gcaggggaac     960
gtcttctcat gctccgtgat gcatgaggct ctgcacaacc actacacgca gaagagcctc    1020
tccctgtctc cgggtaaa                                                   1038

<210> SEQ ID NO 43
<211> LENGTH: 449
<212> TYPE: PRT
<213> ORGANISM: Artificial Sequence
<220> FEATURE:
<223> OTHER INFORMATION: Erb-Knob

<400> SEQUENCE: 43
```

-continued

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
            85                  90                  95

Arg Ala Leu Thr Tyr Tyr Asp Tyr Glu Phe Ala Tyr Trp Gly Gln Gly
        100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Cys Arg Asp Glu Leu Thr Lys Asn Gln Val Ser Leu Trp
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
             420                 425                 430

Ala Leu His Asn His Tyr Thr Gln Lys Ser Leu Ser Leu Ser Pro Gly
        435                 440                 445

Lys

<210> SEQ ID NO 44
<211> LENGTH: 1347
<212> TYPE: DNA
<213> ORGANISM: Artificial Sequence
<220> FEATURE:
<223> OTHER INFORMATION: nucleic acid molecules encoding Erb-Knob

<400> SEQUENCE: 44

```
caggtgcagc tgaagcagag cggccccggc ctggtgcagc ccagccagag cctgagcatc     60
acctgcaccg tgagcggctt cagcctgacc aactacggcg tgcactgggt gcgccagagc    120
cccggcaagg gcctggagtg gctgggcgtg atctggagcg gcggcaacac cgactacaac    180
acccccttca ccagccgcct gagcatcaac aaggacaaca gcaagagcca ggtgttcttc    240
aagatgaaca gcctgcagag caacgacacc gccatctact actgcgcccg cgccctgacc    300
tactacgact acgagttcgc ctactggggc cagggcaccc tggtgaccgt gagcgccgcc    360
agcaccaagg gcccagcgt gttccccctg gcccccagca gcaagagcac cagcggcggc    420
accgccgccc tgggctgcct ggtgaaggac tacttccccg agcccgtgac cgtgagctgg    480
aacagcggcg ccctgaccag cggcgtgcac accttccccg ccgtgctgca gagcagcggc    540
ctgtacagcc tgagcagcgt ggtgaccgtg cccagcagca gcctgggcac ccagacctac    600
atctgcaacg tgaaccacaa gcccagcaac accaaggtgg acaagcgcgt ggagcccaag    660
agctgcgaca gaccccacac ctgccccccc tgccccgccc cgagctgct gggcggcccc    720
agcgtgttcc tgttcccccc caagcccaag gacaccctga tgatcagccg caccccgag    780
gtgacctgcg tggtggtgga cgtgagccac gaggaccccg aggtgaagtt caactggtac    840
gtggacggcg tggaggtgca caacgccaag accaagcccc gcgaggagca gtacaacagc    900
acctaccgcg tggtgagcgt gctgaccgtg ctgcaccagg actggctgaa cggcaaggag    960
tacaagtgca aggtgagcaa caaggccctg ccccgccccca tcgagaagac catcagcaag   1020
gccaagggcc agccccgcga gccccaggtg tacaccctgc ccccctgccg cgacgagctg   1080
accaagaacc aggtgagcct gtggtgcctg gtgaagggct tctaccccag cgacatcgcc   1140
gtggagtggg agagcaacgg ccagcccgag aacaactaca agaccacccc ccccgtgctg   1200
gacagcgacg gcagcttctt cctgtacagc aagctgaccg tggacaagag ccgctggcag   1260
cagggcaacg tgttcagctg cagcgtgatg cacgaggccc tgcacaacca ctacacccag   1320
aagagcctga gcctgagccc cggcaag                                       1347
```

<210> SEQ ID NO 45
<211> LENGTH: 214
<212> TYPE: PRT
<213> ORGANISM: Artificial Sequence
<220> FEATURE:
<223> OTHER INFORMATION: T-LC

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

-continued

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
         50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 46
<211> LENGTH: 708
<212> TYPE: DNA
<213> ORGANISM: Artificial Sequence
<220> FEATURE:
<223> OTHER INFORMATION: nucleic acid molecules encoding T-LC

<400> SEQUENCE: 46
gacatccaga tgacccagag ccccagcagc ctgagcgcca gcgtgggcga ccgcgtgacc      60
atcacctgcc gcgccagcca ggacgtgaac accgccgtgg cctggtacca gcagaagccc     120
ggcaaggccc ccaagctgct gatctacagc gccagcttcc tgtacagcgg cgtgcccagc     180
cgcttcagcg gcagccgcag cggcaccgac ttcaccctga ccatcagcag cctgcagccc     240
gaggacttcg ccacctacta ctgccagcag cactacacca cccccccac cttcggccag     300
ggcaccaagg tggagatcaa atactactgc agcagaaca acaactggcc caccaccttc     360
ggcgccggca ccaagctgga gctgaagcgc accgtggccg ccccagcgt gttcatcttc     420
cccccagcg acgagcagct gaagagcggc accgccagc tggtgtgcct gctgaacaac     480
ttctaccccc gcgaggccaa ggtgcagtgg aaggtggaca cgccctgca gagcggcaac     540
agccaggaga gcgtgaccga gcaggacagc aaggacagca cctacagcct gagcagcacc     600
ctgaccctga gcaaggccga ctacgagaag cacaaggtgt acgcctgcga ggtgacccac     660
cagggcctga gcagccccgt gaccaagagc ttcaaccgcg gcgagtgc               708

<210> SEQ ID NO 47
<211> LENGTH: 450
<212> TYPE: PRT
<213> ORGANISM: Artificial Sequence
<220> FEATURE:
<223> OTHER INFORMATION: T-Fc9

```
<400> SEQUENCE: 47

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
             85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Ala Leu Thr Val Asp
                405                 410                 415
```

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
            435                 440                 445

Gly Lys
    450

<210> SEQ ID NO 48
<211> LENGTH: 1350
<212> TYPE: DNA
<213> ORGANISM: Artificial Sequence
<220> FEATURE:
<223> OTHER INFORMATION: nucleic acid molecules encoding T-Fc9

<400> SEQUENCE: 48

```
gaggtgcagc tggtggagag cggcggcggc ctggtgcagc ccggcggcag cctgcgcctg      60
agctgcgccg ccagcggctt caacatcaag gacacctaca tccactgggt gcgccaggcc     120
cccggcaagg gcctggagtg ggtggcccgc atctacccca ccaacggcta cacccgctac     180
gccgacagcg tgaagggccg cttcaccatc agcgccgaca ccagcaagaa caccgcctac     240
ctgcagatga acagcctgcg cgccgaggac accgccgtgt actactgcag ccgctggggc     300
ggcgacggct tctacgccat ggactactgg ggccagggca ccctggtgac cgtgagcagc     360
gccagcacta aggggccctc tgtgtttcca ctcgccccct tctagcaaaag cacttccgga     420
ggaactgccg ctctgggctg tctggtgaaa gattacttcc ccgaaccagt cactgtgtca     480
tggaactctg gagcactgac atctggagtt cacacctttc ctgctgtgct gcagagttct     540
ggactgtact ccctgtcatc tgtggtcacc gtgccatctt catctctggg acccagacc     600
tacatctgta acgtgaacca caaaccctcc aacacaaaag tggacaaacg agtcgaacca     660
aaatcttgtg acaaaaccca cacatgccca ccgtgcccag ctccggaact cctgggcgga     720
ccgtcagtct tcctcttccc cccaaaaacc caaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag gcagccccg agaaccacag gtgtacaccc tgcccccaag tcgggatgag    1080
ctgaccaaga accaggtcag cctgtggtgc ctggtcaaag gcttctatcc agcgacatc    1140
gccgtggagt gggagagcaa tgggcagccg gagaacaact acaagaccac gcctccgtg    1200
ttggactccg acggctcctt cttcctctac agcgcgctca ccgtggacaa gagcaggtgg    1260
cagcagggga acgtcttctc atgctccgtg atgcatgagg ctctgcacaa ccactacacg    1320
cagaagagcc tctccctgtc tccgggtaaa                                     1350
```

<210> SEQ ID NO 49
<211> LENGTH: 214
<212> TYPE: PRT
<213> ORGANISM: Artificial Sequence
<220> FEATURE:
<223> OTHER INFORMATION: P-LC

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
             20                  25                  30

Val Ala Trp Tyr Gln Gln Lys Pro Gly Lys Ala Pro Lys Leu Leu Ile
         35                  40                  45

Tyr Ser Ala Ser Tyr Arg Tyr Thr Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Tyr Pro Tyr
                 85                  90                  95

Thr Phe Gly Gln Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                 165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
         195                 200                 205

Phe Asn Arg Gly Glu Cys
    210

<210> SEQ ID NO 50
<211> LENGTH: 708
<212> TYPE: DNA
<213> ORGANISM: Artificial Sequence
<220> FEATURE:
<223> OTHER INFORMATION: nucleic acid molecules encoding P-LC

<400> SEQUENCE: 50
gacatccaga tgacccagag ccccagcagc ctgagcgcca gcgtgggcga ccgcgtgacc    60
atcacctgca aggccagcca ggacgtgagc atcggcgtgg cctggtacca gcagaagccc   120
ggcaaggccc ccaagctgct gatctacagc gccagctacc gctacaccgg cgtgcccagc   180
cgcttcagcg gcagcggcag cggcaccgac ttcaccctga ccatcagcag cctgcagccc   240
gaggacttcg ccacctacta ctgccagcag tactacatct accccgacac cttcggccag   300
ggcaccaagg tggagatcaa gtactactgc cagcagaaca caactggcc caccaccttc   360 ggcgccggca ccaagctgga gctgaagcgc accgtggccg cccccagcgt gttcatcttc   420
ccccccagcg acgagcagct gaagagcggc accgccagcg tggtgtgcct gctgaacaac   480 ttctacccc gcgaggccaa ggtgcagtgg aaggtggaca acgccctgca gagcggcaac   540
agccaggaga gcgtgaccga gcaggacagc aaggacagca cctacagcct gagcagcacc   600
ctgaccctga gcaaggccga ctacgagaag cacaaggtgt acgcctgcga ggtgacccac   660
cagggcctga gcagccccgt gaccaagagc ttcaaccgcg gcgagtgc               708

<210> SEQ ID NO 51
<211> LENGTH: 449
<212> TYPE: PRT
<213> ORGANISM: Artificial Sequence
<220> FEATURE:

<223> OTHER INFORMATION: P-Fc9

<400> SEQUENCE: 51

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Ala Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys

<210> SEQ ID NO 52
<211> LENGTH: 1347
<212> TYPE: DNA
<213> ORGANISM: Artificial Sequence
<220> FEATURE:
<223> OTHER INFORMATION: nucleic acid molecules encoding P-Fc9

<400> SEQUENCE: 52
gaggtgcagc tggtggagag cggcggcggc ctggtgcagc ccggcggcag cctgcgcctg      60
agctgcgccg ccagcggctt caccttcacc gactacacca tggactgggt gcgccaggcc     120
cccggcaagg gcctggagtg ggtggccgac gtgaacccca cagcggcgg cagcatctac      180
aaccagcgct tcaagggccg cttcaccctg agcgtggacc gcagcaagaa cacctgtac     240
ctgcagatga acagcctgcg cgccgaggac accgccgtgt actactgcgc ccgcaacctg     300
ggccccagct ctacttcga ctactgggc cagggcaccc tggtgaccgt gagcagcgcc      360
agcactaagg ggccctctgt gtttccactc gccccttcta gcaaaagcac ttccggagga     420
actgccgctc tgggctgtct ggtgaaagat tacttcccg aaccagtcac tgtgtcatgg      480
aactctggag cactgacatc tggagttcac acctttcctg ctgtgctgca gagttctgga     540
ctgtactccc tgtcatctgt ggtcaccgtg ccatcttcat ctctggggac ccagacctac     600
atctgtaacg tgaaccacaa accctccaac acaaaagtgg acaaacgagt cgaaccaaaa     660
tcttgtgaca aaacccacac atgcccaccg tgcccagctc cggaactcct gggcggaccg     720
tcagtcttcc tcttcccccc aaaacccaag gacaccctca tgatctcccg gacccctgag     780
gtcacatgcg tggtggtgga cgtgagccca gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc ccccaagtcg ggatgagctg    1080
accaagaacc aggtcagcct gtggtgcctg gtcaaaggct tctatcccag cgacatcgcc    1140
gtggagtggg agagcaatgg gcagccggag aacaactaca agaccacgcc tcccgtgttg    1200
gactccgacg gctccttctt cctctacagc gcgctcaccg tggacaagag caggtggcag    1260
caggggaacg tcttctcatg ctccgtgatg catgaggctc tgcacaacca ctacacgcag    1320
aagagcctct ccctgtctcc gggtaaa                                        1347

<210> SEQ ID NO 53
<211> LENGTH: 214
<212> TYPE: PRT
<213> ORGANISM: Artificial Sequence
<220> FEATURE:
<223> OTHER INFORMATION: Mab806-LC

<400> SEQUENCE: 53

Asp Ile Leu Met Thr Gln Ser Pro Ser Ser Met Ser Val Ser Leu Gly
1               5                   10                  15
```

```
Asp Thr Val Ser Ile Thr Cys His Ser Ser Gln Asp Ile Asn Ser Asn
         20                  25                  30

Ile Gly Trp Leu Gln Gln Arg Pro Gly Lys Ser Phe Lys Gly Leu Ile
         35                  40                  45

Tyr His Gly Thr Asn Leu Asp Asp Glu Val Pro Ser Arg Phe Ser Gly
     50                  55                  60

Ser Gly Ser Gly Ala Asp Tyr Ser Leu Thr Ile Ser Ser Leu Glu Ser
 65                  70                  75                  80

Glu Asp Phe Ala Asp Tyr Tyr Cys Val Gln Tyr Ala Gln Phe Pro Trp
                 85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 54
<211> LENGTH: 708
<212> TYPE: DNA
<213> ORGANISM: Artificial Sequence
<220> FEATURE:
<223> OTHER INFORMATION: nucleic acid molecules encoding Mab806-LC

<400> SEQUENCE: 54
gacatcctga tgacccagag ccccagcagc atgagcgtga gcctgggcga caccgtgagc      60
atcacctgcc acagcagcca ggacatcaac agcaacatcg gctggctgca gcagcgcccc     120
ggcaagagct tcaagggcct gatctaccac ggcaccaacc tggacgacga ggtgcccagc     180
cgcttcagcg gcagcggcag cggcgccgac tacagcctga ccatcagcag cctggagagc     240
gaggacttcg ccgactacta ctgcgtgcag tacgcccagt tcccctggac cttcggcggc     300
ggcaccaagc tggagatcaa gtactactgc cagcagaaca caactggcc accaccttc      360 ggcgccggca ccaagctgga gctgaagcgc accgtggccg cccccagcgt gttcatcttc     420 cccccagcg acgagcagct gaagagcggc accgccagcg tggtgtgcct gctgaacaac     480
ttctaccccc gcgaggccaa ggtgcagtgg aaggtggaca cgccctgca gagcggcaac     540 agccaggaga gcgtgaccga gcaggacagc aaggacagca cctacagcct gagcagcacc     600
ctgaccctga gcaaggccga ctacgagaag cacaaggtgt acgcctgcga ggtgacccac     660
cagggcctga gcagccccgt gaccaagagc ttcaaccgcg gcgagtgc                 708

<210> SEQ ID NO 55
<211> LENGTH: 446
<212> TYPE: PRT
<213> ORGANISM: Artificial Sequence
```

<220> FEATURE:
<223> OTHER INFORMATION: Mab806-Fc9

<400> SEQUENCE: 55

```
Asp Val Gln Leu Gln Glu Ser Gly Pro Ser Leu Val Lys Pro Ser Gln
1               5                   10                  15

Ser Leu Ser Leu Thr Cys Thr Val Thr Gly Tyr Ser Ile Thr Ser Asp
            20                  25                  30

Phe Ala Trp Asn Trp Ile Arg Gln Phe Pro Gly Asn Lys Leu Glu Trp
        35                  40                  45

Met Gly Tyr Ile Ser Tyr Ser Gly Asn Thr Arg Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ile Glu Asp Thr Ala Thr Tyr Tyr Cys
                85                  90                  95

Val Thr Ala Gly Arg Gly Phe Pro Tyr Trp Gly Gln Gly Thr Leu Val
            100                 105                 110

Thr Val Ser Ala Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400
```

Gly Ser Phe Phe Leu Tyr Ser Ala Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
            435                 440                 445

<210> SEQ ID NO 56
<211> LENGTH: 1338
<212> TYPE: DNA
<213> ORGANISM: Artificial Sequence
<220> FEATURE:
<223> OTHER INFORMATION: nucleic acid molecules encoding Mab806-Fc9

<400> SEQUENCE: 56

```
gacgtgcagc tgcaggagag cggccccagc ctggtgaagc ccagccagag cctgagcctg      60
acctgcaccg tgaccggcta cagcatcacc agcgacttcg cctggaactg gatccgccag     120
ttccccggca acaagctgga gtggatgggc tacatcagct acagcggcaa cacccgctac     180
aaccccagcc tgaagagccg catcagcatc acccgcgaca ccagcaagaa ccagttcttc     240
ctgcagctga cagcgtgac catcgaggac accgccacct actactgcgt gaccgccggc     300
cgcggcttcc cctactgggg ccagggcacc ctggtgaccg tgagcgccgc cagcactaag     360
gggccctctg tgtttccact cgcccttct agcaaaagca cttccggagg aactgccgct     420
ctgggctgtc tggtgaaaga ttacttcccc gaaccagtca ctgtgtcatg gaactctgga     480
gcactgacat ctggagttca cccttttcct gctgtgctgc agagttctgg actgtactcc     540
ctgtcatctg tggtcaccgt gccatcttca tctctgggga cccagaccta catctgtaac     600
gtgaaccaca accctccaa cacaaaagtg gacaaacgag tcgaaccaaa atcttgtgac     660
aaaaacccaca catgcccacc gtgcccagct ccggaactcc tgggcggacc gtcagtcttc     720
ctcttccccc caaaacccaa ggacaccctc atgatctccc ggaccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtacaccctg cccccaagtc gggatgagct gaccaagaac    1080
caggtcagcc tgtggtgcct ggtcaaaggc ttctatccca gcgacatcgc cgtggagtgg    1140
gagagcaatg ggcagccgga gaacaactac aagaccacgc tcccgtgtt ggactccgac    1200
ggctccttct cctctacag cgcgctcacc gtggacaaga gcaggtggca gcagggggaac    1260
gtcttctcat gctccgtgat gcatgaggct ctgcacaacc actacacgca gaagagcctc    1320
tccctgtctc cgggtaaa                                                  1338
```

<210> SEQ ID NO 57
<211> LENGTH: 219
<212> TYPE: PRT
<213> ORGANISM: Artificial Sequence
<220> FEATURE:
<223> OTHER INFORMATION: C-MAB-LC

<400> SEQUENCE: 57

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 58
<211> LENGTH: 657
<212> TYPE: DNA
<213> ORGANISM: Artificial Sequence
<220> FEATURE:
<223> OTHER INFORMATION: nucleic acid molecules encoding C-MAB-LC

<400> SEQUENCE: 58
gacgtggtga tgacccagag ccccctgagc ctgcctgtga cacctggcga gcctgccagc    60
atcagctgca gaagcagcca gtccctggtg cacagcaaca ggaacaccta cctgcactgg   120
tatttacaga gcccggaca gagccccag ctgctgatct acaaggtgag caacaggttc   180
agcggcgtgc ctgacaggtt ttccggcagc ggcagcggca ccgacttcac cctgaagatc   240
agcagggtgg aggccgagga tgtgggcgtg tactactgca gccagaacac ccacgtgccc   300
cctacctttg gccagggcac caagctggag atcaagcgta cggtggctgc accatctgtc   360
ttcatcttcc cgccatctga tgagcagttg aaatctggta ccgctagcgt tgtgtgcctg   420
ctgaataact ttatccacg ggaggctaag gtgcagtgga agtggacaa tgccctccag   480 agcggaaata gccaagagtc cgttaccgaa caggactcta agactctac atactccctg   540 tcctccacac tgaccctctc caaggccgac tatgagaaac acaaggttta cgcatgcgag   600
gtcacacacc agggactctc ctctcccgtg accaagagct tcaaccgggg agaatgc     657

<210> SEQ ID NO 59
<211> LENGTH: 445
<212> TYPE: PRT
<213> ORGANISM: Artificial Sequence
<220> FEATURE:
<223> OTHER INFORMATION: C-MAB-Fc9

<400> SEQUENCE: 59

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Glu Met His Trp Val Arg Gln Ala Pro Gly Gln Gly Leu Glu Trp Met
        35                  40                  45
Gly Ala Leu Asp Pro Lys Thr Gly Asp Thr Ala Tyr Ser Gln Lys Phe
    50                  55                  60
Lys Gly Arg Val Thr Leu Thr Ala Asp Lys Ser Thr Ser Thr Ala Tyr
65                  70                  75                  80
Met Glu Leu Ser Ser Leu Thr Ser Glu Asp Thr Ala Val Tyr Tyr Cys
                85                  90                  95
Thr Arg Phe Tyr Ser Tyr Thr Tyr Trp Gly Gln Gly Thr Leu Val Thr
            100                 105                 110
Val Ser Ser Ala Ser Thr Lys Gly Pro Ser Val Phe Pro Leu Ala Pro
        115                 120                 125
Ser Ser Lys Ser Thr Ser Gly Gly Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Arg Val Glu Pro Lys Ser Cys Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
        275                 280                 285
Pro Arg Glu Glu Gln Tyr Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Asp Glu Leu Thr Lys Asn Gln Val Ser Leu Trp Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Ala Leu Thr Val Asp Lys Ser Arg Trp Gln
                405                 410                 415
```

```
Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440             445

<210> SEQ ID NO 60
<211> LENGTH: 1335
<212> TYPE: DNA
<213> ORGANISM: Artificial Sequence
<220> FEATURE:
<223> OTHER INFORMATION: nucleic acid molecules encoding C-MAB-Fc9

<400> SEQUENCE: 60
caggtgcagc tggtgcagag cggcgccgag gtgaagaaac ctggcgccag cgtgaaggtg      60
agctgcaagg cctccggcta caccttcacc gactacgaga tgcactgggt gaggcaggcc     120
cctggacaag gactggagtg gatgggcgcc ttagatccta agacaggcga caccgcctac     180
tcccagaagt tcaagggcag ggtgaccctg accgccgaca gagcaccag caccgcctac      240
atggagctga gcagcctgac cagcgaggac accgccgtgt actattgcac caggttctac     300
agctacacct actggggcca gggcacactg gtgaccgtga gcagcgccag cactaagggg     360
cccctctgtgt ttccactcgc cccttctagc aaaagcactt ccggaggaac tgccgctctg     420
ggctgtctgg tgaaagatta cttcccccgaa ccagtcactg tgtcatggaa ctctggagca     480
ctgacatctg gagttcacac cttttcctgct gtgctgcaga gttctggact gtactccctg     540
tcatctgtgg tcaccgtgcc atcttcatct ctggggaccc agacctacat ctgtaacgtg     600
aaccacaaac cctccaacac aaaagtggac aaacgagtcg aaccaaaatc ttgtgacaaa     660
acccacacat gcccaccgtg cccagctccg gaactcctgg gcggaccgtc agtcttcctc     720
ttccccccaa aacccaagga caccctcatg atctcccgga cccctgaggt cacatgcgtg     780
gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcaag     960
gtctccaaca agccctcccc agcccccatc gagaaaacca tctccaaagc caaagggcag    1020
ccccgagaac cacaggtgta caccctgccc ccaagtcggg atgagctgac caagaaccag    1080
gtcagcctgt ggtgcctggt caaaggcttc tatcccagcg acatcgccgt ggagtgggag    1140
agcaatgggc agccggagaa caactacaag accacgcctc ccgtgttgga ctccgacggc    1200
tccttcttcc tctacagcgc gctcaccgtg gacaagagca ggtggcagca ggggaacgtc    1260
ttctcatgct ccgtgatgca tgaggctctg cacaaccact acacgcagaa gagcctctcc    1320
ctgtctccgg gtaaa                                                     1335

<210> SEQ ID NO 61
<211> LENGTH: 215
<212> TYPE: PRT
<213> ORGANISM: Artificial Sequence
<220> FEATURE:
<223> OTHER INFORMATION: 28H1-LC

<400> SEQUENCE: 61

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30
```

-continued

```
Tyr Leu Ala Trp Tyr Gln Gln Lys Pro Gly Gln Ala Pro Arg Leu Leu
             35                  40                  45
Ile Ile Gly Ala Ser Thr Arg Ala Thr Gly Ile Pro Asp Arg Phe Ser
 50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Gly Gln Val Ile Pro
                 85                  90                  95
Pro Thr Phe Gly Gln Gly Thr Lys Val Glu Ile Lys Arg Thr Val Ala
                100                 105                 110
Ala Pro Ser Val Phe Ile Phe Pro Pro Ser Asp Glu Gln Leu Lys Ser
            115                 120                 125
Gly Thr Ala Ser Val Val Cys Leu Leu Asn Asn Phe Tyr Pro Arg Glu
        130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys
    210                 215

<210> SEQ ID NO 62
<211> LENGTH: 645
<212> TYPE: DNA
<213> ORGANISM: Artificial Sequence
<220> FEATURE:
<223> OTHER INFORMATION: nucleic acid molecules encoding 28H1-LC

<400> SEQUENCE: 62
gagatcgtgc tgacacagtc tccaggcacc ctgtctctgt ctccaggaga gagagccacc      60
ctgtcttgca gagcctctca gagcgtgtcc aggagctacc tggcttggta tcagcagaag     120
ccaggacagg cccctagact gctgatcatc ggagcctcta caagagccac aggcatccca     180
gacagattca gcggcagcgg aagcggcaca gacttcaccc tgaccatcag caggctggag     240
ccagaggact tcgccgtgta ctattgccag cagggccagg tcatccctcc tacctttgga     300
cagggcacca aggtggagat caagcgtacg gtggctgcac catctgtctt catcttcccg     360
ccatctgatg agcagttgaa atctggtacc gctagcgttg tgtgcctgct gaataacttt     420
tatccacggg aggctaaggt gcagtggaaa gtggacaatg ccctccagag cggaaatagc     480
caagagtccg ttaccgaaca ggactctaaa gactctacat actccctgtc ctccacactg     540
accctctcca aggccgacta tgagaaacac aaggtttacg catgcgaggt cacacaccag     600
ggactctcct ctcccgtgac caagagcttc aaccggggag aatgc                    645

<210> SEQ ID NO 63
<211> LENGTH: 446
<212> TYPE: PRT
<213> ORGANISM: Artificial Sequence
<220> FEATURE:
<223> OTHER INFORMATION: 28H1-Fc9

<400> SEQUENCE: 63

Glu Val Gln Leu Leu Glu Ser Gly Gly Gly Leu Val Gln Pro Gly Gly
```

-continued

```
1               5                   10                  15
Ser Leu Arg Leu Ser Cys Ala Ala Ser Gly Phe Thr Phe Ser Ser His
                20                  25                  30
Ala Met Ser Trp Val Arg Gln Ala Pro Gly Lys Gly Leu Glu Trp Val
                35                  40                  45
Ser Ala Ile Trp Ala Ser Gly Glu Gln Tyr Tyr Ala Asp Ser Val Lys
                50                  55                  60
Gly Arg Phe Thr Ile Ser Arg Asp Asn Ser Lys Asn Thr Leu Tyr Leu
 65                 70                  75                  80
Gln Met Asn Ser Leu Arg Ala Gln Asp Thr Ala Val Tyr Tyr Cys Ala
                85                  90                  95
Lys Gly Trp Leu Gly Asn Phe Asp Tyr Trp Gly Gln Gly Thr Leu Val
                100                 105                 110
Thr Val Ser Ser Ala Ser Thr Lys Gly Pro Ser Val Phe Pro Leu Ala
                115                 120                 125
Pro Ser Ser Lys Ser Thr Ser Gly Gly Thr Ala Ala Leu Gly Cys Leu
                130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
                180                 185                 190
Gly Thr Gln Thr Tyr Ile Cys Asn Val Asn His Lys Pro Ser Asn Thr
                195                 200                 205
Lys Val Asp Lys Arg Val Glu Pro Lys Ser Cys Asp Lys Thr His Thr
210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
                260                 265                 270
Lys Phe Asn Trp Tyr Val Asp Gly Val Glu Val His Asn Ala Lys Thr
                275                 280                 285
Lys Pro Arg Glu Glu Gln Tyr Asn Ser Thr Tyr Arg Val Val Ser Val
                290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
                340                 345                 350
Ser Arg Asp Glu Leu Thr Lys Asn Gln Val Ser Leu Trp Cys Leu Val
                355                 360                 365
Lys Gly Phe Tyr Pro Ser Asp Ile Ala Val Glu Trp Glu Ser Asn Gly
                370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Ala Leu Thr Val Asp Lys Ser Arg Trp
                405                 410                 415
Gln Gln Gly Asn Val Phe Ser Cys Ser Val Met His Glu Ala Leu His
                420                 425                 430
```

Asn His Tyr Thr Gln Lys Ser Leu Ser Leu Ser Pro Gly Lys
        435                 440                 445

<210> SEQ ID NO 64
<211> LENGTH: 1338
<212> TYPE: DNA
<213> ORGANISM: Artificial Sequence
<220> FEATURE:
<223> OTHER INFORMATION: nucleic acid molecules encoding 28H1-Fc9

<400> SEQUENCE: 64

| | | | |
|---|---|---|---|
| gaggtgcagc tgctggaatc aggaggagga ctggtgcagc caggaggatc tctgagactg | 60 |
| tcttgcgccg ccagcggctt tacattcagc tctcacgcca tgtcttgggt ccgacaggct | 120 |
| ccaggcaaag gactgaatg ggtgtccgct atttgggcca gcggagagca gtactacgcc | 180 |
| gacagcgtga agggacggtt caccatcagc cgggacaaca gcaagaacac cctgtacctg | 240 |
| cagatgaaca gcctgagggc ccaggatacc gccgtgtact attgcgccaa gggttggctg | 300 |
| ggcaacttcg actattgggg ccaggaacc ctggtgacag tgtccagcgc cagcactaag | 360 |
| gggccctctg tgttttccact cgccccttct agcaaaagca cttccggagg aactgccgct | 420 |
| ctgggctgtc tggtgaaaga ttacttcccc gaaccagtca ctgtgtcatg gaactctgga | 480 |
| gcactgacat ctggagttca cacctttcct gctgtgctgc agagttctgg actgtactcc | 540 |
| ctgtcatctg tggtcaccgt gccatcttca tctctgggga cccagaccta catctgtaac | 600 |
| gtgaaccaca accctccaa cacaaaagtg gacaaacgag tcgaaccaaa atcttgtgac | 660 |
| aaaacccaca catgcccacc gtgcccagct ccggaactcc tgggcggacc gtcagtcttc | 720 |
| ctcttccccc caaaacccaa ggacaccctc atgatctccc ggacccctga ggtcacatgc | 780 |
| gtggtggtgg acgtgagcca cgaagaccct gaggtcaagt tcaactggta cgtggacggc | 840 |
| gtggaggtgc ataatgccaa gacaaagccg cgggaggagc agtacaacag cacgtaccgt | 900 |
| gtggtcagcg tcctcaccgt cctgcaccag gactggctga atggcaagga gtacaagtgc | 960 |
| aaggtctcca acaaagccct cccagccccc atcgagaaaa ccatctccaa agccaaaggg | 1020 |
| cagccccgag aaccacaggt gtacaccctg cccccaagtc gggatgagct gaccaagaac | 1080 |
| caggtcagcc tgtggtgcct ggtcaaaggc ttctatccca gcgacatcgc cgtggagtgg | 1140 |
| gagagcaatg gcagccgga gaacaactac aagaccacgc ctcccgtgtt ggactccgac | 1200 |
| ggctccttct tcctctacag cgcgctcacc gtggacaaga gcaggtggca gcaggggaac | 1260 |
| gtcttctcat gctccgtgat gcatgaggct ctgcacaacc actacacgca gaagagcctc | 1320 |
| tccctgtctc cgggtaaa | 1338 |

<210> SEQ ID NO 65
<211> LENGTH: 220
<212> TYPE: PRT
<213> ORGANISM: Artificial Sequence
<220> FEATURE:
<223> OTHER INFORMATION: 5E5-LC

<400> SEQUENCE: 65

Glu Leu Val Met Thr Gln Ser Pro Ser Ser Leu Thr Val Thr Ala Gly
1               5                   10                  15

Glu Lys Val Thr Met Ile Cys Lys Ser Ser Gln Ser Leu Leu Asn Ser
            20                  25                  30

Gly Asp Gln Lys Asn Tyr Leu Thr Trp Tyr Gln Gln Lys Pro Gly Gln
        35                  40                  45

```
Pro Pro Lys Leu Leu Ile Phe Trp Ala Ser Thr Arg Glu Ser Gly Val
    50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Ser Tyr Pro Leu Thr Phe Gly Ala Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 66
<211> LENGTH: 660
<212> TYPE: DNA
<213> ORGANISM: Artificial Sequence
<220> FEATURE:
<223> OTHER INFORMATION: nucleic acid molecules encoding 5E5-LC

<400> SEQUENCE: 66

```
gaactcgtga tgacccagag ccccagctct ctgacagtga cagccggcga gaaagtgacc      60
atgatctgca agtcctccca gagcctgctg aactccggcg accagaagaa ctacctgacc     120
tggtatcagc agaaacccgg ccagcccccc aagctgctga tcttttgggc cagcacccgg     180
gaaagcggcg tgcccgatag attcacaggc agcggctccg gcaccgactt taccctgacc     240
atcagctccg tgcaggccga ggacctggcc gtgtattact gccagaacga ctacagctac     300
cccctgacct tcggagccgg caccaagctg gaactgaagc gtacggtggc tgcaccatct     360
gtcttcatct tcccgccatc tgatgagcag ttgaaatctg gtaccgctag cgttgtgtgc     420
ctgctgaata ctttttatcc acgggaggct aaggtgcagt ggaaagtgga caatgccctc     480
cagagcggaa atagccaaga gtccgttacc gaacaggact ctaaagactc tacatactcc     540
ctgtcctcca cactgaccct ctccaaggcc gactatgaga acacaaggt ttacgcatgc      600
gaggtcacac accagggact ctcctctccc gtgaccaaga gcttcaaccg ggagaatgc      660
```

<210> SEQ ID NO 67
<211> LENGTH: 446
<212> TYPE: PRT
<213> ORGANISM: Artificial Sequence
<220> FEATURE:
<223> OTHER INFORMATION: 5E5-Fc9

<400> SEQUENCE: 67

```
Gln Val Gln Leu Gln Gln Ser Asp Ala Glu Leu Val Lys Pro Gly Ser
  1               5                  10                  15

Ser Val Lys Ile Ser Cys Lys Ala Ser Gly Tyr Thr Phe Thr Asp His
```

-continued

```
                20                  25                  30
Ala Ile His Trp Val Lys Gln Lys Pro Glu Gln Gly Leu Glu Trp Ile
                35                  40                  45
Gly His Phe Ser Pro Gly Asn Thr Asp Ile Lys Tyr Asn Asp Lys Phe
                50                  55                  60
Lys Gly Lys Ala Thr Leu Thr Val Asp Arg Ser Ser Thr Ala Tyr
 65                 70                  75                  80
Met Gln Leu Asn Ser Leu Thr Ser Glu Asp Ser Ala Val Tyr Phe Cys
                85                  90                  95
Lys Thr Ser Thr Phe Phe Asp Tyr Trp Gly Gln Gly Thr Thr Leu
                100                 105                 110
Thr Val Ser Ser Ala Ser Thr Lys Gly Pro Ser Val Phe Pro Leu Ala
                115                 120                 125
Pro Ser Ser Lys Ser Thr Ser Gly Gly Thr Ala Ala Leu Gly Cys Leu
                130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
                180                 185                 190
Gly Thr Gln Thr Tyr Ile Cys Asn Val Asn His Lys Pro Ser Asn Thr
                195                 200                 205
Lys Val Asp Lys Arg Val Glu Pro Lys Ser Cys Asp Lys Thr His Thr
                210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
                260                 265                 270
Lys Phe Asn Trp Tyr Val Asp Gly Val Glu Val His Asn Ala Lys Thr
                275                 280                 285
Lys Pro Arg Glu Glu Gln Tyr Asn Ser Thr Tyr Arg Val Val Ser Val
                290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
                340                 345                 350
Ser Arg Asp Glu Leu Thr Lys Asn Gln Val Ser Leu Trp Cys Leu Val
                355                 360                 365
Lys Gly Phe Tyr Pro Ser Asp Ile Ala Val Glu Trp Glu Ser Asn Gly
                370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Ala Leu Thr Val Asp Lys Ser Arg Trp
                405                 410                 415
Gln Gln Gly Asn Val Phe Ser Cys Ser Val Met His Glu Ala Leu His
                420                 425                 430
Asn His Tyr Thr Gln Lys Ser Leu Ser Leu Ser Pro Gly Lys
                435                 440                 445
```

<210> SEQ ID NO 68
<211> LENGTH: 1338
<212> TYPE: DNA
<213> ORGANISM: Artificial Sequence
<220> FEATURE:
<223> OTHER INFORMATION: nucleic acid molecules encoding 5E5-Fc9

<400> SEQUENCE: 68

```
caggtgcagc tgcagcagtc tgatgccgag ctcgtgaagc tggcagcag cgtgaagatc        60
agctgcaagg ccagcggcta caccttcacc gaccacgcca tccactgggt caagcagaag       120
cctgagcagg gcctggaatg gatcggccac ttcagcccg gcaacaccga catcaagtac       180
aacgacaagt tcaagggcaa ggccaccctg accgtggaca agcagcag caccgcctac       240
atgcagctga acagcctgac cagcgaggac agcgccgtgt acttctgcaa gaccagcacc      300
ttcttttcg actactgggg ccagggcaca accctgacag tgtctagcgc cagcactaag      360
gggccctctg tgtttccact cgccccttct agcaaaagca cttccggagg aactgccgct      420
ctgggctgtc tggtgaaaga ttacttcccc gaaccagtca ctgtgtcatg aactctgga      480
gcactgacat ctggagttca cctttcct gctgtgctgc agagttctgg actgtactcc       540
ctgtcatctg tggtcaccgt gccatcttca tctctgggga cccagaccta catctgtaac     600
gtgaaccaca accctccaa cacaaaagtg gacaaacgag tcgaaccaaa atcttgtgac     660
aaaacccaca catgcccacc gtgcccagct ccggaactcc tgggcggacc gtcagtcttc      720
ctcttccccc caaaacccaa ggacaccctc atgatctccc ggacccctga ggtcacatgc      780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca caaagccct cccagccccc atcgagaaaa ccatctccaa agccaaaggg     1020
cagccccgag aaccacaggt gtacaccctg cccccaagtc gggatgagct gaccaagaac     1080
caggtcagcc tgtggtgcct ggtcaaaggc ttctatccca gcgacatcgc cgtggagtgg    1140
gagagcaatg ggcagccgga gaacaactac aagaccacgc ctcccgtgtt ggactccgac    1200
ggctccttct cctctacag cgcgctcacc gtggacaaga gcaggtggca gcaggggaac     1260
gtcttctcat gctccgtgat gcatgaggct ctgcacaacc actacacgca gaagagcctc    1320
tccctgtctc cgggtaaa                                                   1338
```

<210> SEQ ID NO 69
<211> LENGTH: 213
<212> TYPE: PRT
<213> ORGANISM: Artificial Sequence
<220> FEATURE:
<223> OTHER INFORMATION: E-mab-LC

<400> SEQUENCE: 69

```
Gln Val Val Leu Thr Gln Ser Pro Val Ile Met Ser Ala Ser Pro Gly
  1               5                  10                  15

Glu Lys Val Thr Met Thr Cys Ser Ala Ser Ser Ile Ser Tyr Met
             20                  25                  30

Tyr Trp Tyr Gln Gln Lys Pro Gly Thr Ser Pro Lys Arg Trp Ile Tyr
         35                  40                  45

Asp Thr Ser Lys Leu Ala Ser Gly Val Pro Ala Arg Phe Ser Gly Ser
     50                  55                  60
```

Gly Ser Gly Thr Ser Tyr Ser Leu Thr Ile Ser Asn Met Glu Ala Gly
 65                  70                  75                  80

Asp Ala Ala Thr Tyr Tyr Cys His Gln Arg Asp Ser Tyr Pro Trp Thr
                 85                  90                  95

Phe Gly Gly Gly Thr Asn Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 70
<211> LENGTH: 639
<212> TYPE: DNA
<213> ORGANISM: Artificial Sequence
<220> FEATURE:
<223> OTHER INFORMATION: nucleic acid molecules encoding E-mab-LC

<400> SEQUENCE: 70
caggtggtgc tgacccagag ccccgtgatc atgtccgcca gccctggcga gaaggtgacc      60
atgacctgca gcgccagcag cagcatcagc tacatgtact ggtatcaaca gaagcccggc     120
accagcccca gaggtggat ctacgacacc agcaagctgg ctagcggcgt gcctgccaga      180
ttcagcggaa gcggcagcgg caccagctac agcctgacca tcagcaacat ggaggccggc     240
gacgccgcca catactactg ccaccagagg gactcctacc cctggacctt cggcggaggc     300
accaacctgg agatcaagcg tacggtggct gcaccatctg tcttcatctt cccgccatct     360
gatgagcagt tgaaatctgg taccgctagc gttgtgtgcc tgctgaataa ctttatcca     420 cgggaggcta aggtgcagtg gaaagtggac aatgccctcc agagcggaaa tagccaagag     480
tccgttaccg aacaggactc taaagactct acatactccc tgtcctccac actgaccctc     540
tccaaggccg actatgagaa acacaaggtt tacgcatgcg aggtcacaca ccagggactc     600
tcctctcccg tgaccaagag cttcaaccgg ggagaatgc                            639

<210> SEQ ID NO 71
<211> LENGTH: 443
<212> TYPE: PRT
<213> ORGANISM: Artificial Sequence
<220> FEATURE:
<223> OTHER INFORMATION: E-mab-Fc9

<400> SEQUENCE: 71

Gln Val Gln Leu Lys Glu Ser Gly Pro Asp Leu Val Ala Pro Ser Gln
1               5                   10                  15

Ser Leu Ser Ile Thr Cys Thr Val Ser Gly Phe Ser Leu Ser Lys Phe
            20                  25                  30

Gly Val Asn Trp Val Arg Gln Pro Pro Gly Lys Gly Leu Glu Trp Leu 35                  40                  45
Gly Val Ile Trp Gly Asp Gly Ser Thr Ser Tyr Asn Ser Gly Leu Ile
 50                  55                  60

Ser Arg Leu Ser Ile Ser Lys Glu Asn Ser Lys Ser Gln Val Phe Leu
 65                  70                  75                  80

Lys Leu Asn Ser Leu Gln Ala Asp Asp Thr Ala Thr Tyr Tyr Cys Val
                 85                  90                  95

Lys Pro Gly Gly Asp Tyr Trp Gly His Gly Thr Ser Val Thr Val Ser
                100                 105                 110

Ser Ala Ser Thr Lys Gly Pro Ser Val Phe Pro Leu Ala Pro Ser Ser
                115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
                180                 185                 190

Thr Tyr Ile Cys Asn Val Asn His Lys Pro Ser Asn Thr Lys Val Asp
                195                 200                 205

Lys Arg Val Glu Pro Lys Ser Cys Asp Lys Thr His Thr Cys Pro Pro
210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
                260                 265                 270

Trp Tyr Val Asp Gly Val Glu Val His Asn Ala Lys Thr Lys Pro Arg
                275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
                340                 345                 350

Glu Leu Thr Lys Asn Gln Val Ser Leu Trp Cys Leu Val Lys Gly Phe
                355                 360                 365

Tyr Pro Ser Asp Ile Ala Val Glu Trp Glu Ser Asn Gly Gln Pro Glu
                370                 375                 380

Asn Asn Tyr Lys Thr Thr Pro Pro Val Leu Asp Ser Asp Gly Ser Phe
385                 390                 395                 400

Phe Leu Tyr Ser Ala Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
                435                 440

<210> SEQ ID NO 72

<211> LENGTH: 1329
<212> TYPE: DNA
<213> ORGANISM: Artificial Sequence
<220> FEATURE:
<223> OTHER INFORMATION: nucleic acid molecules encoding E-mab-Fc9

<400> SEQUENCE: 72

```
caggtgcagc tgaaggagag cggacctgac ctggtggccc ctagccagag cctgagcatc      60
acctgcaccg tgagcggctt cagcctgagc aagttcggcg tgaactgggt gagacagccc     120
cccggaaagg gactggagtg gctgggagtg atctggggcg acggcagcac cagctacaac     180
agcggcctga tcagcaggct gtccatcagc aaggagaaca gcaagagcca ggtgttcctg     240
aagctgaaca gcctgcaggc cgacgacacc gccacctact actgcgtgaa gcctggcggc     300
gattactggg gccacggaac cagcgtgacc gtgagcagcg ccagcactaa ggggcccctct    360
gtgtttccac tcgccccttc tagcaaaagc acttccggag gaactgccgc tctgggctgt     420
ctggtgaaag attacttccc cgaaccagtc actgtgtcat ggaactctgg agcactgaca     480
tctggagttc acacctttcc tgctgtgctg cagagttctg gactgtactc cctgtcatct     540
gtggtcaccg tgccatcttc atctctgggg acccagacct acatctgtaa cgtgaaccac     600
aaaccctcca cacaaaagt ggacaaacga gtcgaaccaa atcttgtga caaaacccac      660
acatgcccac cgtgcccagc tccggaactc ctgggcggac cgtcagtctt cctcttcccc     720
ccaaaaccca aggacaccct catgatctcc cggaccctg aggtcacatg cgtggtggtg      780
gacgtgagcc acgaagaccc tgaggtcaag ttcaactggt acgtggacgg cgtggaggtg     840
cataatgcca agacaaagcc gcgggaggag cagtacaaca gcacgtaccg tgtggtcagc     900
gtcctcaccg tcctgcacca ggactggctg aatggcaagg agtacaagtg caaggtctcc     960
aacaaagccc tcccagcccc catcgagaaa accatctcca agccaaagg gcagccccga     1020
gaaccacagg tgtacaccct gcccccaagt cgggatgagc tgaccaagaa ccaggtcagc    1080
ctgtggtgcc tggtcaaagg cttctatccc agcgacatcg ccgtggagtg ggagagcaat    1140
gggcagccgg agaacaacta caagaccacg cctcccgtgt ggactccga cggctccttc      1200
ttcctctaca gcgcgctcac cgtggacaag agcaggtggc agcaggggaa cgtcttctca    1260
tgctccgtga tgcatgaggc tctgcacaac cactacacgc agaagagcct ctccctgtct    1320
ccgggtaaa                                                            1329
```

<210> SEQ ID NO 73
<211> LENGTH: 213
<212> TYPE: PRT
<213> ORGANISM: Artificial Sequence
<220> FEATURE:
<223> OTHER INFORMATION: A-mab-LC

<400> SEQUENCE: 73

```
Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Gly Arg Phe Ser Gly Ser
        50                  55                  60

Gly Ser Gly Asn Ser Tyr Ser Leu Thr Ile Ser Ser Val Glu Ala Glu
65                  70                  75                  80
```

Asp Asp Ala Thr Tyr Tyr Cys Gln Gln Trp Ser Lys His Pro Leu Thr
                85                  90                  95

Phe Gly Ser Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 74
<211> LENGTH: 639
<212> TYPE: DNA
<213> ORGANISM: Artificial Sequence
<220> FEATURE:
<223> OTHER INFORMATION: nucleic acid molecules encoding A-mab-LC

<400> SEQUENCE: 74
gacatcgagc tgacacagag ccctgccatc atgtctgcta gccctggcga gaaagtgacc      60
atgacctgta gcgccagcag cagcgtgtcc tacatgcact ggtatcagca gaagtccggc     120
acaagcccca gcggtggat  ctacgataca agcaagctgg cctctggcgt gcccggcaga     180
ttttctggtt ctggcagcgg caacagctac agcctgacaa tcagctccgt ggaagccgag     240
gacgacgcca cctactattg ccagcagtgg tctaagcacc ctctgacctt ggctccggc      300 accaaggtgg aaatcaagcg tacggtggct gcaccatctg tcttcatctt cccgccatct     360
gatgagcagt tgaaatctgg taccgctagc gttgtgtgcc tgctgaataa ctttttatcca    420 cgggaggcta aggtgcagtg gaaagtggac aatgccctcc agagcggaaa tagccaagag     480
tccgttaccg aacaggactc taaagactct acatactccc tgtcctccac actgaccctc     540
tccaaggccg actatgagaa acacaaggtt acgcatgcg  aggtcacaca ccagggactc     600
tcctctcccg tgaccaagag cttcaaccgg ggagaatgc                            639

<210> SEQ ID NO 75
<211> LENGTH: 449
<212> TYPE: PRT
<213> ORGANISM: Artificial Sequence
<220> FEATURE:
<223> OTHER INFORMATION: A-mab-Fc9

<400> SEQUENCE: 75

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe

-continued

```
                50                  55                  60
Arg Gly Lys Ala Thr Leu Thr Val Asp Lys Ser Ser Thr Ala Tyr
 65                  70                  75                  80

Met Asp Leu Leu Ser Leu Thr Ser Glu Asp Ser Ala Val Tyr Phe Cys
                 85                  90                  95

Ala Arg Gly Gly Tyr Asp Gly Arg Gly Phe Asp Tyr Trp Gly Ser Gly
                100                 105                 110

Thr Pro Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Arg Val Glu Pro Lys Ser Cys Asp Lys
                210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Trp
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Ala Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys
```

<210> SEQ ID NO 76
<211> LENGTH: 1347

<212> TYPE: DNA
<213> ORGANISM: Artificial Sequence
<220> FEATURE:
<223> OTHER INFORMATION: nucleic acid molecules encoding A-mab-Fc9

<400> SEQUENCE: 76

```
caggttcagc tgcagcagtc tggacccgag ctggaaaaac tggcgcctc cgtgaagatc        60
agctgcaagg ccagcggcta cagcttcacc ggctacacca tgaactgggt caagcagagc       120
cacggcaaga gcctggaatg gatcggcctg atcacccctt acaatggcgc cagcagctac       180
aaccagaagt tcagaggcaa ggccacactg accgtggaca gagcagcag caccgcctac        240
atggatctgc tgagcctgac cagcgaggac agcgccgtgt actttgtgc cagaggcggc        300
tatgacggca gaggctttga ttactggggc agcggaaccc ctgtgaccgt tcttctgcc        360
agcactaagg ggccctctgt gtttccactc gccccttcta gcaaaagcac ttccggagga       420
actgccgctc tgggctgtct ggtgaaagat tacttccccg aaccagtcac tgtgtcatgg       480
aactctggag cactgacatc tggagttcac acctttcctg ctgtgctgca gagttctgga       540
ctgtactccc tgtcatctgt ggtcaccgtg ccatcttcat ctctgggac ccagacctac        600
atctgtaacg tgaaccacaa accctccaac acaaaagtgg acaaacgagt cgaaccaaaa       660
tcttgtgaca aacccacac atgcccaccg tgcccagctc cggaactcct gggcggaccg        720
tcagtcttcc tcttcccccc aaaacccaag gacaccctca tgatctcccg gaccccgag        780
gtcacatgcg tggtggtgga cgtgagccac gaagaccctg aggtcaagtt caactggtac       840
gtggacggcg tggaggtgca taatgccaag acaaagccgc gggaggagca gtacaacagc       900
acgtaccgtg tggtcagcgt cctcaccgtc ctgcaccagg actggctgaa tggcaaggag       960
tacaagtgca aggtctccaa caaagccctc ccagccccca tcgagaaaac catctccaaa      1020
gccaaagggc agccccgaga accacaggtg tacaccctgc ccccaagtcg ggatgagctg      1080
accaagaacc aggtcagcct gtggtgcctg gtcaaaggct tctatcccag cgacatcgcc      1140
gtggagtggg agagcaatgg gcagccggag aacaactaca agaccacgcc tcccgtgttg      1200
gactccgacg gctccttctt cctctacagc gcgctcaccg tggacaagag caggtggcag      1260
caggggaacg tcttctcatg ctccgtgatg catgaggctc tgcacaacca ctacacgcag      1320
aagagcctct ccctgtctcc gggtaaa                                          1347
```

<210> SEQ ID NO 77
<211> LENGTH: 423
<212> TYPE: PRT
<213> ORGANISM: Artificial Sequence
<220> FEATURE:
<223> OTHER INFORMATION: muIFNa4-Fc6

<400> SEQUENCE: 77

```
Met Ala Arg Leu Cys Ala Phe Leu Met Ile Leu Val Met Met Ser Tyr
1               5                   10                  15

Tyr Trp Ser Ala Cys Ser Leu Gly Cys Asp Leu Pro His Thr Tyr Asn
            20                  25                  30

Leu Gly Asn Lys Arg Ala Leu Thr Val Leu Glu Glu Met Arg Arg Leu
        35                  40                  45

Pro Pro Leu Ser Cys Leu Lys Asp Arg Lys Asp Phe Gly Phe Pro Leu
    50                  55                  60

Glu Lys Val Asp Asn Gln Gln Ile Gln Lys Ala Gln Ala Ile Leu Val
65                  70                  75                  80

Leu Arg Asp Leu Thr Gln Gln Ile Leu Asn Leu Phe Thr Ser Lys Asp
```

| | | | | | 85 | | | | | 90 | | | | | 95 | | |

Leu Ser Ala Thr Trp Asn Ala Thr Leu Leu Asp Ser Phe Cys Asn Asp
            100                    105                110

Leu His Gln Gln Leu Asn Asp Leu Lys Ala Cys Val Met Gln Glu Pro
        115                  120              125

Pro Leu Thr Gln Glu Asp Ser Leu Leu Ala Val Arg Thr Tyr Phe His
    130                  135              140

Arg Ile Thr Val Tyr Leu Arg Lys Lys His Ser Leu Cys Ala Trp
145                150              155              160

Glu Val Ile Arg Ala Glu Val Trp Arg Ala Leu Ser Ser Ser Thr Asn
        165                  170              175

Leu Leu Ala Arg Leu Ser Glu Glu Lys Glu Gly Gly Gly Ser Glu
        180                  185              190

Pro Lys Ser Ser Asp Lys Thr His Thr Cys Pro Pro Cys Pro Ala Pro
        195                  200              205

Glu Leu Leu Gly Gly Pro Ser Val Phe Leu Phe Pro Pro Lys Pro Lys
    210                  215              220

Asp Thr Leu Met Ile Ser Arg Thr Pro Glu Val Thr Cys Val Val Val
225                230              235              240

Asp Val Ser His Glu Asp Pro Glu Val Lys Phe Asn Trp Tyr Val Asp
        245                  250              255

Gly Val Glu Val His Asn Ala Lys Thr Lys Pro Arg Glu Glu Gln Tyr
        260                  265              270

Asn Ser Thr Tyr Arg Val Val Ser Val Leu Thr Val Leu His Gln Asp
        275                  280              285

Trp Leu Asn Gly Lys Glu Tyr Lys Cys Lys Val Ser Asn Lys Ala Leu
    290                  295              300

Pro Ala Pro Ile Glu Lys Thr Ile Ser Lys Ala Lys Gly Gln Pro Arg
305                310              315              320

Glu Pro Gln Val Tyr Thr Leu Pro Pro Ser Arg Asp Glu Leu Thr Lys
            325                330              335

Asn Gln Val Ser Leu Ser Cys Gly Val Lys Gly Phe Tyr Pro Ser Asp
        340                  345              350

Ile Ala Val Glu Trp Glu Ser Asn Gly Gln Pro Glu Asn Asn Tyr Lys
        355                  360              365

Thr Thr Pro Pro Val Leu Asp Ser Asp Gly Ser Phe Lys Leu Ala Ser
    370                  375              380

Lys Leu Thr Val Asp Lys Ser Arg Trp Gln Gln Gly Asn Val Phe Ser
385                390              395              400

Cys Ser Val Met His Glu Ala Leu His Asn His Tyr Thr Gln Lys Ser
                405              410              415

Leu Ser Leu Ser Pro Gly Lys
        420

<210> SEQ ID NO 78
<211> LENGTH: 1269
<212> TYPE: DNA
<213> ORGANISM: Artificial Sequence
<220> FEATURE:
<223> OTHER INFORMATION: nucleic acid molecules encoding muIFNa4-Fc6

<400> SEQUENCE: 78

```
atggctaggc tctgtgcttt cctcatgatc ctggtaatga tgagctacta ctggtcagcc      60
tgttctctag gatgtgacct gcctcacact tataacctcg ggaacaagag ggccttgaca     120
```

-continued

```
gtcctggaag aaatgagaag actccccct ctttcctgcc tgaaggacag gaaggatttt        180
ggattcccct tggagaaggt ggataaccaa cagatccaga aggctcaagc catccttgtg        240
ctaagagatc ttacccagca gattttgaac ctcttcacat caaaagactt gtctgctact        300
tggaatgcaa ctctactaga ctcattctgc aatgacctcc atcagcagct caatgacctc        360
aaagcctgtg tgatgcagga acctcctctg acccaggaag actccctgct ggctgtgagg        420
acatacttcc acaggatcac tgtgtacctg agaaagaaga acacagcct ctgtgcctgg         480
gaggtgatca gagcagaagt ctggagagcc ctctcttcct caaccaactt gctggcaaga        540
ctgagtgagg agaaggaggg aggaggagga agcgaaccta agagcagcga caagacccac        600
acttgccccc cttgtcccgc tccggaactc ctgggcggac cgtcagtctt cctcttcccc        660
ccaaaaccca aggacaccct catgatctcc cggacccctg aggtcacatg cgtggtggtg        720
gacgtgagcc acgaagaccc tgaggtcaag ttcaactggt acgtggacgg cgtggaggtg        780
cataatgcca agacaaagcc gcgggaggag cagtacaaca gcacgtaccg tgtggtcagc        840
gtcctcaccg tcctgcacca ggactggctg aatggcaagg agtacaagtg caaggtctcc        900
aacaaagccc tcccagcccc catcgagaaa accatctcca aagccaaagg gcagccccga        960
gaaccacagg tgtataccct gcccccatcc cgggatgagc tgaccaagaa ccaggtcagc       1020
ctgagttgcg gggtcaaagg cttctatccc agcgacatcg ccgtggagtg ggagagcaat       1080
gggcagccgg agaacaacta caagaccacg cctcccgtgt ggactccga cggctccttc        1140
aagctcgcca gcaagctcac cgtggacaag agcaggtggc agcaggggaa cgtcttctca       1200
tgctccgtga tgcatgaggc tctgcacaac cactacacgc agaagagcct ctccctgtct       1260
ccgggtaaa                                                              1269
```

<210> SEQ ID NO 79
<211> LENGTH: 5
<212> TYPE: PRT
<213> ORGANISM: Artificial Sequence
<220> FEATURE:
<223> OTHER INFORMATION: linker sequence

<400> SEQUENCE: 79

Gly Ser Gly Gly Gly
1               5

<210> SEQ ID NO 80
<211> LENGTH: 425
<212> TYPE: PRT
<213> ORGANISM: Artificial Sequence
<220> FEATURE:
<223> OTHER INFORMATION: huIFNa2-Fc6

<400> SEQUENCE: 80

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
                20                  25                  30

Gly Ser Arg Arg Thr Leu Met Leu Leu Ala Gln Met Arg Arg Ile Ser
            35                  40                  45

Leu Phe Ser Cys Leu Lys Asp Arg His Asp Phe Gly Phe Pro Gln Glu
        50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser 85                  90                  95
Ala Ala Trp Asp Glu Thr Leu Leu Asp Lys Phe Tyr Thr Glu Leu Tyr
                100                 105                 110

Gln Gln Leu Asn Asp Leu Glu Ala Cys Val Ile Gln Gly Val Gly Val
            115                 120                 125

Thr Glu Thr Pro Leu Met Lys Glu Asp Ser Ile Leu Ala Val Arg Lys
        130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu Gly Gly Gly Gly
            180                 185                 190

Ser Glu Pro Lys Ser Ser Asp Lys Thr His Thr Cys Pro Pro Cys Pro
        195                 200                 205

Ala Pro Glu Leu Leu Gly Gly Pro Ser Val Phe Leu Phe Pro Pro Lys
210                 215                 220

Pro Lys Asp Thr Leu Met Ile Ser Arg Thr Pro Glu Val Thr Cys Val
225                 230                 235                 240

Val Val Asp Val Ser His Glu Asp Pro Glu Val Lys Phe Asn Trp Tyr
                245                 250                 255

Val Asp Gly Val Glu Val His Asn Ala Lys Thr Lys Pro Arg Glu Glu
            260                 265                 270

Gln Tyr Asn Ser Thr Tyr Arg Val Val Ser Val Leu Thr Val Leu His
        275                 280                 285

Gln Asp Trp Leu Asn Gly Lys Glu Tyr Lys Cys Lys Val Ser Asn Lys
290                 295                 300

Ala Leu Pro Ala Pro Ile Glu Lys Thr Ile Ser Lys Ala Lys Gly Gln
305                 310                 315                 320

Pro Arg Glu Pro Gln Val Tyr Thr Leu Pro Pro Ser Arg Asp Glu Leu
                325                 330                 335

Thr Lys Asn Gln Val Ser Leu Ser Cys Gly Val Lys Gly Phe Tyr Pro
            340                 345                 350

Ser Asp Ile Ala Val Glu Trp Glu Ser Asn Gly Gln Pro Glu Asn Asn
        355                 360                 365

Tyr Lys Thr Thr Pro Pro Val Leu Asp Ser Asp Gly Ser Phe Lys Leu
370                 375                 380

Ala Ser Lys Leu Thr Val Asp Lys Ser Arg Trp Gln Gln Gly Asn Val
385                 390                 395                 400

Phe Ser Cys Ser Val Met His Glu Ala Leu His Asn His Tyr Thr Gln
                405                 410                 415

Lys Ser Leu Ser Leu Ser Pro Gly Lys
            420                 425

<210> SEQ ID NO 81
<211> LENGTH: 1275
<212> TYPE: DNA
<213> ORGANISM: Artificial Sequence
<220> FEATURE:
<223> OTHER INFORMATION: nucleic acid molecules encoding huIFNa2-Fc6

<400> SEQUENCE: 81
atggccttga cctttgcttt actggtggcc ctcctggtgc tcagctgcaa gtcaagctgc      60
tctgtgggct gtgatctgcc tcaaacccac agcctgggta gcaggaggac cttgatgctc     120

```
ctggcacaga tgaggagaat ctctcttttc tcctgcttga aggacagaca tgactttgga    180
tttccccagg aggagtttgg caaccagttc caaaaggctg aaaccatccc tgtcctccat    240
gagatgatcc agcagatctt caatctcttc agcacaaagg actcatctgc tgcttgggat    300
gagaccctcc tagacaaatt ctacactgaa ctctaccagc agctgaatga cctggaagcc    360
tgtgtgatac aggggtggg ggtgacagag actcccctga tgaaggagga ctccattctg    420
gctgtgagga aatacttcca agaatcact ctctatctga agagaagaa atacagccct    480 tgtgcctggg aggttgtcag agcagaaatc atgagatctt tttctttgtc aacaaacttg    540
caagaaagtt taagaagtaa ggaggaggag ggaggaagcg aacctaagag cagcgacaag    600
acccacactt gccccccttg tcccgctccg gaactcctgg gcggaccgtc agtcttcctc    660
ttccccccaa acccaagga caccctcatg atctcccgga cccctgaggt cacatgcgtg    720
gtggtggacg tgagccacga agaccctgag gtcaagttca actggtacgt ggacggcgtg    780
gaggtgcata atgccaagac aaagccgcgg gaggagcagt acaacagcac gtaccgtgtg    840
gtcagcgtcc tcaccgtcct gcaccaggac tggctgaatg gcaaggagta caagtgcaag    900
gtctccaaca aagccctccc agcccccatc gagaaaacca tctccaaagc caagggcag    960 ccccgagaac acaggtgta ccctgcccc catcccggg atgagctgac caagaaccag    1020
gtcagcctga gttgcgggt caaaggcttc tatcccagcg acatcgccgt ggagtgggag    1080
agcaatgggc agccggagaa caactacaag accacgcctc ccgtgttgga ctccgacggc    1140
tccttcaagc tcgccagcaa gctcaccgtg gacaagagca ggtggcagca ggggaacgtc    1200
ttctcatgct ccgtgatgca tgaggctctg cacaaccact acacgcagaa gagcctctcc    1260
ctgtctccgg gtaaa                                                     1275
```

<210> SEQ ID NO 82
<211> LENGTH: 419
<212> TYPE: PRT
<213> ORGANISM: Artificial Sequence
<220> FEATURE:
<223> OTHER INFORMATION: muIFNb-Fc6

<400> SEQUENCE: 82

```
Met Asn Asn Arg Trp Ile Leu His Ala Ala Phe Leu Leu Cys Phe Ser
1               5                  10                  15

Thr Thr Ala Leu Ser Ile Asn Tyr Lys Gln Leu Gln Leu Gln Glu Arg
            20                  25                  30

Thr Asn Ile Arg Lys Cys Gln Glu Leu Leu Glu Gln Leu Asn Gly Lys
        35                  40                  45

Ile Asn Leu Thr Tyr Arg Ala Asp Phe Lys Ile Pro Met Glu Met Thr
    50                  55                  60

Glu Lys Met Gln Lys Ser Tyr Thr Ala Phe Ala Ile Gln Glu Met Leu
65                  70                  75                  80

Gln Asn Val Phe Leu Val Phe Arg Asn Asn Phe Ser Ser Thr Gly Trp
                85                  90                  95

Asn Glu Thr Ile Val Val Arg Leu Leu Asp Glu Leu His Gln Gln Thr
            100                 105                 110

Val Phe Leu Lys Thr Val Leu Glu Glu Lys Gln Glu Glu Arg Leu Thr
        115                 120                 125

Trp Glu Met Ser Ser Thr Ala Leu His Leu Lys Ser Tyr Tyr Trp Arg
    130                 135                 140

Val Gln Arg Tyr Leu Lys Leu Met Lys Tyr Asn Ser Tyr Ala Trp Met
145                 150                 155                 160
```

Val Val Arg Ala Glu Ile Phe Arg Asn Phe Leu Ile Ile Arg Arg Leu
             165                 170                 175

Thr Arg Asn Phe Gln Asn Gly Gly Gly Ser Glu Pro Lys Ser Ser
            180                 185                 190

Asp Lys Thr His Thr Cys Pro Pro Cys Pro Ala Pro Glu Leu Leu Gly
            195                 200                 205

Gly Pro Ser Val Phe Leu Phe Pro Pro Lys Pro Lys Asp Thr Leu Met
            210                 215                 220

Ile Ser Arg Thr Pro Glu Val Thr Cys Val Val Val Asp Val Ser His
225                 230                 235                 240

Glu Asp Pro Glu Val Lys Phe Asn Trp Tyr Val Asp Gly Val Glu Val
            245                 250                 255

His Asn Ala Lys Thr Lys Pro Arg Glu Glu Gln Tyr Asn Ser Thr Tyr
            260                 265                 270

Arg Val Val Ser Val Leu Thr Val Leu His Gln Asp Trp Leu Asn Gly
            275                 280                 285

Lys Glu Tyr Lys Cys Lys Val Ser Asn Lys Ala Leu Pro Ala Pro Ile
            290                 295                 300

Glu Lys Thr Ile Ser Lys Ala Lys Gly Gln Pro Arg Glu Pro Gln Val
305                 310                 315                 320

Tyr Thr Leu Pro Pro Ser Arg Asp Glu Leu Thr Lys Asn Gln Val Ser
            325                 330                 335

Leu Ser Cys Gly Val Lys Gly Phe Tyr Pro Ser Asp Ile Ala Val Glu
            340                 345                 350

Trp Glu Ser Asn Gly Gln Pro Glu Asn Asn Tyr Lys Thr Thr Pro Pro
            355                 360                 365

Val Leu Asp Ser Asp Gly Ser Phe Lys Leu Ala Ser Lys Leu Thr Val
            370                 375                 380

Asp Lys Ser Arg Trp Gln Gln Gly Asn Val Phe Ser Cys Ser Val Met
385                 390                 395                 400

His Glu Ala Leu His Asn His Tyr Thr Gln Lys Ser Leu Ser Leu Ser
            405                 410                 415

Pro Gly Lys

<210> SEQ ID NO 83
<211> LENGTH: 1257
<212> TYPE: DNA
<213> ORGANISM: Artificial Sequence
<220> FEATURE:
<223> OTHER INFORMATION: nucleic acid molecules encoding muIFNb-Fc6

<400> SEQUENCE: 83
atgaacaaca ggtggattct ccacgctgcg ttcctgctgt gcttctccac cacagccctc      60
tccatcaact ataagcagct ccagctccaa gaaaggacga acattcggaa atgtcaggag     120
ctcctggagc agctgaatgg aaagatcaac ctcacctaca gggcggactt caagatccct     180
atggagatga cggagaagat gcagaagagt tacactgcct ttgccatcca agagatgctc     240
cagaatgtct tccttgtctt cagaaacaat ttctccagca ctgggtggaa tgagactatt     300
gttgtacgtc tcctggatga actccaccag cagacagtgt tctgaagac agtactagag     360 gaaaagcaag aggaaagatt gacgtgggag atgtcctcaa ctgctctcca cttgaagagc     420
tattactgga gggtgcaaag gtatcttaaa ctcatgaagt acaacagcta cgcctggatg     480
gtggtccgag cagagatctt caggaacttt ctcatcattc gaagacttac cagaaacttc     540

-continued

```
caaaacggag gaggaggaag cgaacctaag agcagcgaca agacccacac ttgcccccct   600
tgtcccgctc cggaactcct gggcggaccg tcagtcttcc tcttcccccc aaaacccaag   660
gacaccctca tgatctcccg gacccctgag gtcacatgcg tggtggtgga cgtgagccac   720
gaagaccctg aggtcaagtt caactggtac gtggacggcg tggaggtgca taatgccaag   780
acaaagccgc gggaggagca gtacaacagc acgtaccgtg tggtcagcgt cctcaccgtc   840
ctgcaccagg actggctgaa tggcaaggag tacaagtgca aggtctccaa caaagccctc   900
ccagccccca tcgagaaaac catctccaaa gccaagggc agccccgaga ccacaggtg     960 tatacccthgc cccatcccg ggatgagctg accaagaacc aggtcagcct gagttgcggg  1020
gtcaaaggct tctatcccag cgacatcgcc gtggagtggg agagcaatgg gcagccggag  1080
aacaactaca agaccacgcc tcccgtgttg gactccgacg gctccttcaa gctcgccagc  1140
aagctcaccg tggacaagag caggtggcag caggggaacg tcttctcatg ctccgtgatg  1200
catgaggctc tgcacaacca ctacacgcag aagagcctct ccctgtctcc gggtaaa     1257
```

<210> SEQ ID NO 84
<211> LENGTH: 424
<212> TYPE: PRT
<213> ORGANISM: Artificial Sequence
<220> FEATURE:
<223> OTHER INFORMATION: huIFNb-Fc6

<400> SEQUENCE: 84

```
Met Thr Asn Lys Cys Leu Leu Gln Ile Ala Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn Gly Gly Gly Ser
            180                 185                 190

Glu Pro Lys Ser Ser Asp Lys Thr His Thr Cys Pro Pro Cys Pro Ala
        195                 200                 205

Pro Glu Leu Leu Gly Gly Pro Ser Val Phe Leu Phe Pro Pro Lys Pro
    210                 215                 220

Lys Asp Thr Leu Met Ile Ser Arg Thr Pro Glu Val Thr Cys Val Val
225                 230                 235                 240
```

```
Val Asp Val Ser His Glu Asp Pro Glu Val Lys Phe Asn Trp Tyr Val
            245                 250                 255
Asp Gly Val Glu Val His Asn Ala Lys Thr Lys Pro Arg Glu Glu Gln
        260                 265                 270
Tyr Asn Ser Thr Tyr Arg Val Val Ser Val Leu Thr Val Leu His Gln
    275                 280                 285
Asp Trp Leu Asn Gly Lys Glu Tyr Lys Cys Lys Val Ser Asn Lys Ala
290                 295                 300
Leu Pro Ala Pro Ile Glu Lys Thr Ile Ser Ala Lys Gly Gln Pro
305                 310                 315                 320
Arg Glu Pro Gln Val Tyr Thr Leu Pro Pro Ser Arg Asp Glu Leu Thr
                325                 330                 335
Lys Asn Gln Val Ser Leu Ser Cys Gly Val Lys Gly Phe Tyr Pro Ser
            340                 345                 350
Asp Ile Ala Val Glu Trp Glu Ser Asn Gly Gln Pro Glu Asn Asn Tyr
        355                 360                 365
Lys Thr Thr Pro Pro Val Leu Asp Ser Asp Gly Ser Phe Lys Leu Ala
    370                 375                 380
Ser Lys Leu Thr Val Asp Lys Ser Arg Trp Gln Gln Gly Asn Val Phe
385                 390                 395                 400
Ser Cys Ser Val Met His Glu Ala Leu His Asn His Tyr Thr Gln Lys
                405                 410                 415
Ser Leu Ser Leu Ser Pro Gly Lys
            420
```

```
<210> SEQ ID NO 85
<211> LENGTH: 1272
<212> TYPE: DNA
<213> ORGANISM: Artificial Sequence
<220> FEATURE:
<223> OTHER INFORMATION: nucleic acid molecules encoding huIFNb-Fc6

<400> SEQUENCE: 85
ttggattcct acaaagaagc agcaatttc agtgtcagaa gctcctgtgg caattgaatg      60
ggaggcttga atactgcctc aaggacagga tgaactttga catccctgag agattaagc   120
agctgcagca gttccagaag gaggacgccg cattgaccat ctatgagatg ctccagaaca   180
tctttgctat tttcagacaa gattcatcta gcactggctg aatgagact attgttgaga   240
acctcctggc taatgtctat catcagataa accatctgaa gacagtcctg gaagaaaaac   300
tggagaaaga agatttcacc aggggaaaac tcatgagcag tctgcacctg aaaagatatt   360
atgggaggat tctgcattac ctgaaggcca aggagtacag tcactgtgcc tggaccatag   420
tcagagtgga atcctaagg aactttact tcattaacag acttacaggt tacctccgaa   480
acggatccgg tggaggtgac aagacccaca cctgccccc ctgccccgcc cccgagctgc   540
tgggcggccc cagcgtgttc cggaggagga ggaagcgaac ctaagagcag cgacaagacc   600
cacacttgcc cccttgtcc cgctccggaa ctcctgggcg accgtcagt cttcctcttc   660
cccccaaaac ccaaggacac cctcatgatc tcccggaccc ctgaggtcac atgcgtggtg   720
gtggacgtga gccacgaaga ccctgaggtc aagttcaact ggtacgtgga cggcgtggag   780
gtgcataatg ccaagacaaa gccgcgggag gagcagtaca acagcacgta ccgtgtggtc   840
agcgtcctca ccgtcctgca ccaggactgg ctgaatggca aggagtacaa gtgcaaggtc   900
tccaacaaag ccctcccagc ccccatcgag aaaaccatct ccaaagccaa agggcagccc   960
cgagaaccac aggtgtatac cctgccccca tcccgggatg agctgaccaa gaaccaggtc  1020
```

-continued

```
agcctgagtt gcggggtcaa aggcttctat cccagcgaca tcgccgtgga gtgggagagc    1080
aatgggcagc cggagaacaa ctacaagacc acgcctcccg tgttggactc cgacggctcc    1140
ttcaagctcg ccagcaagct caccgtggac aagagcaggt ggcagcaggg gaacgtcttc    1200
tcatgctccg tgatgcatga ggctctgcac aaccactaca cgcagaagag cctctccctg    1260
tctccgggta aa                                                        1272
```

<210> SEQ ID NO 86
<211> LENGTH: 437
<212> TYPE: PRT
<213> ORGANISM: Artificial Sequence
<220> FEATURE:
<223> OTHER INFORMATION: huIFNL-Fc6

<400> SEQUENCE: 86

```
Met Ala Ala Ala Trp Thr Val Val Leu Val Thr Leu Val Leu Gly Leu
1               5                   10                  15

Ala Val Ala Gly Pro Val Pro Thr Ser Lys Pro Thr Thr Thr Gly Lys
                20                  25                  30

Gly Cys His Ile Gly Arg Phe Lys Ser Leu Ser Pro Gln Glu Leu Ala
            35                  40                  45

Ser Phe Lys Lys Ala Arg Asp Ala Leu Glu Glu Ser Leu Lys Leu Lys
        50                  55                  60

Asn Trp Ser Cys Ser Ser Pro Val Phe Pro Gly Asn Trp Asp Leu Arg
65                  70                  75                  80

Leu Leu Gln Val Arg Glu Arg Pro Val Ala Leu Glu Ala Glu Leu Ala
                85                  90                  95

Leu Thr Leu Lys Val Leu Glu Ala Ala Ala Gly Pro Ala Leu Glu Asp
            100                 105                 110

Val Leu Asp Gln Pro Leu His Thr Leu His His Ile Leu Ser Gln Leu
        115                 120                 125

Gln Ala Cys Ile Gln Pro Gln Pro Thr Ala Gly Pro Arg Pro Arg Gly
    130                 135                 140

Arg Leu His His Trp Leu His Arg Leu Gln Glu Ala Pro Lys Lys Glu
145                 150                 155                 160

Ser Ala Gly Cys Leu Glu Ala Ser Val Thr Phe Asn Leu Phe Arg Leu
                165                 170                 175

Leu Thr Arg Asp Leu Lys Tyr Val Ala Asp Gly Asn Leu Cys Leu Arg
            180                 185                 190

Thr Ser Thr His Pro Glu Ser Thr Gly Gly Gly Ser Glu Pro Lys
        195                 200                 205

Ser Ser Asp Lys Thr His Thr Cys Pro Pro Cys Pro Ala Pro Glu Leu
    210                 215                 220

Leu Gly Gly Pro Ser Val Phe Leu Phe Pro Pro Lys Pro Lys Asp Thr
225                 230                 235                 240

Leu Met Ile Ser Arg Thr Pro Glu Val Thr Cys Val Val Val Asp Val
                245                 250                 255

Ser His Glu Asp Pro Glu Val Lys Phe Asn Trp Tyr Val Asp Gly Val
            260                 265                 270

Glu Val His Asn Ala Lys Thr Lys Pro Arg Glu Glu Gln Tyr Asn Ser
        275                 280                 285

Thr Tyr Arg Val Val Ser Val Leu Thr Val Leu His Gln Asp Trp Leu
    290                 295                 300

Asn Gly Lys Glu Tyr Lys Cys Lys Val Ser Asn Lys Ala Leu Pro Ala
```

```
                305                 310                 315                 320
Pro Ile Glu Lys Thr Ile Ser Lys Ala Lys Gly Gln Pro Arg Glu Pro
                325                 330                 335

Gln Val Tyr Thr Leu Pro Pro Ser Arg Asp Glu Leu Thr Lys Asn Gln
                340                 345                 350

Val Ser Leu Ser Cys Gly Val Lys Gly Phe Tyr Pro Ser Asp Ile Ala
                355                 360                 365

Val Glu Trp Glu Ser Asn Gly Gln Pro Glu Asn Asn Tyr Lys Thr Thr
            370                 375                 380

Pro Pro Val Leu Asp Ser Asp Gly Ser Phe Lys Leu Ala Ser Lys Leu
385                 390                 395                 400

Thr Val Asp Lys Ser Arg Trp Gln Gln Gly Asn Val Phe Ser Cys Ser
                405                 410                 415

Val Met His Glu Ala Leu His Asn His Tyr Thr Gln Lys Ser Leu Ser
            420                 425                 430

Leu Ser Pro Gly Lys
            435

<210> SEQ ID NO 87
<211> LENGTH: 1311
<212> TYPE: DNA
<213> ORGANISM: Artificial Sequence
<220> FEATURE:
<223> OTHER INFORMATION: nucleic acid molecules encoding huIFNL-Fc6

<400> SEQUENCE: 87
atggctgcag cttggaccgt ggtgctggtg actttggtgc taggcttggc cgtggcaggc      60
cctgtcccca cttccaagcc caccacaact gggaagggct gccacattgg caggttcaaa    120
tctctgtcac acaggagct agcgagcttc aagaaggcca gggacgcctt ggaagagtca    180
ctcaagctga aaaactggag ttgcagctct cctgtcttcc ccgggaattg ggacctgagg    240
cttctccagg tgagggagcg ccctgtggcc ttggaggctg agctggccct gacgctgaag    300
gtcctggagg ccgctgctgg cccagccctg gaggacgtcc tagaccagcc ccttcacacc    360
ctgcaccaca tcctctccca gctccaggcc tgtatccagc ctcagcccac agcagggccc    420
aggccccggg gccgcctcca ccactggctg accggctccc aggaggcccc caaaaaggag    480
tccgctggct gcctggaggc atctgtcacc ttcaacctct ccgcctcct cacgcgagac    540 ctcaaatatg tggccgatgg gaacctgtgt ctgagaacgt caacccaccc tgagtccacc    600
ggaggaggag gaagcgaacc taagagcagc gacaagaccc acacttgccc cccttgtccc    660
gctccggaac tcctgggcgg accgtcagtc ttcctcttcc ccccaaaacc caaggacacc    720
ctcatgatct cccggacccc tgaggtcaca tgcgtggtgg tggacgtgag ccacgaagac    780
cctgaggtca agttcaactg gtacgtggac ggcgtggagg tgcataatgc caagacaaag    840
ccgcgggagg agcagtacaa cagcacgtac cgtgtggtca gcgtcctcac cgtcctgcac    900
caggactggc tgaatggcaa ggagtacaag tgcaaggtct ccaacaaagc cctcccagcc    960
cccatcgaga aaaccatctc caaagccaaa gggcagcccc gagaaccaca ggtgtatacc   1020
ctgcccccat cccgggatga gctgaccaag aaccaggtca gcctgagttg cggggtcaaa   1080
ggcttctatc ccagcgacat cgccgtggag tgggagagca atgggcagcc ggagaacaac   1140
tacaagacca cgcctcccgt gttggactcc gacggctcct tcaagctcgc cagcaagctc   1200
accgtggaca gagcaggtg gcagcagggg aacgtcttct catgctccgt gatgcatgag   1260
gctctgcaca accactacac gcagaagagc ctctccctgt ctccgggtaa a            1311
```

<210> SEQ ID NO 88
<211> LENGTH: 15
<212> TYPE: PRT
<213> ORGANISM: Artificial Sequence
<220> FEATURE:
<223> OTHER INFORMATION: linker sequence

<400> SEQUENCE: 88

Gly Gly Gly Gly Ser Gly Gly Gly Gly Ser Gly Gly Gly Gly Ser
1               5                   10                  15

<210> SEQ ID NO 89
<211> LENGTH: 407
<212> TYPE: PRT
<213> ORGANISM: Artificial Sequence
<220> FEATURE:
<223> OTHER INFORMATION: huIL10-Fc6

<400> SEQUENCE: 89

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Gly Gly Ser Gly Gly Gly Ser Gly Gly Gly Ser Glu
                165                 170                 175

Pro Lys Ser Ser Asp Lys Thr His Thr Cys Pro Pro Cys Pro Ala Pro
            180                 185                 190

Glu Leu Leu Gly Gly Pro Ser Val Phe Leu Phe Pro Pro Lys Pro Lys
        195                 200                 205

Asp Thr Leu Met Ile Ser Arg Thr Pro Glu Val Thr Cys Val Val Val
    210                 215                 220

Asp Val Ser His Glu Asp Pro Glu Val Lys Phe Asn Trp Tyr Val Asp
225                 230                 235                 240

Gly Val Glu Val His Asn Ala Lys Thr Lys Pro Arg Glu Glu Gln Tyr
                245                 250                 255

Asn Ser Thr Tyr Arg Val Val Ser Val Leu Thr Val Leu His Gln Asp
            260                 265                 270

Trp Leu Asn Gly Lys Glu Tyr Lys Cys Lys Val Ser Asn Lys Ala Leu
        275                 280                 285

Pro Ala Pro Ile Glu Lys Thr Ile Ser Lys Ala Lys Gly Gln Pro Arg

```
                290                 295                 300
Glu Pro Gln Val Tyr Thr Leu Pro Pro Ser Arg Asp Glu Leu Thr Lys
305                 310                 315                 320

Asn Gln Val Ser Leu Ser Cys Gly Val Lys Gly Phe Tyr Pro Ser Asp
            325                 330                 335

Ile Ala Val Glu Trp Glu Ser Asn Gly Gln Pro Glu Asn Asn Tyr Lys
            340                 345                 350

Thr Thr Pro Pro Val Leu Asp Ser Asp Gly Ser Phe Lys Leu Ala Ser
        355                 360                 365

Lys Leu Thr Val Asp Lys Ser Arg Trp Gln Gln Gly Asn Val Phe Ser
    370                 375                 380

Cys Ser Val Met His Glu Ala Leu His Asn His Tyr Thr Gln Lys Ser
385                 390                 395                 400

Leu Ser Leu Ser Pro Gly Lys
            405
```

<210> SEQ ID NO 90
<211> LENGTH: 1221
<212> TYPE: DNA
<213> ORGANISM: Artificial Sequence
<220> FEATURE:
<223> OTHER INFORMATION: nucleic acid molecules encoding huIL10-Fc6

<400> SEQUENCE: 90

```
agccccggcc agggcacaca gtccgagaac agctgcaccc actttcccgg caacctgcct      60
aacatgctga gggacctgag ggacgccttc agcagggtga agaccttctt ccagatgaag     120
gaccagctgg ataacctgct gctgaaggag agcctgctgg aggacttcaa gggctacctg     180
ggctgccagg ccctgagcga gatgatccag ttctacctgg aggaggtgat gccccaggcc     240
gagaaccagg accccgacat caaggcccac gtgaacagct gggcgagaa cctgaagacc     300
ctgaggctga ggctgaggag gtgccacagg ttcctgccct gtgagaacaa atccaaggcc     360
gtggagcagg tgaagaacgc cttcaacaag ctgcaggaaa agggcatcta caaggccatg     420
agcgagttcg acatctttat caactatatc gaggcctaca tgacaatgaa gatcaggaac     480
ggcggcggcg gcagcggggg cggcggcagc ggaggaggcg gcagcgaacc taagagcagc     540
gacaagaccc acacttgccc cccttgtccc gctccggaac tcctgggcgg accgtcagtc     600
ttcctcttcc ccccaaaacc caaggacacc ctcatgatct cccggacccc tgaggtcaca     660
tgcgtggtgg tggacgtgag ccacgaagac cctgaggtca agttcaactg gtacgtggac     720
ggcgtggagg tgcataatgc caagacaaag ccgcgggagg agcagtacaa cagcacgtac     780
cgtgtggtca gcgtcctcac cgtcctgcac caggactggc tgaatggcaa ggagtacaag     840
tgcaaggtct ccaacaaagc cctcccagcc cccatcgaga aaaccatctc caaagccaaa     900
gggcagcccc gagaaccaca ggtgtatacc ctgcccccat cccgggatga gctgaccaag     960
aaccaggtca gcctgagttg cggggtcaaa ggcttctatc ccagcgacat cgccgtggag    1020
tgggagagca atgggcagcc ggagaacaac tacaagacca cgcctcccgt gttggactcc    1080
gacggctcct tcaagctcgc cagcaagctc accgtggaca agagcaggtg gcagcagggg    1140
aacgtcttct catgctccgt gatgcatgag gctctgcaca accactacac gcagaagagc    1200
ctctccctgt ctccgggtaa a                                              1221
```

<210> SEQ ID NO 91
<211> LENGTH: 582
<212> TYPE: PRT

<213> ORGANISM: Artificial Sequence
<220> FEATURE:
<223> OTHER INFORMATION: (huIL10)2-Fc6

<400> SEQUENCE: 91

```
Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
130                 135                 140

Ile Phe Ile Asn Tyr Ile Glu Ala Tyr Met Thr Met Lys Ile Arg Asn
145                 150                 155                 160

Gly Gly Gly Gly Ser Gly Gly Gly Ser Gly Gly Gly Gly Ser Ser
                165                 170                 175

Pro Gly Gln Gly Thr Gln Ser Glu Asn Ser Cys Thr His Phe Pro Gly
            180                 185                 190

Asn Leu Pro Asn Met Leu Arg Asp Leu Arg Asp Ala Phe Ser Arg Val
        195                 200                 205

Lys Thr Phe Phe Gln Met Lys Asp Gln Leu Asp Asn Leu Leu Leu Lys
        210                 215                 220

Glu Ser Leu Leu Glu Asp Phe Lys Gly Tyr Leu Gly Cys Gln Ala Leu
225                 230                 235                 240

Ser Glu Met Ile Gln Phe Tyr Leu Glu Glu Val Met Pro Gln Ala Glu
                245                 250                 255

Asn Gln Asp Pro Asp Ile Lys Ala His Val Asn Ser Leu Gly Glu Asn
            260                 265                 270

Leu Lys Thr Leu Arg Leu Arg Leu Arg Arg Cys His Arg Phe Leu Pro
        275                 280                 285

Cys Glu Asn Lys Ser Lys Ala Val Glu Gln Val Lys Asn Ala Phe Asn
        290                 295                 300

Lys Leu Gln Glu Lys Gly Ile Tyr Lys Ala Met Ser Glu Phe Asp Ile
305                 310                 315                 320

Phe Ile Asn Tyr Ile Glu Ala Tyr Met Thr Met Lys Ile Arg Asn Gly
                325                 330                 335

Gly Gly Gly Ser Gly Gly Gly Ser Gly Gly Gly Ser Glu Pro
            340                 345                 350

Lys Ser Ser Asp Lys Thr His Thr Cys Pro Pro Cys Pro Ala Pro Glu
        355                 360                 365

Leu Leu Gly Gly Pro Ser Val Phe Leu Phe Pro Pro Lys Pro Lys Asp
        370                 375                 380

Thr Leu Met Ile Ser Arg Thr Pro Glu Val Thr Cys Val Val Val Asp
```

```
                385                 390                 395                 400
Val Ser His Glu Asp Pro Glu Val Lys Phe Asn Trp Tyr Val Asp Gly
                405                 410                 415
Val Glu Val His Asn Ala Lys Thr Lys Pro Arg Glu Glu Gln Tyr Asn
                420                 425                 430
Ser Thr Tyr Arg Val Val Ser Val Leu Thr Val Leu His Gln Asp Trp
                435                 440                 445
Leu Asn Gly Lys Glu Tyr Lys Cys Lys Val Ser Asn Lys Ala Leu Pro
450                 455                 460
Ala Pro Ile Glu Lys Thr Ile Ser Lys Ala Lys Gly Gln Pro Arg Glu
465                 470                 475                 480
Pro Gln Val Tyr Thr Leu Pro Pro Ser Arg Asp Glu Leu Thr Lys Asn
                485                 490                 495
Gln Val Ser Leu Ser Cys Gly Val Lys Gly Phe Tyr Pro Ser Asp Ile
                500                 505                 510
Ala Val Glu Trp Glu Ser Asn Gly Gln Pro Glu Asn Asn Tyr Lys Thr
                515                 520                 525
Thr Pro Pro Val Leu Asp Ser Asp Gly Ser Phe Lys Leu Ala Ser Lys
                530                 535                 540
Leu Thr Val Asp Lys Ser Arg Trp Gln Gln Gly Asn Val Phe Ser Cys
545                 550                 555                 560
Ser Val Met His Glu Ala Leu His Asn His Tyr Thr Gln Lys Ser Leu
                565                 570                 575
Ser Leu Ser Pro Gly Lys
                580

<210> SEQ ID NO 92
<211> LENGTH: 1746
<212> TYPE: DNA
<213> ORGANISM: Artificial Sequence
<220> FEATURE:
<223> OTHER INFORMATION: nucleic acid molecules encoding (huIL10)2-Fc6

<400> SEQUENCE: 92
agccccggcc agggcacaca gtccgagaac agctgcaccc actttcccgg caacctgcct      60
aacatgctga gggacctgag gacgccttc agcagggtga gaccttctt ccagatgaag      120 gaccagctgg ataacctgct gctgaaggag agcctgctgg aggacttcaa gggctacctg      180
ggctgccagg ccctgagcga gatgatccag ttctacctgg aggaggtgat gccccaggcc      240
gagaaccagg accccgacat caaggcccac gtgaacagcc tgggcgagaa cctgaagacc      300
ctgaggctga ggctgaggag gtgccacagg ttcctgccct gtgagaacaa atccaaggcc      360
gtggagcagg tgaagaacgc cttcaacaag ctgcaggaaa agggcatcta caaggccatg      420
agcgagttcg acatctttat caactatatc gaggcctaca tgacaatgaa gatcaggaac      480
ggcggcggcg gcagcggggg cggcggcagc ggaggaggcg gcagcagccc cggccagggc      540
acacagtccg agaacagctg cacccacttt cccggcaacc tgcctaacat gctgagggac      600
ctgagggacg ccttcagcag ggtgaagacc ttcttccaga tgaaggacca gctggataac      660
ctgctgctga aggagagcct gctggaggac ttcaagggct acctgggctg ccaggccctg      720
agcgagatga tccagttcta cctggaggag gtgatgcccc aggccgagaa ccaggacccc      780
gacatcaagg cccacgtgaa cagcctgggc gagaacctga gaccctgag gctgaggctg      840 aggaggtgcc acaggttcct gccctgtgag aacaaatcca aggccgtgga gcaggtgaag      900
aacgccttca caagctgca ggaaaagggc atctacaagg ccatgagcga gttcgacatc      960
```

```
tttatcaact atatcgaggc ctacatgaca atgaagatca ggaacggcgg cggcggcagc   1020
ggggcggcg gcagcggagg aggcggcagc gaacctaaga gcagcgacaa gacccacact   1080
tgccccctt gtcccgctcc ggaactcctg ggcggaccgt cagtcttcct cttccccca    1140
aaacccaagg acaccctcat gatctcccgg accctgagg tcacatgcgt ggtggtggac    1200
gtgagccacg aagaccctga ggtcaagttc aactggtacg tggacggcgt ggaggtgcat   1260
aatgccaaga caaagccgcg ggaggagcag tacaacagca cgtaccgtgt ggtcagcgtc   1320
ctcaccgtcc tgcaccagga ctggctgaat ggcaaggagt acaagtgcaa ggtctccaac   1380
aaagccctcc cagcccccat cgagaaaacc atctccaaag ccaagggca gccccgagaa    1440
ccacaggtgt ataccctgcc cccatcccgg gatgagctga ccaagaacca ggtcagcctg   1500
agttgcgggg tcaaaggctt ctatcccagc gacatcgccg tggagtggga gagcaatggg   1560
cagccggaga acaactacaa gaccacgcct cccgtgttgg actccgacgg ctccttcaag   1620
ctcgccagca agctcaccgt ggacaagagc aggtggcagc aggggaacgt cttctcatgc   1680
tccgtgatgc atgaggctct gcacaaccac tacacgcaga agagcctctc cctgtctccg   1740
ggtaaa                                                              1746

<210> SEQ ID NO 93
<211> LENGTH: 577
<212> TYPE: PRT
<213> ORGANISM: Artificial Sequence
<220> FEATURE:
<223> OTHER INFORMATION: (huIL10)2-Fc9

<400> SEQUENCE: 93

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
                20                  25                  30

Val Lys Thr Phe Phe Gln Met Lys Asp Gln Leu Asp Asn Leu Leu Leu
            35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
                100                 105                 110

Pro Cys Glu Asn Lys Ser Lys Ala Val Glu Gln Val Lys Asn Ala Phe
            115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Gly Gly Ser Gly Gly Gly Ser Gly Gly Gly Ser Ser
                165                 170                 175

Pro Gly Gln Gly Thr Gln Ser Glu Asn Ser Cys Thr His Phe Pro Gly
                180                 185                 190

Asn Leu Pro Asn Met Leu Arg Asp Leu Arg Asp Ala Phe Ser Arg Val
            195                 200                 205

Lys Thr Phe Phe Gln Met Lys Asp Gln Leu Asp Asn Leu Leu Leu Lys
```

```
     210                 215                 220
Glu Ser Leu Leu Glu Asp Phe Lys Gly Tyr Leu Gly Cys Gln Ala Leu
225                 230                 235                 240

Ser Glu Met Ile Gln Phe Tyr Leu Glu Glu Val Met Pro Gln Ala Glu
                245                 250                 255

Asn Gln Asp Pro Asp Ile Lys Ala His Val Asn Ser Leu Gly Glu Asn
                260                 265                 270

Leu Lys Thr Leu Arg Leu Arg Leu Arg Arg Cys His Arg Phe Leu Pro
                275                 280                 285

Cys Glu Asn Lys Ser Lys Ala Val Glu Gln Val Lys Asn Ala Phe Asn
            290                 295                 300

Lys Leu Gln Glu Lys Gly Ile Tyr Lys Ala Met Ser Glu Phe Asp Ile
305                 310                 315                 320

Phe Ile Asn Tyr Ile Glu Ala Tyr Met Thr Met Lys Ile Arg Asn Gly
                325                 330                 335

Gly Gly Gly Ser Gly Gly Gly Ser Gly Gly Gly Ser Asp Lys
                340                 345                 350

Thr His Thr Cys Pro Pro Cys Pro Ala Pro Glu Leu Leu Gly Gly Pro
                355                 360                 365

Ser Val Phe Leu Phe Pro Pro Lys Pro Lys Asp Thr Leu Met Ile Ser
370                 375                 380

Arg Thr Pro Glu Val Thr Cys Val Val Val Asp Val Ser His Glu Asn
385                 390                 395                 400

Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
                420                 425                 430

Val Ser Val Leu Thr Val Leu His Gln Asp Trp Leu Asn Gly Lys Glu
                435                 440                 445

Tyr Lys Cys Lys Val Ser Asn Lys Ala Leu Pro Ala Pro Ile Glu Lys
                450                 455                 460

Thr Ile Ser Lys Ala Lys Gly Gln Pro Arg Glu Pro Gln Val Tyr Thr
465                 470                 475                 480

Leu Pro Pro Ser Arg Asp Glu Leu Thr Lys Asn Gln Val Ser Leu Trp
                485                 490                 495

Cys Leu Val Lys Gly Phe Tyr Pro Ser Asp Ile Ala Val Glu Trp Glu
                500                 505                 510

Ser Asn Gly Gln Pro Glu Asn Asn Tyr Lys Thr Thr Pro Pro Val Leu
                515                 520                 525

Asp Ser Asp Gly Ser Phe Phe Leu Tyr Ser Ala Leu Thr Val Asp Lys
                530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
                565                 570                 575

Lys
```

<210> SEQ ID NO 94
<211> LENGTH: 1731
<212> TYPE: DNA
<213> ORGANISM: Artificial Sequence
<220> FEATURE:
<223> OTHER INFORMATION: nucleic acid molecules encoding (huIL10)2-Fc9

<400> SEQUENCE: 94

```
agccccggcc agggcacaca gtccgagaac agctgcaccc actttcccgg caacctgcct      60
aacatgctga gggacctgag ggacgccttc agcagggtga agaccttctt ccagatgaag     120
gaccagctgg ataacctgct gctgaaggag agcctgctgg aggacttcaa gggctacctg     180
ggctgccagg ccctgagcga gatgatccag ttctacctgg aggaggtgat gccccaggcc     240
gagaaccagg accccgacat caaggcccac gtgaacagcc tgggcgagaa cctgaagacc     300
ctgaggctga ggctgaggag gtgccacagg ttcctgccct gtgagaacaa atccaaggcc     360
gtggagcagg tgaagaacgc cttcaacaag ctgcaggaaa agggcatcta caaggccatg     420
agcgagttcg acatctttat caactatatc gaggcctaca tgacaatgaa gatcaggaac     480
ggcggcggcg gcagcggggg cggcggcagc ggaggaggcg gcagcagccc cggccagggc     540
acacagtccg agaacagctg cacccacttt cccggcaacc tgcctaacat gctgagggac     600
ctgagggacg ccttcagcag ggtgaagacc ttcttccaga tgaaggacca gctggataac     660
ctgctgctga aggagagcct gctggaggac ttcaagggct acctgggctg ccaggccctg     720
agcgagatga tccagttcta cctggaggag gtgatgcccc aggccgagaa ccaggacccc     780
gacatcaagg cccacgtgaa cagcctgggc gagaacctga gaccctgag gctgaggctg     840
aggaggtgcc acaggttcct gccctgtgag aacaaatcca aggccgtgga gcaggtgaag     900
aacgccttca acaagctgca ggaaaagggc atctacaagg ccatgagcga gttcgacatc     960
tttatcaact atatcgaggc ctacatgaca atgaagatca ggaacggcgg cggcggcagc    1020
gggggcggcg gcagcggagg aggcggcagc gacaaaaccc acacatgccc accgtgccca    1080
gctccggaac tcctgggcgg accgtcagtc ttcctcttcc cccaaaaacc caaggacacc    1140
ctcatgatct cccggacccc tgaggtcaca tgcgtggtgg tggacgtgag ccacgaagac    1200
cctgaggtca agttcaactg gtacgtggac ggcgtggagg tgcataatgc caagacaaag    1260
ccgcgggagg agcagtacaa cagcacgtac cgtgtggtca gcgtcctcac cgtcctgcac    1320
caggactggc tgaatggcaa ggagtacaag tgcaaggtct ccaacaaagc cctcccagcc    1380
cccatcgaga aaaccatctc caaagccaaa gggcagcccc gagaaccaca ggtgtacacc    1440
ctgcccccaa gtcgggatga gctgaccaag aaccaggtca gcctgtggtg cctggtcaaa    1500
ggcttctatc ccagcgacat cgccgtggag tgggagagca atgggcagcc ggagaacaac    1560
tacaagacca cgcctcccgt gttggactcc gacggctcct tcttcctcta cagcgcgctc    1620
accgtggaca gagcaggtg gcagcagggg aacgtcttct catgctccgt gatgcatgag    1680
gctctgcaca accactacac gcagaagagc ctctccctgt ctccgggtaa a             1731
```

<210> SEQ ID NO 95  
<211> LENGTH: 577  
<212> TYPE: PRT  
<213> ORGANISM: Artificial Sequence  
<220> FEATURE:  
<223> OTHER INFORMATION: (huIL10)2-Fc-hole

<400> SEQUENCE: 95

```
Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
```

```
                    50                  55                  60
Leu Ser Glu Met Ile Gln Phe Tyr Leu Glu Glu Val Met Pro Gln Ala
 65                  70                  75                  80

Glu Asn Gln Asp Pro Asp Ile Lys Ala His Val Asn Ser Leu Gly Glu
                 85                  90                  95

Asn Leu Lys Thr Leu Arg Leu Arg Leu Arg Arg Cys His Arg Phe Leu
                100                 105                 110

Pro Cys Glu Asn Lys Ser Lys Ala Val Glu Gln Val Lys Asn Ala Phe
                115                 120                 125

Asn Lys Leu Gln Glu Lys Gly Ile Tyr Lys Ala Met Ser Glu Phe Asp
130                 135                 140

Ile Phe Ile Asn Tyr Ile Glu Ala Tyr Met Thr Met Lys Ile Arg Asn
145                 150                 155                 160

Gly Gly Gly Gly Ser Gly Gly Gly Ser Gly Gly Gly Gly Ser Ser
                165                 170                 175

Pro Gly Gln Gly Thr Gln Ser Glu Asn Ser Cys Thr His Phe Pro Gly
                180                 185                 190

Asn Leu Pro Asn Met Leu Arg Asp Leu Arg Asp Ala Phe Ser Arg Val
                195                 200                 205

Lys Thr Phe Phe Gln Met Lys Asp Gln Leu Asp Asn Leu Leu Leu Lys
210                 215                 220

Glu Ser Leu Leu Glu Asp Phe Lys Gly Tyr Leu Gly Cys Gln Ala Leu
225                 230                 235                 240

Ser Glu Met Ile Gln Phe Tyr Leu Glu Glu Val Met Pro Gln Ala Glu
                245                 250                 255

Asn Gln Asp Pro Asp Ile Lys Ala His Val Asn Ser Leu Gly Glu Asn
                260                 265                 270

Leu Lys Thr Leu Arg Leu Arg Leu Arg Arg Cys His Arg Phe Leu Pro
                275                 280                 285

Cys Glu Asn Lys Ser Lys Ala Val Glu Gln Val Lys Asn Ala Phe Asn
                290                 295                 300

Lys Leu Gln Glu Lys Gly Ile Tyr Lys Ala Met Ser Glu Phe Asp Ile
305                 310                 315                 320

Phe Ile Asn Tyr Ile Glu Ala Tyr Met Thr Met Lys Ile Arg Asn Gly
                325                 330                 335

Gly Gly Gly Ser Gly Gly Gly Ser Gly Gly Gly Ser Asp Lys
                340                 345                 350

Thr His Thr Cys Pro Pro Cys Pro Ala Pro Glu Leu Leu Gly Gly Pro
                355                 360                 365

Ser Val Phe Leu Phe Pro Pro Lys Pro Lys Asp Thr Leu Met Ile Ser
370                 375                 380

Arg Thr Pro Glu Val Thr Cys Val Val Val Asp Val Ser His Glu Asp
385                 390                 395                 400

Pro Glu Val Lys Phe Asn Trp Tyr Val Asp Gly Val Glu Val His Asn
                405                 410                 415

Ala Lys Thr Lys Pro Arg Glu Glu Gln Tyr Asn Ser Thr Tyr Arg Val
                420                 425                 430

Val Ser Val Leu Thr Val Leu His Gln Asp Trp Leu Asn Gly Lys Glu
                435                 440                 445

Tyr Lys Cys Lys Val Ser Asn Lys Ala Leu Pro Ala Pro Ile Glu Lys
                450                 455                 460

Thr Ile Ser Lys Ala Lys Gly Gln Pro Arg Glu Pro Gln Val Cys Thr
465                 470                 475                 480
```

```
Leu Pro Pro Ser Arg Asp Glu Leu Thr Lys Asn Gln Val Ser Leu Ser
            485                 490                 495

Cys Ala Val Lys Gly Phe Tyr Pro Ser Asp Ile Ala Val Glu Trp Glu
            500                 505                 510

Ser Asn Gly Gln Pro Glu Asn Asn Tyr Lys Thr Thr Pro Pro Val Leu
            515                 520                 525

Asp Ser Asp Gly Ser Phe Phe Leu Val Ser Lys Leu Thr Val Asp Lys
            530                 535                 540

Ser Arg Trp Gln Gln Gly Asn Val Phe Ser Cys Ser Val Met His Glu
545                 550                 555                 560

Ala Leu His Asn His Tyr Thr Gln Lys Ser Leu Ser Leu Ser Pro Gly
            565                 570                 575

Lys

<210> SEQ ID NO 96
<211> LENGTH: 1731
<212> TYPE: DNA
<213> ORGANISM: Artificial Sequence
<220> FEATURE:
<223> OTHER INFORMATION: nucleic acid molecules encoding
      (huIL10)2-Fc-hole

<400> SEQUENCE: 96
agccccggcc agggcacaca gtccgagaac agctgcaccc actttcccgg caacctgcct      60
aacatgctga gggacctgag ggacgccttc agcagggtga agaccttctt ccagatgaag     120
gaccagctgg ataacctgct gctgaaggag agcctgctgg aggacttcaa gggctacctg     180
ggctgccagg ccctgagcga gatgatccag ttctacctgg aggaggtgat gccccaggcc     240
gagaaccagg accccgacat caaggcccac gtgaacagcc tgggcgagaa cctgaagacc     300
ctgaggctga ggctgaggag gtgccacagg ttcctgccct gtgagaacaa atccaaggcc     360
gtggagcagg tgaagaacgc cttcaacaag ctgcaggaaa agggcatcta caaggccatg     420
agcgagttcg acatctttat caactatatc gaggcctaca tgacaatgaa gatcaggaac     480
ggcggcggcg gcagcggggg cggcggcagc ggaggaggcg gcagcagccc cggccagggc     540
acacagtccg agaacagctg cacccacttt cccggcaacc tgcctaacat gctgagggac     600
ctgagggacg ccttcagcag ggtgaagacc ttcttccaga tgaaggacca gctggataac     660
ctgctgctga aggagagcct gctggaggac ttcaagggct acctgggctg ccaggccctg     720
agcgagatga tccagttcta cctggaggag gtgatgcccc aggccgagaa ccaggacccc     780
gacatcaagg cccacgtgaa cagcctgggc gagaacctga gaccctgag gctgaggctg     840 aggaggtgcc acaggttcct gccctgtgag aacaaatcca aggccgtgga gcaggtgaag     900
aacgccttca caagctgca ggaaaagggc atctacaagg ccatgagcga gttcgacatc     960
tttatcaact atatcgaggc ctacatgaca atgaagatca ggaacggcgg cggcggcagc    1020
gggggcggcg gcagcggagg aggcggcagc gacaagaccc acacctgccc cccttgcccc    1080
gctccggagc tgctgggcgg ccccagcgtg ttcctgttcc ccccaagcc caaggacacc    1140 ctgatgatca gccgcacccc cgaggtgacc tgcgtggtgg tggacgtgag ccacgaggac    1200
cccgaggtga agttcaactg gtacgtggac ggcgtggagg tgcacaacgc caagaccaag    1260
ccccgcgagg agcagtacaa cagcacctac cgcgtggtga gcgtgctgac cgtgctgcac    1320
caggactggc tgaacggcaa ggagtacaag tgcaaggtgg caacaaggc cctgcccgcc    1380 cccatcgaga agaccatcag caaggccaag ggccagcccc gcgagcccca ggtgtgcacc    1440
```

```
ctgcccccca gccgcgacga gctgaccaag aaccaggtga gcctgagctg cgccgtgaag    1500
ggcttctacc ccagcgacat cgccgtggag tgggagagca cggccagcc cgagaacaac    1560 tacaagacca cccccccgt gctggacagc gacggcagct tcttcctggt gagcaagctg    1620
accgtggaca gagccgctg gcagcagggc aacgtgttca gctgcagcgt gatgcacgag    1680
gccctgcaca accactacac ccagaagagc ctgagcctga gccccggcaa g            1731
```

<210> SEQ ID NO 97
<211> LENGTH: 370
<212> TYPE: PRT
<213> ORGANISM: Artificial Sequence
<220> FEATURE:
<223> OTHER INFORMATION: husIL2-Fc6

<400> SEQUENCE: 97

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Pro Lys Ser Ser Asp
    130                 135                 140

Lys Thr His Thr Cys Pro Pro Cys Pro Ala Pro Glu Leu Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser His Glu
            180                 185                 190

Asp Pro Glu Val Lys Phe Asn Trp Tyr Val Asp Gly Val Glu Val His
        195                 200                 205

Asn Ala Lys Thr Lys Pro Arg Glu Glu Gln Tyr Asn Ser Thr Tyr Arg
    210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Ala Leu Pro Ala Pro Ile Glu
                245                 250                 255

Lys Thr Ile Ser Lys Ala Lys Gly Gln Pro Arg Glu Pro Gln Val Tyr
            260                 265                 270

Thr Leu Pro Pro Ser Arg Asp Glu Leu Thr Lys Asn Gln Val Ser Leu
        275                 280                 285

Ser Cys Gly Val Lys Gly Phe Tyr Pro Ser Asp Ile Ala Val Glu Trp
    290                 295                 300

Glu Ser Asn Gly Gln Pro Glu Asn Asn Tyr Lys Thr Thr Pro Pro Val
```

```
                305                 310                 315                 320
Leu Asp Ser Asp Gly Ser Phe Lys Leu Ala Ser Lys Leu Thr Val Asp
                    325                 330                 335

Lys Ser Arg Trp Gln Gln Gly Asn Val Phe Ser Cys Ser Val Met His
            340                 345                 350

Glu Ala Leu His Asn His Tyr Thr Gln Lys Ser Leu Ser Leu Ser Pro
        355                 360                 365

Gly Lys
    370

<210> SEQ ID NO 98
<211> LENGTH: 1110
<212> TYPE: DNA
<213> ORGANISM: Artificial Sequence
<220> FEATURE:
<223> OTHER INFORMATION: nucleic acid molecules encoding husIL2-Fc6

<400> SEQUENCE: 98
gcccctacaa gcagcagcac caagaagacc cagctgcagc tggaacacct gctgctggat      60
ctgcagatga tcctgaacgg catcaacaac tacaagaacc ccaagctgac ccggatgctg     120
accttcaagt tctacatgcc caagaaggcc accgagctga agcacctcca gtgtctggag     180
gaggagctga agcctctgga ggaagtgctg aacctggccc agagcaagaa cttccacttc     240
gaccccaggg acgtggtgtc caacatcaac gtgttcgtgc tggaactgaa gggcagcgag     300
accaccttca tgtgcgagta cgccgacgag accgctacca tcgtggagtt cctgaaccgc     360
tggatcacct tttgccagag catcatcagc acactgaccg aggaggagga aagcgaacct     420
aagagcagcg acaagaccca cacttgcccc ccttgtcccg ctccggaact cctgggcgga     480
ccgtcagtct tcctcttccc cccaaaaccc aaggacaccc tcatgatctc ccggacccct     540
gaggtcacat gcgtggtggt ggacgtgagc cacgaagacc ctgaggtcaa gttcaactgg     600
tacgtggacg gcgtggaggt gcataatgcc aagacaaagc cgcgggagga gcagtacaac     660
agcacgtacc gtgtggtcag cgtcctcacc gtcctgcacc aggactggct gaatggcaag     720
gagtacaagt gcaaggtctc caacaaagcc ctcccagccc ccatcgagaa aaccatctcc     780
aaagccaaag ggcagccccg agaaccacag gtgtataccc tgcccccatc ccgggatgag     840
ctgaccaaga accaggtcag cctgagttgc ggggtcaaag gcttctatcc cagcgacatc     900
gccgtggagt gggagagcaa tgggcagccg gagaacaact acaagaccac gcctcccgtg     960
ttggactccg acggctcctt caagctcgcc agcaagctca ccgtggacaa gagcaggtgg    1020
cagcagggga acgtcttctc atgctccgtg atgcatgagg ctctgcacaa ccactacacg    1080
cagaagagcc tctccctgtc tccgggtaaa                                     1110

<210> SEQ ID NO 99
<211> LENGTH: 370
<212> TYPE: PRT
<213> ORGANISM: Artificial Sequence
<220> FEATURE:
<223> OTHER INFORMATION: husIL2-Fc-hole

<400> SEQUENCE: 99

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
```

```
            35                  40                  45
Lys Ala Thr Glu Leu Lys His Leu Gln Cys Leu Glu Glu Leu Lys
 50                  55                  60
Pro Leu Glu Glu Val Leu Asn Leu Ala Gln Ser Lys Asn Phe His Phe
65                  70                  75                  80
Asp Pro Arg Asp Val Val Ser Asn Ile Asn Val Phe Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr Gly Gly Gly Gly Ser Glu Pro Lys Ser Ser Asp
    130                 135                 140
Lys Thr His Thr Cys Pro Pro Cys Pro Ala Pro Glu Leu Leu Gly Gly
145                 150                 155                 160
Pro Ser Val Phe Leu Phe Pro Pro Lys Pro Lys Asp Thr Leu Met Ile
                165                 170                 175
Ser Arg Thr Pro Glu Val Thr Cys Val Val Val Asp Val Ser His Glu
            180                 185                 190
Asp Pro Glu Val Lys Phe Asn Trp Tyr Val Asp Gly Val Glu Val His
        195                 200                 205
Asn Ala Lys Thr Lys Pro Arg Glu Glu Gln Tyr Asn Ser Thr Tyr Arg
    210                 215                 220
Val Val Ser Val Leu Thr Val Leu His Gln Asp Trp Leu Asn Gly Lys
225                 230                 235                 240
Glu Tyr Lys Cys Lys Val Ser Asn Lys Ala Leu Pro Ala Pro Ile Glu
                245                 250                 255
Lys Thr Ile Ser Lys Ala Lys Gly Gln Pro Arg Glu Pro Gln Val Tyr
            260                 265                 270
Thr Leu Pro Pro Ser Arg Cys Glu Leu Thr Lys Asn Gln Val Ser Leu
        275                 280                 285
Ser Cys Ala Val Lys Gly Phe Tyr Pro Ser Asp Ile Ala Val Glu Trp
    290                 295                 300
Glu Ser Asn Gly Gln Pro Glu Asn Asn Tyr Lys Thr Thr Pro Pro Val
305                 310                 315                 320
Leu Asp Ser Asp Gly Ser Phe Phe Leu Val Ser Lys Leu Thr Val Asp
                325                 330                 335
Lys Ser Arg Trp Gln Gln Gly Asn Val Phe Ser Cys Ser Val Met His
            340                 345                 350
Glu Ala Leu His Asn His Tyr Thr Gln Lys Ser Leu Ser Leu Ser Pro
        355                 360                 365
Gly Lys
    370

<210> SEQ ID NO 100
<211> LENGTH: 1110
<212> TYPE: DNA
<213> ORGANISM: Artificial Sequence
<220> FEATURE:
<223> OTHER INFORMATION: nucleic acid molecules encoding husIL2-Fc-hole

<400> SEQUENCE: 100
gcccctacaa gcagcagcac caagaagacc cagctgcagc tggaacaccct gctgctggat      60 ctgcagatga tcctgaacgg catcaacaac tacaagaacc ccaagctgac ccggatgctg     120
```

-continued

```
accttcaagt tctacatgcc caagaaggcc accgagctga agcacctcca gtgtctggag    180
gaggagctga agcctctgga ggaagtgctg aacctggccc agagcaagaa cttccacttc    240
gaccccaggg acgtggtgtc caacatcaac gtgttcgtgc tggaactgaa gggcagcgag    300
accaccttca tgtgcgagta cgccgacgag accgctacca tcgtggagtt cctgaaccgc    360
tggatcacct tttgccagag catcatcagc acactgaccg gaggaggagg aagcgagcct    420
aagtccagcg acaagaccca cacctgcccc ccttgccccg ctccggaact cctgggcgga    480
ccgtcagtct tcctcttccc cccaaaaccc aaggacaccc tcatgatctc ccggacccct    540
gaggtcacat gcgtggtggt ggacgtgagc cacgaagacc ctgaggtcaa gttcaactgg    600
tacgtggacg gcgtggaggt gcataatgcc aagacaaagc cgcgggagga gcagtacaac    660
agcacgtacc gtgtggtcag cgtcctcacc gtcctgcacc aggactggct gaatggcaag    720
gagtacaagt gcaaggtctc caacaaagcc ctcccagccc ccatcgagaa aaccatctcc    780
aaagccaaag ggcagccccg agaaccacag gtgtataccc tgcccccatc ccggtgtgag    840
ctgaccaaga accaggtcag cctgagttgc gcggtcaaag gcttctatcc cagcgacatc    900
gccgtggagt gggagagcaa tgggcagccg gagaacaact acaagaccac gcctcccgtg    960
ttggactccg acggctcctt cttcctcgtc agcaagctca ccgtggacaa gagcaggtgg   1020
cagcagggga acgtcttctc atgctccgtg atgcatgagg ctctgcacaa ccactacacg   1080
cagaagagcc tctccctgtc tccgggtaaa                                    1110
```

<210> SEQ ID NO 101
<211> LENGTH: 11
<212> TYPE: PRT
<213> ORGANISM: Artificial Sequence
<220> FEATURE:
<223> OTHER INFORMATION: Cetuximab light chain CDR1

<400> SEQUENCE: 101

Arg Ala Ser Gln Ser Ile Gly Thr Asn Ile His
1               5                   10

<210> SEQ ID NO 102
<211> LENGTH: 7
<212> TYPE: PRT
<213> ORGANISM: Artificial Sequence
<220> FEATURE:
<223> OTHER INFORMATION: Cetuximab light chain CDR2

<400> SEQUENCE: 102

Tyr Ala Ser Glu Ser Ile Ser
1               5

<210> SEQ ID NO 103
<211> LENGTH: 9
<212> TYPE: PRT
<213> ORGANISM: Artificial Sequence
<220> FEATURE:
<223> OTHER INFORMATION: Cetuximab light chain CDR3

<400> SEQUENCE: 103

Gln Gln Asn Asn Asn Trp Pro Thr Thr
1               5

<210> SEQ ID NO 104
<211> LENGTH: 107
<212> TYPE: PRT
<213> ORGANISM: Artificial Sequence
<220> FEATURE:

<223> OTHER INFORMATION: Cetuximab light chain variable region

<400> SEQUENCE: 104

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105

<210> SEQ ID NO 105
<211> LENGTH: 5
<212> TYPE: PRT
<213> ORGANISM: Artificial Sequence
<220> FEATURE:
<223> OTHER INFORMATION: Cetuximab heavy chain CDR1

<400> SEQUENCE: 105

Asn Tyr Gly Val His
1               5

<210> SEQ ID NO 106
<211> LENGTH: 16
<212> TYPE: PRT
<213> ORGANISM: Artificial Sequence
<220> FEATURE:
<223> OTHER INFORMATION: Cetuximab heavy chain CDR2

<400> SEQUENCE: 106

Val Ile Trp Ser Gly Gly Asn Thr Asp Tyr Asn Thr Pro Phe Thr Ser
1               5                   10                  15

<210> SEQ ID NO 107
<211> LENGTH: 11
<212> TYPE: PRT
<213> ORGANISM: Artificial Sequence
<220> FEATURE:
<223> OTHER INFORMATION: Cetuximab heavy chain CDR3

<400> SEQUENCE: 107

Ala Leu Thr Tyr Tyr Asp Tyr Glu Phe Ala Tyr
1               5                   10

<210> SEQ ID NO 108
<211> LENGTH: 119
<212> TYPE: PRT
<213> ORGANISM: Artificial Sequence
<220> FEATURE:
<223> OTHER INFORMATION: Cetuximab heavy chain variable region

<400> SEQUENCE: 108

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

```
Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 109
<211> LENGTH: 11
<212> TYPE: PRT
<213> ORGANISM: Artificial Sequence
<220> FEATURE:
<223> OTHER INFORMATION: Mab806 light chain CDR1

<400> SEQUENCE: 109

His Ser Ser Gln Asp Ile Asn Ser Asn Ile Gly
1               5                   10

<210> SEQ ID NO 110
<211> LENGTH: 7
<212> TYPE: PRT
<213> ORGANISM: Artificial Sequence
<220> FEATURE:
<223> OTHER INFORMATION: Mab806 light chain CDR2

<400> SEQUENCE: 110

His Gly Thr Asn Leu Asp Asp
1               5

<210> SEQ ID NO 111
<211> LENGTH: 9
<212> TYPE: PRT
<213> ORGANISM: Artificial Sequence
<220> FEATURE:
<223> OTHER INFORMATION: Mab806 light chain CDR3

<400> SEQUENCE: 111

Val Gln Tyr Ala Gln Phe Pro Trp Thr
1               5

<210> SEQ ID NO 112
<211> LENGTH: 107
<212> TYPE: PRT
<213> ORGANISM: Artificial Sequence
<220> FEATURE:
<223> OTHER INFORMATION: Mab806 light chain variable region

<400> SEQUENCE: 112

Asp Ile Leu Met Thr Gln Ser Pro Ser Ser Met Ser Val Ser Leu Gly
1               5                   10                  15

Asp Thr Val Ser Ile Thr Cys His Ser Ser Gln Asp Ile Asn Ser Asn
            20                  25                  30

Ile Gly Trp Leu Gln Gln Arg Pro Gly Lys Ser Phe Lys Gly Leu Ile
        35                  40                  45

Tyr His Gly Thr Asn Leu Asp Asp Glu Val Pro Ser Arg Phe Ser Gly
    50                  55                  60
```

```
Ser Gly Ser Gly Ala Asp Tyr Ser Leu Thr Ile Ser Ser Leu Glu Ser
 65                  70                  75                  80

Glu Asp Phe Ala Asp Tyr Tyr Cys Val Gln Tyr Ala Gln Phe Pro Trp
                 85                  90                  95

Thr Phe Gly Gly Gly Thr Lys Leu Glu Ile Lys
            100                 105

<210> SEQ ID NO 113
<211> LENGTH: 6
<212> TYPE: PRT
<213> ORGANISM: Artificial Sequence
<220> FEATURE:
<223> OTHER INFORMATION: Mab806 heavy chain CDR1

<400> SEQUENCE: 113

Ser Asp Phe Ala Trp Asn
1               5

<210> SEQ ID NO 114
<211> LENGTH: 16
<212> TYPE: PRT
<213> ORGANISM: Artificial Sequence
<220> FEATURE:
<223> OTHER INFORMATION: Mab806 heavy chain CDR2

<400> SEQUENCE: 114

Tyr Ile Ser Tyr Ser Gly Asn Thr Arg Tyr Asn Pro Ser Leu Lys Ser
1               5                  10                  15

<210> SEQ ID NO 115
<211> LENGTH: 7
<212> TYPE: PRT
<213> ORGANISM: Artificial Sequence
<220> FEATURE:
<223> OTHER INFORMATION: Mab806 heavy chain CDR3

<400> SEQUENCE: 115

Ala Gly Arg Gly Phe Pro Tyr
1               5

<210> SEQ ID NO 116
<211> LENGTH: 116
<212> TYPE: PRT
<213> ORGANISM: Artificial Sequence
<220> FEATURE:
<223> OTHER INFORMATION: Mab806 heavy chain variable region

<400> SEQUENCE: 116

Asp Val Gln Leu Gln Glu Ser Gly Pro Ser Leu Val Lys Pro Ser Gln
1               5                  10                  15

Ser Leu Ser Leu Thr Cys Thr Val Thr Gly Tyr Ser Ile Thr Ser Asp
                20                  25                  30

Phe Ala Trp Asn Trp Ile Arg Gln Phe Pro Gly Asn Lys Leu Glu Trp
            35                  40                  45

Met Gly Tyr Ile Ser Tyr Ser Gly Asn Thr Arg Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ile Glu Asp Thr Ala Thr Tyr Tyr Cys
                85                  90                  95

Val Thr Ala Gly Arg Gly Phe Pro Tyr Trp Gly Gln Gly Thr Leu Val
                100                 105                 110
```

Thr Val Ser Ala
        115

<210> SEQ ID NO 117
<211> LENGTH: 11
<212> TYPE: PRT
<213> ORGANISM: Artificial Sequence
<220> FEATURE:
<223> OTHER INFORMATION: Trastuzumab light chain CDR1

<400> SEQUENCE: 117

Arg Ala Ser Gln Asp Val Asn Thr Ala Val Ala
1               5                   10

<210> SEQ ID NO 118
<211> LENGTH: 7
<212> TYPE: PRT
<213> ORGANISM: Artificial Sequence
<220> FEATURE:
<223> OTHER INFORMATION: Trastuzumab light chain CDR2

<400> SEQUENCE: 118

Ser Ala Ser Phe Leu Tyr Ser
1               5

<210> SEQ ID NO 119
<211> LENGTH: 9
<212> TYPE: PRT
<213> ORGANISM: Artificial Sequence
<220> FEATURE:
<223> OTHER INFORMATION: Trastuzumab light chain CDR3

<400> SEQUENCE: 119

Gln Gln His Tyr Thr Thr Pro Pro Thr
1               5

<210> SEQ ID NO 120
<211> LENGTH: 107
<212> TYPE: PRT
<213> ORGANISM: Artificial Sequence
<220> FEATURE:
<223> OTHER INFORMATION: Trastuzumab light chain variable region

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 121
<211> LENGTH: 5
<212> TYPE: PRT
<213> ORGANISM: Artificial Sequence -continued

```
<220> FEATURE:
<223> OTHER INFORMATION: Trastuzumab heavy chain CDR1

<400> SEQUENCE: 121

Asp Thr Tyr Ile His
1               5

<210> SEQ ID NO 122
<211> LENGTH: 17
<212> TYPE: PRT
<213> ORGANISM: Artificial Sequence
<220> FEATURE:
<223> OTHER INFORMATION: Trastuzumab heavy chain CDR2

<400> SEQUENCE: 122

Arg Ile Tyr Pro Thr Asn Gly Tyr Thr Arg Tyr Ala Asp Ser Val Lys
1               5                   10                  15

Gly

<210> SEQ ID NO 123
<211> LENGTH: 11
<212> TYPE: PRT
<213> ORGANISM: Artificial Sequence
<220> FEATURE:
<223> OTHER INFORMATION: Trastuzumab heavy chain CDR3

<400> SEQUENCE: 123

Trp Gly Gly Asp Gly Phe Tyr Ala Met Asp Tyr
1               5                   10

<210> SEQ ID NO 124
<211> LENGTH: 120
<212> TYPE: PRT
<213> ORGANISM: Artificial Sequence
<220> FEATURE:
<223> OTHER INFORMATION: Trastuzumab heavy chain variable region

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 125
<211> LENGTH: 11
<212> TYPE: PRT
<213> ORGANISM: Artificial Sequence
<220> FEATURE:
<223> OTHER INFORMATION: Pertuzumab light chain CDR1

<400> SEQUENCE: 125
```

```
Lys Ala Ser Gln Asp Val Ser Ile Gly Val Ala
1               5                   10

<210> SEQ ID NO 126
<211> LENGTH: 7
<212> TYPE: PRT
<213> ORGANISM: Artificial Sequence
<220> FEATURE:
<223> OTHER INFORMATION: Pertuzumab light chain CDR2

<400> SEQUENCE: 126

Ser Ala Ser Tyr Arg Tyr Thr
1               5

<210> SEQ ID NO 127
<211> LENGTH: 9
<212> TYPE: PRT
<213> ORGANISM: Artificial Sequence
<220> FEATURE:
<223> OTHER INFORMATION: Pertuzumab light chain CDR3

<400> SEQUENCE: 127

Gln Gln Tyr Tyr Ile Tyr Pro Tyr Thr
1               5

<210> SEQ ID NO 128
<211> LENGTH: 107
<212> TYPE: PRT
<213> ORGANISM: Artificial Sequence
<220> FEATURE:
<223> OTHER INFORMATION: Pertuzumab light chain variable region

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 129
<211> LENGTH: 5
<212> TYPE: PRT
<213> ORGANISM: Artificial Sequence
<220> FEATURE:
<223> OTHER INFORMATION: Pertuzumab heavy chain CDR1

<400> SEQUENCE: 129

Asp Tyr Thr Met Asp
1               5

<210> SEQ ID NO 130
<211> LENGTH: 17
<212> TYPE: PRT
<213> ORGANISM: Artificial Sequence
```

<220> FEATURE:
<223> OTHER INFORMATION: Pertuzumab heavy chain CDR2

<400> SEQUENCE: 130

Asp Val Asn Pro Asn Ser Gly Gly Ser Ile Tyr Asn Gln Arg Phe Lys
1               5                   10                  15

Gly

<210> SEQ ID NO 131
<211> LENGTH: 10
<212> TYPE: PRT
<213> ORGANISM: Artificial Sequence
<220> FEATURE:
<223> OTHER INFORMATION: Pertuzumab heavy chain CDR3

<400> SEQUENCE: 131

Asn Leu Gly Pro Ser Phe Tyr Phe Asp Tyr
1               5                   10

<210> SEQ ID NO 132
<211> LENGTH: 119
<212> TYPE: PRT
<213> ORGANISM: Artificial Sequence
<220> FEATURE:
<223> OTHER INFORMATION: Pertuzumab heavy chain variable region

<400> SEQUENCE: 132

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 133
<211> LENGTH: 16
<212> TYPE: PRT
<213> ORGANISM: Artificial Sequence
<220> FEATURE:
<223> OTHER INFORMATION: C-MAB light chain CDR1

<400> SEQUENCE: 133

Arg Ser Ser Gln Ser Leu Val His Ser Asn Arg Asn Thr Tyr Leu His
1               5                   10                  15

<210> SEQ ID NO 134
<211> LENGTH: 7
<212> TYPE: PRT
<213> ORGANISM: Artificial Sequence
<220> FEATURE:
<223> OTHER INFORMATION: C-MAB light chain CDR2

<400> SEQUENCE: 134

```
Lys Val Ser Asn Arg Phe Ser
1               5
```

<210> SEQ ID NO 135
<211> LENGTH: 9
<212> TYPE: PRT
<213> ORGANISM: Artificial Sequence
<220> FEATURE:
<223> OTHER INFORMATION: C-MAB light chain CDR3

<400> SEQUENCE: 135

```
Ser Gln Asn Thr His Val Pro Pro Thr
1               5
```

<210> SEQ ID NO 136
<211> LENGTH: 112
<212> TYPE: PRT
<213> ORGANISM: Artificial Sequence
<220> FEATURE:
<223> OTHER INFORMATION: C-MAB light chain variable region

<400> SEQUENCE: 136

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110
```

<210> SEQ ID NO 137
<211> LENGTH: 5
<212> TYPE: PRT
<213> ORGANISM: Artificial Sequence
<220> FEATURE:
<223> OTHER INFORMATION: C-MAB heavy chain CDR1

<400> SEQUENCE: 137

```
Asp Tyr Glu Met His
1               5
```

<210> SEQ ID NO 138
<211> LENGTH: 17
<212> TYPE: PRT
<213> ORGANISM: Artificial Sequence
<220> FEATURE:
<223> OTHER INFORMATION: C-MAB heavy chain CDR2

<400> SEQUENCE: 138

```
Ala Leu Asp Pro Lys Thr Gly Asp Thr Ala Tyr Ser Gln Lys Phe Lys
1               5                   10                  15

Gly
```

<210> SEQ ID NO 139
<211> LENGTH: 6

```
<212> TYPE: PRT
<213> ORGANISM: Artificial Sequence
<220> FEATURE:
<223> OTHER INFORMATION: C-MAB heavy chain CDR3

<400> SEQUENCE: 139

Phe Tyr Ser Tyr Thr Tyr
1               5

<210> SEQ ID NO 140
<211> LENGTH: 115
<212> TYPE: PRT
<213> ORGANISM: Artificial Sequence
<220> FEATURE:
<223> OTHER INFORMATION: C-MAB heavy chain variable region

<400> SEQUENCE: 140

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 141
<211> LENGTH: 6
<212> TYPE: PRT
<213> ORGANISM: Artificial Sequence
<220> FEATURE:
<223> OTHER INFORMATION: 28H1 light chain CDR1

<400> SEQUENCE: 141

Ser Arg Ser Tyr Leu Ala
1               5

<210> SEQ ID NO 142
<211> LENGTH: 7
<212> TYPE: PRT
<213> ORGANISM: Artificial Sequence
<220> FEATURE:
<223> OTHER INFORMATION: 28H1 light chain CDR2

<400> SEQUENCE: 142

Gly Ala Ser Thr Arg Ala Thr
1               5

<210> SEQ ID NO 143
<211> LENGTH: 9
<212> TYPE: PRT
<213> ORGANISM: Artificial Sequence
<220> FEATURE:
<223> OTHER INFORMATION: 28H1 light chain CDR3

<400> SEQUENCE: 143
```

Gln Gln Gly Gln Val Ile Pro Pro Thr
1               5

<210> SEQ ID NO 144
<211> LENGTH: 108
<212> TYPE: PRT
<213> ORGANISM: Artificial Sequence
<220> FEATURE:
<223> OTHER INFORMATION: 28H1 light chain variable region

<400> SEQUENCE: 144

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105

<210> SEQ ID NO 145
<211> LENGTH: 5
<212> TYPE: PRT
<213> ORGANISM: Artificial Sequence
<220> FEATURE:
<223> OTHER INFORMATION: 28H1 heavy chain CDR1

<400> SEQUENCE: 145

Ser His Ala Met Ser
1               5

<210> SEQ ID NO 146
<211> LENGTH: 16
<212> TYPE: PRT
<213> ORGANISM: Artificial Sequence
<220> FEATURE:
<223> OTHER INFORMATION: 28H1 heavy chain CDR2

<400> SEQUENCE: 146

Ala Ile Trp Ala Ser Gly Glu Gln Tyr Tyr Ala Asp Ser Val Lys Gly
1               5                   10                  15

<210> SEQ ID NO 147
<211> LENGTH: 8
<212> TYPE: PRT
<213> ORGANISM: Artificial Sequence
<220> FEATURE:
<223> OTHER INFORMATION: 28H1 heavy chain CDR3

<400> SEQUENCE: 147

Gly Trp Leu Gly Asn Phe Asp Tyr
1               5

<210> SEQ ID NO 148
<211> LENGTH: 116
<212> TYPE: PRT
<213> ORGANISM: Artificial Sequence

```
<220> FEATURE:
<223> OTHER INFORMATION: 28H1 heavy chain variable region

<400> SEQUENCE: 148

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Gln Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser
        115

<210> SEQ ID NO 149
<211> LENGTH: 17
<212> TYPE: PRT
<213> ORGANISM: Artificial Sequence
<220> FEATURE:
<223> OTHER INFORMATION: 5E5 light chain CDR1

<400> SEQUENCE: 149

Lys Ser Ser Gln Ser Leu Leu Asn Ser Gly Asp Gln Lys Asn Tyr Leu
1               5                   10                  15

Thr

<210> SEQ ID NO 150
<211> LENGTH: 7
<212> TYPE: PRT
<213> ORGANISM: Artificial Sequence
<220> FEATURE:
<223> OTHER INFORMATION: 5E5 light chain CDR2

<400> SEQUENCE: 150

Trp Ala Ser Thr Arg Glu Ser
1               5

<210> SEQ ID NO 151
<211> LENGTH: 9
<212> TYPE: PRT
<213> ORGANISM: Artificial Sequence
<220> FEATURE:
<223> OTHER INFORMATION: 5E5 light chain CDR3

<400> SEQUENCE: 151

Gln Asn Asp Tyr Ser Tyr Pro Leu Thr
1               5

<210> SEQ ID NO 152
<211> LENGTH: 113
<212> TYPE: PRT
<213> ORGANISM: Artificial Sequence
<220> FEATURE:
<223> OTHER INFORMATION: 5E5 light chain variable region

<400> SEQUENCE: 152
```

```
Glu Leu Val Met Thr Gln Ser Pro Ser Ser Leu Thr Val Thr Ala Gly
1               5                   10                  15

Glu Lys Val Thr Met Ile Cys Lys Ser Ser Gln Ser Leu Leu Asn Ser
            20                  25                  30

Gly Asp Gln Lys Asn Tyr Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys

<210> SEQ ID NO 153
<211> LENGTH: 5
<212> TYPE: PRT
<213> ORGANISM: Artificial Sequence
<220> FEATURE:
<223> OTHER INFORMATION: 5E5 heavy chain CDR1

<400> SEQUENCE: 153

Asp His Ala Ile His
1               5

<210> SEQ ID NO 154
<211> LENGTH: 17
<212> TYPE: PRT
<213> ORGANISM: Artificial Sequence
<220> FEATURE:
<223> OTHER INFORMATION: 5E5 heavy chain CDR2

<400> SEQUENCE: 154

His Phe Ser Pro Gly Asn Thr Asp Ile Lys Tyr Asn Asp Lys Phe Lys
1               5                   10                  15

Gly

<210> SEQ ID NO 155
<211> LENGTH: 7
<212> TYPE: PRT
<213> ORGANISM: Artificial Sequence
<220> FEATURE:
<223> OTHER INFORMATION: 5E5 heavy chain CDR3

<400> SEQUENCE: 155

Ser Thr Phe Phe Phe Asp Tyr
1               5

<210> SEQ ID NO 156
<211> LENGTH: 116
<212> TYPE: PRT
<213> ORGANISM: Artificial Sequence
<220> FEATURE:
<223> OTHER INFORMATION: 5E5 heavy chain variable region

<400> SEQUENCE: 156

Gln Val Gln Leu Gln Gln Ser Asp Ala Glu Leu Val Lys Pro Gly Ser
1               5                   10                  15

Ser Val Lys Ile Ser Cys Lys Ala Ser Gly Tyr Thr Phe Thr Asp His
```

```
                    20                  25                  30
Ala Ile His Trp Val Lys Gln Lys Pro Glu Gln Gly Leu Glu Trp Ile
                35                  40                  45

Gly His Phe Ser Pro Gly Asn Thr Asp Ile Lys Tyr Asn Asp Lys Phe
            50                  55                  60

Lys Gly Lys Ala Thr Leu Thr Val Asp Arg Ser Ser Thr Ala Tyr
65                  70                  75                  80

Met Gln Leu Asn Ser Leu Thr Ser Glu Asp Ser Ala Val Tyr Phe Cys
                85                  90                  95

Lys Thr Ser Thr Phe Phe Phe Asp Tyr Trp Gly Gln Gly Thr Thr Leu
                100                 105                 110

Thr Val Ser Ser
        115

<210> SEQ ID NO 157
<211> LENGTH: 10
<212> TYPE: PRT
<213> ORGANISM: Artificial Sequence
<220> FEATURE:
<223> OTHER INFORMATION: E-mab light chain CDR1

<400> SEQUENCE: 157

Ser Ala Ser Ser Ser Ile Ser Tyr Met Tyr
1               5                   10

<210> SEQ ID NO 158
<211> LENGTH: 7
<212> TYPE: PRT
<213> ORGANISM: Artificial Sequence
<220> FEATURE:
<223> OTHER INFORMATION: E-mab light chain CDR2

<400> SEQUENCE: 158

Asp Thr Ser Lys Leu Ala Ser
1               5

<210> SEQ ID NO 159
<211> LENGTH: 9
<212> TYPE: PRT
<213> ORGANISM: Artificial Sequence
<220> FEATURE:
<223> OTHER INFORMATION: E-mab light chain CDR3

<400> SEQUENCE: 159

His Gln Arg Asp Ser Tyr Pro Trp Thr
1               5

<210> SEQ ID NO 160
<211> LENGTH: 106
<212> TYPE: PRT
<213> ORGANISM: Artificial Sequence
<220> FEATURE:
<223> OTHER INFORMATION: E-mab light chain variable region

<400> SEQUENCE: 160

Gln Val Val Leu Thr Gln Ser Pro Val Ile Met Ser Ala Ser Pro Gly
1               5                   10                  15

Glu Lys Val Thr Met Thr Cys Ser Ala Ser Ser Ser Ile Ser Tyr Met
                20                  25                  30

Tyr Trp Tyr Gln Gln Lys Pro Gly Thr Ser Pro Lys Arg Trp Ile Tyr
            35                  40                  45

Asp Thr Ser Lys Leu Ala Ser Gly Val Pro Ala Arg Phe Ser Gly Ser
```

```
                50                  55                  60
Gly Ser Gly Thr Ser Tyr Ser Leu Thr Ile Ser Asn Met Glu Ala Gly
 65                  70                  75                  80

Asp Ala Ala Thr Tyr Tyr Cys His Gln Arg Asp Ser Tyr Pro Trp Thr
                 85                  90                  95

Phe Gly Gly Gly Thr Asn Leu Glu Ile Lys
            100                 105

<210> SEQ ID NO 161
<211> LENGTH: 5
<212> TYPE: PRT
<213> ORGANISM: Artificial Sequence
<220> FEATURE:
<223> OTHER INFORMATION: E-mab heavy chain CDR1

<400> SEQUENCE: 161

Lys Phe Gly Val Asn
 1               5

<210> SEQ ID NO 162
<211> LENGTH: 16
<212> TYPE: PRT
<213> ORGANISM: Artificial Sequence
<220> FEATURE:
<223> OTHER INFORMATION: E-mab heavy chain CDR2

<400> SEQUENCE: 162

Val Ile Trp Gly Asp Gly Ser Thr Ser Tyr Asn Ser Gly Leu Ile Ser
 1               5                  10                  15

<210> SEQ ID NO 163
<211> LENGTH: 5
<212> TYPE: PRT
<213> ORGANISM: Artificial Sequence
<220> FEATURE:
<223> OTHER INFORMATION: E-mab heavy chain CDR3

<400> SEQUENCE: 163

Pro Gly Gly Asp Tyr
 1               5

<210> SEQ ID NO 164
<211> LENGTH: 113
<212> TYPE: PRT
<213> ORGANISM: Artificial Sequence
<220> FEATURE:
<223> OTHER INFORMATION: E-mab heavy chain variable region

<400> SEQUENCE: 164

Gln Val Gln Leu Lys Glu Ser Gly Pro Asp Leu Val Ala Pro Ser Gln
 1               5                  10                  15

Ser Leu Ser Ile Thr Cys Thr Val Ser Gly Phe Ser Leu Ser Lys Phe
                20                  25                  30

Gly Val Asn Trp Val Arg Gln Pro Pro Gly Lys Gly Leu Glu Trp Leu
             35                  40                  45

Gly Val Ile Trp Gly Asp Gly Ser Thr Ser Tyr Asn Ser Gly Leu Ile
         50                  55                  60

Ser Arg Leu Ser Ile Ser Lys Glu Asn Ser Lys Ser Gln Val Phe Leu
 65                  70                  75                  80

Lys Leu Asn Ser Leu Gln Ala Asp Asp Thr Ala Thr Tyr Tyr Cys Val
                 85                  90                  95

Lys Pro Gly Gly Asp Tyr Trp Gly His Gly Thr Ser Val Thr Val Ser
```

Ser

<210> SEQ ID NO 165
<211> LENGTH: 5
<212> TYPE: PRT
<213> ORGANISM: Artificial Sequence
<220> FEATURE:
<223> OTHER INFORMATION: A-mab light chain CDR1

<400> SEQUENCE: 165

Ser Tyr Met His Trp
1               5

<210> SEQ ID NO 166
<211> LENGTH: 7
<212> TYPE: PRT
<213> ORGANISM: Artificial Sequence
<220> FEATURE:
<223> OTHER INFORMATION: A-mab light chain CDR2

<400> SEQUENCE: 166

Asp Thr Ser Lys Leu Ala Ser
1               5

<210> SEQ ID NO 167
<211> LENGTH: 9
<212> TYPE: PRT
<213> ORGANISM: Artificial Sequence
<220> FEATURE:
<223> OTHER INFORMATION: A-mab light chain CDR3

<400> SEQUENCE: 167

Gln Gln Trp Ser Lys His Pro Leu Thr
1               5

<210> SEQ ID NO 168
<211> LENGTH: 106
<212> TYPE: PRT
<213> ORGANISM: Artificial Sequence
<220> FEATURE:
<223> OTHER INFORMATION: A-mab light chain variable region

<400> SEQUENCE: 168

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Val Glu Ala Glu
65                  70                  75                  80

Asp Asp Ala Thr Tyr Tyr Cys Gln Gln Trp Ser Lys His Pro Leu Thr
                85                  90                  95

Phe Gly Ser Gly Thr Lys Val Glu Ile Lys
            100                 105

<210> SEQ ID NO 169
<211> LENGTH: 5
<212> TYPE: PRT
<213> ORGANISM: Artificial Sequence
<220> FEATURE:
<223> OTHER INFORMATION: A-mab heavy chain CDR1

<400> SEQUENCE: 169

Gly Tyr Thr Met Asn
1               5

<210> SEQ ID NO 170
<211> LENGTH: 17
<212> TYPE: PRT
<213> ORGANISM: Artificial Sequence
<220> FEATURE:
<223> OTHER INFORMATION: A-mab heavy chain CDR2

<400> SEQUENCE: 170

Leu Ile Thr Pro Tyr Asn Gly Ala Ser Ser Tyr Asn Gln Lys Phe Arg
1               5                   10                  15

Gly

<210> SEQ ID NO 171
<211> LENGTH: 10
<212> TYPE: PRT
<213> ORGANISM: Artificial Sequence
<220> FEATURE:
<223> OTHER INFORMATION: A-mab heavy chain CDR3

<400> SEQUENCE: 171

Gly Gly Tyr Asp Gly Arg Gly Phe Asp Tyr
1               5                   10

<210> SEQ ID NO 172
<211> LENGTH: 119
<212> TYPE: PRT
<213> ORGANISM: Artificial Sequence
<220> FEATURE:
<223> OTHER INFORMATION: A-mab heavy chain variable region

<400> SEQUENCE: 172

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Ser Gly
            100                 105                 110

Thr Pro Val Thr Val Ser Ser
        115

<210> SEQ ID NO 173
<211> LENGTH: 133
<212> TYPE: PRT
<213> ORGANISM: Artificial Sequence
<220> FEATURE:
<223> OTHER INFORMATION: husIL2

<400> SEQUENCE: 173

```
Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
            130
```

<210> SEQ ID NO 174
<211> LENGTH: 186
<212> TYPE: PRT
<213> ORGANISM: Artificial Sequence
<220> FEATURE:
<223> OTHER INFORMATION: muIFNa4

<400> SEQUENCE: 174

```
Met Ala Arg Leu Cys Ala Phe Leu Met Ile Leu Val Met Met Ser Tyr
1               5                   10                  15

Tyr Trp Ser Ala Cys Ser Leu Gly Cys Asp Leu Pro His Thr Tyr Asn
                20                  25                  30

Leu Gly Asn Lys Arg Ala Leu Thr Val Leu Glu Glu Met Arg Arg Leu
            35                  40                  45

Pro Pro Leu Ser Cys Leu Lys Asp Arg Lys Asp Phe Gly Phe Pro Leu
50                  55                  60

Glu Lys Val Asp Asn Gln Gln Ile Gln Lys Ala Gln Ala Ile Leu Val
65                  70                  75                  80

Leu Arg Asp Leu Thr Gln Gln Ile Leu Asn Leu Phe Thr Ser Lys Asp
                85                  90                  95

Leu Ser Ala Thr Trp Asn Ala Thr Leu Leu Asp Ser Phe Cys Asn Asp
            100                 105                 110

Leu His Gln Gln Leu Asn Asp Leu Lys Ala Cys Val Met Gln Glu Pro
            115                 120                 125

Pro Leu Thr Gln Glu Asp Ser Leu Leu Ala Val Arg Thr Tyr Phe His
            130                 135                 140

Arg Ile Thr Val Tyr Leu Arg Lys Lys His Ser Leu Cys Ala Trp
145                 150                 155                 160

Glu Val Ile Arg Ala Glu Val Trp Arg Ala Leu Ser Ser Ser Thr Asn
                165                 170                 175

Leu Leu Ala Arg Leu Ser Glu Glu Lys Glu
            180                 185
```

<210> SEQ ID NO 175
<211> LENGTH: 188
<212> TYPE: PRT
<213> ORGANISM: Artificial Sequence
<220> FEATURE:
<223> OTHER INFORMATION: huIFNa2

<400> SEQUENCE: 175

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
            180                 185

<210> SEQ ID NO 176
<211> LENGTH: 182
<212> TYPE: PRT
<213> ORGANISM: Artificial Sequence
<220> FEATURE:
<223> OTHER INFORMATION: muIFNb

<400> SEQUENCE: 176

Met Asn Asn Arg Trp Ile Leu His Ala Ala Phe Leu Leu Cys Phe Ser
1               5                   10                  15

Thr Thr Ala Leu Ser Ile Asn Tyr Lys Gln Leu Gln Leu Gln Glu Arg
            20                  25                  30

Thr Asn Ile Arg Lys Cys Gln Glu Leu Leu Glu Gln Leu Asn Gly Lys
        35                  40                  45

Ile Asn Leu Thr Tyr Arg Ala Asp Phe Lys Ile Pro Met Glu Met Thr
    50                  55                  60

Glu Lys Met Gln Lys Ser Tyr Thr Ala Phe Ala Ile Gln Glu Met Leu
65                  70                  75                  80

Gln Asn Val Phe Leu Val Phe Arg Asn Asn Phe Ser Ser Thr Gly Trp
                85                  90                  95

Asn Glu Thr Ile Val Val Arg Leu Leu Asp Glu Leu His Gln Gln Thr
            100                 105                 110

Val Phe Leu Lys Thr Val Leu Glu Glu Lys Gln Glu Glu Arg Leu Thr
        115                 120                 125

Trp Glu Met Ser Ser Thr Ala Leu His Leu Lys Ser Tyr Tyr Trp Arg
130                 135                 140

Val Gln Arg Tyr Leu Lys Leu Met Lys Tyr Asn Ser Tyr Ala Trp Met

```
145                 150                 155                 160
Val Val Arg Ala Glu Ile Phe Arg Asn Phe Leu Ile Ile Arg Arg Leu
                165                 170                 175
Thr Arg Asn Phe Gln Asn
            180
```

<210> SEQ ID NO 177
<211> LENGTH: 187
<212> TYPE: PRT
<213> ORGANISM: Artificial Sequence
<220> FEATURE:
<223> OTHER INFORMATION: huIFNb

<400> SEQUENCE: 177

```
Met Thr Asn Lys Cys Leu Leu Gln Ile Ala Leu Leu Cys Phe Ser
1               5                   10                  15
Thr Thr Ala Leu Ser Met Ser Tyr Asn Leu Leu Gly Phe Leu Gln Arg
                20                  25                  30
Ser Ser Asn Phe Gln Cys Gln Lys Leu Leu Trp Gln Leu Asn Gly Arg
            35                  40                  45
Leu Glu Tyr Cys Leu Lys Asp Arg Met Asn Phe Asp Ile Pro Glu Glu
50                  55                  60
Ile Lys Gln Leu Gln Gln Phe Gln Lys Glu Asp Ala Ala Leu Thr Ile
65                  70                  75                  80
Tyr Glu Met Leu Gln Asn Ile Phe Ala Ile Phe Arg Gln Asp Ser Ser
                85                  90                  95
Ser Thr Gly Trp Asn Glu Thr Ile Val Glu Asn Leu Leu Ala Asn Val
            100                 105                 110
Tyr His Gln Ile Asn His Leu Lys Thr Val Leu Glu Glu Lys Leu Glu
        115                 120                 125
Lys Glu Asp Phe Thr Arg Gly Lys Leu Met Ser Ser Leu His Leu Lys
130                 135                 140
Arg Tyr Tyr Gly Arg Ile Leu His Tyr Leu Lys Ala Lys Glu Tyr Ser
145                 150                 155                 160
His Cys Ala Trp Thr Ile Val Arg Val Glu Ile Leu Arg Asn Phe Tyr
                165                 170                 175
Phe Ile Asn Arg Leu Thr Gly Tyr Leu Arg Asn
            180                 185
```

<210> SEQ ID NO 178
<211> LENGTH: 200
<212> TYPE: PRT
<213> ORGANISM: Artificial Sequence
<220> FEATURE:
<223> OTHER INFORMATION: huIFNL

<400> SEQUENCE: 178

```
Met Ala Ala Ala Trp Thr Val Val Leu Val Thr Leu Val Leu Gly Leu
1               5                   10                  15
Ala Val Ala Gly Pro Val Pro Thr Ser Lys Pro Thr Thr Thr Gly Lys
                20                  25                  30
Gly Cys His Ile Gly Arg Phe Lys Ser Leu Ser Pro Gln Glu Leu Ala
            35                  40                  45
Ser Phe Lys Lys Ala Arg Asp Ala Leu Glu Glu Ser Leu Lys Leu Lys
        50                  55                  60
Asn Trp Ser Cys Ser Ser Pro Val Phe Pro Gly Asn Trp Asp Leu Arg
65                  70                  75                  80
```

```
Leu Leu Gln Val Arg Glu Arg Pro Val Ala Leu Glu Ala Glu Leu Ala
             85                  90                  95

Leu Thr Leu Lys Val Leu Glu Ala Ala Gly Pro Ala Leu Glu Asp
            100                 105                 110

Val Leu Asp Gln Pro Leu His Thr Leu His His Ile Leu Ser Gln Leu
            115                 120                 125

Gln Ala Cys Ile Gln Pro Gln Pro Thr Ala Gly Pro Arg Pro Arg Gly
            130                 135                 140

Arg Leu His His Trp Leu His Arg Leu Gln Glu Ala Pro Lys Lys Glu
145                 150                 155                 160

Ser Ala Gly Cys Leu Glu Ala Ser Val Thr Phe Asn Leu Phe Arg Leu
            165                 170                 175

Leu Thr Arg Asp Leu Lys Tyr Val Ala Asp Gly Asn Leu Cys Leu Arg
            180                 185                 190

Thr Ser Thr His Pro Glu Ser Thr
            195                 200

<210> SEQ ID NO 179
<211> LENGTH: 160
<212> TYPE: PRT
<213> ORGANISM: Artificial Sequence
<220> FEATURE:
<223> OTHER INFORMATION: huIL10

<400> SEQUENCE: 179

Ser Pro Gly Gln Gly Thr Gln Ser Glu Asn Ser Cys Thr His Phe Pro
1               5                  10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
            35                  40                  45

Lys Glu Ser Leu Leu Glu Asp Phe Lys Gly Tyr Leu Gly Cys Gln Ala
            50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
            85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
            115                 120                 125

Asn Lys Leu Gln Glu Lys Gly Ile Tyr Lys Ala Met Ser Glu Phe Asp
            130                 135                 140

Ile Phe Ile Asn Tyr Ile Glu Ala Tyr Met Thr Met Lys Ile Arg Asn
145                 150                 155                 160

<210> SEQ ID NO 180
<211> LENGTH: 335
<212> TYPE: PRT
<213> ORGANISM: Artificial Sequence
<220> FEATURE:
<223> OTHER INFORMATION: (huIL10)2

<400> SEQUENCE: 180

Ser Pro Gly Gln Gly Thr Gln Ser Glu Asn Ser Cys Thr His Phe Pro
1               5                  10                  15

Gly Asn Leu Pro Asn Met Leu Arg Asp Leu Arg Asp Ala Phe Ser Arg
            20                  25                  30
```

```
Val Lys Thr Phe Phe Gln Met Lys Asp Gln Leu Asp Asn Leu Leu Leu
        35                  40                  45
Lys Glu Ser Leu Leu Glu Asp Phe Lys Gly Tyr Leu Gly Cys Gln Ala
    50                  55                  60
Leu Ser Glu Met Ile Gln Phe Tyr Leu Glu Glu Val Met Pro Gln Ala
65                  70                  75                  80
Glu Asn Gln Asp Pro Asp Ile Lys Ala His Val Asn Ser Leu Gly Glu
                85                  90                  95
Asn Leu Lys Thr Leu Arg Leu Arg Leu Arg Arg Cys His Arg Phe Leu
                100                 105                 110
Pro Cys Glu Asn Lys Ser Lys Ala Val Glu Gln Val Lys Asn Ala Phe
            115                 120                 125
Asn Lys Leu Gln Glu Lys Gly Ile Tyr Lys Ala Met Ser Glu Phe Asp
    130                 135                 140
Ile Phe Ile Asn Tyr Ile Glu Ala Tyr Met Thr Met Lys Ile Arg Asn
145                 150                 155                 160
Gly Gly Gly Gly Ser Gly Gly Gly Gly Ser Gly Gly Gly Gly Ser Ser
                165                 170                 175
Pro Gly Gln Gly Thr Gln Ser Glu Asn Ser Cys Thr His Phe Pro Gly
            180                 185                 190
Asn Leu Pro Asn Met Leu Arg Asp Leu Arg Asp Ala Phe Ser Arg Val
        195                 200                 205
Lys Thr Phe Phe Gln Met Lys Asp Gln Leu Asp Asn Leu Leu Leu Lys
    210                 215                 220
Glu Ser Leu Leu Glu Asp Phe Lys Gly Tyr Leu Gly Cys Gln Ala Leu
225                 230                 235                 240
Ser Glu Met Ile Gln Phe Tyr Leu Glu Glu Val Met Pro Gln Ala Glu
                245                 250                 255
Asn Gln Asp Pro Asp Ile Lys Ala His Val Asn Ser Leu Gly Glu Asn
            260                 265                 270
Leu Lys Thr Leu Arg Leu Arg Leu Arg Arg Cys His Arg Phe Leu Pro
    275                 280                 285
Cys Glu Asn Lys Ser Lys Ala Val Glu Gln Val Lys Asn Ala Phe Asn
    290                 295                 300
Lys Leu Gln Glu Lys Gly Ile Tyr Lys Ala Met Ser Glu Phe Asp Ile
305                 310                 315                 320
Phe Ile Asn Tyr Ile Glu Ala Tyr Met Thr Met Lys Ile Arg Asn
                325                 330                 335
```

PROTEINACEOUS HETERODIMER AND USE THEREOF

BACKGROUND

Although immune responses against tumor antigens can be detected (Disis et al. (1997) J. Clin. Oncol. 15: 3363-3367), malignant cells causing diseases often fail to elicit an immune response that leads to rejection. Studies have demonstrated that it is possible to enhance the immunogenicity of tumor cells by introducing immunoregulatory molecules such as cytokines and costimulatory molecules into them; however, eradication of residual cancer cells may require the targeting of widely scattered micrometastatic tumor deposits that are not accessible to direct gene transfer. In addition, the expression and stability of the immunoregulatory molecules introduced are often far from satisfactory. Immunoregulators, such as cytokines, produced by cells of the immune system can, directly or indirectly, activate the cells of the adaptive immune response and can play an important role in eliciting protective antitumor immunity. The innate immune system can be triggered by bacterial products or "danger" signals that lead to the release of proinflammatory cytokines, such as IFN-$\alpha$, TNF-$\alpha$, and interleukins.

Multiple studies have shown that immunoregulators may be useful in exerting antitumor effects in both animal models and cancer patients. However, short half-life and systemic toxicity related with application of the immunoregulators have greatly limited their usage. In CN200880117225.8, a chimeric construct comprising an interferon attached to the c-terminus of an antibody targeting a tumor associated antigen has been described. However, fusion proteins expressed from such a chimeric construct are typically very unstable in vivo, and the expression yield thereof is typically not high enough for industrial-scale production.

Recently, heterodimeric proteins (such as bispecific antibodies) have been developed to permit co-engagement of two distinct targets. Traditionally, bispecific antibodies were generated by fusing two cell lines that each produced a single monoclonal antibody (mAb). However, in such a process, the bispecifc antibodies (or heterodimeric proteins) are only a minor population and extensive purification would be required to isolate the desired product.

In the 1990s, Carter et al. developed a "knob-and-hole" model that increased the yield of bispecific antibodies by introducing asymmetrical modifications in the CH3 regions of the two monospecific starting proteins (Ridgway, Presta et al. 1996; Carter et al., 2001). However, even with the "knob-and-hole" modifications, protein homodimer formation still could not be very effectively controlled or eliminated, and the yield of heterodimeric proteins is difficult to be further increased.

SUMMARY

As such, there is a considerable need for targeted expression of immunoregulators, which could be produced with relatively high yield at industrial-scale and would have a relatively long half-life in vivo to be useful in treating disorders or diseases related with hyper proliferation of cells and/or tissues, e.g., various neoplasms, different types of cancer, and/or tumors. In addition, the yield of such a product shall be sufficiently high to avoid complicated purification process and/or to reduce the risks associated with undesired impurities.

The present disclosure addresses such a need and provides related advantages as well.

The present disclosure encompasses proteinaceous heterodimers useful in inhibiting tumor growth, and compositions, medicaments and/or kits comprising the proteinaceous heterodimers. In addition, the present disclosure provides protein mixtures comprising said proteinaceous heterodimers and with little (if any) undesired impurities (such as undesired protein homodimers). The disclosure also provides methods to produce the proteinaceous heterodimers or protein mixtures, as well as pharmaceutical uses of the proteinaceous heterodimers and/or protein mixtures in inhibiting tumor growth, including but not limited to treatment of cancers.

In some aspects, the proteinaceous heterodimers of the present disclosure have significant anti-tumor activity. In some aspects, the proteinaceous heterodimers of the present disclosure have high expression yield. In some aspects, the proteinaceous heterodimers of the present disclosure have long in vivo half-life. In some aspects, the proteinaceous heterodimers of the present disclosure are particularly suitable for large scale industrial production. In some aspects, the protein mixtures of the present disclosure comprising said proteinaceous heterodimers contain little or substantially no undesired impurities.

In one aspect, the present disclosure provides a proteinaceous heterodimer. The proteinaceous heterodimer may comprise a first member and a second member different from the first member, the first member may comprise a light chain and a heavy chain comprising a first Fc region, the light chain may be complexed with the heavy chain to form a targeting moiety exhibiting binding specificity to a tumor antigen; the second member may comprise a polypeptide comprising an immunoregulator fused to a second Fc region; the first member may associate with the second member to form the heterodimer through complexation of the first Fc region with the second Fc region; and the first Fc region may comprise a first modification and/or the second Fc region may comprise a second modification, wherein the first modification and/or the second modification may more effectively promote heterodimerization between the first member and the second member than a knob-and-hole modification comprising a knob modification and a hole modification. For the knob-and-hole modification comprising a knob modification and a hole modification, the first Fc region may comprise the knob modification, and the second Fc region may comprise the hole modification. Alternatively, the first Fc region may comprise the hole modification, and the second Fc region may comprise the knob modification In some embodiments, the first modification is different from the knob modification or the hole modification, and/or the second modification is different from the knob modification or the hole modification.

In some embodiments, when expressed in a mammalian cell, a yield of the proteinaceous heterodimer is at least 10% higher than that of a reference protein, and the reference protein differs from the proteinaceous heterodimer in that the reference protein: i) comprises the knob modification in the first Fc region, ii) comprises the hole modification in the second Fc region, and iii) does not comprise said first modification and said second modification of the proteinaceous heterodimer of the present application simultaneously. The mammalian cell may be selected from the group consisting of a HEK293 cell, a CHO cell, a COS-1 cell and a NS0 cell.

In some embodiments, the first Fc region comprises the first modification, the second Fc region comprises the second modification, and neither the first modification nor the second modification is the same as the knob modification or the hole modification.

In some embodiments, the polypeptide comprised in the second member is a fusion protein, and a C-terminus of the immunoregulator is directly or indirectly fused to a N-terminus of the second Fc region to form the fusion protein.

In some embodiments, the tumor antigen is selected from the group consisting of EGFR, an EGFR mutant, HER2/neu, GPC3, FAP, Muc1, MUC5AC and Mesothelin.

In some embodiments, the light chain of the targeting moiety contains CDRs comprising an amino acid sequence that is at least 60%, 70%, 75%, 80%, 85%, 90%, 95%, 96%, 97%, 98%, 99% or 100% identical to that comprised in corresponding CDRs of a light chain of an antibody specifically directed to a tumor antigen.

In some embodiments, the light chain of the targeting moiety contains variable regions comprising an amino acid sequence that is at least 60%, 70%, 75%, 80%, 85%, 90%, 95%, 96%, 97%, 98%, 99% or 100% identical to that comprised in corresponding variable regions of a light chain of an antibody specifically directed to a tumor antigen.

In some embodiments, the light chain of the targeting moiety contains an amino acid sequence that is at least 60%, 70%, 75%, 80%, 85%, 90%, 95%, 96%, 97%, 98%, 99% or 100% identical to that comprised in corresponding the amino acid sequence of a light chain of an antibody specifically directed to a tumor antigen.

In some embodiments, the heavy chain of the targeting moiety contains CDRs comprising an amino acid sequence that is at least 60%, 70%, 75%, 80%, 85%, 90%, 95%, 96%, 97%, 98%, 99% or 100% identical to that comprised in corresponding CDRs of a heavy chain of an antibody specifically directed to a tumor antigen.

In some embodiments, the heavy chain of the targeting moiety contains variable regions comprising an amino acid sequence that is at least 60%, 70%, 75%, 80%, 85%, 90%, 95%, 96%, 97%, 98%, 99% or 100% identical to that comprised in corresponding variable regions of a heavy chain of an antibody specifically directed to a tumor antigen.

In some embodiments, the heavy chain of the targeting moiety contains an amino acid sequence that is at least 60%, 70%, 75%, 80%, 85%, 90%, 95%, 96%, 97%, 98%, 99% or 100% identical to that comprised in corresponding the amino acid sequence of a heavy chain of an antibody specifically directed to a tumor antigen.

In some embodiments, the light chain of the targeting moiety contains CDRs comprising an amino acid sequence that is at least 60%, 70%, 75%, 80%, 85%, 90%, 95%, 96%, 97%, 98%, 99% or 100% identical to that comprised in corresponding CDRs of a light chain of an antibody specifically directed to a tumor antigen; and the heavy chain of the targeting moiety contains CDRs comprising an amino acid sequence that is at least 60%, 70%, 75%, 80%, 85%, 90%, 95%, 96%, 97%, 98%, 99% or 100% identical to that comprised in corresponding CDRs of a heavy chain of an antibody specifically directed to a tumor antigen.

In some embodiments, the light chain of the targeting moiety contains variable regions comprising an amino acid sequence that is at least 60%, 70%, 75%, 80%, 85%, 90%, 95%, 96%, 97%, 98%, 99% or 100% identical to that comprised in corresponding variable regions of a light chain of an antibody specifically directed to a tumor antigen; and the heavy chain of the targeting moiety contains variable regions comprising an amino acid sequence that is at least 60%, 70%, 75%, 80%, 85%, 90%, 95%, 96%, 97%, 98%, 99% or 100% identical to that comprised in corresponding variable regions of a heavy chain of an antibody specifically directed to a tumor antigen.

In some embodiments, the light chain of the targeting moiety contains an amino acid sequence comprising an amino acid sequence that is at least 60%, 70%, 75%, 80%, 85%, 90%, 95%, 96%, 97%, 98%, 99% or 100% identical to that comprised in corresponding the amino acid sequence of a light chain of an antibody specifically directed to a tumor antigen; and the heavy chain of the targeting moiety contains an amino acid sequence comprising an amino acid sequence that is at least 60%, 70%, 75%, 80%, 85%, 90%, 95%, 96%, 97%, 98%, 99% or 100% identical to that comprised in corresponding the amino acid sequence of a heavy chain of an antibody specifically directed to a tumor antigen.

In some embodiments, the antibody specifically directed to a tumor antigen is selected from the group consisting of anti-EGFR, anti-EGFR mutant, anti-HER2/neu, anti-GPC3, anti-FAP, anti-Muc1, anti-MUC5AC and anti-Mesothelin.

In some embodiments, the immunoregulator augments an immune response. In some embodiments, the immunoregulator reduces an immune response.

In some embodiments, the immunoregulator is a cytokine. For example, the immunoregulator may be a cytokine selected from the group consisting of an interferon, an interleukin, a chemokine, a lymphokine, and a tumor necrosis factor.

In some embodiments, the immunoregulator is an interferon selected from the group consisting of interferon alpha, interferon lambda and interferon beta.

In some embodiments, the immunoregulator is an interleukin, and the interleukin comprises interleukin 10, interleukin 2 and/or super interleukin 2.

In some embodiments, the first Fc region and the second Fc region is from an Fc region of an immunoglobulin.

For example, the immunoglobulin may be selected from the group consisting of IgG1, IgG2, IgG3 and IgG4.

In some embodiments, the first Fc region and the second Fc region are from an Fc region of an immunoglobulin, and the immunoglobulin is a human IgG1.

In some embodiments, the second Fc region is fused in frame to the immunoregulator.

In some embodiments, the second Fc region is fused in frame to the immunoregulator via a linker.

In some embodiments, the polypeptide comprised in the second member comprises two or more immunoregulators, the two or more immunoregulators are fused in frame to each other and to the second Fc region, and wherein the two or more immunoregulators are located N-terminal to the second Fc region. For example, the two or more immunoregulators may be the same.

In some embodiments, the first modification comprises an amino acid substitution at position T366, and an amino acid substitution at one or more positions selected from the group consisting of: Y349, F405, K409, D399, K360, Q347, K392 and S354, wherein the position of the amino acid is determined according to the EU index of the KABAT number.

In some embodiments, the first modification comprises an amino acid substitution selected from the group consisting of Y349C, Y349D, D399S, F405K, K360E, K409A, K409E, Q347E, Q347R, S354D, K392D and T366W.

In some embodiments, the first modification comprises 2-5 amino acid substitutions.

In some embodiments, the first modification comprises an amino acid substitution at a group of positions selected from any of the following groups: 1) Y349 and T366; 2) Y349, T366 and F405; 3) Y349, T366 and K409; 4) Y349, T366, F405, K360 and Q347; 5) Y349, T366, F405 and Q347; 6) Y349, T366, K409, K360 and Q347; 7) Y349, T366, K409 and Q347; 8) T366, K409 and K392; 9) T366 and K409; 10) T366, K409, Y349 and S354; 11) T366 and F405; 12) T366, F405 and D399; and 13) T366, F405, Y349 and S354.

In some embodiments, the first modification comprises a group of amino acid substitutions selected from any of the following groups: 1) Y349C and T366W; 2) Y349C, T366W and F405K; 3) Y349C, T366W and K409E; 4) Y349C, T366W and K409A; 5) Y349C, T366W, F405K, K360E and Q347E; 6) Y349C, T366W, F405K and Q347R; 7) Y349C, T366W, K409A, K360E and Q347E; 8) Y349C, T366W, K409A and Q347R; 9) T366W, K409A and K392D; 10) T366W and K409A; 11) T366W, K409A and Y349D; 12) T366W, K409A, Y349D and S354D; 13) T366W and F405K; 14) T366W, F405K and D399S; 15) T366W, F405K and Y349D; and 16) T366W, F405K, Y349D and S354D.

In some embodiments, the second modification comprises amino acid substitutions at positions T366, L368 and Y407, as well as an amino acid substitution at one or more positions selected from the group consisting of D356, D399, E357, F405, K360, K392, K409 and Q347, wherein the position of the amino acid is determined according to the EU index of the KABAT number.

In some embodiments, the amino acid substitution comprised by the second modification is selected from the group consisting of D356C, D399S, E357A, F405K, K360E, K392D, K409A, L368A, L368G, Q347E, Q347R, T366S, Y407A and Y407V.

In some embodiments, the second modification comprises an amino acid substitution at 4-6 positions.

In some embodiments, the second modification comprises an amino acid substitution at a group of positions selected from any of the following groups: 1) D356, T366, L368, Y407 and F405; 2) D356, T366, L368 and Y407; 3) D356, T366, L368, Y407 and Q347; 4) D356, T366, L368, Y407, K360 and Q347; 5) D356, T366, L368, Y407, F405 and Q347; 6) D356, T366, L368, Y407, F405, K360 and Q347; 7) T366, L368, Y407, D399 and F405; 8) T366, L368, Y407 and F405; 9) T366, L368, Y407, F405 and E357; 10) T366, L368, Y407 and K409; 11) T366, L368, Y407, K409 and K392; and 12) T366, L368, Y407, K409 and E357.

In some embodiments, the second modification comprises a group of amino acid substitutions selected from any of the following groups: 1) D356C, T366S, L368A, Y407V and F405K; 2) D356C, T366S, L368A and Y407V; 3) D356C, T366S, L368A, Y407V and Q347R; 4) D356C, T366S, L368A, Y407V, K360E and Q347E; 5) D356C, T366S, L368A, Y407V, F405K and Q347R; 6) D356C, T366S, L368A, Y407V, F405K, K360E and Q347E; 7) T366S, L368A, Y407V, D399S and F405K; 8) T366S, L368G, Y407A and F405K; 9) T366S, L368A, Y407V, F405K and E357A; 10) T366S, L368A, Y407V and K409A; 11) T366S, L368A, Y407V, K409A and K392D; 12) T366S, L368G, Y407A and K409A; 13) T366S, L368A, Y407V, K409A and E357A.

In some embodiments, the first Fc region comprises the first modification, and the second Fc region comprises the second modification. The first modification comprises an amino acid substitution at position T366, and an amino acid substitution at one or more positions selected from the group consisting of: Y349, F405, K409, D399, K360, Q347, K392 and S354, wherein the position of the amino acid is determined according to the EU index of the KABAT number; and the second modification comprises amino acid substitutions at positions T366, L368 and Y407, as well as an amino acid substitution at one or more positions selected from the group consisting of D356, D399, E357, F405, K360, K392, K409 and Q347, wherein the position of the amino acid is determined according to the EU index of the KABAT number. The first modification and the second modification may be as defined in the present application.

In some embodiments, the first Fc region comprises the first modification, the second Fc region comprises the second modification, and the first modification and the second modification comprise an amino acid substitution at a group of positions selected from any of the following groups: 1) the first modification: Y349 and T366; and the second modification: D356, T366, L368, Y407 and F405; 2) the first modification: Y349, T366 and F405; and the second modification: D356, T366, L368 and Y407; 3) the first modification: Y349, T366 and K409; and the second modification: D356, T366, L368, Y407 and F405; 4) the first modification: Y349, T366, F405, K360 and Q347; and the second modification: D356, T366, L368, Y407 and Q347; 5) the first modification: Y349, T366, F405 and Q347; and the second modification: D356, T366, L368, Y407, K360 and Q347; 6) the first modification: Y349, T366, K409, K360 and Q347; and the second modification: D356, T366, L368, Y407, F405 and Q347; 7) the first modification: Y349, T366, K409 and Q347; and the second modification: D356, T366, L368, Y407, F405, K360 and Q347; 8) the first modification: T366, K409 and K392; and the second modification: T366, L368, Y407, D399 and F405; 9) the first modification: T366 and K409; and the second modification: T366, L368, Y407 and F405; 10) the first modification: T366, K409 and Y349; and the second modification: T366, L368, Y407, F405 and E357; 11) the first modification: T366, K409, Y349 and S354; and the second modification: T366, L368, Y407, F405 and E357; 12) the first modification: T366 and F405; and the second modification: T366, L368, Y407 and K409; 13) the first modification: T366, F405 and D399; and the second modification: T366, L368, Y407, K409 and K392; 14) the first modification: T366, F405 and Y349; and the second modification: T366, L368, Y407, K409 and E357; 15) the first modification: T366, F405, Y349 and S354; and the second modification: T366, L368, Y407, K409 and E357; wherein the position of the amino acid is determined according to the EU index of the KABAT number.

In some embodiments, the first Fc region comprises the first modification, the second Fc region comprises the second modification, wherein the first modification and the second modification comprise a group of amino acid substitutions selected from any of the following groups: 1) the first modification: Y349C and T366W; and the second modification: D356C, T366S, L368A, Y407V and F405K; 2) the first modification: Y349C, T366W and F405K; and the second modification: D356C, T366S, L368A and Y407V; 3) the first modification: Y349C, T366W and K409E; and the second modification: D356C, T366S, L368A, Y407V and F405K; 4) the first modification: Y349C, T366W and K409A; and the second modification: D356C, T366S, L368A, Y407V and F405K; 5) the first modification: Y349C, T366W, F405K, K360E and Q347E; and the second modification: D356C, T366S, L368A, Y407V and Q347R; 6) the first modification: Y349C, T366W, F405K and Q347R; and the second modification: D356C, T366S, L368A, Y407V, K360E and Q347E; 7) the first modification: Y349C, T366W, K409A, K360E and Q347E; and the second modification: D356C, T366S, L368A, Y407V, F405K and Q347R; 8) the first modification: Y349C, T366W, K409A and Q347R; and the second modification: D356C, T366S, L368A, Y407V, F405K, K360E and Q347E; 9) the first modification: T366W, K409A and K392D; and the second modification: T366S, L368A, Y407V, D399S and F405K; 10) the first modification: T366W and K409A; and the second modification: T366S, L368G, Y407A and F405K; 11) the first modification: T366W, K409A and Y349D; and the second modification: T366S, L368A, Y407V, F405K and E357A; 12) the first modification: T366W, K409A, Y349D and S354D; and the second modification: T366S, L368A, Y407V, F405K and E357A; 13) the first modification: T366W and F405K; and the second modification: T366S, L368A, Y407V and K409A; 14) the first modification: T366W, F405K and D399S; and the second modification: T366S, L368A, Y407V, K409A and K392D; 15) the first modification: T366W and F405K; and the second modification: T366S, L368G, Y407A and K409A; 16) the first modification: T366W, F405K and Y349D; and the second modification: T366S, L368A, Y407V, K409A and E357A; 17) the first modification: T366W, F405K, Y349D and S354D; and the second modification: T366S, L368A, Y407V, K409A and E357A; wherein the position of the amino acid is determined according to the EU index of the KABAT number.

In some embodiments, the first Fc region comprises the first modification, the second Fc region comprises the second modification, the first modification comprises the amino acid substitutions T366W and K409A, and the second modification comprises the amino acid substitutions T366S, L368G, Y407A and F405K, wherein the position of the amino acid is determined according to the EU index of the KABAT number.

In some embodiments, the targeting moiety specifically binds to EGFR, the light chain of the first member comprises CDR1-3, the amino acid sequence of the CDR1 is as set forth in SEQ ID NO: 101, the amino acid sequence of the CDR2 is as set forth in SEQ ID NO:102, and the amino acid sequence of the CDR3 is as set forth in SEQ ID NO: 103.

In some embodiments, the targeting moiety specifically binds to EGFR, the light chain of the first member comprises a light chain variable region, and the amino acid sequences of the light chain variable region is as set forth in SEQ ID NO: 104.

In some embodiments, the targeting moiety specifically binds to EGFR, and the amino acid sequence of the light chain of the first member is as set forth in SEQ ID NO: 37.

In some embodiments, the targeting moiety specifically binds to EGFR, the heavy chain of the first member comprises CDR1-3, the amino acid sequence of the CDR1 is as set forth in SEQ ID NO: 105, the amino acid sequence of the CDR2 is as set forth in SEQ ID NO: 106, the amino acid sequence of the CDR3 is as set forth in SEQ ID NO: 107.

In some embodiments, the targeting moiety specifically binds to EGFR, the heavy chain of the first member comprises a heavy chain variable region, and the amino acid sequence of the heavy chain variable region is as set forth in SEQ ID NO: 108.

In some embodiments, the targeting moiety specifically binds to EGFR, and the amino acid sequence of the heavy chain of the first member is as set forth in SEQ ID NO: 39.

In some embodiments, the targeting moiety specifically binds to an EGFR mutant, the light chain of the first member comprises CDR1-3, the amino acid sequence of the CDR1 is as set forth in SEQ ID NO: 109, the amino acid sequence of the CDR2 is as set forth in SEQ ID NO: 110, and the amino acid sequence of the CDR3 is as set forth in SEQ ID NO: 111.

In some embodiments, the targeting moiety specifically binds to an EGFR mutant, the light chain of the first member comprises a light chain variable region, and the amino acid sequence of the light chain variable region is as set forth in SEQ ID NO: 112.

In some embodiments, the targeting moiety specifically binds to an EGFR mutant, and the amino acid sequence of the light chain of the first member is as set forth in SEQ ID NO: 53.

In some embodiments, the targeting moiety specifically binds to an EGFR mutant, the heavy chain of the first member comprises CDR1-3, the amino acid sequence of the CDR1 is as set forth in SEQ ID NO: 113, the amino acid sequence of the CDR2 is as set forth in SEQ ID NO: 114, and the amino acid sequence of the CDR3 is as set forth in SEQ ID NO: 115.

In some embodiments, the targeting moiety specifically binds to an EGFR mutant, the heavy chain of the first member comprises a heavy chain variable region, and the amino acid sequence of the heavy chain variable region is as set forth in SEQ ID NO: 116.

In some embodiments, the targeting moiety specifically binds to an EGFR mutant, and the amino acid sequence of the heavy chain of the first member is as set forth in SEQ ID NO: 55.

In some embodiments, the targeting moiety specifically binds to HER2/neu, the light chain of the first member comprises CDR1-3, the amino acid sequence of the CDR1 is selected from SEQ ID NO: 117 and SEQ ID NO: 125, the amino acid sequence of the CDR2 is selected from SEQ ID NO: 118 and SEQ ID NO: 126, and the amino acid sequence of the CDR3 is selected from SEQ ID NO: 119 and SEQ ID NO: 127.

In some embodiments, the targeting moiety specifically binds to HER2/neu, the light chain of the first member comprises a light chain variable region, and the amino acid sequence of the light chain variable region is selected from SEQ ID NO: 120 and SEQ ID NO: 128.

In some embodiments, the targeting moiety specifically binds to HER2/neu, and the amino acid sequence of the light chain of the first member is selected from SEQ ID NO: 45 and SEQ ID NO: 49.

In some embodiments, the targeting moiety specifically binds to HER2/neu, the heavy chain of the first member comprises CDR1-3, the amino acid sequence of the CDR1 is selected from SEQ ID NO: 121 and SEQ ID NO: 129, the amino acid sequence of the CDR2 is selected from SEQ ID NO: 122 and SEQ ID NO: 130, and the amino acid sequence of the CDR3 is selected from SEQ ID NO: 123 and SEQ ID NO: 131.

In some embodiments, the targeting moiety specifically binds to HER2/neu, the heavy chain of the first member comprises a heavy chain variable region, and the amino acid sequence of the heavy chain variable region is selected from SEQ ID NO: 124 and SEQ ID NO: 132.

In some embodiments, the targeting moiety specifically binds to HER2/neu, and the amino acid sequence of the heavy chain of the first member is selected from SEQ ID NO: 47 and SEQ ID NO: 51.

In some embodiments, the targeting moiety specifically binds to GPC3, the antibody light chain of the first member comprises CDR1-3, the amino acid sequence of the CDR1 is as set forth in SEQ ID NO: 133, the amino acid sequence of the CDR2 is as set forth in SEQ ID NO: 134, and the amino acid sequence of the CDR3 is as set forth in SEQ ID NO: 135.

In some embodiments, the targeting moiety specifically binds to GPC3, the light chain of the first member comprises a light chain variable region, and the amino acid sequence of the light chain variable region is as set forth in SEQ ID NO: 136.

In some embodiments, the targeting moiety specifically binds to GPC3, and the amino acid sequence of the light chain of the first member is as set forth in SEQ ID NO: 57.

In some embodiments, the targeting moiety specifically binds to GPC3, the heavy chain of the first member comprises CDR1-3, the amino acid sequence of the CDR1 is as set forth in SEQ ID NO: 137, the amino acid sequence of the CDR2 is as set forth in SEQ ID NO: 138, and the amino acid sequence of the CDR3 is as set forth in SEQ ID NO: 139.

In some embodiments, the targeting moiety specifically binds to GPC3, the antibody heavy chain of the first member comprises a heavy chain variable region, and the amino acid sequence of the heavy chain variable region is as set forth in SEQ ID NO: 140.

In some embodiments, the targeting moiety specifically binds to GPC3, and the amino acid sequence of the heavy chain of the first member is as set forth in SEQ ID NO: 59.

In some embodiments, the targeting moiety specifically binds to FAP, the light chain of the first member comprises CDR1-3, the amino acid sequence of the CDR1 is as set forth in SEQ ID NO: 141, the amino acid sequence of the CDR2 is as set forth in SEQ ID NO: 142, and the amino acid sequence of the CDR3 is as set forth in SEQ ID NO: 143.

In some embodiments, the targeting moiety specifically binds to FAP, the light chain of the first member comprises a light chain variable region, and the amino acid sequence of the light chain variable region is as set forth in SEQ ID NO: 144.

In some embodiments, the targeting moiety specifically binds to FAP, and the amino acid sequence of the light chain of the first member is as set forth in SEQ ID NO: 61.

In some embodiments, the targeting moiety specifically binds to FAP, the heavy chain of the first member comprises CDR1-3, the amino acid sequence of the CDR1 is as set forth in SEQ ID NO: 145, the amino acid sequence of the CDR2 is as set forth in SEQ ID NO: 146, and the amino acid sequence of the CDR3 is as set forth in SEQ ID NO: 147.

In some embodiments, the targeting moiety specifically binds to FAP, the heavy chain of the first member comprises a heavy chain variable region, and the amino acid sequence of the heavy chain variable region is as set forth in SEQ ID NO: 148.

In some embodiments, the targeting moiety specifically binds to FAP, and the amino acid sequence of the heavy chain of the first member is as set forth in SEQ ID NO: 63.

In some embodiments, the targeting moiety specifically binds to Muc1, the light chain of the first member comprises CDR1-3, the amino acid sequence of the CDR1 is as set forth in SEQ ID NO: 149, the amino acid sequence of the CDR2 is as set forth in SEQ ID NO: 150, and the amino acid sequence of the CDR3 is as set forth in SEQ ID NO: 151.

In some embodiments, the targeting moiety specifically binds to Muc1, the light chain of the first member comprises a light chain variable region, and the amino acid sequence of the light chain variable region is as set forth in SEQ ID NO: 152.

In some embodiments, the targeting moiety specifically binds to Muc1, and the amino acid sequence of the light chain of the first member is as set forth in SEQ ID NO: 65.

In some embodiments, the targeting moiety specifically binds to Muc1, the heavy chain of the first member comprises CDR1-3, the amino acid sequence of the CDR1 is as set forth in SEQ ID NO: 153, the amino acid sequence of the CDR2 is as set forth in SEQ ID NO: 154, and the amino acid sequence of the CDR3 is as set forth in SEQ ID NO: 155.

In some embodiments, the targeting moiety specifically binds to Muc1, the heavy chain of the first member comprises a heavy chain variable region, and the amino acid sequence of the heavy chain variable region is as set forth in SEQ ID NO: 156.

In some embodiments, the targeting moiety specifically binds to Muc1, and the amino acid sequence of the heavy chain of the first member is as set forth in SEQ ID NO: 67.

In some embodiments, the targeting moiety specifically binds to Mesothelin, the light chain of the first member comprises CDR1-3, the amino acid sequence of the CDR1 is as set forth in SEQ ID NO: 165, the amino acid sequence of the CDR2 is as set forth in SEQ ID NO: 166, and the amino acid sequence of the CDR3 is as set forth in SEQ ID NO: 167.

In some embodiments, the targeting moiety specifically binds to Mesothelin, the light chain of the first member comprises a light chain variable region, and the amino acid sequence of the light chain variable region is as set forth in SEQ ID NO: 168.

In some embodiments, the targeting moiety specifically binds to Mesothelin, and the amino acid sequence of the light chain of the first member is as set forth in SEQ ID NO: 73.

In some embodiments, the targeting moiety specifically binds to Mesothelin, the heavy chain of the first member comprises CDR1-3, the amino acid sequence of the CDR1 is as set forth in SEQ ID NO: 169, the amino acid sequence of the CDR2 is as set forth in SEQ ID NO: 170, and the amino acid sequence of the CDR3 is as set forth in SEQ ID NO: 171.

In some embodiments, the targeting moiety specifically binds to Mesothelin, the heavy chain of the first member comprises a heavy chain variable region, and the amino acid sequence of the heavy chain variable region is as set forth in SEQ ID NO: 172

In some embodiments, the targeting moiety specifically binds to Mesothelin, and the amino acid sequence of the heavy chain of the first member is as set forth in SEQ ID NO: 75.

In some embodiments, the targeting moiety specifically binds to MUCSAC, the light chain of the first member comprises CDR1-3, the amino acid sequence of the CDR1 is as set forth in SEQ ID NO: 157, the amino acid sequence of the CDR2 is as set forth in SEQ ID NO: 158, and the amino acid sequence of the CDR3 is as set forth in SEQ ID NO: 159.

In some embodiments, the targeting moiety specifically binds to MUCSAC, the light chain of the first member comprises a light chain variable region, and the amino acid sequence of the light chain variable region is as set forth in SEQ ID NO: 160.

In some embodiments, the targeting moiety specifically binds to MUCSAC, and the amino acid sequence of the light chain of the first member is as set forth in SEQ ID NO: 69.

In some embodiments, the targeting moiety specifically binds to MUCSAC, the heavy chain of the first member comprises CDR1-3, the amino acid sequence of the CDR1 is as set forth in SEQ ID NO: 161, the amino acid sequence of the CDR2 is as set forth in SEQ ID NO: 162, and the amino acid sequence of the CDR3 is as set forth in SEQ ID NO: 163.

In some embodiments, the targeting moiety specifically binds to MUCSAC, the heavy chain of the first member comprises a heavy chain variable region, and the amino acid sequence of the heavy chain variable region is as set forth in SEQ ID NO: 164.

In some embodiments, the targeting moiety specifically binds to MUCSAC, and the amino acid sequence of the heavy chain of the first member is as set forth in SEQ ID NO:71.

In some embodiments, in the heavy chain of the first member, the amino acid sequence of the first Fc region is selected from SEQ ID NO:1, 4, 5, 6, 7, 9, 11, 13, 15, 17, 19, 21, 22, 24, 26, 27, and 29.

In some embodiments, the amino acid sequence of the immunoregulator comprised in the second member is selected from SEQ ID NO:173-180.

In some embodiments, the amino acid sequence of the second Fc region comprised in the second member is selected from SEQ ID NO:2, 3, 8, 10, 12, 14, 16, 18, 20, 23, 25, and 28.

In some embodiments, the amino acid sequence of the polypeptide comprised in the second member is selected from SEQ ID NO:77, 80, 82, 84, 86, 89, 91, and 97.

In some embodiments, the amino acid sequence of the light chain comprised in the first member is selected from SEQ ID NO: 37, 45, 49, 53, 57, 61, 65, 69, and 73, the amino acid sequence of the heavy chain comprised in the first member is selected from SEQ ID NO: 39, 47, 51, 55, 59, 63, 67, 71, and 75, and the amino acid sequence of the polypeptide comprised in the second member is selected from SEQ ID NO: 77, 80, 82, 84, 86, 89, 91, and 97.

In some embodiments, the knob-and-hole modification comprises a knob modification and a hole modification, wherein the knob modification comprises the amino acid substitutions Y349C and T366W, and the hole modification comprises the amino acid substitutions D356C, T366S, L368A and Y407V, wherein the position of the amino acid is determined according to the EU index of the KABAT number. In some cases, the knob modification is comprised in the first Fc region, and the hole modification is comprised in the second Fc region. In some cases, the knob modification is comprised in the second Fc region, and the hole modification is comprised in the first Fc region.

In another aspect, the present disclosure provides an isolated polynucleotide encoding the proteinaceous heterodimer according to the present disclosure. In some embodiments, the isolated polynucleotide encodes a subunit (e.g., a member) or a fragment of the proteinaceous heterodimer according to the present disclosure.

In another aspect, the present disclosure provides a vector comprising the isolated polynucleotide of the present disclosure.

In another aspect, the present disclosure provides an isolated host cell, comprising the isolated polynucleotide or the vector of the present disclosure.

In another aspect, the present disclosure provides a protein mixture, comprising: 1) the proteinaceous heterodimer according to the present disclosure; 2) a first homodimer formed by two of the first member of the proteinaceous heterodimer; and 3) a second homodimer formed by two of the second member of the proteinaceous heterodimer; wherein the percentage of the proteinaceous heterodimer in the protein mixture is at least 50%. In some embodiments, the percentage of the second homodimer is less than the percentage of the first homodimer. In some embodiments, the percentage of the second homodimer is at most 10%. In some embodiments, the protein mixture substantially comprises none of the second homodimer. For example, the protein mixture may be obtained directly from the cells expressing it. For example, the proteinaceous heterodimers in the protein mixture has not been purified post expression. For example, undesired protein dimers or multimers (e.g., protein homodimers) have not been removed from the mixture after protein expression.

In another aspect, the present disclosure provides a pharmaceutical composition comprising the proteinaceous heterodimer according to the present disclosure; or the protein mixture according to the present disclosure, and optionally a pharmaceutically acceptable excipient.

In some embodiments, the pharmaceutical composition is formulated for oral administration, intravenous administration, intramuscular administration, in-situ administration at the site of a tumor, inhalation, rectal administration, vaginal administration, transdermal administration, or administration via subcutaneous repository.

In another aspect, the present disclosure provides a use of the proteinaceous heterodimer, or the protein mixture according to the present disclosure in the manufacture of a medicament and/or a kit for inhibiting growth of a tumor or a tumor cell.

In another aspect, the present disclosure provides a method for inhibiting growth of a tumor or a tumor cell, comprising contacting the tumor or tumor cell with an effective amount of the proteinaceous heterodimer according to the present disclosure, or the protein mixture according to the present disclosure. In some embodiments, the contacting occurs in vitro or in vivo.

For example, the present disclosure provides a method for treating a tumor/cancer in a subject in need thereof, the method comprising administering an effective amount of the proteinaceous heterodimer according to the present disclosure, or the protein mixture according to the present disclosure to the subject.

In another aspect, the present disclosure provides a method of producing a proteinaceous heterodimer or a protein mixture comprising the proteinaceous heterodimer, comprising (i) culturing the host cell of the present disclosure under conditions to effect expression of the proteinaceous heterodimer, and (ii) harvesting the expressed proteinaceous heterodimer or a protein mixture comprising the expressed proteinaceous heterodimer.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Figure 1:
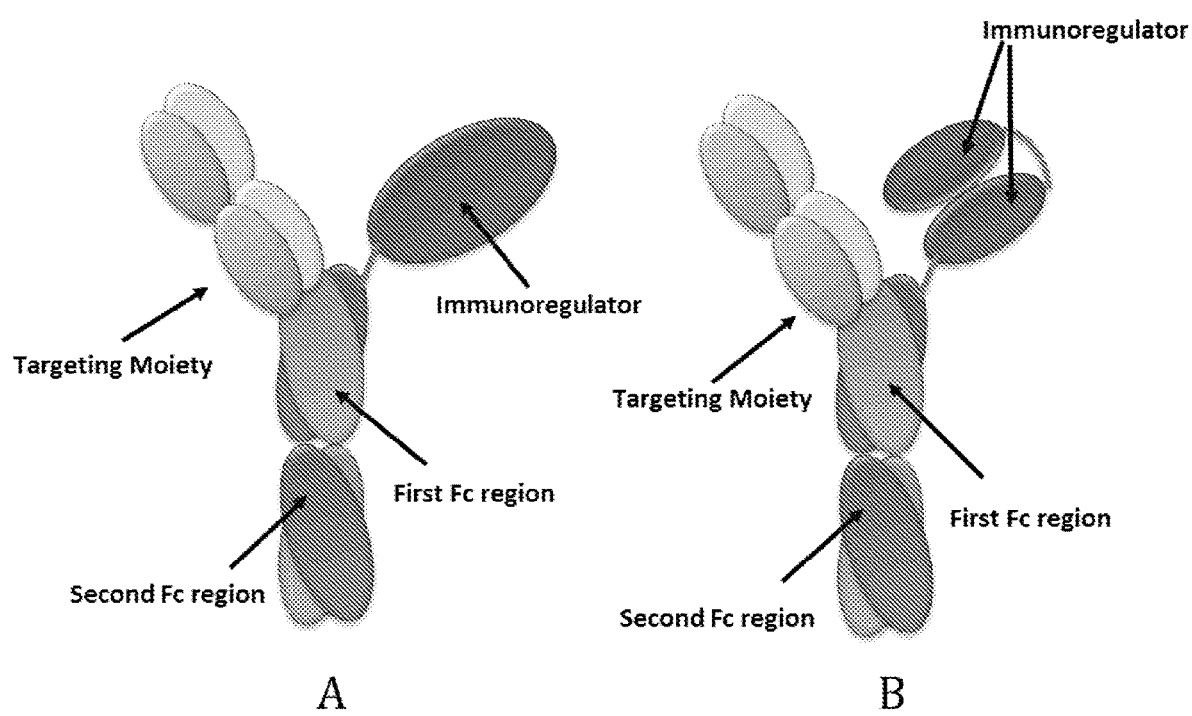
FIG. 1 illustrates examples of the proteinaceous heterodimers according to the present application.

Before the embodiments of the disclosure are described, it is to be understood that such embodiments are provided by way of example only, and that various alternatives to the embodiments of the disclosure described herein may be employed in practicing the disclosure. Numerous variations, changes, and substitutions will now occur to those skilled in the art without departing from the disclosure.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. In case of conflict, the patent specification, including definitions, will control. In addition, the materials, methods, and examples are illustrative only and not intended to be limiting. Numerous variations, changes, and substitutions will now occur to those skilled in the art without departing from the disclosure.

The singular form "a," "an" and "the," as used herein, generally include plural references unless the context clearly dictates otherwise.

The term "proteinaceous," as used herein, generally refers to a material or molecule that is of, relating to, resembling, or being a polypeptide or a protein. For example, a proteinaceous heterodimer of the present disclosure may be a heterodimer protein, or a heterodimer comprising two or more polypeptides.

The term "heterodimer," as used herein, generally refers to a molecule (e.g. a proteinaceous molecule) composed of two different members. The two members of a heterodimer may differ in structure, function, activity and/or composition. For example, the two different members may comprise polypeptides differing in the order, number, or kind of amino acid residues forming these polypeptides. Each of the two different members of a heterodimer may independently comprise one, two or more units, polypeptide chains, or moieties.

The term "targeting moiety," as used herein, generally refers to a molecule, complex or aggregate, that binds specifically, selectively or preferentially to a target molecule, cell, particle, tissue or aggregate. For example, a targeting moiety may be an antibody, antigen-binding antibody fragment, bispecific antibody or other antibody-based molecule or compound. Other examples of targeting moieties may include, but are not limited to, aptamers, avimers, receptor-binding ligands, nucleic acids, biotin-avidin binding pairs, binding peptides or proteins, etc. The terms "targeting moiety" and "binding moiety" are used interchangeably herein.

The term "tumor antigen," as used herein, generally refers to an antigenic substance produced in or by tumor cells, which may have an ability to trigger an immune response in a host.

For example, a tumor antigen may be a protein, a polypeptide, a peptide, or a fragment thereof, which constitutes part of a tumor cell and is capable of inducing tumor-specific cytotoxic T lymphocytes. A tumor antigen peptide may be a peptide that is generated as a result of degradation of the tumor antigen in a tumor cell and can induce or activate tumor-specific cytotoxic T lymphocytes upon being expressed on cell surface by binding to an HLA molecule.

In some embodiments, the term "tumor antigen" may also refer to biomolecules (e.g., proteins, carbohydrates, glycoproteins, etc.) that are exclusively or preferentially or differentially expressed on a cancer cell and/or are found in association with a cancer cell and thereby provide targets preferential or specific to the cancer. For example, the preferential expression can be preferential expression as compared to any other cell in the organism, or preferential expression within a particular area of the organism (e.g. within a particular organ or tissue).

The terms "tumor antigen epitope" and "tumor antigen determinant" are used interchangeably herein and generally refer to the site of an amino acid sequence present in a tumor antigen that induces tumor-specific cytotoxic T lymphocytes.

The terms "immunoregulator" and "immunomodulator," are used interchangeably herein, and generally refer to a substance that affects the functioning of the immune system. An immunoregulator may augment or reduce an immune response. For example, an immunoregulator may be an active agent of immunotherapy, including but not limited to, e.g., recombinant, synthetic and/or natural preparations of cytokines, granulocyte colony-stimulating factors (G-CSF), interferons, imiquimod, cellular membrane fractions from bacteria, chemokines, interleukins, cytosine phosphateguanosine (CpG) oligodeoxynucleotides, and glucans. In some examples, the immunoregulator is a cytokine. In some cases, the immunoregulator is not an antibody or an antigen binding fragment thereof. In some cases, the immunoregulator is not an immunoglobulin molecule or a fragment (such as an antigen binding fragment) thereof.

In some embodiments, the immunoregulator is selected from the group consisting of interferon, interleukin, chemokine, lymphokine, and tumor necrosis factor. For example, the immunoregulator may be selected from the group consisting of interferon alpha, interferon lambda, interferon beta, interleukin 10, interleukin 2, and super interleukin 2.

The term "expression yield," as used in the context of proteinaceous heterodimers herein, generally refers to an amount of a proteinaceous heterodimer being produced in functional form upon expression, e.g., when expressed by a host cell.

The term "dimerization sequence," as used herein, generally refers to an amino acid sequence capable of forming a dimer, or undergoing dimerization. In some embodiments, a dimer is a heterodimer formed by two different members. In some cases, the two different members of a heterodimer may comprise different dimerization sequences.

The term "heterodimerization," as used herein, generally refers to the process of forming a heterodimer between two different members (e.g., two different polypeptides), such as through complexation, association, or aggregation, with or without formation of covalent bonds between the two different members.

The term "covalent bond," as used herein, generally refers to a chemical bond formed between atoms by the sharing of electrons. For example, a covalent bond may be polar or non-polar. In some embodiments, a covalent bond is a disulfide bond.

The term "non-covalent pairwise affinity," as used herein, generally refers to that dimerization sequences or heterodimerization sequences capable of binding each other via non-covalent interaction, e.g., via ion pairs, hydrogen bonds, dipole-dipole interactions, charge transfer interactions, π-π interactions, cation-π-electron interactions, van der Waals interactions and disperse interactions, hydrophobic (lipophilic) interactions, complex formation (e.g., complex formation of transition metal cations), or a combination of these interactions.

The term "linker," as used herein, generally refers to a synthetic amino acid sequence that connects or links two polypeptide sequences, e.g., that link two polypeptide domains. A linker may connect two amino acid sequences via peptide bonds. In some embodiments, a linker of the present disclosure connects a biologically active moiety to a second moiety in a linear sequence.

The terms "polypeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified, for example, by disulfide bond formation, glycosylation, lipidation, acetylation, phosphorylation, or any other manipulation, such as conjugation with a labeling component. The terms may apply to amino acid polymers in which one or more amino acid residue is an artificial chemical analogue of a corresponding naturally occurring amino acid, as well as to naturally occurring amino acid polymers. The terms may also include variants on the traditional peptide linkage joining the amino acids making up the polypeptide. For example, the "peptides," "polypeptides," and "proteins" may be chains of amino acids whose alpha carbons are linked through peptide bonds. The terminal amino acid at one end of the chain (amino terminal) therefore may have a free amino group, while the terminal amino acid at the other end of the chain (carboxy terminal) may have a free carboxyl group. As used herein, the term "amino terminus" (abbreviated N-terminus) generally refers to the free α-amino group on an amino acid at the amino terminal of a peptide or to the α-amino group (imino group when participating in a peptide bond) of an amino acid at any other location within the peptide. Similarly, the term "carboxy terminus" generally refers to the free carboxyl group on the carboxy terminus of a peptide or the carboxyl group of an amino acid at any other location within the peptide. Peptides may also include essentially any poly-amino acid including, but not limited to peptide mimetics such as amino acids joined by a ether as opposed to an amide bond.

The term "amino acid," as used herein, generally refers to either natural and/or unnatural or synthetic amino acids, including but not limited to, the D or L optical isomers or both, amino acid analogs and peptidomimetics. Standard single or three letter codes are used to designate amino acids.

The term "natural L-amino acid," as used herein, generally refers to the L optical isomer forms of glycine (G), proline (P), alanine (A), valine (V), leucine (L), isoleucine (I), methionine (M), cysteine (C), phenylalanine (F), tyrosine (Y), tryptophan (W), histidine (H), lysine (K), arginine (R), glutamine (Q), asparagine (N), glutamic acid (E), aspartic acid (D), serine (S), and threonine (T).

The term "non-naturally occurring," as used herein, generally refers to polypeptide or polynucleotide sequences that do not have a counterpart to, are not complementary to, or do not have a high degree of homology with a wild-type or naturally-occurring sequence (e.g., those found in a subject). For example, a non-naturally occurring polypeptide or fragment may share less than 99%, 98%, 95%, 90%, 80%, 70%, 60%, 50% or even less amino acid sequence identity as compared to a natural sequence when suitably aligned. Alternatively, a non-naturally occurring polypeptide or fragment may share more than 99%, 98%, 95%, 90%, 80%, 70%, 60%, 50% or even more amino acid sequence identity as compared to a natural sequence when suitably aligned.

The terms "hydrophilic" and "hydrophobic," as used herein, generally refer to the degree of affinity that a substance has with water. A hydrophilic substance has a strong affinity for water, tending to dissolve in, mix with, or be wetted by water, while a hydrophobic substance substantially lacks affinity for water, tending to repel and not absorb water and tending not to dissolve in or mix with or be wetted by water. Amino acids can be characterized based on their hydrophobicity. A number of scales have been developed. An example is a scale developed by Levitt, M, et al., J Mol Biol (1976) 104:59, which is listed in Hopp, T P, et al., Proc Natl Acad Sci USA (1981) 78:3824. Examples of "hydrophilic amino acids" are arginine, lysine, threonine, alanine, asparagine, and glutamine. Of particular interest are the hydrophilic amino acids aspartate, glutamate, and serine, and glycine. Examples of "hydrophobic amino acids" are tryptophan, tyrosine, phenylalanine, methionine, leucine, isoleucine, and valine.

The term "fragment," when used in the context of a proteinaceous molecule (e.g., a polypeptide or a protein), generally refers to a truncated form of a native biologically active protein that may or may not retain a portion of the therapeutic and/or biological activity.

The term "variant," when used in the context of a proteinaceous molecule (e.g., a polypeptide or a protein), generally refers to a proteinaceous molecule with sequence homology to the native biologically active protein that retains at least a portion of the therapeutic and/or biological activity of the biologically active protein. For example, a variant protein may share at least 60%, 65%, 70%, 75%, 80%, 85%, 90%, 95%, 96%, 97%, 98% or 99% amino acid sequence identity compared with the reference biologically active protein. In some embodiments, the "variant" may include proteins modified deliberately, as for example, by site directed mutagenesis, synthesis of the encoding gene, insertions, or accidentally through mutations.

The terms "conjugated," "linked," "fused," and "fusion" are used interchangeably herein, and generally refer to the joining together of two or more chemical elements, sequences or components, e.g., by means including chemical conjugation or recombinant means. For example, a promoter or enhancer is operably linked to a coding sequence if it effects the transcription of the sequence. Generally, "operably linked" means that the DNA sequences being linked are contiguous, and in reading phase or in-frame. An "in-frame fusion" refers to the joining of two or more open reading frames (ORFs) to form a continuous longer ORF, in a manner that maintains the correct reading frame of the original ORFs. Thus, the resulting "fusion polypeptide" is a single protein containing two or more fragments that correspond to polypeptides encoded by the original ORFs (which segments are not normally so joined in nature). The "fusion site" refers to the sequence where the two or more fragments are joined together. In some cases, the fusion site can be a sequence that is identical to sequences in the two or more fragments being joined. In some cases, the fusion site can further comprise a gap segment that is not identical to either of the sequences of the two or more fragments being joined.

In the context of polypeptides, a "linear sequence" or a "sequence" is an order of amino acids in a polypeptide in an amino to carboxyl terminus direction in which residues next to each other in the sequence are contiguous in the primary structure of the polypeptide. A "partial sequence" is a linear sequence forming part of a polypeptide that is known to comprise additional residues in one or both directions.

The terms "polynucleotides," "nucleic acids," "nucleotides" and "oligonucleotides" are used interchangeably herein, and they generally refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The terms "gene" and "gene fragment" are used interchangeably herein and generally refer to a polynucleotide containing at least one open reading frame that is capable of encoding a particular protein after being transcribed and translated. A gene or gene fragment may be genomic or cDNA, as long as the polynucleotide contains at least one open reading frame, which may cover the entire coding region or a segment thereof. A "fusion gene" is a gene composed of at least two heterologous polynucleotides that are linked together.

The term "antibody," as used herein, generally refers to a protein comprising one or more polypeptides substantially encoded by immunoglobulin genes or fragments of immunoglobulin genes. The immunoglobulin genes may include the kappa, lambda, alpha, gamma, delta, epsilon and mu constant region genes, as well as myriad immunoglobulin variable region genes. As used herein, light chains may be classified as either kappa or lambda. Heavy chains may be classified as gamma, mu, alpha, delta, or epsilon, which in turn define the immunoglobulin classes, IgG, IgM, IgA, IgD and IgE, respectively. An antibody as used in the present disclosure may have a structural unit comprising a tetramer. Each tetramer may be composed of two identical pairs of polypeptide chains, each pair having one "light" (about 25 KD) and one "heavy" chain (about 50-70 KD). The N-terminus of each chain may define a variable region of about 100 to 110 or more amino acids primarily responsible for antigen recognition. The terms "light chain variable region" (VL) and "heavy chain variable region" (VH), as used herein, generally refer to these regions of the light and heavy chains respectively. Antibodies may exist as intact immunoglobulins or as a number of well characterized fragments produced by digestion with various peptidases or expressed de novo. Thus, for example, pepsin may digest an antibody below the disulfide linkages in the hinge region to produce F(ab)'2 (a dimer of Fab which itself is a light chain joined to VH—CH1 by a disulfide bond). The F(ab)'2 may be reduced under mild conditions to break the disulfide linkage in the hinge region thereby converting the (Fab')2 dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of ordinary skill in the art will appreciate that such Fab' fragments may be synthesized de novo either chemically or by utilizing recombinant DNA methodology. Thus, the term antibody, as used herein, may also include antibody fragments either produced by the modification of whole antibodies or synthesized de novo using recombinant DNA methodologies, including, but are not limited to, Fab'2, IgG, IgM, IgA, IgE, scFv, dAb, nanobodies, unibodies, and diabodies. In some embodiments, the antibodies include, but are not limited to Fab'2, IgG, IgM, IgA, IgE, and single chain antibodies, for example, single chain Fv (scFv) antibodies in which a variable heavy and a variable light chain are joined together (directly or through a peptide linker) to form a continuous polypeptide.

The term "antigen-binding site" or "binding portion," as used herein, generally refers to a part of an antibody that participates in antigen binding. An antigen binding site may be formed by amino acid residues of the N-terminal variable ("V") regions of a heavy ("H") chain and/or a light ("L") chain. Three highly divergent stretches within the V regions of the heavy and light chains are referred to as "hypervariable regions" which are interposed between more conserved flanking stretches known as "framework regions" or "FRs". Thus, the term "FR," as used herein, generally refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three-dimensional space to form an antigen binding "surface". This surface may mediate recognition and binding of the target antigen. The three hypervariable regions of each of the heavy and light chains are referred to as "complementarity determining regions" or "CDRs" and are characterized, for example by Kabat et al. *Sequences of proteins of immunological interest*, 4$^{th}$ ed. U.S. Dept. Health and Human Services, Public Health Services, Bethesda, Md. (1987).

In some embodiments, antibodies and fragments thereof used herein can be bispecific. Bispecific antibodies or fragments thereof can be of various configurations. For example, bispecific antibodies may resemble single antibodies (or antibody fragments) but have two different antigen binding sites (variable regions). In various embodiments, bispecific antibodies can be produced by chemical techniques (Kranz et al. (1981) Proc. Natl. Acad. Sci., USA, 78: 5807), by "polyoma" techniques (see, e.g., U.S. Pat. No. 4,474,893), or by recombinant DNA techniques. In some embodiments, bispecific antibodies as used herein may have binding specificities for at least two different epitopes and at least one of which is a tumor antigen. In some embodiments, the antibodies and fragments thereof may also be heteroantibodies. Heteroantibodies are two or more antibodies, or antibody binding fragments (e.g., Fab) linked together, each antibody or fragment having a different specificity.

The term "homology," "homologous" or "sequence identity," as used herein, generally refers to sequence similarity or interchangeability between two or more polynucleotide sequences or between two or more polypeptide sequences. When using a program (e.g. Emboss Needle or BestFit) to determine sequence identity, similarity or homology between two different amino acid sequences, the default settings may be used, or an appropriate scoring matrix, such as blosum45 or blosum80, may be selected to optimize identity, similarity or homology scores. In some embodiments, polynucleotides that are homologous are those which hybridize under stringent conditions and have at least 60%, at least 65%, at least 70%, at least 80%, at least 90%, at least 95%, at least 97%, at least 98%, at least 99%, and even 100% sequence identity compared to those sequences. Polypeptides that are homologous have sequence identities of at least 80%, or at least 90%, or at least 95%, or at least 97%, or at least 98%, or have at least 99% sequence identity when sequences of comparable length are optimally aligned.

The terms "percent identity" and "% identity," as used in the context of polynucleotide sequences, generally refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity may be measured over the length of an entire defined polynucleotide sequence, or may be measured over a shorter length, for example, over the length of a fragment taken from a larger, defined polynucleotide sequence. It is understood that any fragment length supported by the sequences shown herein, in the tables, figures or Sequence Listing, may be used to describe a length over which percentage identity may be measured.

The term "percent (%) sequence identity," as used in the context of polypeptide sequences identified herein, generally refers to the percentage of amino acid residues in a query sequence that are identical with the amino acid residues of a second, reference polypeptide sequence or a portion thereof, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, NEEDLE or Megalign (DNASTAR) software. Those skilled in the art can determine appropriate parameters for measuring alignment, including any algorithms needed to achieve maximal alignment over the full length of the sequences being compared. Percent identity may be measured over the length of an entire defined polypeptide sequence, or may be measured over a shorter length, for example, over the length of a fragment taken from a larger, defined polypeptide sequence. It is understood that any fragment length supported by the sequences shown herein, in the tables, figures or Sequence Listing, may be used to describe a length over which percentage identity may be measured.

The term "host cell," as used herein, generally includes an individual cell, a cell line or cell culture which can be or has been a recipient for the subject plasmids or vectors, comprise the polynucleotide of the present disclosure, or express the proteinaceous heterodimer (e.g. heterodimer protein) of the present disclosure. Host cells may include progeny of a single host cell. The progeny may not necessarily be completely identical (in morphology or in genomic of total DNA complement) to the original parent cell due to natural, accidental, or deliberate mutation. A host cell may include cells transfected in vitro with a vector of the present disclosure. A host cell may be a bacterial cell (e.g., *E. coli*), a yeast cell or other eukaryotic cells, e.g., a COS cell, a Chinese hamster ovary (CHO) cell, a HeLa cell, a HEK293 cell, a COS-1 cell, an NS0 cell, or a myeloma cell. In some embodiments, a host cell is a mammalian cell. In some embodiments, the mammalian cell is a HEK293 cell.

The term "vector," as used herein, generally refers to a nucleic acid molecule capable of self-replicating in an appropriate host, which transfers an inserted nucleic acid molecule into and/or between host cells. The term may include vectors that function primarily for insertion of DNA or RNA into a cell, replication of vectors that function primarily for the replication of DNA or RNA, and expression vectors that function for transcription and/or translation of the DNA or RNA. Also included are vectors that provide more than one of the above functions. An "expression vector" is a polynucleotide which, when introduced into an appropriate host cell, can be transcribed and translated into a polypeptide(s). An "expression system" usually connotes a suitable host cell comprising an expression vector that can function to yield a desired expression product.

The term "effective amount" or "therapeutically effective amount" refers to an amount of a composition (e.g., a proteinaceous heterodimer described herein) that is sufficient to effect the intended application, including but not limited to disease treatment. The therapeutically effective amount may vary depending upon the intended application (e.g., in vitro or in vivo), or the subject and disease condition being treated, e.g., the weight and age of the subject, the severity of the disease condition, the manner of administration and the like, which can readily be determined by one of ordinary skill in the art. The term may also apply to a dose that will induce a particular response in target cells, e.g. target gene induction, proliferation, and/or apoptosis. The specific dose will vary depending on the particular compounds chosen, the dosing regimen to be followed, whether it is administered in combination with other compounds, timing of administration, the tissue to which it is administered, and the physical delivery system in which it is carried.

The terms "treatment" or "treating," or "palliating" or "ameliorating" is used interchangeably herein, and refer to an approach for obtaining beneficial or desired results including but not limited to a therapeutic benefit and/or a prophylactic benefit. As used herein, therapeutic benefit generally refers to eradication or reduced severity of the underlying disorder being treated. Also, a therapeutic benefit is achieved with the eradication, reduced severity or reduced incidence of one or more of the physiological symptoms associated with the underlying disorder such that an improvement is observed in the subject, notwithstanding that the subject may still be afflicted with the underlying disorder. For prophylactic benefit, the compositions may be administered to a subject at risk of developing a particular disease, or to a subject reporting one or more of the physiological symptoms of a disease, even though a diagnosis of this disease may not have been made.

The term "therapeutic effect," as used herein, generally encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, generally encompass administration of two or more agents to an animal so that both agents and/or their metabolites are present in the subject at the same time. Co-administration includes simultaneous administration in separate compositions, administration at different times in separate compositions, or administration in a composition in which both agents are present.

The terms "antagonist" and "inhibitor" are used interchangeably herein, and they generally refer to a compound having the ability to inhibit a biological function of a target protein, whether by inhibiting the activity or expression of the target protein. Accordingly, the terms "antagonist" and "inhibitors" are defined in the context of the biological role of the target protein. While preferred antagonists herein specifically interact with (e.g. bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist," as used herein, generally refers to a compound having the ability to initiate or enhance a biological function of a target protein, whether by inhibiting or enhancing the activity or expression of the target protein. Accordingly, the term "agonist" is defined in the context of the biological role of the target polypeptide. While preferred agonists herein specifically interact with (e.g. bind to) the target, compounds that initiate or enhance a biological activity of the target polypeptide by interacting with other members of the signal transduction pathway of which the target polypeptide is a member are also specifically included within this definition.

The term "agent" or "biologically active agent," as used herein, generally refers to a biological, pharmaceutical, or chemical compound or other moieties. Non-limiting examples include a simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

The term "anti-cancer agent," "anti-tumor agent" or "chemotherapeutic agent," as used herein, generally refers to any agent useful in the treatment of a neoplastic condition. One class of anti-cancer agents comprises chemotherapeutic agents.

The term "chemotherapy," as used herein, generally refers to the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation," as used herein, generally refers to a phenomenon by which the cell number has changed as a result of division. For example, cell proliferation may result in an increase in number of cells. This term also encompasses cell growth by which the cell morphology has changed (e.g., increased in size) consistent with a proliferative signal.

The term "in vivo," as used herein, generally refers to an event that takes place in a subject's body.

The term "in vitro," as used herein, generally refers to an event that takes places outside of a subject's body. For example, an in vitro assay encompasses any assay conducted outside of a subject. In vitro assays encompass cell-based assays in which dead or living cells are employed. In vitro assays also encompass a cell-free assay in which no intact cells are employed.

The term "interferon" (IFN), as used herein, generally refers to a signaling protein made and released by a host cell in response to the presence of pathogens, such as viruses, bacteria, parasites, or tumor cells. There are three major types of interferons, i.e. type I, type II and type III, wherein type I interferons may include IFN-α and IFN-β, and IFN-α may further comprise IFN-α subtypes, e.g., IFN-α2, IFN-α4, etc. Type I interferons may inhibit virus replication, have anti-parasitic activity, inhibit cell proliferation, stimulate cytotoxic activity of immune cells, be involved in immune regulation, and exhibit anti-tumor effects. Type II and Type III interferons may include IFN-γ, IFN-λ2(IL-28a) and IFN-λ3(IL-28b). As used herein, the term "interferon" may include full length interferons, or a fragment (e.g., a truncated form) or variant thereof substantially maintaining the biological activities of a corresponding wild-type interferon (e.g., having a biological activity that is at least 80%, at least 90%, at least 95%, at least 98%, at least 99%, or even at least 100% of the biological activity of a corresponding wild-type interferon). An interferon, as used herein, may be from any mammalian species. In some embodiments, the interferon is from a species selected from the group consisting of human, horse, cattle, murine, pig, rabbit, cat, dog, rat, goat, sheep, and non-human primate.

The term "interleukin," as used herein, generally refers to a secreted protein or a signaling molecule capable of promoting the development and differentiation of T and/or B lymphocytes and/or hematopoietic cells. An interleukin may be synthesized by helper CD4 T lymphocytes, as well as through monocytes, macrophages, and endothelial cells. As used herein, an interleukin (IL) may include IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, and/or IL-36. As used herein, the term "interleukin" may include full length interleukins, or a fragment (e.g., a truncated form) or variant thereof substantially maintaining the biological activities of a corresponding wild-type interleukin (e.g., having a biological activity that is at least 80%, at least 90%, at least 95%, at least 98%, at least 99%, or even at least 100% of the biological activity of a corresponding wild-type interleukin). An interleukin, as used herein, may be from any mammalian species. In some embodiments, the interleukin is from a species selected from the group consisting of human, horse, cattle, murine, pig, rabbit, cat, dog, rat, goat, sheep, and non-human primate. In some embodiments, the interleukin can be in a mutated form, for example, with increased or decreased affinity to its receptors. In specific embodiments, the interleukin can be a super IL-2 (also known as sIL2, see Nature 484, 529-533, 26 Apr. 2012), which may be obtained by modifying IL-2 to increase its binding affinity for IL-2Rμ. Mutations in sIL-2 are principally in the core of the cytokine, and molecular dynamics simulations indicated that the evolved mutations stabilized IL-2, reducing the flexibility of a helix in the IL-2Rμ binding site, into an optimized receptor-binding conformation resembling that when bound to CD25. Compared to IL-2, sIL-2 induced superior expansion of cytotoxic T cells, leading to improved anti-tumor responses in vivo, and elicited proportionally less expansion of T regulatory cells and reduced pulmonary edema.

The term "anti-HER2/neu antibody," as used herein, generally refers to an antibody that specifically or preferentially binds a HER2/neu receptor. For example, an anti-HER2/neu antibody or anti-HER2 antibody could be Trastuzumab, Pertuzumab, or antigen binding fragments thereof.

The term "anti-EGFR antibody," as used herein, generally refers to an antibody that specifically or preferentially binds an EGFR. In some cases, and anti-EGFR antibody may bind to a mutated form of EGFR (e.g., EGFR variant III (also known as EGFRvIII), which is the most common extracellular domain mutation of EGFR, this mutation leads to a deletion of exons 2-7 of the EGFR gene, which is characterized by a truncated extracellular domain with ligand-independent constitutive activity). For example, an anti-EGFR antibody may be Cetuximab, Mab806, or antigen binding fragments thereof.

The term "subject," as used herein, generally refers to a human or non-human animal, including, but not limited to, a cat, dog, horse, pig, cow, sheep, goat, rabbit, mouse, rat, or monkey.

The term "anti-EGFR family antibody," as used herein, generally refers to an antibody that specifically binds to a member of the epidermal growth factor receptor family. For example, it may be an antibody that binds to ErbB-1 (also named as epidermal growth factor receptor (EGFR)), ErbB-2 (also named as HER2 in humans and as neu in rodents), ErbB-3 (also named as HER3), and/or to ErbB-4 (also named as HER4). Examples of anti-EGFR family antibodies include, but are not limited to one or more of the following antibodies: C6.5, C6mL3-9, C6 MH3-B1, C6-B1D2, F5, HER3.A5, HER3.F4, HER3.H1, HER3.H3, HER3.E12, HER3.B12, EGFR.E12, EGFR.C10, EGFR.B11, EGFR.E8, HER4.B4, HER4.G4, HER4.F4, HER4.A8, HER4.B6, HER4.D4, HER4.D7, HER4.D11, HER4.D12, HER4.E3, HER4.E7, HER4.F8 and HER4.C7, etc., also see, e.g., U.S. Patent publications US 2006/0099205 A1 and US 2004/0071696 A1, which are incorporated herein by reference.

The term "single chain Fv" ("sFv" or "scFv") polypeptide, as used herein, generally refers to a covalently linked VH (heavy chain variable region):VL (light chain variable region) heterodimer, which may be expressed from a nucleic acid including VH- and VL-encoding sequences either joined directly or joined by a peptide-encoding linker. (see Huston, et al. Proc. Nat. Acad. Sci. USA, 85: 5879-5883 (1988)).

The term "inhibition of growth and/or proliferation," when used with cancer cells, generally refers to decrease in the growth rate and/or proliferation rate of a cancer cell. For example, this may include death of a cancer cell (e.g. via apoptosis). In some embodiments, this term may also refer to inhibiting the growth and/or proliferation of a solid tumor and/or inducing tumor size reduction or elimination of the tumor.

The term "a cancer cell surface marker" or "a cancer cell associated marker," as used herein, generally refers to biomolecules such as proteins, carbohydrates, glycoproteins, and the like that are exclusively or preferentially or differentially expressed on a cancer cell and/or are found to be associated with a cancer cell and thereby provide targets preferential or specific to the cancer. In some embodiments, the preferential expression can be preferential expression as compared to any other cell in the organism, or preferential expression within a particular area of the organism (e.g. within a particular organ or tissue).

The term "member" as used herein, generally refers to a polypeptide, subunit, or moiety which is one component of the proteinaceous heterodimer.

The term "Fc region" as used herein, generally refers to the carboxyl terminal portion of an immunoglobulin heavy chain constant region, or an analog or portion thereof capable of binding an Fc receptor. As is known, each immunoglobulin heavy chain constant region comprises four or five domains. The domains are named sequentially as follows: CH1-hinge-CH2-CH3(-CH4). CH4 is present in IgM, which has no hinge region. The immunoglobulin heavy chain constant region useful in the present disclosure may comprise an immunoglobulin hinge region, and may also include a CH3 domain. For example, the immunoglobulin heavy chain constant region may comprise an immunoglobulin hinge region, a CH2 domain and a CH3 domain. In some embodiments, the Fc region according to the present disclosure consists of the hinge-CH2-CH3 domain.

The term "complexed with" as used herein, generally refers to the association (e.g., binding) of one member/subunit with another member/subunit of a molecule (e.g., an antibody). For example, a light chain may be complexed with a heavy chain to form a targeting moiety.

The term "binding specificity" as used herein, generally refers to the ability to specifically bind (e.g., immunoreact with) a given target (while not binding or substantially not binding a non-target). A targeting moiety of the present disclosure may be monospecific and contain one or more binding sites which specifically bind a target or may be multispecific (e.g., bispecific or trispecific) and contain two or more binding sites which specifically bind the same or different targets.

The term "associates with" or "associated with" as used herein, generally refers to that one entity is in physical association or contact with another. For example, a first member of the proteinaceous heterodimer may "associate with" a second member covalently or non-covalently. In some embodiments, a first member of the proteinaceous heterodimer associates with a second member via an interface, and the interface is formed by amino acid residues (i.e., interface residues) from the first member and the second member, respectively.

The term "modification" as used herein, generally refers to any manipulation of the peptide backbone (e.g. amino acid sequence) or any post-translational modifications (e.g. glycosylation) of a polypeptide. For example, a modification is in comparison to the sequence of a corresponding wild-type polypeptide. A modification may be a substitution, an addition, and/or a deletion of one or more amino acids (e.g., 1, 2, 3, 4, 5, 6, 7, 8, 9, 10, or more).

The term "knob-and-hole modification" as used herein, generally refers to introducing a modification at the interface of a polypeptide to form a bulge (knob modification) and introducing a modification at a corresponding position of another polypeptide to form a cavity (hole-modification), and the size of the bulge is the same or similar to that of the cavity. For example, the knob-and-hole modification enables the formation of a heterodimer, while inhibiting the formation of homodimers. See the reference of U.S. Pat. Nos. 5,731,168; 7,695,936; Ridgway et al., Prot Eng 9, 617-621 (1996) and Carter, J Immunol Meth 248, 7-15 (2001). Accordingly, the term "knob modification" as used herein, generally refers to a modification at the interface of a polypeptide to replace an amino acid having a smaller side chain (e.g., alanine or threonine) with an amino acid having a larger side chain (e.g., tyrosine or tryptophan) to form a bulge. The term "hole modification" as used herein, generally refers to a modification at a corresponding position of another polypeptide to replace an amino acid having a larger side chain (e.g., tyrosine or tryptophan) with an amino acid having a smaller side chain (e.g., alanine or threonine) to form a cavity. The knob modification and the hole modification can be made by altering the nucleic acid encoding the polypeptides, e.g. by site-specific mutagenesis, or by peptide synthesis. In a specific embodiment, a knob modification comprises the amino acid substitutions Y349C and T366W in one of the two subunits of the Fc region, and the hole modification comprises the amino acid substitutions D356C, T366S, L368A and Y407V in the other one of the two subunits of the Fc region.

The term "HEK293 cell" as used herein, generally refers to clonal isolates derived from transformed human embryonal kidney (HEK) cells. The HEK293 strain is a variant of the 293 cell line that demonstrates better adherence in monolayer culture and ease of use for plaque assays and other anchorage dependent applications. They have been adapted to suspension culture in serum-free media, e.g., 293 SFM II.

The term "CHO cell" as used herein, generally refers to Chinese hamster ovary cells, which are non-secretory, immortal fibroblasts. The CHO cells rarely secrete CHO endogenous protein, so is favorable to the separation and purification for a target protein.

The term "COS-1 cell" as used herein, generally refers to fibroblast-like cell lines derived from monkey kidney tissue. COS cells are obtained by immortalizing CV-1 cells with a version of the SV40 virus that can produce large T antigen but has a defect in genomic replication. One form of COS cell lines commonly used is COS-1.

The term "NS0 cell" as used herein, generally refers to a model cell line derived from the non-secreting murine myeloma. The cell line is a cholesterol-dependent cell line that was generated from a subline of NSI/1.

The term "fusion protein" as used herein, generally refers to a polypeptide that comprises, or alternatively consists of, an amino acid sequence of a polypeptide fused directly or indirectly (e.g., via a linker) to an amino acid sequence of a heterologous polypeptide (i.e., a polypeptide unrelated to the former polypeptide or the domain thereof).

The term "C-terminus" as used herein, generally refers to the carboxy terminus of a polypeptide.

The term "N-terminus" as used herein, generally refers to the amino terminus of a polypeptide.

The term "EGFR" as used herein, generally refers to epidermal growth factor receptor. for example, see in Carpenter et al. Ann. Rev. Biochem. 56:881-914 (1987), including naturally occurring mutant forms thereof.

The term "EGFR mutant" as used herein, generally refers to a mutated form of EGFR (e.g., EGFR variant III (also known as EGFRvIII), which is the most common extracellular domain mutation of EGFR, this mutation leads to a deletion of exons 2-7 of the EGFR gene which is characterized by a truncated extracellular domain with ligand-independent constitutive activity.

The term "HER2/neu" as used herein, generally refers to a human HER2 protein, for example, in Semba et al., PNAS (USA) 82:6497-6501 (1985) and Yamamoto et al. Nature 319:230-234 (1986) (GenBank accession number X03363).

The term "GPC3" as used herein, generally refers to a protein encoding by the gene glypican 3 (NCBI database Gene ID: 2719), which is an early marker of liver cancer. GPC3 is highly expressed in hepatocellular carcinoma and is detected in the tissues of patients with early hepatocellular carcinoma.

The term "anti-GPC3 antibody," as used herein, generally refers to an antibody that specifically or preferentially binds GPC3. For example, an anti-GPC3 antibody could be codrituzumab, or antigen binding fragments thereof.

The term "FAP" as used herein, generally refers to Fibroblast Activation Protein (FAP). FAP exists in tumor matrix fibroblasts and plays a role in the cell surface. It is a membrane serine peptidase which is a member of the type II serine protease family and has dipeptidyl peptidase and collagenase activity.

The term "anti-FAP antibody," as used herein, generally refers to an antibody that specifically or preferentially binds FAP. For example, an anti-FAP antibody could be antibody 28H1 or antigen binding fragments thereof.

The term "Muc1" as used herein, generally refers to a glycoprotein encoded by the muc1 gene. Muc1 is mainly present in the epithelial tissues and organs of mammary gland, pancreas, ovary, etc. It is highly expressed on the surface of cancer epithelial cells, and accordingly becomes the target of immune response.

The term "anti-Muc1 antibody," as used herein, generally refers to an antibody that specifically or preferentially binds Muc1. For example, an anti-Muc1 antibody could be antibody 5E5, a humanized version of the antibody 5E5, or antigen binding fragments thereof.

The term "MUC5AC" as used herein, generally refers to the mucin MUC5AC. MUC5AC is highly expressed in colorectal cancer, gastric signet ring cell carcinoma, colon cancer, rectal cancer and pancreatic cancer.

The term "anti-MUC5AC antibody," as used herein, generally refers to an antibody that specifically or preferentially binds MUC5AC. For example, an anti-MUC5AC antibody could be antibody ensituximab, or antigen binding fragments thereof.

The term "Mesothelin" as used herein, generally refers to a cell surface glycoprotein with a molecular weight of 40 KD. Mesothelin is highly expressed in a variety of tumor tissues, such as early pancreatic tumors, and it can be expressed in normal pleura, pericardium and peritoneal mesothelial cells.

The term "anti-Mesothelin antibody," as used herein, generally refers to an antibody that specifically or preferentially binds Mesothelin. For example, an anti-Mesothelin antibody could be antibody amatuximab, a humanized version of the antibody amatuximab, or antigen binding fragments thereof.

The term "chemokine" as used herein, generally refers to some low molecular weight (mostly 8-10 KD) proteins capable of attracting white blood cells to the site of infection. For example, the common structural features of chemokine proteins may include small molecular weight and four cysteine residues at the conserved positions ensuring the tertiary structure. Some chemokines are involved in promoting inflammatory responses, and some are involved in controlling cell migration during normal process of repair or development.

The term "lymphokine" as used herein, generally refers to a hormone-like polypeptide produced by activated lymphocytes, which can act on the corresponding target cells, causing changes in the characteristics or functions of the target cells. The lymphocytes act on adjacent or distant target cells via lymphokines to achieve immunomodulatory and immune effects. Common lymphokines include, but are not limited to, monocyte-macrophage migration inhibitory factor (MIF), leukocyte motility inhibitory factor (LIF), natural killer cell cytotoxin (NKCF) and lymphotoxin (LB).

The term "tumor necrosis factor" as used herein, generally refers to tumor necrosis factors produced by activated macrophages, NK cells and T lymphocytes. Among them, TNF produced by macrophages is called TNF-α, T lymphocytes produced by lymphotoxin (lymphotoxin, LT) is named TNF-β.

The term "immunoglobulin" as used herein, generally refers to a protein consisting of one or more polypeptides substantially encoded by immunoglobulin genes. The recognized immunoglobulin genes include the κ, λ, α, γ (IgG1, IgG2, IgG3, IgG4), δ, ε and μ constant region genes, as well as the myriad immunoglobulin variable region genes. One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions. In addition to antibodies, immunoglobulins may exist in a variety of other forms including, for example, Fv, Fab, Fab' and (Fab')2.

The term "fused in frame" as used herein, generally refers to the joining of two or more open reading frames (ORFs) to form a continuous longer ORF, in a manner that maintains the correct reading frame of the original ORFs.

The term "linker" as used herein, generally refers to a synthetic amino acid sequence that connects or links two polypeptide sequences, e.g., that links two polypeptide domains. A linker may connect two amino acid sequences via peptide bonds. In some embodiments, a linker of the present disclosure connects an immunoregulator to the second Fc region in a linear sequence.

The term "located N-terminal to" as used herein, generally refers to locating at a position N-terminal to another molecule (e.g., another polypeptide). For example, according to the present disclosure, two or more immunoregulators may be located N-terminal to the second Fc region.

The term "amino acid substitution" as used herein, generally refers to that one amino acid at a specific position of a polypeptide is replaced by another amino acid.

The term "EU index of the KABAT number" as used herein, generally refers to the index of the EU number corresponding to the amino acid sequence according to Kabat et al. (1971) Ann. N.Y. Acad, Sci. 190:382-391 and Kabat, E. A., et al. (1991) Sequences of Proteins of Immunological Interest, Fifth Edition, U.S. Department of Health and Human Services, NIH Publication No. 91-3242.

The term "isolated polynucleotide" as used herein, generally refers to a polymeric form of nucleotides of any length, either deoxyribonucleotides or ribonucleotides, or analogs thereof, isolated from its native environment, or that is artificially synthesized.

The term "protein mixture" as used herein, generally refers to a mixture of two or more types of proteins.

The term "homodimer" as used herein, generally refers to a molecule formed by two identical monomers (e.g., two identical members or subunits). The two monomers may aggregate, complex or associate with each other via covalent and/or non-covalent interactions. For example, the two monomers of a proteinaceous homodimer may associate with each other via interactions between interface amino acid residues from each of said two monomers.

The term "substantially comprises no" as used herein, generally refers that a composition (e.g., a mixture) comprises little or almost none of a substance. For example, said substance is present with a percentage of e.g., less than 10%, less than 9%, less than 8%, less than 7%, less than 6%, less than 5%, less than 4%, less than 3%, less than 2%, less than 1%, less than 0.5%, less than 0.1%, or less than 0.01%.

The term "pharmaceutically acceptable excipient" as used herein, generally refers to any and all solvents, dispersion media, coatings, isotonic and absorption delaying agents, etc., that are compatible with pharmaceutical administration.

Proteinaceous Heterodimers, Protein Mixtures, Isolated Polynucleotides, Vectors and Host Cells In one aspect, the present disclosure provides a proteinaceous heterodimer. The proteinaceous heterodimer may comprise a first member and a second member different from the first member. The first member may comprise a light chain and a heavy chain comprising a first Fc region, and the light chain may be complexed with the heavy chain to form a targeting moiety exhibiting binding specificity to a tumor antigen. The second member may comprise a polypeptide comprising an immunoregulator fused to a second Fc region. The first member may associate with the second member to form the heterodimer through complexation of the first Fc region with the second Fc region.

In some cases, the proteinaceous heterodimer of the present disclosure may be a proteinaceous complex. The complex may comprise at least three polypeptide chains, e.g., a first polypeptide chain, a second polypeptide chain, and a third polypeptide chain. In some embodiments, the complex consists of, or consists essentially of, three polypeptide chains. For example, the first polypeptide chain may comprise a heavy chain of an antibody specific for a tumor antigen, the second polypeptide chain may comprise a light chain of the antibody specific for the tumor antigen. The heavy chain may comprise the first Fc region. The heavy chain (i.e., of the first polypeptide chain) and the light chain (i.e., of the second polypeptide chain) may be complexed to form the first member of the proteinaceous heterodimer. The third polypeptide chain may comprise (e.g., from N-terminus to C-terminus) one or more immunoregulators fused to the second Fc region, optionally via one or more linkers. The third polypeptide chain may be the second member of the proteinaceous heterodimer. The first member may associate with the second member to form the heterodimer through complexation of the first Fc region with the second Fc region.

For example, the proteinaceous heterodimer of the present disclosure may be a proteinaceous complex, the complex may comprise (1) a heavy chain and a light chain of an antibody specific for a tumor antigen; and (2) a fusion protein comprising, from N-terminus to C-terminus, one or more immunoregulators fused to an antibody Fc region, optionally via one or more linkers.

The first Fc region may comprise a first modification and/or the second Fc region may comprise a second modification, wherein the first modification and/or the second modification may more effectively promote heterodimerization between the first member and the second member than a knob-and-hole modification comprising a knob modification and a hole modification. For example, the first modification may be in the CH3 domain of the first Fc region, and the second modification may be in the CH3 domain of the second Fc region. For example, the first modification and/or the second modification is in comparison to the sequence of its corresponding wildtype Fc region, respectively.

In some embodiments, the first Fc region comprises the first modification while the second Fc region does not comprise any modification, and said first modification more effectively promotes heterodimerization between the first member and the second member than the knob-and-hole modification comprising a knob modification and a hole modification.

In some embodiments, the second Fc region comprises the second modification while the first Fc region does not comprise any modification, and said second modification more effectively promotes heterodimerization between the first member and the second member than the knob-and-hole modification comprising a knob modification and a hole modification.

In some embodiments, the first Fc region comprises the first modification and the second Fc region comprises the second modification, wherein said first modification and said second modification more effectively promote heterodimerization between the first member and the second member than the knob-and-hole modification comprising a knob modification and a hole modification.

In some embodiments, the first modification is different from the knob modification or the hole modification, and/or the second modification is different from the knob modification or the hole modification. For example, the first modification may be different from the knob modification or the hole modification, while the second modification is the same as the hole modification. In some cases, the first modification is the same as the knob modification, while the second modification is different from the knob modification or the hole modification. In some embodiments, the first Fc region comprises the first modification, the second Fc region comprises the second modification, and neither the first modification nor the second modification is the same as the knob modification or the hole modification.

In some embodiments, the first modification comprises an amino acid substitution at position T366, and an amino acid substitution at one or more positions selected from the group consisting of: Y349, F405, K409, D399, K360, Q347, K392 and S354, wherein the position of the amino acid is determined according to the EU index of the KABAT number.

In some embodiments, the first modification comprises an amino acid substitution selected from the group consisting of Y349C, Y349D, D399S, F405K, K360E, K409A, K409E, Q347E, Q347R, S354D, K392D and T366W, wherein the position of the amino acid is determined according to the EU index of the KABAT number.

In some embodiments, the first modification comprises 2-5 amino acid substitutions.

In some embodiments, the first modification comprises an amino acid substitution at a group of positions selected from any of the following groups: 1) Y349 and T366; 2) Y349, T366 and F405; 3) Y349, T366 and K409; 4) Y349, T366, F405, K360 and Q347; 5) Y349, T366, F405 and Q347; 6) Y349, T366, K409, K360 and Q347; 7) Y349, T366, K409 and Q347; 8) T366, K409 and K392; 9) T366 and K409; 10) T366, K409, Y349 and S354; 11) T366 and F405; 12) T366, F405 and D399; and 13) T366, F405, Y349 and S354, wherein the position of the amino acid is determined according to the EU index of the KABAT number.

In some embodiments, the first modification comprises a group of amino acid substitutions selected from any of the following groups: 1) Y349C and T366W; 2) Y349C, T366W and F405K; 3) Y349C, T366W and K409E; 4) Y349C, T366W and K409A; 5) Y349C, T366W, F405K, K360E and Q347E; 6) Y349C, T366W, F405K and Q347R; 7) Y349C, T366W, K409A, K360E and Q347E; 8) Y349C, T366W, K409A and Q347R; 9) T366W, K409A and K392D; 10) T366W and K409A; 11) T366W, K409A and Y349D; 12) T366W, K409A, Y349D and S354D; 13) T366W and F405K; 14) T366W, F405K and D399S; 15) T366W, F405K and Y349D; and 16) T366W, F405K, Y349D and S354D, wherein the position of the amino acid is determined according to the EU index of the KABAT number.

In some embodiments, the second modification comprises amino acid substitutions at positions T366, L368 and Y407, as well as an amino acid substitution at one or more positions selected from the group consisting of D356, D399, E357, F405, K360, K392, K409 and Q347, wherein the position of the amino acid is determined according to the EU index of the KABAT number.

In some embodiments, the amino acid substitution comprised by the second modification is selected from the group consisting of D356C, D399S, E357A, F405K, K360E, K392D, K409A, L368A, L368G, Q347E, Q347R, T366S, Y407A and Y407V, wherein the position of the amino acid is determined according to the EU index of the KABAT number.

In some embodiments, the second modification comprises an amino acid substitution at 4-6 positions.

In some embodiments, the second modification comprises an amino acid substitution at a group of positions selected from any of the following groups: 1) D356, T366, L368, Y407 and F405; 2) D356, T366, L368 and Y407; 3) D356, T366, L368, Y407 and Q347; 4) D356, T366, L368, Y407, K360 and Q347; 5) D356, T366, L368, Y407, F405 and Q347; 6) D356, T366, L368, Y407, F405, K360 and Q347; 7) T366, L368, Y407, D399 and F405; 8) T366, L368, Y407 and F405; 9) T366, L368, Y407, F405 and E357; 10) T366, L368, Y407 and K409; 11) T366, L368, Y407, K409 and K392; and 12) T366, L368, Y407, K409 and E357, wherein the position of the amino acid is determined according to the EU index of the KABAT number.

In some embodiments, the second modification comprises a group of amino acid substitutions selected from any of the following groups: 1) D356C, T366S, L368A, Y407V and F405K; 2) D356C, T366S, L368A and Y407V; 3) D356C, T366S, L368A, Y407V and Q347R; 4) D356C, T366S, L368A, Y407V, K360E and Q347E; 5) D356C, T366S, L368A, Y407V, F405K and Q347R; 6) D356C, T366S, L368A, Y407V, F405K, K360E and Q347E; 7) T366S, L368A, Y407V, D399S and F405K; 8) T366S, L368G, Y407A and F405K; 9) T366S, L368A, Y407V, F405K and E357A; 10) T366S, L368A, Y407V and K409A; 11) T366S, L368A, Y407V, K409A and K392D; 12) T366S, L368G, Y407A and K409A; 13) T366S, L368A, Y407V, K409A and E357A, wherein the position of the amino acid is determined according to the EU index of the KABAT number.

In some embodiments, the first Fc region comprises the first modification, the second Fc region comprises the second modification, and the first modification and the second modification comprise an amino acid substitution at a group of positions selected from any of the following groups: 1) the first modification: Y349 and T366; and the second modification: D356, T366, L368, Y407 and F405; 2) the first modification: Y349, T366 and F405; and the second modification: D356, T366, L368 and Y407; 3) the first modification: Y349, T366 and K409; and the second modification: D356, T366, L368, Y407 and F405; 4) the first modification: Y349, T366, F405, K360 and Q347; and the second modification: D356, T366, L368, Y407 and Q347; 5) the first modification: Y349, T366, F405 and Q347; and the second modification: D356, T366, L368, Y407, K360 and Q347; 6) the first modification: Y349, T366, K409, K360 and Q347; and the second modification: D356, T366, L368, Y407, F405 and Q347; 7) the first modification: Y349, T366, K409 and Q347; and the second modification: D356, T366, L368, Y407, F405, K360 and Q347; 8) the first modification: T366, K409 and K392; and the second modification: T366, L368, Y407, D399 and F405; 9) the first modification: T366 and K409; and the second modification: T366, L368, Y407 and F405; 10) the first modification: T366, K409 and Y349; and the second modification: T366, L368, Y407, F405 and E357; 11) the first modification: T366, K409, Y349 and S354; and the second modification: T366, L368, Y407, F405 and E357; 12) the first modification: T366 and F405; and the second modification: T366, L368, Y407 and K409; 13) the first modification: T366, F405 and D399; and the second modification: T366, L368, Y407, K409 and K392; 14) the first modification: T366, F405 and Y349; and the second modification: T366, L368, Y407, K409 and E357; 15) the first modification: T366, F405, Y349 and S354; and the second modification: T366, L368, Y407, K409 and E357; wherein the position of the amino acid is determined according to the EU index of the KABAT number.

In some embodiments, the first Fc region comprises the first modification, the second Fc region comprises the second modification, wherein the first modification and the second modification comprise a group of amino acid substitutions selected from any of the following groups: 1) the first modification: Y349C and T366W; and the second modification: D356C, T366S, L368A, Y407V and F405K; 2) the first modification: Y349C, T366W and F405K; and the second modification: D356C, T366S, L368A and Y407V; 3) the first modification: Y349C, T366W and K409E; and the second modification: D356C, T366S, L368A, Y407V and F405K; 4) the first modification: Y349C, T366W and K409A; and the second modification: D356C, T366S, L368A, Y407V and F405K; 5) the first modification: Y349C, T366W, F405K, K360E and Q347E; and the second modification: D356C, T366S, L368A, Y407V and Q347R; 6) the first modification: Y349C, T366W, F405K and Q347R; and the second modification: D356C, T366S, L368A, Y407V, K360E and Q347E; 7) the first modification: Y349C, T366W, K409A, K360E and Q347E; and the second modification: D356C, T366S, L368A, Y407V, F405K and Q347R; 8) the first modification: Y349C, T366W, K409A and Q347R; and the second modification: D356C, T366S, L368A, Y407V, F405K, K360E and Q347E; 9) the first modification: T366W, K409A and K392D; and the second modification: T366S, L368A, Y407V, D399S and F405K; 10) the first modification: T366W and K409A; and the second modification: T366S, L368G, Y407A and F405K; 11) the first modification: T366W, K409A and Y349D; and the second modification: T366S, L368A, Y407V, F405K and E357A; 12) the first modification: T366W, K409A, Y349D and S354D; and the second modification: T366S, L368A, Y407V, F405K and E357A; 13) the first modification: T366W and F405K; and the second modification: T366S, L368A, Y407V and K409A; 14) the first modification: T366W, F405K and D399S; and the second modification: T366S, L368A, Y407V, K409A and K392D; 15) the first modification: T366W and F405K; and the second modification: T366S, L368G, Y407A and K409A; 16) the first modification: T366W, F405K and Y349D; and the second modification: T366S, L368A, Y407V, K409A and E357A; 17) the first modification: T366W, F405K, Y349D and S354D; and the second modification: T366S, L368A, Y407V, K409A and E357A; wherein the position of the amino acid is determined according to the EU index of the KABAT number.

In some embodiments, the first Fc region comprises the first modification, the second Fc region comprises the second modification, the first modification comprises the amino acid substitutions T366W and K409A, and the second modification comprises the amino acid substitutions T366S, L368G, Y407A and F405K, wherein the position of the amino acid is determined according to the EU index of the KABAT number.

In some embodiments, the knob-and-hole modification comprises a knob modification and a hole modification, wherein the knob modification comprises the amino acid substitutions Y349C and T366W, and the hole modification comprises the amino acid substitutions D356C, T366S, L368A and Y407V, wherein the position of the amino acid is determined according to the EU index of the KABAT number.

In some embodiments, when expressed in a mammalian cell, a yield of the proteinaceous heterodimer of the present disclosure is at least 10% (e.g., at least 15%, at least 20%, at least 25%, at least 30%, at least 35%, at least 40%, at least 45%, at least 50%, at least 55%, at least 60%, at least 65%, at least 70%, at least 75%, at least 80%, at least 85% or more) higher than that of a reference protein. The reference protein differs from the proteinaceous heterodimer in that the reference protein: i) comprises the knob modification in the first Fc region, ii) comprises the hole modification in the second Fc region, and iii) does not comprise the first modification and the second modification simultaneously. The mammalian cell may be selected from the group consisting of a HEK293 cell, a CHO cell, a COS-1 cell and a NS0 cell. In some embodiments, the knob modification comprises the amino acid substitutions Y349C and T366W, and the hole modification comprises the amino acid substitutions D356C, T366S, L368A and Y407V, wherein the position of the amino acid is determined according to the EU index of the KABAT number.

In some embodiments, the polypeptide comprised in the second member is a fusion protein, and a C-terminus of the immunoregulator is directly or indirectly fused to a N-terminus of the second Fc region to form the fusion protein. In some embodiments, the C-terminus of the immunoregulator is indirectly fused to the N-terminus of the second Fc region. For example, the second Fc region may be fused in frame to the immunoregulator via a linker. The linker may be a synthetic amino acid sequence that connects or links two polypeptide sequences, e.g., via peptide bonds. In some embodiments, a linker is a peptide comprising 1, 2, 3, 4, 5, 6, 7, 8, 9, 10, 11, 12, 13, 14, 15, 16, 17, 18, 19, 20, 21, 22, 23, 24, 25 or more amino acids. For example, the linker may comprise 1-10 amino acids (e.g., 1, 2, 3, 4, 5, 6, 7, 8, 9, 10 or more amino acids), 1-15 amino acids (e.g., 1-11, 12, 13, 14, 15 amino acids), 1-20 amino acids, 1-30 amino acids or more. In some embodiments, the linker comprises an amino acid sequence as set forth in SEQ ID NO: 79 or 88. In some embodiments, the linker is resistant to proteolysis or substantially resistant to proteolysis.

In some embodiments, the tumor antigen is selected from the group consisting of EGFR, an EGFR mutant, HER2/neu, GPC3, FAP, Muc1, MUC5AC and Mesothelin.

The light chain of the targeting moiety may contain CDRs comprising an amino acid sequence that is at least 60%, 70%, 75%, 80%, 85%, 90%, 95%, 96%, 97%, 98%, 99% or 100% identical to that comprised in corresponding CDRs of a light chain of an antibody specifically directed to a tumor antigen. In some embodiments, the light chain of the targeting moiety contains variable regions comprising an amino acid sequence that is at least 60%, 70%, 75%, 80%, 85%, 90%, 95%, 96%, 97%, 98%, 99% or 100% identical to that comprised in corresponding variable regions of a light chain of an antibody specifically directed to a tumor antigen. In some embodiments, the light chain of the targeting moiety contains an amino acid sequence that is at least 60%, 70%, 75%, 80%, 85%, 90%, 95%, 96%, 97%, 98%, 99% or 100% identical to that comprised in corresponding the amino acid sequence of a light chain of an antibody specifically directed to a tumor antigen.

The heavy chain of the targeting moiety may contain CDRs comprising an amino acid sequence that is at least 60%, 70%, 75%, 80%, 85%, 90%, 95%, 96%, 97%, 98%, 99% or 100% identical to that comprised in corresponding CDRs of a heavy chain of an antibody specifically directed to a tumor antigen. In some embodiments, the heavy chain of the targeting moiety contains variable regions comprising an amino acid sequence that is at least 60%, 70%, 75%, 80%, 85%, 90%, 95%, 96%, 97%, 98%, 99% or 100% identical to that comprised in corresponding variable regions of a heavy chain of an antibody specifically directed to a tumor antigen. In some embodiments, the heavy chain of the targeting moiety contains an amino acid sequence that is at least 60%, 70%, 75%, 80%, 85%, 90%, 95%, 96%, 97%, 98%, 99% or 100% identical to that comprised in corresponding the amino acid sequence of a heavy chain of an antibody specifically directed to a tumor antigen.

In some embodiments, the light chain of the targeting moiety contains CDRs comprising an amino acid sequence that is at least 60%, 70%, 75%, 80%, 85%, 90%, 95%, 96%, 97%, 98%, 99% or 100% identical to that comprised in corresponding CDRs of a light chain of an antibody specifically directed to a tumor antigen; and the heavy chain of the targeting moiety contains CDRs comprising an amino acid sequence that is at least 60%, 70%, 75%, 80%, 85%, 90%, 95%, 96%, 97%, 98%, 99% or 100% identical to that comprised in corresponding CDRs of a heavy chain of an antibody specifically directed to a tumor antigen.

In some embodiments, the light chain of the targeting moiety contains variable regions comprising an amino acid sequence that is at least 60%, 70%, 75%, 80%, 85%, 90%, 95%, 96%, 97%, 98%, 99% or 100% identical to that comprised in corresponding variable regions of a light chain of an antibody specifically directed to a tumor antigen; and the heavy chain of the targeting moiety contains variable regions comprising an amino acid sequence that is at least 60%, 70%, 75%, 80%, 85%, 90%, 95%, 96%, 97%, 98%, 99% or 100% identical to that comprised in corresponding variable regions of a heavy chain of an antibody specifically directed to a tumor antigen.

In some embodiments, the light chain of the targeting moiety contains an amino acid sequence comprising an amino acid sequence that is at least 60%, 70%, 75%, 80%, 85%, 90%, 95%, 96%, 97%, 98%, 99% or 100% identical to that comprised in corresponding the amino acid sequence of a light chain of an antibody specifically directed to a tumor antigen; and the heavy chain of the targeting moiety contains an amino acid sequence comprising an amino acid sequence that is at least 60%, 70%, 75%, 80%, 85%, 90%, 95%, 96%, 97%, 98%, 99% or 100% identical to that comprised in corresponding the amino acid sequence of a heavy chain of an antibody specifically directed to a tumor antigen.

The antibody specifically directed to a tumor antigen may be selected from the group consisting of anti-EGFR, anti-EGFR mutant, anti-HER2/neu, anti-GPC3, anti-FAP, anti-Muc1, anti-MUC5AC and anti-Mesothelin. In some embodiments, an anti-EGFR antibody is Cetuximab. In some embodiments, an anti-EGFR mutant antibody is an anti-EGFR variant III antibody, such as Mab806. In some embodiments, an anti-HER2/neu antibody is Trastuzumab or Pertuzumab. In some embodiments, an anti-GPC3 antibody is antibody codrituzumab. In some embodiments, an anti-FAP antibody is antibody 28H1. In some embodiments, an anti-Muc1 antibody is antibody 5E5, or a humanized version of antibody 5E5. In some embodiments, an anti-MUC5AC antibody is antibody ensituximab. In some embodiments, an anti-Mesothelin antibody is antibody amatuximab or a humanized version of the antibody amatuximab.

In some embodiments, the targeting moiety specifically binds to EGFR, the light chain of the first member comprises CDR1-3, the amino acid sequence of the CDR1 is as set forth in SEQ ID NO: 101 the amino acid sequence of the CDR2 is as set forth in SEQ ID NO: 102, and the amino acid sequence of the CDR3 is as set forth in SEQ ID NO: 103.

In some embodiments, the targeting moiety specifically binds to EGFR, the light chain of the first member comprises a light chain variable region, and the amino acid sequences of the light chain variable region is as set forth in SEQ ID NO: 104.

In some embodiments, the targeting moiety specifically binds to EGFR, and the amino acid sequence of the light chain of the first member is as set forth in SEQ ID NO: 37.

In some embodiments, the targeting moiety specifically binds to EGFR, the heavy chain of the first member comprises CDR1-3, the amino acid sequence of the CDR1 is as set forth in SEQ ID NO: 105, the amino acid sequence of the CDR2 is as set forth in SEQ ID NO: 106, the amino acid sequence of the CDR3 is as set forth in SEQ ID NO: 107.

In some embodiments, the targeting moiety specifically binds to EGFR, the heavy chain of the first member comprises a heavy chain variable region, and the amino acid sequence of the heavy chain variable region is as set forth in SEQ ID NO: 108.

In some embodiments, the targeting moiety specifically binds to EGFR, and the amino acid sequence of the heavy chain of the first member is as set forth in SEQ ID NO: 39.

In some embodiments, the targeting moiety specifically binds to EGFR, the light chain of the first member comprises light chain CDR1-3, the amino acid sequence of the light chain CDR1 is as set forth in SEQ ID NO: 101 the amino acid sequence of the light chain CDR2 is as set forth in SEQ ID NO: 102, and the amino acid sequence of the light chain CDR3 is as set forth in SEQ ID NO: 103; and the heavy chain of the first member comprises heavy chain CDR1-3, the amino acid sequence of the heavy chain CDR1 is as set forth in SEQ ID NO: 105, the amino acid sequence of the heavy chain CDR2 is as set forth in SEQ ID NO: 106, and the amino acid sequence of the heavy chain CDR3 is as set forth in SEQ ID NO: 107.

In some embodiments, the targeting moiety specifically binds to EGFR, the light chain of the first member comprises a light chain variable region, and the amino acid sequences of the light chain variable region is as set forth in SEQ ID NO: 104; and the heavy chain of the first member comprises a heavy chain variable region, and the amino acid sequence of the heavy chain variable region is as set forth in SEQ ID NO: 108.

In some embodiments, the targeting moiety specifically binds to EGFR, and the amino acid sequence of the light chain of the first member is as set forth in SEQ ID NO:37; and the amino acid sequence of the heavy chain of the first member is as set forth in SEQ ID NO: 39.

In some embodiments, the targeting moiety specifically binds to an EGFR mutant, the light chain of the first member comprises CDR1-3, the amino acid sequence of the CDR1 is as set forth in SEQ ID NO: 109, the amino acid sequence of the CDR2 is as set forth in SEQ ID NO: 110, and the amino acid sequence of the CDR3 is as set forth in SEQ ID NO: 111.

In some embodiments, the targeting moiety specifically binds to an EGFR mutant, the light chain of the first member comprises a light chain variable region, and the amino acid sequence of the light chain variable region is as set forth in SEQ ID NO: 112.

In some embodiments, the targeting moiety specifically binds to an EGFR mutant, and the amino acid sequence of the light chain of the first member is as set forth in SEQ ID NO: 53.

In some embodiments, the targeting moiety specifically binds to an EGFR mutant, the heavy chain of the first member comprises CDR1-3, the amino acid sequence of the CDR1 is as set forth in SEQ ID NO: 113, the amino acid sequence of the CDR2 is as set forth in SEQ ID NO: 114, and the amino acid sequence of the CDR3 is as set forth in SEQ ID NO: 115.

In some embodiments, the targeting moiety specifically binds to an EGFR mutant, the heavy chain of the first member comprises a heavy chain variable region, and the amino acid sequence of the heavy chain variable region is as set forth in SEQ ID NO: 116.

In some embodiments, the targeting moiety specifically binds to an EGFR mutant, and the amino acid sequence of the heavy chain of the first member is as set forth in SEQ ID NO: 55.

In some embodiments, the targeting moiety specifically binds to an EGFR mutant, the light chain of the first member comprises light chain CDR1-3, the amino acid sequence of the light chain CDR1 is as set forth in SEQ ID NO: 109, the amino acid sequence of the light chain CDR2 is as set forth in SEQ ID NO: 110, and the amino acid sequence of the light chain CDR3 is as set forth in SEQ ID NO: 111; and the heavy chain of the first member comprises heavy chain CDR1-3, the amino acid sequence of the heavy chain CDR1 is as set forth in SEQ ID NO: 113, the amino acid sequence of the heavy chain CDR2 is as set forth in SEQ ID NO: 114, and the amino acid sequence of the heavy chain CDR3 is as set forth in SEQ ID NO: 115.

In some embodiments, the targeting moiety specifically binds to an EGFR mutant, the light chain of the first member comprises a light chain variable region, and the amino acid sequences of the light chain variable region is as set forth in SEQ ID NO: 112; and the heavy chain of the first member comprises a heavy chain variable region, and the amino acid sequence of the heavy chain variable region is as set forth in SEQ ID NO: 116.

In some embodiments, the targeting moiety specifically binds to an EGFR mutant, and the amino acid sequence of the light chain of the first member is as set forth in SEQ ID NO: 53; and the amino acid sequence of the heavy chain of the first member is as set forth in SEQ ID NO: 55.

In some embodiments, the targeting moiety specifically binds to HER2/neu, the light chain of the first member comprises CDR1-3, the amino acid sequence of the CDR1 is selected from SEQ ID NO: 117 and 125, the amino acid sequence of the CDR2 is selected from SEQ ID NO: 118 and 126, the amino acid sequence of the CDR3 is selected from SEQ ID NO: 119 and 127.

In some embodiments, the targeting moiety specifically binds to HER2/neu, the light chain of the first member comprises a light chain variable region, and the amino acid sequence of the light chain variable region is selected from SEQ ID NO: 120 and 128.

In some embodiments, the targeting moiety specifically binds to HER2/neu, and the amino acid sequence of the light chain of the first member is selected from SEQ ID NO: 45 and 49.

In some embodiments, the targeting moiety specifically binds to HER2/neu, the heavy chain of the first member comprises CDR1-3, the amino acid sequence of the CDR1 is selected from SEQ ID NO: 121 and 129, the amino acid sequence of the CDR2 is selected from SEQ ID NO: 122 and 130, and the amino acid sequence of the CDR3 is selected from SEQ ID NO: 123 and 131.

In some embodiments, the targeting moiety specifically binds to HER2/neu, the antibody heavy chain of the first member comprises a heavy chain variable region, and the amino acid sequence of the heavy chain variable region is selected from SEQ ID NO: 124 and 132.

In some embodiments, the targeting moiety specifically binds to HER2/neu, and the amino acid sequence of the heavy chain of the first member is selected from SEQ ID NO: 47 and In some embodiments, the targeting moiety specifically binds to HER2/neu, the light chain of the first member comprises light chain CDR1-3, the amino acid sequence of the light chain CDR1 is selected from SEQ ID NO: 117 and 125, the amino acid sequence of the light chain CDR2 is selected from SEQ ID NO: 118 and 126, and the amino acid sequence of the light chain CDR3 is selected from SEQ ID NO: 119 and 127; and the heavy chain of the first member comprises heavy chain CDR1-3, the amino acid sequence of the heavy chain CDR1 is selected from SEQ ID NO: 121 and 129, the amino acid sequence of the heavy chain CDR2 is selected from SEQ ID NO: 122 and 130, and the amino acid sequence of the heavy chain CDR3 is selected from SEQ ID NO: 123 and 131.

In some embodiments, the targeting moiety specifically binds to HER2/neu, the light chain of the first member comprises a light chain variable region, and the amino acid sequences of the light chain variable region is selected from SEQ ID NO: 120 and 128; and the heavy chain of the first member comprises a heavy chain variable region, and the amino acid sequence of the heavy chain variable region is selected from SEQ ID NO: 124 and 132.

In some embodiments, the targeting moiety specifically binds to HER2/neu, and the amino acid sequence of the light chain of the first member is selected from SEQ ID NO: 45 and 49; and the amino acid sequence of the heavy chain of the first member is selected from SEQ ID NO: 47 and 51.

In some embodiments, the targeting moiety specifically binds to GPC3, the light chain of the first member comprises CDR1-3, the amino acid sequence of the CDR1 is as set forth in SEQ ID NO: 133, the amino acid sequence of the CDR2 is as set forth in SEQ ID NO: 134, and the amino acid sequence of the CDR3 is as set forth in SEQ ID NO: 135.

In some embodiments, the targeting moiety specifically binds to GPC3, the light chain of the first member comprises a light chain variable region, and the amino acid sequence of the light chain variable region is as set forth in SEQ ID NO: 136.

In some embodiments, the targeting moiety specifically binds to GPC3, and the amino acid sequence of the light chain of the first member is as set forth in SEQ ID NO: 57.

In some embodiments, the targeting moiety specifically binds to GPC3, the heavy chain of the first member comprises CDR1-3, the amino acid sequence of the CDR1 is as set forth in SEQ ID NO: 137, the amino acid sequence of the CDR2 is as set forth in SEQ ID NO: 138, and the amino acid sequence of the CDR3 is as set forth in SEQ ID NO: 139.

In some embodiments, the targeting moiety specifically binds to GPC3, the heavy chain of the first member comprises a heavy chain variable region, and the amino acid sequence of the heavy chain variable region is as set forth in SEQ ID NO: 140.

In some embodiments, the targeting moiety specifically binds to GPC3, and the amino acid sequence of the heavy chain of the first member is as set forth in SEQ ID NO: 59.

In some embodiments, the targeting moiety specifically binds to GPC3, the light chain of the first member comprises light chain CDR1-3, the amino acid sequence of the light chain CDR1 is as set forth in SEQ ID NO: 133, the amino acid sequence of the light chain CDR2 is as set forth in SEQ ID NO: 134, and the amino acid sequence of the light chain CDR3 is as set forth in SEQ ID NO: 135; and the heavy chain of the first member comprises heavy chain CDR1-3, the amino acid sequence of the heavy chain CDR1 is as set forth in SEQ ID NO: 137, the amino acid sequence of the heavy chain CDR2 is as set forth in SEQ ID NO: 138, and the amino acid sequence of the heavy chain CDR3 is as set forth in SEQ ID NO: 139.

In some embodiments, the targeting moiety specifically binds to GPC3, the light chain of the first member comprises a light chain variable region, and the amino acid sequences of the light chain variable region is as set forth in SEQ ID NO: 136; and the heavy chain of the first member comprises a heavy chain variable region, and the amino acid sequence of the heavy chain variable region is as set forth in SEQ ID NO: 140.

In some embodiments, the targeting moiety specifically binds to GPC3, and the amino acid sequence of the light chain of the first member is as set forth in SEQ ID NO: 57; and the amino acid sequence of the heavy chain of the first member is as set forth in SEQ ID NO: 59.

In some embodiments, the targeting moiety specifically binds to FAP, the light chain of the first member comprises CDR1-3, the amino acid sequence of the CDR1 is as set forth in SEQ ID NO: 141, the amino acid sequence of the CDR2 is as set forth in SEQ ID NO: 142, and the amino acid sequence of the CDR3 is as set forth in SEQ ID NO: 143.

In some embodiments, the targeting moiety specifically binds to FAP, the light chain of the first member comprises a light chain variable region, and the amino acid sequence of the light chain variable region is as set forth in SEQ ID NO: 144.

In some embodiments, the targeting moiety specifically binds to FAP, and the amino acid sequence of the light chain of the first member is as set forth in SEQ ID NO: 61.

In some embodiments, the targeting moiety specifically binds to FAP, the heavy chain of the first member comprises CDR1-3, the amino acid sequence of the CDR1 is as set forth in SEQ ID NO: 145, the amino acid sequence of the CDR2 is as set forth in SEQ ID NO: 146, and the amino acid sequence of the CDR3 is as set forth in SEQ ID NO: 147.

In some embodiments, the targeting moiety specifically binds to FAP, the heavy chain of the first member comprises a heavy chain variable region, and the amino acid sequence of the heavy chain variable region is as set forth in SEQ ID NO: 148.

In some embodiments, the targeting moiety specifically binds to FAP, and the amino acid sequence of the heavy chain of the first member is as set forth in SEQ ID NO: 63.

In some embodiments, the targeting moiety specifically binds to FAP, the light chain of the first member comprises light chain CDR1-3, the amino acid sequence of the light chain CDR1 is as set forth in SEQ ID NO: 141, the amino acid sequence of the light chain CDR2 is as set forth in SEQ ID NO: 142, and the amino acid sequence of the light chain CDR3 is as set forth in SEQ ID NO: 143; and the heavy chain of the first member comprises heavy chain CDR1-3, the amino acid sequence of the heavy chain CDR1 is as set forth in SEQ ID NO: 145, the amino acid sequence of the heavy chain CDR2 is as set forth in SEQ ID NO:146, and the amino acid sequence of the heavy chain CDR3 is as set forth in SEQ ID NO: 147.

In some embodiments, the targeting moiety specifically binds to FAP, the light chain of the first member comprises a light chain variable region, and the amino acid sequences of the light chain variable region is as set forth in SEQ ID NO: 148; and the chain of the first member comprises a heavy chain variable region, and the amino acid sequence of the heavy chain variable region is as set forth in SEQ ID NO: 152.

In some embodiments, the targeting moiety specifically binds to FAP, and the amino acid sequence of the light chain of the first member is as set forth in SEQ ID NO: 61; and the amino acid sequence of the heavy chain of the first member is as set forth in SEQ ID NO: 63.

In some embodiments, the targeting moiety specifically binds to Muc1, the antibody light chain of the first member comprises CDR1-3, the amino acid sequence of the CDR1 is as set forth in SEQ ID NO: 149, the amino acid sequence of the CDR2 is as set forth in SEQ ID NO: 150, and the amino acid sequence of the CDR3 is as set forth in SEQ ID NO: 151.

In some embodiments, the targeting moiety specifically binds to Muc1, the antibody light chain of the first member comprises a light chain variable region, and the amino acid sequence of the light chain variable region is as set forth in SEQ ID NO: 152.

In some embodiments, the targeting moiety specifically binds to Muc1, and the amino acid sequence of the light chain of the first member is as set forth in SEQ ID NO: 65.

In some embodiments, the targeting moiety specifically binds to Muc1, the heavy chain of the first member comprises CDR1-3, the amino acid sequence of the CDR1 is as set forth in SEQ ID NO: 153, the amino acid sequence of the CDR2 is as set forth in SEQ ID NO: 154, and the amino acid sequence of the CDR3 is as set forth in SEQ ID NO: 155.

In some embodiments, the targeting moiety specifically binds to Muc1, the heavy chain of the first member comprises a heavy chain variable region, and the amino acid sequence of the heavy chain variable region is as set forth in SEQ ID NO: 156.

In some embodiments, the targeting moiety specifically binds to Muc1, and the amino acid sequence of the heavy chain of the first member is as set forth in SEQ ID NO:67.

In some embodiments, the targeting moiety specifically binds to Muc1, the light chain of the first member comprises light chain CDR1-3, the amino acid sequence of the light chain CDR1 is as set forth in SEQ ID NO: 149, the amino acid sequence of the light chain CDR2 is as set forth in SEQ ID NO: 150, and the amino acid sequence of the light chain CDR3 is as set forth in SEQ ID NO: 151; and the heavy chain of the first member comprises heavy chain CDR1-3, the amino acid sequence of the heavy chain CDR1 is as set forth in SEQ ID NO: 153, the amino acid sequence of the heavy chain CDR2 is as set forth in SEQ ID NO: 154, and the amino acid sequence of the heavy chain CDR3 is as set forth in SEQ ID NO: 155.

In some embodiments, the targeting moiety specifically binds to Muc1, the light chain of the first member comprises a light chain variable region, and the amino acid sequences of the light chain variable region is as set forth in SEQ ID NO: 152; and the heavy chain of the first member comprises a heavy chain variable region, and the amino acid sequence of the heavy chain variable region is as set forth in SEQ ID NO: 156.

In some embodiments, the targeting moiety specifically binds to Muc1, and the amino acid sequence of the light chain of the first member is as set forth in SEQ ID NO: 65; and the amino acid sequence of the heavy chain of the first member is as set forth in SEQ ID NO: 67.

In some embodiments, the targeting moiety specifically binds to Mesothelin, the light chain of the first member comprises CDR1-3, the amino acid sequence of the CDR1 is as set forth in SEQ ID NO: 165, the amino acid sequence of the CDR2 is as set forth in SEQ ID NO: 166, and the amino acid sequence of the CDR3 is as set forth in SEQ ID NO: 167.

In some embodiments, the targeting moiety specifically binds to Mesothelin, the light chain of the first member comprises a light chain variable region, and the amino acid sequence of the light chain variable region is as set forth in SEQ ID NO: 168.

In some embodiments, the targeting moiety specifically binds to Mesothelin, and the amino acid sequence of the light chain of the first member is as set forth in SEQ ID NO: 73.

In some embodiments, the targeting moiety specifically binds to Mesothelin, the heavy chain of the first member comprises CDR1-3, the amino acid sequence of the CDR1 is as set forth in SEQ ID NO: 169, the amino acid sequence of the CDR2 is as set forth in SEQ ID NO:
170, and the amino acid sequence of the CDR3 is as set forth in SEQ ID NO: 171.

In some embodiments, the targeting moiety specifically binds to Mesothelin, the heavy chain of the first member comprises a heavy chain variable region, and the amino acid sequence of the heavy chain variable region is as set forth in SEQ ID NO: 172.

In some embodiments, the targeting moiety specifically binds to Mesothelin, and the amino acid sequence of the heavy chain of the first member is as set forth in SEQ ID NO: 75.

In some embodiments, the targeting moiety specifically binds to Mesothelin, the light chain of the first member comprises light chain CDR1-3, the amino acid sequence of the light chain CDR1 is as set forth in SEQ ID NO: 165, the amino acid sequence of the light chain CDR2 is as set forth in SEQ ID NO: 166, and the amino acid sequence of the light chain CDR3 is as set forth in SEQ ID NO: 167; and the heavy chain of the first member comprises heavy chain CDR1-3, the amino acid sequence of the heavy chain CDR1 is as set forth in SEQ ID NO: 169, the amino acid sequence of the heavy chain CDR2 is as set forth in SEQ ID NO: 170, and the amino acid sequence of the heavy chain CDR3 is as set forth in SEQ ID NO: 171.

In some embodiments, the targeting moiety specifically binds to Mesothelin, the light chain of the first member comprises a light chain variable region, and the amino acid sequences of the light chain variable region is as set forth in SEQ ID NO: 168; and the heavy chain of the first member comprises a heavy chain variable region, and the amino acid sequence of the heavy chain variable region is as set forth in SEQ ID NO: 172.

In some embodiments, the targeting moiety specifically binds to Mesothelin, and the amino acid sequence of the light chain of the first member is as set forth in SEQ ID NO: 73; and the amino acid sequence of the heavy chain of the first member is as set forth in SEQ ID NO: 75.

In some embodiments, the targeting moiety specifically binds to MUC5AC, the light chain of the first member comprises CDR1-3, the amino acid sequence of the CDR1 is as set forth in SEQ ID NO: 157, the amino acid sequence of the CDR2 is as set forth in SEQ ID NO:158, and the amino acid sequence of the CDR3 is as set forth in SEQ ID NO: 159.

In some embodiments, the targeting moiety specifically binds to MUC5AC, the light chain of the first member comprises a light chain variable region, and the amino acid sequence of the light chain variable region is as set forth in SEQ ID NO: 160.

In some embodiments, the targeting moiety specifically binds to MUC5AC, and the amino acid sequence of the light chain of the first member is as set forth in SEQ ID NO: 69.

In some embodiments, the targeting moiety specifically binds to MUC5AC, the heavy chain of the first member comprises CDR1-3, the amino acid sequence of the CDR1 is as set forth in SEQ ID NO: 161, the amino acid sequence of the CDR2 is as set forth in SEQ ID NO: 162, and the amino acid sequence of the CDR3 is as set forth in SEQ ID NO: 163.

In some embodiments, the targeting moiety specifically binds to MUC5AC, the heavy chain of the first member comprises a heavy chain variable region, and the amino acid sequence of the heavy chain variable region is as set forth in SEQ ID NO: 164.

In some embodiments, the targeting moiety specifically binds to MUC5AC, and the amino acid sequence of the heavy chain of the first member is as set forth in SEQ ID NO:71.

In some embodiments, the targeting moiety specifically binds to MUC5AC, the light chain of the first member comprises light chain CDR1-3, the amino acid sequence of the light chain CDR1 is as set forth in SEQ ID NO: 157, the amino acid sequence of the light chain CDR2 is as set forth in SEQ ID NO: 158, and the amino acid sequence of the light chain CDR3 is as set forth in SEQ ID NO: 159; and the heavy chain of the first member comprises heavy chain CDR1-3, the amino acid sequence of the heavy chain CDR1 is as set forth in SEQ ID NO: 161, the amino acid sequence of the heavy chain CDR2 is as set forth in SEQ ID NO: 162, and the amino acid sequence of the heavy chain CDR3 is as set forth in SEQ ID NO: 163.

In some embodiments, the targeting moiety specifically binds to MUC5AC, the light chain of the first member comprises a light chain variable region, and the amino acid sequences of the light chain variable region is as set forth in SEQ ID NO: 160; and the heavy chain of the first member comprises a heavy chain variable region, and the amino acid sequence of the heavy chain variable region is as set forth in SEQ ID NO: 164.

In some embodiments, the targeting moiety specifically binds to MUC5AC, and the amino acid sequence of the light chain of the first member is as set forth in SEQ ID NO: 69; and the amino acid sequence of the heavy chain of the first member is as set forth in SEQ ID NO:71.

In some embodiments, the immunoregulator augments an immune response. Examples of immunoregulators capable of augmenting an immune response include, without limitation, IL-2, IFNα, IFNβ, IFNγ, IFNλ, Tumor Necrosis Factor (TNF) α, IL-12, and IL-10.

In some embodiments, the immunoregulator reduces an immune response. Non-limiting examples of immunoregulators capable of reducing an immune response include IL-10, and Transforming Growth Factor (TGF)-β.

In some embodiments, the immunoregulator is a cytokine. For example, the immunoregulator may be a cytokine selected from the group consisting of an interferon, an interleukin, a chemokine, a lymphokine, and a tumor necrosis factor.

In some embodiments, the immunoregulator is an interferon selected from the group consisting of interferon alpha, interferon lambda and interferon beta.

In some embodiments, the immunoregulator is an interleukin, and the interleukin comprises interleukin 10, interleukin 2 and/or super interleukin 2.

In some embodiments, the first Fc region and the second Fc region is from an Fc region of an immunoglobulin. For example, the immunoglobulin may be selected from the group consisting of IgG1, IgG2, IgG3 and IgG4. In some embodiments, the first Fc region and the second Fc region are from an Fc region of an immunoglobulin, and the immunoglobulin is a human IgG1.

In some embodiments, the first modification and/or the second modification is in comparison to the wildtype amino acid sequence of the Fc region of human IgG1.

In some embodiments, the second Fc region is fused in frame to the immunoregulator.

In some embodiments, the polypeptide comprised in the second member comprises two or more immunoregulators, the two or more immunoregulators are fused in frame to each other and to the second Fc region, and wherein the two or more immunoregulators are located N-terminal to the second Fc region. In some embodiments, the two or more immunoregulators may be fused in-frame to each other and/or to the second Fc region via a linker. The linker may be a synthetic amino acid sequence that connects or links two polypeptide sequences, e.g., via peptide bonds. In some embodiments, a linker is a peptide comprising e.g., 1, 2, 3, 4, 5, 6, 7, 8, 9, 10, 11, 12, 13, 14, 15, 16, 17, 18, 19, 20, 21, 22, 23, 24, 25 or more amino acids. The two or more immunoregulators may be of the same type or may be of different types. For example, the two or more immunoregulators may be the same. In some embodiments, the two or more immunoregulators are interleukin 10.

In some embodiments, in the heavy chain of the first member, the amino acid sequence of the first Fc region is selected from SEQ ID NO:1, 4, 5, 6, 7, 9, 11, 13, 15, 17, 19, 21, 22, 24, 26, 27, and 29.

In some embodiments, the amino acid sequence of the immunoregulator comprised in the second member is selected from SEQ ID NO:173-180.

In some embodiments, the amino acid sequence of the second Fc region comprised in the second member is selected from SEQ ID NO:2, 3, 8, 10, 12, 14, 16, 18, 20, 23, 25, and 28.

In some embodiments, the amino acid sequence of the polypeptide comprised in the second member is selected from SEQ ID NO:77, 80, 82, 84, 86, 89, 91, and 97.

In some embodiments, the amino acid sequence of the light chain comprised in the first member is selected from SEQ ID NO: 37, 45, 49, 53, 57, 61, 65, 69, and 73, the amino acid sequence of the heavy chain comprised in the first member is selected from SEQ ID NO: 39, 47, 51, 55, 59, 63, 67, 71, and 75, and the amino acid sequence of the polypeptide comprised in the second member is selected from SEQ ID NO: 77, 80, 82, 84, 86, 89, 91, and 97.

In another aspect, the present disclosure provides a protein mixture, comprising: 1) the proteinaceous heterodimer according to the present disclosure; 2) a first homodimer formed by two of the first member of the proteinaceous heterodimer; and 3) a second homodimer formed by two of the second member of the proteinaceous heterodimer. The percentage of the proteinaceous heterodimer in the protein mixture may be at least 50% (e.g., at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, or more).

In some embodiments, in the protein mixture, the percentage of the second homodimer is less than the percentage of the first homodimer. For example, the percentage of the first homodimer may be at least 1.1 fold, at least 1.2 fold, at least 1.3 fold, at least 1.4 fold, at least 1.5 fold, at least 1.6 fold, at least 1.7 fold, at least 1.8 fold, at least 1.9 fold, at least 2.0 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3.0 fold, at least 3.1 fold, at least 3.2 fold, at least 3.5 fold, at least 4.0 fold, at least 4.5 fold, at least 5.0 fold, at least 5.5 fold, at least 6.0 fold, at least 7.0 fold, at least 8.0 fold or more than that of the second homodimer.

In some embodiments, the percentage of the second homodimer in the protein mixture is at most 10% (e.g., at most 0.0%, at most 0.01%, at most 0.1%, at most 0.5%, at most 1%, at most 1.5%, at most 2%, at most 3%, at most 4%, at most 5%, at most 6%, at most 7%, at most 8%, at most 9%). In some embodiments, the protein mixture substantially comprises none of the second homodimer.

In another aspect, the present disclosure provides an isolated polynucleotide encoding the proteinaceous heterodimer according to the present disclosure. In some embodiments, the isolated polynucleotide encodes a subunit (e.g., a member) or a fragment of the proteinaceous heterodimer according to the present disclosure.

The polynucleotide may be synthesized using recombinant techniques well known in the art. For example, the polynucleotide may be synthesized by use of an automated DNA synthesizer.

Standard recombinant DNA and molecular cloning techniques include those described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987). Briefly, the subject nucleic acids can be prepared from genomic DNA fragments, cDNAs, and RNAs, all of which can be extracted directly from a cell or recombinantly produced by various amplification processes including but not limited to PCR and RT-PCR.

Direct chemical synthesis of nucleic acids typically involves sequential addition of 3'-blocked and 5'-blocked nucleotide monomers to the terminal 5'-hydroxyl group of a growing nucleotide polymer chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. See for example, Matteuci et al., *Tet. Lett.* 521:719 (1980); U.S. Pat. No. 4,500,707 to Caruthers et al.; and U.S. Pat. Nos. 5,436,327 and 5,700,637 to Southern et al.

In another aspect, the present disclosure provides a vector comprising the isolated polynucleotide of the present disclosure.

The vector may be any linear nucleic acids, plasmids, phagemids, cosmids, RNA vectors, viral vectors and the like. Non-limiting examples of a viral vector may include a retrovirus, an adenovirus and an adeno-associated virus. In some embodiments, the vector is an expression vector, e.g. a phage display vector.

An expression vector may be suitable for use in particular types of host cells and not others. For example, the expression vector can be introduced into the host organism, which is then monitored for viability and expression of any genes/polynucleotides contained in the vector.

The expression vector may also contain one or more selectable marker genes that, upon expression, confer one or more phenotypic traits useful for selecting or otherwise identifying host cells that carry the expression vector. Non-limiting examples of suitable selectable markers for eukaryotic cells include dihydrofolate reductase and neomycin resistance.

The subject vectors can be introduced into a host cell stably or transiently by a variety of established techniques. For example, one method involves a calcium chloride treatment wherein the expression vector is introduced via a calcium precipitate. Other salts, for example calcium phosphate, may also be used following a similar procedure. In addition, electroporation (that is, the application of current to increase the permeability of cells to nucleic acids) may be used. Other examples of transformation methods include microinjection, DEAE dextran mediated transformation, and heat shock in the presence of lithium acetate. Lipid complexes, liposomes, and dendrimers may also be employed to transfect the host cells.

Upon introduction of the heterologous sequence into a host cell, a variety of methods can be practiced to identify the host cells into which the subject vectors have been introduced. One exemplary selection method involves subculturing individual cells to form individual colonies, followed by testing for expression of the desired protein product. Another method entails selecting host cells containing the heterologous sequence based upon phenotypic traits conferred through the expression of selectable marker genes contained within the expression vector.

For example, the introduction of various heterologous sequences of the disclosure into a host cell can be confirmed by methods such as PCR, Southern blot or Northern blot hybridization.

For example, nucleic acids can be prepared from the resultant host cells, and the specific sequences of interest can be amplified by PCR using primers specific for the sequences of interest. The amplified product is subjected to agarose gel electrophoresis, polyacrylamide gel electrophoresis or capillary electrophoresis, followed by staining with ethidium bromide, SYBR Green solution or the like, or detection of DNA with a UV detection. Alternatively, nucleic acid probes specific for the sequences of interest can be employed in a hybridization reaction. The expression of a specific gene sequence can be ascertained by detecting the corresponding mRNA via reverse-transcription coupled with PCR, Northern blot hybridization, or by immunoassays using antibodies reactive with the encoded gene product. Exemplary immunoassays include but are not limited to ELISA, radioimmunoassays, and sandwich immunoassays.

Furthermore, the introduction of various heterologous sequences of the disclosure into a host cell can be confirmed by the enzymatic activity of an enzyme (e.g., an enzymatic marker) that the heterologous sequence encodes. The enzyme can be assayed by a variety of methods known in the art. In general, the enzymatic activity can be ascertained by the formation of the product or conversion of a substrate of an enzymatic reaction that is under investigation. The reaction can take place in vitro or in vivo.

In another aspect, the present disclosure provides an isolated host cell, comprising the isolated polynucleotide or the vector of the present disclosure, and/or capable of expressing the proteinaceous heterodimer, and/or the isolated polynucleotide encoding the proteinaceous heterodimer, and/or the protein mixture of the present disclosure.

In some embodiments, the cell expresses the heterodimer protein of the present disclosure, the isolated polynucleotide encoding the heterodimer protein and/or the protein mixture of the present disclosure. The cell may be a eukaryotic cell or a prokaryotic cell. An appropriate cell may be transformed or transfected with the polynucleotide or vector of the present disclosure, and utilized for the expression and/or secretion of the heterodimer protein and/or protein mixtures. For example, the cell may be *E. coli* cells, other bacterial host cells, yeast cells, or various higher eukaryotic cells (e.g., immortal hybridoma cells, NS0 myeloma cells, HEK293 cells, Chinese hamster ovary cells, HeLa cells, COS cells, etc.). In some embodiments, polynucleotides encoding the proteinaceous heterodimer (e.g., a heterodimer protein) are operably connected to an expression control sequence suitable for expression in specific host cells.

Pharmaceutical Compositions

In another aspect, the present disclosure provides a pharmaceutical composition comprising the proteinaceous heterodimer according to the present disclosure, or the protein mixture according to the present disclosure. The pharmaceutical composition may further comprise a pharmaceutically acceptable excipient.

Examples of pharmaceutically acceptable excipients include, but are not limited to inert solid diluents and fillers, diluents, sterile aqueous solution and various organic solvents, permeation enhancers, solubilizers and adjuvants.

In some embodiments, the pharmaceutical composition is formulated for oral administration, intravenous administration, intramuscular administration, in-situ administration at the site of a tumor, inhalation, rectal administration, vaginal administration, transdermal administration, or administration via subcutaneous repository.

The pharmaceutical composition may be used for inhibiting tumor growth. For example, the pharmaceutical compositions may inhibit or delay the development or progress of a disease, may reduce tumor size (and even substantially eliminate tumors), and may alleviate and/or stabilize a disease condition.

Described below are non-limiting exemplary pharmaceutical compositions and methods for preparing the same.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition can further comprise a proteinaceous heterodimer (e.g., a heterodimer protein) or a protein mixture according to the present disclosure as an active ingredient and may include a conventional pharmaceutical carrier or excipient.

Further, it may include other medicinal or pharmaceutical agents, carriers, adjuvants, etc.

Exemplary parenteral administration forms include, but not limited to, solutions or suspensions of an active proteinaceous heterodimer (e.g., a heterodimer protein) in sterile aqueous solutions, for example, aqueous propylene glycol or dextrose solutions. Such dosage forms can be suitably buffered with salts such as histidine and/or phosphate, if desired.

In some embodiments, the present disclosure provides a pharmaceutical composition for injection containing a proteinaceous heterodimer (e.g., a heterodimer protein) or a protein mixture of the present disclosure and a pharmaceutical excipient suitable for injection.

Components and amounts of agents in the compositions are as described herein.

The forms in which the pharmaceutical compositions of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline may also be used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions can be prepared by incorporating the proteinaceous heterodimer (e.g., heterodimer protein) or a protein mixture of the present disclosure in a suitable amount in the appropriate solvent with various other ingredients as enumerated above, as needed, followed by filtered sterilization. Generally, dispersions are prepared by incorporating the various sterilized active ingredients into a sterile vehicle which contains the basic dispersion medium and other ingredients from those enumerated above, as needed or desired. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

In some embodiments, the present disclosure provides a pharmaceutical composition for oral administration containing a proteinaceous heterodimer (e.g., a heterodimer protein) or a protein mixture of the present disclosure, and a pharmaceutical excipient suitable for oral administration.

In some embodiments, the present disclosure provides a solid pharmaceutical composition for oral administration containing: (i) an amount of a proteinaceous heterodimer (e.g., a heterodimer protein) or a protein mixture of the disclosure; optionally (ii) an amount of a second agent; and (iii) a pharmaceutical excipient suitable for oral administration. In some embodiments, the composition further contains: (iv) an amount of a third agent. In some embodiments, amounts of the proteinaceous heterodimer or the protein mixture, second agent, and optional third agent are amounts that, alone or in combination, are effective in treating a condition of a subject.

In some embodiments, the pharmaceutical composition may be a liquid pharmaceutical composition suitable for oral consumption. Pharmaceutical compositions of the disclosure suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or nonaqueous liquid, an oil-in-water emulsion, or a water-in-oil liquid emulsion. Such dosage forms can be prepared by any of the methods of pharmacy, but all methods typically include the step of bringing the active ingredient into association with the carrier, which constitutes one or more other ingredients. In general, the compositions are prepared by uniformly and intimately admixing the active ingredient with liquid carriers or finely divided solid carriers or both, and then, if necessary, shaping the product into the desired presentation.

The present disclosure further encompasses anhydrous pharmaceutical compositions and dosage forms comprising an active ingredient (e.g., a proteinaceous heterodimer or a heterodimer protein of the present disclosure), since water can facilitate the degradation of some polypeptides. For example, water may be added (e.g., 5%) in the pharmaceutical arts as a means of simulating long-term storage in order to determine characteristics such as shelf-life or the stability of formulations over time. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

A proteinaceous heterodimer (e.g., a heterodimer protein or complex) or a protein mixture of the present disclosure can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period.

Surfactant which can be used to form pharmaceutical compositions and dosage forms of the disclosure include, but are not limited to, hydrophilic surfactants, lipophilic surfactants, and mixtures thereof. A mixture of hydrophilic surfactants may be employed, a mixture of lipophilic surfactants may be employed, or a mixture of at least one hydrophilic surfactant and at least one lipophilic surfactant may be employed.

In some embodiments, the composition includes a solubilizer to ensure good solubilization and/or dissolution of the proteinaceous heterodimer or the protein mixture of the present disclosure and to minimize precipitation of the proteinaceous heterodimer or protein mixture of the present disclosure. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons.

The pharmaceutical compositions of the present disclosure may comprise a therapeutically effective amount of the active agent (e.g., the proteinaceous heterodimer or the protein mixture of the present disclosure). A therapeutically effective amount is an amount of the subject pharmaceutical composition capable of preventing and/or curing (at least partially) a condition or disorder (e.g., cancer) and/or any complications thereof in a subject suffering from or having a risk of developing said condition or disorder. The specific amount/concentration of the active agent comprised may vary according to the method of administration and the need of a patient, and can be determined based on e.g., volume, viscosity, and/or body weight of a patient etc. For example, an appropriate dosage may be about 0.1 mg or 1 mg/kg/day to about 50 mg/kg/day; sometimes, the dosage can be even higher. In some embodiments, the dosage applied may be from about 3 mg/kg/day to about 3.5 mg/kg/day, from 3.5 mg/kg/day to about 7.2 mg/kg/day, from about 7.2 mg/kg/day to about 11.0 mg/kg/day, from about 11.0 mg/kg/day to about 15.0 mg/kg/day. In some embodiments, the dosage applied is from about 10 mg/kg/day to about 50 mg/kg/day, for example, from about 20 mg to about 50 mg per day, administered twice/day. It shall be understood that these specific doses may be conveniently adjusted by a skilled person in the art (e.g., a doctor or a pharmacist) based on conditions of a specific patient, formulation, and/or disease.

The proteinaceous heterodimer or the pharmaceutical composition of the present disclosure may also comprise one or more additional therapeutically active component. Such additional therapeutically active component may be present separately in the composition, or may be attached to, conjugated to or associated with the proteinaceous heterodimer of the present disclosure.

Medical Use and Methods of Treatment

In another aspect, the present disclosure provides a use of the proteinaceous heterodimer, or the protein mixture according to the present disclosure in the manufacture of a medicament and/or a kit for inhibiting growth of a tumor or a tumor cell. In some embodiments, the medicament and/or kit is used for specifically and/or preferentially inhibiting growth or differentiation of target cells (e.g., cancer cells) or killing target cells (e.g., cancer cells).

In another aspect, the present disclosure provides a method for inhibiting growth of a tumor or a tumor cell. The method may comprise contacting the tumor or tumor cell with an effective amount of the proteinaceous heterodimer according to the present disclosure, or the protein mixture according to the present disclosure. In some embodiments, the contacting occurs in vitro. In some embodiments, the contacting occurs in vivo.

In some embodiments, said contacting includes systemically or locally administering the proteinaceous heterodimer (e.g., a heterodimer protein), the protein mixture, the pharmaceutical composition or the medicament of the present disclosure to a subject (e.g., a mammal). In some embodiments, said contacting includes administering the proteinaceous heterodimer (e.g., a heterodimer protein), the protein mixture, the pharmaceutical composition, or the medicament of the present disclosure directly at the site of a tumor. In some embodiments, the administering is conducted by oral administration, intravenous administration, intramuscular administration, in-situ administration at the site of a tumor, inhalation, rectal administration, vaginal administration, transdermal administration or administration via subcutaneous repository.

In some embodiments, the tumor (e.g., cancer) or tumor cell (e.g., a cancer cell) is or is from a solid tumor. For example, the cancer may be selected from the group consisting of a B cell lymphoma, a lung cancer, a bronchus cancer, a colorectal cancer, a prostate cancer, a breast cancer, a pancreas cancer, a stomach cancer, an ovarian cancer, a urinary bladder cancer, a brain or central nervous system cancer, a peripheral nervous system cancer, an esophageal cancer, a cervical cancer, a melanoma, a uterine or endometrial cancer, a cancer of the oral cavity or pharynx, a liver cancer, a kidney cancer, a biliary tract cancer, a small bowel or appendix cancer, a salivary gland cancer, a thyroid gland cancer, an adrenal gland cancer, an osteosarcoma, a chondrosarcoma, a liposarcoma, a testes cancer, and a malignant fibrous histiocytoma.

In some embodiments, the cancer or cancer cell is within the body of a subject, e.g., a cancer or cancer cell within a human or in a non-human animal (e.g., a mammal).

In some embodiments, the mammal is a human. In some embodiments, the mammal is a mouse, a rat, a cat, a dog, a rabbit, a pig, a sheep, a horse, a bovine, a goat, a gerbil, a hamster, a guinea pig, a monkey or any other mammal. Many such mammals may be subjects that are known to the art as preclinical models for certain diseases or disorders, including solid tumors and/or other cancers (e.g., Talmadge et al., 2007 Am. J. Pathol. 170:793; Kerbel, 2003 Canc. Biol. Therap. 2(4 Suppl 1):S134; Man et al., 2007 Canc. Met. Rev. 26:737; Cespedes et al., 2006 Clin. TransL Oncol. 8:318).

Method for Preparing Proteinaceous Heterodimers or Protein Mixtures

In another aspect, the present disclosure provides a method of producing a proteinaceous heterodimer or a protein mixture comprising the proteinaceous heterodimer, comprising (i) culturing the host cell of the present disclosure under conditions to effect expression of the proteinaceous heterodimer, and (ii) harvesting the expressed proteinaceous heterodimer or a protein mixture (such as the protein mixture of the present disclosure) comprising the expressed proteinaceous heterodimer.

In some embodiments, the method of producing a proteinaceous heterodimer comprises the following steps:

(1) providing a first member of the heterodimer, wherein the first member comprises a light chain and a heavy chain comprising a first Fc region, wherein the light chain is complexed with the heavy chain to form a targeting moiety exhibiting binding specificity to a tumor antigen;

(2) providing a second member of said heterodimer, the second member is different from the first member, wherein the second member comprises a polypeptide comprising an immunoregulator fused to a second Fc region; the first member associates with the second member to form the heterodimer through complexation of the first Fc region with the second Fc region; and the first Fc region comprises a first modification and/or the second Fc region comprises a second modification, wherein the first modification and/or the second modification more effectively promote heterodimerization between the first member and the second member than a knob-and-hole modification comprising a knob modification and a hole modification; and 3) obtaining the proteinaceous heterodimer.

In some embodiments, the method further comprises the steps of isolating and/or purifying the proteinaceous heterodimer or the protein mixture.

In some embodiments, the method further comprises the steps of transfecting/transforming host cells with polynucleotides/vectors encoding/expressing the heterodimer of the present disclosure, one or more members thereof, or fragments thereof.

In some embodiments, the proteinaceous heterodimer or the protein mixture of the present disclosure is produced by expressing a vector in a cell under conditions suitable for protein expression. In some embodiments, the proteinaceous heterodimer or the protein mixture of the present disclosure is produced in a single cell clone.

Factors that may vary among suitable conditions for protein expression include factors such as incubation time, temperature, and medium, and may depend on cell type and will be readily determined by one of ordinary skill in the art.

In some embodiments, during the process of producing the proteinaceous heterodimer or the protein mixture of the present disclosure, the host cells are grown in cultures, and in any apparatus that may be used to grow cultures, including fermenters. Cells may be grown as monolayers or attached to a surface. Alternatively, the host cells may be grown in suspension. The cells can be grown in a culture medium that is serum-free. The media can be a commercially available media, such as, but not limited to, Opti-CHO (Invitrogen, Catalogue #12681) supplemented with glutamine, such as 8 mM L-glutamine; RPMI 1640 medium, supplemented with 10% bovine calf serum, 10.5 ng/ml mIL-3 and L-glutamine; or 5% FCS medium.

The present disclosure includes the following embodiments:

1. A proteinaceous heterodimer comprising a first member and a second member different from said first member, wherein: said first member comprises a light chain and a heavy chain comprising a first Fc region, the light chain is complexed with the heavy chain to form a targeting moiety exhibiting binding specificity to a tumor antigen; said second member comprises a polypeptide comprising an immunoregulator fused to a second Fc region; said first member associates with said second member to form said heterodimer through complexation of said first Fc region with said second Fc region; and said first Fc region comprises a first modification and/or said second Fc region comprises a second modification, wherein said first modification and/or said second modification more effectively promotes heterodimerization between said first member and said second member than a knob-and-hole modification comprising a knob modification and a hole modification.

2. The proteinaceous heterodimer according to embodiment 1, wherein said first modification is different from said knob modification or said hole modification, and/or said second modification is different from said knob modification or said hole modification.

3. The proteinaceous heterodimer according to any one of the preceding embodiments, wherein when expressed in a mammalian cell, a yield of the proteinaceous heterodimer is at least 10% higher than that of a reference protein, and the reference protein differs from the proteinaceous heterodimer in that the reference protein: i) comprises the knob modification in said first Fc region, ii) comprises the hole modification in said second Fc region, and iii) does not comprise said first modification and said second modification simultaneously.

4. The proteinaceous heterodimer of embodiment 3, wherein said mammalian cell is selected from the group consisting of a HEK293 cell, a CHO cell, a COS-1 cell and a NS0 cell.

5. The proteinaceous heterodimer according to any one of the preceding embodiments, wherein said first Fc region comprises the first modification, said second Fc region comprises the second modification, and neither the first modification nor the second modification is the same as the knob modification or the hole modification.

6. The proteinaceous heterodimer according to any one of the preceding embodiments, wherein the polypeptide comprised in the second member is a fusion protein, and a C-terminus of the immunoregulator is directly or indirectly fused to a N-terminus of the second Fc region to form the fusion protein.

7. The proteinaceous heterodimer according to any one of the preceding embodiments, wherein the tumor antigen is selected from the group consisting of EGFR, an EGFR mutant, HER2/neu, GPC3, FAP, Muc1, MUC5AC and Mesothelin.

8. The proteinaceous heterodimer according to any one of the preceding embodiments, wherein the light chain of the targeting moiety contains CDRs comprising an amino acid sequence that is at least 60%, 70%, 75%, 80%, 85%, 90%, 95%, 96%, 97%, 98%, 99% or 100% identical to that comprised in corresponding CDRs of a light chain of an antibody specifically directed to a tumor antigen.

9. The proteinaceous heterodimer according to any one of the preceding embodiments, wherein the light chain of the targeting moiety contains variable regions comprising an amino acid sequence that is at least 60%, 70%, 75%, 80%, 85%, 90%, 95%, 96%, 97%, 98%, 99% or 100% identical to that comprised in corresponding variable regions of a light chain of an antibody specifically directed to a tumor antigen.

10. The proteinaceous heterodimer according to any one of the preceding embodiments, wherein the light chain of the targeting moiety contains an amino acid sequence that is at least 60%, 70%, 75%, 80%, 85%, 90%, 95%, 96%, 97%, 98%, 99% or 100% identical to that comprised in corresponding the amino acid sequence of a light chain of an antibody specifically directed to a tumor antigen.

11. The proteinaceous heterodimer according to any one of the preceding embodiments, wherein the heavy chain of the targeting moiety contains CDRs comprising an amino acid sequence that is at least 60%, 70%, 75%, 80%, 85%, 90%, 95%, 96%, 97%, 98%, 99% or 100% identical to that comprised in corresponding CDRs of a heavy chain of an antibody specifically directed to a tumor antigen.

12. The proteinaceous heterodimer according to any one of the preceding embodiments, wherein the heavy chain of the targeting moiety contains variable regions comprising an amino acid sequence that is at least 60%, 70%, 75%, 80%, 85%, 90%, 95%, 96%, 97%, 98%, 99% or 100% identical to that comprised in corresponding variable regions of a heavy chain of an antibody specifically directed to a tumor antigen.

13. The proteinaceous heterodimer according to any one of the preceding embodiments, wherein the heavy chain of the targeting moiety contains an amino acid sequence that is at least 60%, 70%, 75%, 80%, 85%, 90%, 95%, 96%, 97%, 98%, 99% or 100% identical to that comprised in corresponding the amino acid sequence of a heavy chain of an antibody specifically directed to a tumor antigen.

14. The proteinaceous heterodimer according to any one of the preceding embodiments, wherein the light chain of the targeting moiety contains CDRs comprising an amino acid sequence that is at least 60%, 70%, 75%, 80%, 85%, 90%, 95%, 96%, 97%, 98%, 99% or 100% identical to that comprised in corresponding CDRs of a light chain of an antibody specifically directed to a tumor antigen; and the heavy chain of the targeting moiety contains CDRs comprising an amino acid sequence that is at least 60%, 70%, 75%, 80%, 85%, 90%, 95%, 96%, 97%, 98%, 99% or 100% identical to that comprised in corresponding CDRs of a heavy chain of an antibody specifically directed to a tumor antigen.

15. The proteinaceous heterodimer according to any one of the preceding embodiments, wherein the light chain of the targeting moiety contains variable regions comprising an amino acid sequence that is at least 60%, 70%, 75%, 80%, 85%, 90%, 95%, 96%, 97%, 98%, 99% or 100% identical to that comprised in corresponding variable regions of a light chain of an antibody specifically directed to a tumor antigen; and the heavy chain of the targeting moiety contains variable regions comprising an amino acid sequence that is at least 60%, 70%, 75%, 80%, 85%, 90%, 95%, 96%, 97%, 98%, 99% or 100% identical to that comprised in corresponding variable regions of a heavy chain of an antibody specifically directed to a tumor antigen.

16. The proteinaceous heterodimer according to any one of the preceding embodiments, wherein the light chain of the targeting moiety contains an amino acid sequence comprising an amino acid sequence that is at least 60%, 70%, 75%, 80%, 85%, 90%, 95%, 96%, 97%, 98%, 99% or 100% identical to that comprised in corresponding the amino acid sequence of a light chain of an antibody specifically directed to a tumor antigen; and the heavy chain of the targeting moiety contains an amino acid sequence comprising an amino acid sequence that is at least 60%, 70%, 75%, 80%, 85%, 90%, 95%, 96%, 97%, 98%, 99% or 100% identical to that comprised in corresponding the amino acid sequence of a heavy chain of an antibody specifically directed to a tumor antigen.

17. The proteinaceous heterodimer of anyone of embodiments 8-16, wherein the antibody specifically directed to a tumor antigen is selected from the group consisting of anti-EGFR, anti-EGFR mutant, anti-HER2/neu, anti-GPC3, anti-FAP, anti-Muc1, anti-MUC5AC and anti-Mesothelin.

18. The proteinaceous heterodimer according to any one of the preceding embodiments, wherein the immunoregulator augments an immune response.

19. The proteinaceous heterodimer according to any one of embodiments 1-17, wherein the immunoregulator reduces an immune response.

20. The proteinaceous heterodimer according to any one of the preceding embodiments, wherein the immunoregulator is a cytokine.

21. The proteinaceous heterodimer according to embodiment 20, wherein the immunoregulator is a cytokine selected from the group consisting of an interferon, an interleukin, a chemokine, a lymphokine, and a tumor necrosis factor.

22. The proteinaceous heterodimer according to embodiment 21, wherein the immunoregulator is an interferon selected from the group consisting of interferon alpha, interferon lambda and interferon beta.

23. The proteinaceous heterodimer according to embodiment 21, wherein the immunoregulator is an interleukin, and the interleukin comprises interleukin 10, interleukin 2 and/or super interleukin 2.

24. The proteinaceous heterodimer according to any one of the preceding embodiments, wherein the first Fc region and the second Fc region is from an Fc region of an immunoglobulin, and said immunoglobulin is selected from the group consisting of IgG1, IgG2, IgG3 and IgG4.

25. The proteinaceous heterodimer according to embodiment 24, wherein the first Fc region and the second Fc region is from an Fc region of an immunoglobulin, and the immunoglobulin is a human IgG1.

26. The proteinaceous heterodimer according to any one of the preceding embodiments, wherein the second Fc region is fused in frame to the immunoregulator.

27. The proteinaceous heterodimer according to any one of the preceding embodiments, wherein the second Fc region is fused in frame to the immunoregulator via a linker.

28. The proteinaceous heterodimer according to any one of the preceding embodiments, wherein the polypeptide comprised in the second member comprises two or more immunoregulators, said two or more immunoregulators are fused in frame to each other and to the second Fc region, and wherein said two or more immunoregulators are located N-terminal to the second Fc region.

29. The proteinaceous heterodimer according to embodiment 28, wherein said two or more immunoregulators are the same.

30. The proteinaceous heterodimer according to any one of the preceding embodiments, wherein the first modification comprises an amino acid substitution at position T366, and an amino acid substitution at one or more positions selected from the group consisting of: Y349, F405, K409, D399, K360, Q347, K392 and S354, wherein the position of the amino acid is determined according to the EU index of the KABAT number.

31. The proteinaceous heterodimer according to embodiment 30, wherein the first modification comprises an amino acid substitution selected from the group consisting of Y349C, Y349D, D399S, F405K, K360E, K409A, K409E, Q347E, Q347R, S354D, K392D and T366W.

32. The proteinaceous heterodimer according to embodiment 30 or 31, wherein the first modification comprises 2-5 amino acid substitutions.

33. The proteinaceous heterodimer of any one of embodiments 30-32, wherein the first modification comprises an amino acid substitution at a group of positions selected from any of the following groups: 1) Y349 and T366; 2) Y349, T366 and F405; 3) Y349, T366 and K409; 4) Y349, T366, F405, K360 and Q347; 5) Y349, T366, F405 and Q347; 6) Y349, T366, K409, K360 and Q347; 7) Y349, T366, K409 and Q347; 8) T366, K409 and K392; 9) T366 and K409; 10) T366, K409, Y349 and S354; 11) T366 and F405; 12) T366, F405 and D399; and 13) T366, F405, Y349 and S354.

34. The proteinaceous heterodimer of any one of embodiments 30-33, wherein the first modification comprises a group of amino acid substitutions selected from any of the following groups: 1) Y349C and T366W; 2) Y349C, T366W and F405K; 3) Y349C, T366W and K409E; 4) Y349C, T366W and K409A; 5) Y349C, T366W, F405K, K360E and Q347E; 6) Y349C, T366W, F405K and Q347R; 7) Y349C, T366W, K409A, K360E and Q347E; 8) Y349C, T366W, K409A and Q347R; 9) T366W, K409A and K392D; 10) T366W and K409A; 11) T366W, K409A and Y349D; 12) T366W, K409A, Y349D and S354D; 13) T366W and F405K; 14) T366W, F405K and D399S; 15) T366W, F405K and Y349D; and 16) T366W, F405K, Y349D and S354D.

35. The proteinaceous heterodimer of any one of embodiments 30-34, wherein the second modification comprises amino acid substitutions at positions T366, L368 and Y407, as well as an amino acid substitution at one or more positions selected from the group consisting of D356, D399, E357, F405, K360, K392, K409 and Q347, wherein the position of the amino acid is determined according to the EU index of the KABAT number.

36. The proteinaceous heterodimer according to embodiment 35, wherein the amino acid substitution comprised by the second modification is selected from the group consisting of D356C, D399S, E357A, F405K, K360E, K392D, K409A, L368A, L368G, Q347E, Q347R, T366S, Y407A and Y407V.

37. The proteinaceous heterodimer according to embodiment 35 or 36, wherein the second modification comprises an amino acid substitution at 4-6 positions.

38. The proteinaceous heterodimer of any one of embodiments 35-37, wherein the second modification comprises an amino acid substitution at a group of positions selected from any of the following groups: 1) D356, T366, L368, Y407 and F405; 2) D356, T366, L368 and Y407; 3) D356, T366, L368, Y407 and Q347; 4) D356, T366, L368, Y407, K360 and Q347; 5) D356, T366, L368, Y407, F405 and Q347; 6) D356, T366, L368, Y407, F405, K360 and Q347; 7) T366, L368, Y407, D399 and F405; 8) T366, L368, Y407 and F405; 9) T366, L368, Y407, F405 and E357; 10) T366, L368, Y407 and K409; 11) T366, L368, Y407, K409 and K392; and 12) T366, L368, Y407, K409 and E357.

39. The proteinaceous heterodimer of any one of embodiments 35-38, wherein the second modification comprises a group of amino acid substitutions selected from any of the following groups: 1) D356C, T366S, L368A, Y407V and F405K; 2) D356C, T366S, L368A and Y407V; 3) D356C, T366S, L368A, Y407V and Q347R; 4) D356C, T366S, L368A, Y407V, 360E and Q347E; 5) D356C, T366S, L368A, Y407V, F405K and Q347R; 6) D356C, T366S, L368A, Y407V, F405K, K360E and Q347E; 7) T366S, L368A, Y407V, D399S and F405K; 8) T366S, L368G, Y407A and F405K; 9) T366S, L368A, Y407V, F405K and E357A; 10) T366S, L368A, Y407V and K409A; 11) T366S, L368A, Y407V, K409A and K392D; 12) T366S, L368G, Y407A and K409A; 13) T366S, L368A, Y407V, K409A and E357A.

40. The proteinaceous heterodimer according to any one of the preceding embodiments, wherein the first Fc region comprises the first modification, the second Fc region comprises the second modification, and the first modification and the second modification comprise an amino acid substitution at a group of positions selected from any of the following groups: 1) the first modification: Y349 and T366; and the second modification: D356, T366, L368, Y407 and F405; 2) the first modification: Y349, T366 and F405; and the second modification: D356, T366, L368 and Y407; 3) the first modification: Y349, T366 and K409; and the second modification: D356, T366, L368, Y407 and F405; 4) the first modification: Y349, T366, F405, K360 and Q347; and the second modification: D356, T366, L368, Y407 and Q347; 5) the first modification: Y349, T366, F405 and Q347; and the second modification: D356, T366, L368, Y407, K360 and Q347; 6) the first modification: Y349, T366, K409, K360 and Q347; and the second modification: D356, T366, L368, Y407, F405 and Q347; 7) the first modification: Y349, T366, K409 and Q347; and the second modification: D356, T366, L368, Y407, F405, K360 and Q347; 8) the first modification: T366, K409 and K392; and the second modification: T366, L368, Y407, D399 and F405; 9) the first modification: T366 and K409; and the second modification: T366, L368, Y407 and F405; 10) the first modification: T366, K409 and Y349; and the second modification: T366, L368, Y407, F405 and E357; 11) the first modification: T366, K409, Y349 and S354; and the second modification: T366, L368, Y407, F405 and E357; 12) the first modification: T366 and F405; and the second modification: T366, L368, Y407 and K409; 13) the first modification: T366, F405 and D399; and the second modification: T366, L368, Y407, K409 and K392; 14) the first modification: T366, F405 and Y349; and the second modification: T366, L368, Y407, K409 and E357; 15) the first modification: T366, F405, Y349 and S354; and the second modification: T366, L368, Y407, K409 and E357; wherein the position of the amino acid is determined according to the EU index of the KABAT number.

41. The proteinaceous heterodimer according to any one of the preceding embodiments, wherein the first Fc region comprises the first modification, the second Fc region comprises the second modification, wherein the first modification and the second modification comprise a group of amino acid substitutions selected from any of the following groups: 1) the first modification: Y349C and T366W; and the second modification: D356C, T366S, L368A, Y407V and F405K; 2) the first modification: Y349C, T366W and F405K; and the second modification: D356C, T366S, L368A and Y407V; 3) the first modification: Y349C, T366W and K409E; and the second modification: D356C, T366S, L368A, Y407V and F405K; 4) the first modification: Y349C, T366W and K409A; and the second modification: D356C, T366S, L368A, Y407V and F405K; 5) the first modification: Y349C, T366W, F405K, K360E and Q347E; and the second modification: D356C, T366S, L368A, Y407V and Q347R; 6) the first modification: Y349C, T366W, F405K and Q347R; and the second modification: D356C, T366S, L368A, Y407V, K360E and Q347E; 7) the first modification: Y349C, T366W, K409A, K360E and Q347E; and the second modification: D356C, T366S, L368A, Y407V, F405K and Q347R; 8) the first modification: Y349C, T366W, K409A and Q347R; and the second modification: D356C, T366S, L368A, Y407V, F405K, K360E and Q347E; 9) the first modification: T366W, K409A and K392D; and the second modification: T366S, L368A, Y407V, D399S and F405K; 10) the first modification: T366W and K409A; and the second modification: T366S, L368G, Y407A and F405K; 11) the first modification: T366W, K409A and Y349D; and the second modification: T366S, L368A, Y407V, F405K and E357A; 12) the first modification: T366W, K409A, Y349D and S354D; and the second modification: T366S, L368A, Y407V, F405K and E357A; 13) the first modification: T366W and F405K; and the second modification: T366S, L368A, Y407V and K409A; 14) the first modification: T366W, F405K and D399S; and the second modification: T366S, L368A, Y407V, K409A and K392D; 15) the first modification: T366W and F405K; and the second modification: T366S, L368G, Y407A and K409A; 16) the first modification: T366W, F405K and Y349D; and the second modification: T366S, L368A, Y407V, K409A and E357A; 17) the first modification: T366W, F405K, Y349D and S354D; and the second modification: T366S, L368A, Y407V, K409A and E357A; wherein the position of the amino acid is determined according to the EU index of the KABAT number.

42. The proteinaceous heterodimer according to embodiment 41, wherein the first Fc region comprises the first modification, the second Fc region comprises the second modification, the first modification comprises the amino acid substitutions T366W and K409A, and the second modification comprises the amino acid substitutions T366S, L368G, Y407A and F405K, wherein the position of the amino acid is determined according to the EU index of the KABAT number.

43. The proteinaceous heterodimer according to any one of the preceding embodiments, wherein the targeting moiety specifically binds to EGFR, the light chain of the first member comprises CDR1-3, the amino acid sequence of the CDR1 is selected from SEQ ID NO: 101, the amino acid sequence of the CDR2 is selected from SEQ ID NO: 102, and the amino acid sequence of the CDR3 is selected from SEQ ID NO: 103.

44. The proteinaceous heterodimer according to any one of the preceding embodiments, wherein the targeting moiety specifically binds to EGFR, the light chain of the first member comprises a light chain variable region, and the amino acid sequences of the light chain variable region is selected from SEQ ID NO:104.

45. The proteinaceous heterodimer according to any one of the preceding embodiments, wherein the targeting moiety specifically binds to EGFR, and the amino acid sequence of the light chain of the first member is selected from SEQ ID NO: 37.

46. The proteinaceous heterodimer according to any one of embodiments 43-45, wherein the targeting moiety specifically binds to EGFR, the heavy chain of the first member comprises CDR1-3, the amino acid sequence of the CDR1 is selected from SEQ ID NO:105, the amino acid sequence of the CDR2 is selected from SEQ ID NO: 106, the amino acid sequence of the CDR3 is selected from SEQ ID NO: 107.

47. The proteinaceous heterodimer according to any one of embodiments 43-45, wherein the targeting moiety specifically binds to EGFR, the heavy chain of the first member comprises a heavy chain variable region, and the amino acid sequence of the heavy chain variable region is selected from SEQ ID NO: 108.

48. The proteinaceous heterodimer according to any one of embodiments 43-45, wherein the targeting moiety specifically binds to EGFR, and the amino acid sequence of the heavy chain of the first member is selected from SEQ ID NO: 39.

49. The proteinaceous heterodimer according to any one of embodiments 1-42, wherein the targeting moiety specifically binds to an EGFR mutant, the light chain of the first member comprises CDR1-3, the amino acid sequence of the CDR1 is selected from SEQ ID NO: 109, the amino acid sequence of the CDR2 is selected from SEQ ID NO: 110, and the amino acid sequence of the CDR3 is selected from SEQ ID NO: 111.

50. The proteinaceous heterodimer according to any one of embodiments 1-42, wherein the targeting moiety specifically binds to an EGFR mutant, the light chain of the first member comprises a light chain variable region, and the amino acid sequence of the light chain variable region is selected from SEQ ID NO: 112.

51. The proteinaceous heterodimer according to any one of embodiments 1-42, wherein the targeting moiety specifically binds to an EGFR mutant, and the amino acid sequence of the light chain of the first member is selected from SEQ ID NO: 53.

52. The proteinaceous heterodimer according to any one of embodiments 49-51, wherein the targeting moiety specifically binds to an EGFR mutant, the heavy chain of the first member comprises CDR1-3, the amino acid sequence of the CDR1 is selected from SEQ ID NO: 113, the amino acid sequence of the CDR2 is selected from SEQ ID NO: 114, and the amino acid sequence of the CDR3 is selected from SEQ ID NO: 115.

53. The proteinaceous heterodimer according to any one of embodiments 49-51, wherein the targeting moiety specifically binds to an EGFR mutant, the heavy chain of the first member comprises a heavy chain variable region, and the amino acid sequence of the heavy chain variable region is selected from SEQ ID NO: 116.

54. The proteinaceous heterodimer according to any one of embodiments 49-51, wherein the targeting moiety specifically binds to an EGFR mutant, and the amino acid sequence of the heavy chain of the first member is selected from SEQ ID NO: 55.

55. The proteinaceous heterodimer according to any one of embodiments 1-42, wherein the targeting moiety specifically binds to HER2/neu, the light chain of the first member comprises CDR1-3, the amino acid sequence of the CDR1 is selected from SEQ ID NO: 117 and 125, the amino acid sequence of the CDR2 is selected from SEQ ID NO: 118 and 126, the amino acid sequence of the CDR3 is selected from SEQ ID NO: 119 and 127.

56. The proteinaceous heterodimer according to any one of embodiments 1-42, wherein the targeting moiety specifically binds to HER2/neu, the light chain of the first member comprises a light chain variable region, and the amino acid sequence of the light chain variable region is selected from SEQ ID NO: 120 and 128.

57. The proteinaceous heterodimer according to any one of embodiments 1-42, wherein the targeting moiety specifically binds to HER2/neu, and the amino acid sequence of the light chain of the first member is selected from SEQ ID NO: 45 and 49.

58. The proteinaceous heterodimer according to any one of embodiments 55-57, wherein the targeting moiety specifically binds to HER2/neu, the heavy chain of the first member comprises CDR1-3, the amino acid sequence of the CDR1 is selected from SEQ ID NO: 121 and 129, the amino acid sequence of the CDR2 is selected from SEQ ID NO: 122 and 130, and the amino acid sequence of the CDR3 is selected from SEQ ID NO: 123 and 131.

59. The proteinaceous heterodimer according to any one of embodiments 55-57, wherein the targeting moiety specifically binds to HER2/neu, the antibody heavy chain of the first member comprises a heavy chain variable region, and the amino acid sequence of the heavy chain variable region is selected from SEQ ID NO: 124 and 132.

60. The proteinaceous heterodimer according to any one of embodiments 55-57, wherein the targeting moiety specifically binds to HER2/neu, and the amino acid sequence of the heavy chain of the first member is selected from SEQ ID NO: 47 and 51.

61. The proteinaceous heterodimer according to any one of embodiments 1-42, wherein the targeting moiety specifically binds to GPC3, the antibody light chain of the first member comprises CDR1-3, the amino acid sequence of the CDR1 is selected from SEQ ID NO: 133, the amino acid sequence of the CDR2 is selected from SEQ ID NO: 134, and the amino acid sequence of the CDR3 is selected from SEQ ID NO: 135.

62. The proteinaceous heterodimer according to any one of embodiments 1-42, wherein the targeting moiety specifically binds to GPC3, the antibody light chain of the first member comprises a light chain variable region, and the amino acid sequence of the light chain variable region is selected from SEQ ID NO: 136.

63. The proteinaceous heterodimer according to any one of embodiments 1-42, wherein the targeting moiety specifically binds to GPC3, and the amino acid sequence of the light chain of the first member is selected from SEQ ID NO: 57.

64. The proteinaceous heterodimer according to any one of embodiments 61-63, wherein the targeting moiety specifically binds to GPC3, the antibody heavy chain of the first member comprises CDR1-3, the amino acid sequence of the CDR1 is selected from SEQ ID NO: 137, the amino acid sequence of the CDR2 is selected from SEQ ID NO: 138, and the amino acid sequence of the CDR3 is selected from SEQ ID NO: 139.

65. The proteinaceous heterodimer according to any one of embodiments 61-63, wherein the targeting moiety specifically binds to GPC3, the antibody heavy chain of the first member comprises a heavy chain variable region, and the amino acid sequence of the heavy chain variable region is selected from SEQ ID NO: 140.

66. The proteinaceous heterodimer according to any one of embodiments 61-63, wherein the targeting moiety specifically binds to GPC3, and the amino acid sequence of the heavy chain of the first member is selected from SEQ ID NO: 59.

67. The proteinaceous heterodimer according to any one of embodiments 1-42, wherein the targeting moiety specifically binds to FAP, the antibody light chain of the first member comprises CDR1-3, the amino acid sequence of the CDR1 is selected from SEQ ID NO: 141, the amino acid sequence of the CDR2 is selected from SEQ ID NO: 142, and the amino acid sequence of the CDR3 is selected from SEQ ID NO: 143.

68. The proteinaceous heterodimer according to any one of embodiments 1-42, wherein the targeting moiety specifically binds to FAP, the antibody light chain of the first member comprises a light chain variable region, and the amino acid sequence of the light chain variable region is selected from SEQ ID NO:144.

69. The proteinaceous heterodimer according to any one of embodiments 1-42, wherein the targeting moiety specifically binds to FAP, and the amino acid sequence of the light chain of the first member is selected from SEQ ID NO:61.

70. The proteinaceous heterodimer according to any one of embodiments 67-69, wherein the targeting moiety specifically binds to FAP, the antibody heavy chain of the first member comprises CDR1-3, the amino acid sequence of the CDR1 is selected from SEQ ID NO: 145, the amino acid sequence of the CDR2 is selected from SEQ ID NO: 146, and the amino acid sequence of the CDR3 is selected from SEQ ID NO: 147.

71. The proteinaceous heterodimer according to any one of embodiments 67-69, wherein the targeting moiety specifically binds to FAP, the antibody heavy chain of the first member comprises a heavy chain variable region, and the amino acid sequence of the heavy chain variable region is selected from SEQ ID NO:148.

72. The proteinaceous heterodimer according to any one of embodiments 67-69, wherein the targeting moiety specifically binds to FAP, and the amino acid sequence of the heavy chain of the first member is selected from SEQ ID NO: 63.

73. The proteinaceous heterodimer according to any one of embodiments 1-42, wherein the targeting moiety specifically binds to Muc1, the antibody light chain of the first member comprises CDR1-3, the amino acid sequence of the CDR1 is selected from SEQ ID NO: 149, the amino acid sequence of the CDR2 is selected from SEQ ID NO: 150, and the amino acid sequence of the CDR3 is selected from SEQ ID NO: 151.

74. The proteinaceous heterodimer according to any one of embodiments 1-42, wherein the targeting moiety specifically binds to Muc1, the antibody light chain of the first member comprises a light chain variable region, and the amino acid sequence of the light chain variable region is selected from SEQ ID NO: 152.

75. The proteinaceous heterodimer according to any one of embodiments 1-42, wherein the targeting moiety specifically binds to Muc1, and the amino acid sequence of the light chain of the first member is selected from SEQ ID NO: 65.

76. The proteinaceous heterodimer according to any one of embodiments 73-75, wherein the targeting moiety specifically binds to Muc1, the antibody heavy chain of the first member comprises CDR1-3, the amino acid sequence of the CDR1 is selected from SEQ ID NO: 153, the amino acid sequence of the CDR2 is selected from SEQ ID NO: 154, and the amino acid sequence of the CDR3 is selected from SEQ ID NO: 155.

77. The proteinaceous heterodimer according to any one of embodiments 73-75, wherein the targeting moiety specifically binds to Muc1, the antibody heavy chain of the first member comprises a heavy chain variable region, and the amino acid sequence of the heavy chain variable region is selected from SEQ ID NO: 156.

78. The proteinaceous heterodimer according to any one of embodiments 73-75, wherein the targeting moiety specifically binds to Muc1, and the amino acid sequence of the heavy chain of the first member is selected from SEQ ID NO:67.

79. The proteinaceous heterodimer according to any one of embodiments 1-42, wherein the targeting moiety specifically binds to Mesothelin, the antibody light chain of the first member comprises CDR1-3, the amino acid sequence of the CDR1 is selected from SEQ ID NO: 165, the amino acid sequence of the CDR2 is selected from SEQ ID NO: 166, and the amino acid sequence of the CDR3 is selected from SEQ ID NO: 167.

80. The proteinaceous heterodimer according to any one of embodiments 1-42, wherein the targeting moiety specifically binds to Mesothelin, the antibody light chain of the first member comprises a light chain variable region, and the amino acid sequence of the light chain variable region is selected from SEQ ID NO: 168.

81. The proteinaceous heterodimer according to any one of embodiments 1-42, wherein the targeting moiety specifically binds to Mesothelin, and the amino acid sequence of the light chain of the first member is selected from SEQ ID NO: 73.

82. The proteinaceous heterodimer according to any one of embodiments 79-81, wherein the targeting moiety specifically binds to Mesothelin, the antibody heavy chain of the first member comprises CDR1-3, the amino acid sequence of the CDR1 is selected from SEQ ID NO: 169, the amino acid sequence of the CDR2 is selected from SEQ ID NO: 170, and the amino acid sequence of the CDR3 is selected from SEQ ID NO: 171.

83. The proteinaceous heterodimer according to any one of embodiments 79-81, wherein the targeting moiety specifically binds to Mesothelin, the antibody heavy chain of the first member comprises a heavy chain variable region, and the amino acid sequence of the heavy chain variable region is selected from SEQ ID NO: 172.

84. The proteinaceous heterodimer according to any one of embodiments 79-81, wherein the targeting moiety specifically binds to Mesothelin, and the amino acid sequence of the heavy chain of the first member is selected from SEQ ID NO: 75.

85. The proteinaceous heterodimer according to any one of embodiments 1-42, wherein the targeting moiety specifically binds to MUC5AC, the antibody light chain of the first member comprises CDR1-3, the amino acid sequence of the CDR1 is selected from SEQ ID NO: 157, the amino acid sequence of the CDR2 is selected from SEQ ID NO: 158, and the amino acid sequence of the CDR3 is selected from SEQ ID NO: 159.

86. The proteinaceous heterodimer according to any one of embodiments 1-42, wherein the targeting moiety specifically binds to MUC5AC, the antibody light chain of the first member comprises a light chain variable region, and the amino acid sequence of the light chain variable region is selected from SEQ ID NO: 160.

87. The proteinaceous heterodimer according to any one of embodiments 1-42, wherein the targeting moiety specifically binds to MUC5AC, and the amino acid sequence of the light chain of the first member is selected from SEQ ID NO: 69.

88. The proteinaceous heterodimer according to any one of embodiments 85-87, wherein the targeting moiety specifically binds to MUC5AC, the antibody heavy chain of the first member comprises CDR1-3, the amino acid sequence of the CDR1 is selected from SEQ ID NO: 161, the amino acid sequence of the CDR2 is selected from SEQ ID NO: 162, and the amino acid sequence of the CDR3 is selected from SEQ ID NO: 163.

89. The proteinaceous heterodimer according to any one of embodiments 85-87, wherein the targeting moiety specifically binds to MUC5AC, the antibody heavy chain of the first member comprises a heavy chain variable region, and the amino acid sequence of the heavy chain variable region is selected from SEQ ID NO: 164.

90. The proteinaceous heterodimer according to any one of embodiments 85-87, wherein the targeting moiety specifically binds to MUC5AC, and the amino acid sequence of the heavy chain of the first member is selected from SEQ ID NO:71.

91. The proteinaceous heterodimer according to any one of the preceding embodiments, wherein in the heavy chain of the first member, the amino acid sequence of the first Fc region is selected from SEQ ID NO: 1, 4, 5, 6, 7, 9, 11, 13, 15, 17, 19, 21, 22, 24, 26, 27, and 29.

92. The proteinaceous heterodimer according to any one of the preceding embodiments, wherein the amino acid sequence of the immunoregulator comprised in the second member is selected from SEQ ID NO: 173-180.

93. The proteinaceous heterodimer according to any one of the preceding embodiments, wherein the amino acid sequence of the second Fc region comprised in the second member is selected from SEQ ID NO: 2, 3, 8, 10, 12, 14, 16, 18, 20, 23, 25, and 28.

94. The proteinaceous heterodimer according to any one of the preceding embodiments, wherein the amino acid sequence of the polypeptide comprised in the second member is selected from SEQ ID NO: 77, 80, 82, 84, 86, 89, 91, and 97.

95. The proteinaceous heterodimer according to any one of the preceding embodiments, wherein the amino acid sequence of the light chain comprised in the first member is SEQ ID NO: 37, 45, 49, 53, 57, 61, 65, 69, and 73, the amino acid sequence of the heavy chain comprised in the first member is SEQ ID NO: 39, 47, 51, 55, 59, 63, 67, 71, and 75, and the amino acid sequence of the polypeptide comprised in the second member is SEQ ID NO: 77, 80, 82, 84, 86, 89, 91, and 97.

96. The proteinaceous heterodimer according to any one of the preceding embodiments, wherein said knob-and-hole modification comprises a knob modification and a hole modification, wherein the knob modification comprises the amino acid substitutions Y349C and T366W, and the hole modification comprises the amino acid substitutions D356C, T366S, L368A and Y407V, wherein the position of the amino acid is determined according to the EU index of the KABAT number.

97. An isolated polynucleotide encoding the proteinaceous heterodimer according to any one of the preceding embodiments.

98. A vector comprising the isolated polynucleotide of embodiment 97.

99. An isolated host cell, comprising the isolated polynucleotide of embodiment 97 or the vector of embodiment 98.

100. A protein mixture, comprising: 1) the proteinaceous heterodimer according to any one of embodiments 1-96; 2) a first homodimer formed by two of said first member of said proteinaceous heterodimer; and 3) a second homodimer formed by two of said second member of said proteinaceous heterodimer; wherein the percentage of said proteinaceous heterodimer in said protein mixture is at least 50%.

101. The protein mixture of embodiment 100, wherein the percentage of the second homodimer is less than the percentage of the first homodimer.

102. The protein mixture of embodiment 100 or 101, where the percentage of the second homodimer is at most 10%.

103. The protein mixture of embodiment 102, wherein the protein mixture substantially comprises no said second homodimer.

104. A pharmaceutical composition comprising the proteinaceous heterodimer according to any one of embodiments 1-96; or the protein mixture according to any one of embodiments 100-103, and optionally a pharmaceutically acceptable excipient.

105. The pharmaceutical composition of embodiment 104, wherein the composition is formulated for oral administration, intravenous administration, intramuscular administration, in-situ administration at the site of a tumor, inhalation, rectal administration, vaginal administration, transdermal administration, or administration via subcutaneous repository.

106. Use of the proteinaceous heterodimer according to any one of embodiments 1-96, or the protein mixture according to any one of embodiments 100-103 in the manufacture of a medicament and/or a kit for inhibiting growth of a tumor or a tumor cell.

107. A method for inhibiting growth of a tumor or a tumor cell, comprising contacting said tumor or tumor cell with an effective amount of the proteinaceous heterodimer according to any one of embodiments 1-96, or the protein mixture according to any one of embodiments 100-103.

108. The method of embodiment 107, wherein said contacting occurs in vitro or in vivo.

109. A method of producing a proteinaceous heterodimer or a protein mixture comprising a proteinaceous heterodimer, comprising (i) culturing the host cell of claim 99 under conditions to effect expression of the proteinaceous heterodimer, and (ii) harvesting the expressed proteinaceous heterodimer or a protein mixture comprising said proteinaceous heterodimer.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

It is intended that the following claims define the scope of the disclosure and that methods and structures within the scope of these claims and their equivalents be covered thereby.

EXAMPLES

The examples and preparations provided below further illustrate and exemplify the proteinaceous heterodimer of the present disclosure and methods of using and preparing thereof. It is to be understood that the scope of the present disclosure is not limited in any way by the scope of the following examples and preparations.

Example 1 Modification and Preparation of Polypeptides 1.1 Determining Amino Acid Modifications in the Fc Regions CH3-CH3 domain interface amino acid residues were determined for human IgG1. Wildtype human IgG1 comprises a first heavy chain (chain A) and a second heavy chain (chain B), and the interface amino acids in each of chain A and chain B are shown in table 1 below, the position of the amino acid is determined according to the EU index of the KABAT number:

TABLE 1

| CH3-CH3 interface residues in wildtype human IgG1 antibody Fc regions (PDB No. 1DN2) ||
|---|---|
| Interface residues in chain A | Interface residues in chain B |
| Gln347 | Lys360 |
| Val348 | Glu356 |
| Tyr349 | Ser354, Glu356, Glu357, Lys360 |
| Thr350 | Ser354, Glu356 |
| Leu351 | Leu351, Pro352, Pro353, Ser354, Thr366 |
| Pro352 | Leu351, Pro352 |
| Pro353 | Leu351 |
| Ser354 | Tyr349, Thr350, Leu351 |
| Glu356 | Val348, Tyr349, Thr350, Lys439 |
| Glu357 | Tyr349, Leu368, Lys370 |
| Lys360 | Gln347, Tyr349, Lys370 |
| Gln362 | Lys370 |
| Val363 | Lys370 |
| Ser364 | Leu368, Lys370, Tyr407 |
| Leu365 | Tyr407 |
| Thr366 | Leu351, Leu368, Tyr407 |
| Leu368 | Glu357, Ser364, Thr366, Lys409 |

TABLE 1-continued

CH3-CH3 interface residues in wildtype human
IgG1 antibody Fc regions (PDB No. 1DN2)

| Interface residues in chain A | Interface residues in chain B |
|---|---|
| Lys370 | Glu357, Lys360, Gln362, Ser364, Lys409, Thr411 |
| Asn390 | Ser400 |
| Lys392 | Val397, Leu398, Asp399, Ser400, Phe405 |
| Thr393 | Val397 |
| Thr394 | Thr394, Val397, Phe405, Tyr407 |
| Pro395 | Pro395, Val397 |
| Val397 | Lys392, Thr393, Thr394, Pro395 |
| Leu398 | Lys392 |
| Asp399 | Lys392, Lys409, Thr411 |
| Ser400 | Asn390, Lys392 |
| Phe405 | Lys392, Thr394, Tyr407, Lys409 |
| Leu406 | Thr394 |
| Tyr407 | Thr366, Thr394, Phe405, Tyr407, Lys409 |
| Ser408 | Tyr407 |
| Lys409 | Leu368, Lys370, Asp399, Phe405, Tyr407 |
| Thr411 | Lys370, Asp399 |
| Lys439A | Glu356B |

Then, amino acid modifications (e.g., amino acid substitutions) were made to the interface residues to obtain the following groups of modifications (as shown in table 2 below, the reference KH refers to the knob-and-hole modifications), chain A is also referred to as Fc9 or the first Fc region, and chain B is also referred to as Fc6 or the second Fc region in the present disclosure:

Subsequently, formation of heterodimer proteins comprising the groups of modifications listed in Table 2 above were examined using a ScFv-Fc/Fc system, as explained in detail below.

First of all, human immunoglobulin gamma 1 (IgG1) constant region amino acid sequence was obtained from the database Uniprot (P01857), to get wildtype human IgG1-Fc region amino acid sequence (SEQ ID NO: 30). The polynucleotide fragment encoding wild type human IgG1-Fc was obtained by RT-PCR from human PBMC total RNA (SEQ ID NO: 31, named as the Fc gene fragment). A polynucleotide fragment encoding a mouse kappaIII signal peptide (SEQ ID NO: 32) was added to the 5' end of the Fc gene by overlapping PCR, and then subcloned into the vector pcDNA4 (Invitrogen, Cat V86220), to obtain a recombinant expression vector for expressing human IgG1-Fc in mammalian cells.

In some cases, a polypeptide encoding a variable region of a camel single domain antibody (VhH) was fused to the N terminal of the Fc gene fragment to obtain a fusion gene fragment (as set forth in SEQ ID NO: 33) encoding the fusion protein VhH-Fc (as set forth in SEQ ID NO: 34). It was then subcloned into the vector pcDNA4 (Invitrogen, Cat V86220), to obtain a recombinant expression vector for expressing the fusion protein VhH-Fc in mammalian cells.

A nucleic acid molecule encoding a ScFv-Fc fusion protein (SEQ ID NO: 35) was synthesized, wherein the ScFv refers to an anti-Her2 single chain antibody, the amino acid

TABLE 2

Groups of amino acid modifications

| Group | Fc Chain | Modifications | SEQ ID NO |
|---|---|---|---|
| Reference (KH) | A | Y349C + T366W | 1 |
| | B | D356C + T366S + L368A + Y407V | 2 |
| 1 | A | Y349C + T366W | 1 |
| | B | D356C + T366S + L368A + Y407V + F405K | 3 |
| 2 | A | Y349C + T366W + F405K | 4 |
| | B | D356C + T366S + L368A + Y407V | 2 |
| 3 | A | Y349C + T366W + K409E | 5 |
| | B | D356C + T366S + L368A + Y407V + F405K | 3 |
| 4 | A | Y349C + T366W + K409A | 6 |
| | B | D356C + T366S + L368A + Y407V + F405K | 3 |
| 5 | A | Y349C + T366W + F405K + K360E + Q347E | 7 |
| | B | D356C + T366S + L368A + Y407V + Q347R | 8 |
| 6 | A | Y349C + T366W + F405K + Q347R | 9 |
| | B | D356C + T366S + L368A + Y407V + K360E + Q347E | 10 |
| 7 | A | Y349C + T366W + K409A + K360E + Q347E | 11 |
| | B | D356C + T366S + L368A + Y407V + F405K + Q347R | 12 |
| 8 | A | Y349C + T366W + K409A + Q347R | 13 |
| | B | D356C + T366S + L368A + Y407V + F405K + K360E + Q347E | 14 |
| 9 | A | T366W + K409A + K392D | 15 |
| | B | T366S + L368A + Y407V + D399S + F405K | 16 |
| 10 | A | T366W + K409A | 17 |
| | B | T366S + L368G + Y407A + F405K | 18 |
| 11 | A | T366W + K409A + Y349D | 19 |
| | B | T366S + L368A + Y407V + F405K + E357A | 20 |
| 12 | A | T366W + K409A + Y349D + S354D | 21 |
| | B | T366S + L368A + Y407V + F405K + E357A | 20 |
| 13 | A | T366W + F405K | 22 |
| | B | T366S + L368A + Y407V + K409A | 23 |
| 14 | A | T366W + F405K + D399S | 24 |
| | B | T366S + L368A + Y407V + K409A + K392D | 25 |
| 15 | A | T366W + F405K | 22 |
| | B | T366S + L368G + Y407A + K409A | 26 |
| 16 | A | T366W + F405K + Y349D | 27 |
| | B | T366S + L368A + Y407V + K409A + E357A | 28 |
| 17 | A | T366W + F405K + Y349D + S354D | 29 |
| | B | T366S + L368A + Y407V + K409A + E357A | 28 | sequence of the ScFv-Fc fusion protein is as set forth in SEQ ID NO: 36. The ScFv-Fc gene fragment was then subcloned into the vector pcDNA4 (Invitrogen, Cat V86220), to obtain a recombinant expression vector for expressing the ScFv-Fc fusion protein in mammalian cells.

Then, the amino acid modifications as listed in Table 2 above were respectively introduced into the ScFv-Fc (groups KH and 1-17), the VhH-Fc (groups 9-12, 14, 15 and 17), and the Fc gene fragment (groups KH and 1-8) by overlapping PCR, wherein chain A refers to the Fc region in ScFv-Fc and chain B refers to the independent Fc region or the Fc region in VhH-Fc. The gene fragments with amino acid modifications were respectively subcloned into the vector pcDNA4 (Invitrogen, Cat V86220), to obtain recombinant expression vectors for expressing the modified ScFv-Fc fusion proteins, the modified Fc proteins, and the modified VhH-Fc fusion proteins in mammalian cells.

Then, suspend-cultured HEK293 cells (ATCC CRL-1573™) were transfected with the constructed expression vectors with PEI. For each group, the expression vector expressing the A chain (ScFv-Fc fusion protein) and that expressing the B chain (Fc protein or VhH-Fc fusion protein) were co-transfected at a ratio of 1:1. After culturing for 5-6 days, supernatant of the transient expression products was collected, and the expression products comprising corresponding protein heterodimers were preliminarily purified using Protein A affinity chromatography. Each of the preliminarily purified expression products comprises the homodimer protein ScFv-Fc/ScFv-Fc, the homodimer protein Fc/Fc (or the homodimer protein VhH-Fc/VhH-Fc) and the heterodimer protein ScFv-Fc/Fc (or the heterodimer protein ScFv-Fc/VhH-Fc), present in various percentages, respectively. Since the molecular weight of these proteins (i.e., the homodimers and the heterodimers) are different, their corresponding percentage could be determined according to corresponding band intensities reflected on non-reduced SDS-PAGE gels. The intensities were quantified and the results are summarized in tables 3-6 below.

TABLE 3

Percentage of homodimer proteins and heterodimer proteins in expression products

| Group | ScFv-Fc homodimer (%) | ScFv-Fc/Fc heterodimer (%) | Fc homodimer (%) |
|---|---|---|---|
| KH | 29 | 51 | 20 |
| 1 | 24 | 58 | 18 |
| 2 | 10 | 70 | 20 |
| 3 | 25 | 57 | 18 |
| 4 | 10 | 77 | 13 |

TABLE 4

Percentage of homodimer proteins and heterodimer proteins in expression products

| Group | ScFv-Fc homodimer (%) | ScFv-Fc/Fc heterodimer (%) | Fc homodimer (%) |
|---|---|---|---|
| 2 | 17 | 60 | 23 |
| 5 | 14 | 72 | 14 |
| 6 | 14 | 62 | 24 |
| 4 | 21 | 69 | 10 |
| 7 | 24 | 64 | 12 |
| 8 | 21 | 71 | 8 |

TABLE 5

Percentage of homodimer proteins and heterodimer proteins in expression products

| Group | ScFv-Fc homodimer (%) | ScFv-Fc/VhH-Fc heterodimer (%) | VhH-Fc homodimer (%) |
|---|---|---|---|
| 4 | 13 | 68 | 19 |
| 9 | 7 | 80 | 13 |
| 10 | 15 | 85 | 0 |
| 11 | 14 | 83 | 3 |
| 12 | 10 | 84 | 6 |

TABLE 6

Percentage of homodimer proteins and heterodimer proteins in expression products

| Group | ScFv-Fc homodimer (%) | ScFv-Fc/VhH-Fc heterodimer (%) | VhH-Fc homodimer (%) |
|---|---|---|---|
| 2 | 9 | 64 | 27 |
| 14 | 6 | 81 | 13 |
| 15 | 5 | 88 | 7 |
| 17 | 9 | 84 | 7 |

As can be seen from tables 3-6 above, all groups of modifications promoted heterodimer formation more effectively than the reference modification knob-and-hole. For illustrative purposes, the modifications in group 10 (modifications in chain A: T366W+K409A; modifications in chain B: T366S+L368G+Y407A+F405K) were used in the following examples to generate the proteinaceous heterodimers or the protein mixtures of the present disclosure.

1.2 Preparation of Anti-EGFR (Cetuximab)

Full length amino acid sequences of the heavy chain and light chain of Cetuximab (also known as Erbitux or Erb, which is an antibody against epidermal growth factor receptor EGFR) were obtained, and corresponding DNA sequences encoding these amino acid sequences were obtained using online tool DNAworks (helixweb.nih.gov/dnaworks/). Then, nucleic acid molecules encoding the light chain of Cetuximab (Erb-LC) were synthesized. The amino acid sequence of Erb-LC is as set forth in SEQ ID NO: 37, and the corresponding polynucleotide sequence encoding it is as set forth in SEQ ID NO: 38. Then, point mutations (T366W and K409A) were introduced into the polynucleotide sequences encoding the Fc region of Cetuximab heavy chain gene, and nucleic acid molecules encoding the modified Cetuximab heavy chain were synthesized (referred to herein as erb-Fc9), the corresponding polypeptide encoding it was named as Erb-Fc9. The amino acid sequences of Erb-Fc9 is as set forth in SEQ ID NO: 39, and the polynucleotide sequence encoding it is as set forth in SEQ ID NO: 40.

In another experiment, point mutations (T366S, L368G, Y407A and F405K) were introduced into the polynucleotide sequences encoding the Fc region of Cetuximab heavy chain gene, and nucleic acid molecules encoding the modified Cetuximab heavy chain were synthesized (referred to herein as erb-Fc6), the corresponding polypeptide encoding it was named as Erb-Fc6. The amino acid sequences of Erb-Fc6 is as set forth in SEQ ID NO: 41, and the polynucleotide sequence encoding it is as set forth in SEQ ID NO: 42.

In another experiment, to prepare the reference protein, point mutations (Y349C and T366W) were introduced into the polynucleotide sequences encoding the Fc region of Cetuximab heavy chain gene, and nucleic acid molecules encoding the modified Cetuximab heavy chain were synthesized (referred to herein as erb-knob), the corresponding polypeptide encoding it was named as Erb-Knob. The amino acid sequence of Erb-Knob is as set forth in SEQ ID NO: 43, and the polynucleotide sequence encoding it is as set forth in SEQ ID NO: 44.

1.3 Preparation of Anti-HER2 (Trastuzumab)

Full length amino acid sequences of the heavy chain and light chain of Trastuzumab were obtained according to U.S. Pat. No. 7,879,325B2 (incorporated herein by reference). Then, corresponding DNA sequences encoding these amino acid sequences were obtained using online tool DNAworks (helixweb.nih.gov/dnaworks/). Nucleic acid molecules encoding the light chain of Trastuzumab (T-LC) were then synthesized. The amino acid sequence of T-LC is as set forth in SEQ ID NO: 45, and the corresponding polynucleotide sequence encoding it is as set forth in SEQ ID NO: 46. Then, point mutations (T366W and K409A) were introduced into the polynucleotide sequences encoding the Fc region of Trastuzumab heavy chain gene, and nucleic acid molecules encoding the modified Trastuzumab heavy chain were synthesized (referred to herein as t-Fc9), the corresponding polypeptide encoding it was named as T-Fc9. The amino acid sequences of T-Fc9 is as set forth in SEQ ID NO: 47, and the polynucleotide sequence encoding it is as set forth in SEQ ID NO: 48.

1.4 Preparation of Anti-HER2 (Pertuzumab)

Full length amino acid sequences of the heavy chain and light chain of Pertuzumab were obtained according to U.S. Pat. No. 7,879,325B2 (incorporated herein by reference). Then, corresponding DNA sequences encoding these amino acid sequences were obtained using online tool DNAworks (helixweb.nih.gov/dnaworks/). Nucleic acid molecules encoding the light chain of Pertuzumab (P-LC) were then synthesized. The amino acid sequence of P-LC is as set forth in SEQ ID NO: 49, and the corresponding polynucleotide sequence encoding it is as set forth in SEQ ID NO: 50. Then, point mutations (T366W and K409A) were introduced into the polynucleotide sequences encoding the Fc region of Pertuzumab heavy chain gene, and nucleic acid molecules encoding the modified Pertuzumab heavy chain were synthesized (referred to herein as p-Fc9), the corresponding polypeptide encoding it was named as P-Fc9. The amino acid sequences of P-Fc9 is as set forth in SEQ ID NO:51, and the polynucleotide sequence encoding it is as set forth in SEQ ID NO:52.

1.5 Preparation of Anti-EGFR mutant (Mab806)

Full length amino acid sequences of the heavy chain and light chain of Mab806 were obtained according to U.S. Pat. No. 7,589,180B2 (incorporated herein by reference). Then, corresponding DNA sequences encoding these amino acid sequences were obtained using online tool DNAworks (helixweb.nih.gov/dnaworks/). Nucleic acid molecules encoding the light chain of Mab806 (Mab806-LC) were then synthesized. The amino acid sequence of Mab806-LC is as set forth in SEQ ID NO: 53, and the corresponding polynucleotide sequence encoding it is as set forth in SEQ ID NO:54. Then, point mutations (T366W and K409A) were introduced into the polynucleotide sequences encoding the Fc region of Mab806 heavy chain gene, and nucleic acid molecules encoding the modified Mab806 heavy chain were synthesized (referred to herein as mab806-Fc9), the corresponding polypeptide encoding it was named as Mab806-Fc9. The amino acid sequences of Mab806-Fc9 is as set forth in SEQ ID NO: 55, and the polynucleotide sequence encoding it is as set forth in SEQ ID NO: 56.

1.6 Preparation of Anti-GPC3 (Codrituzumab)

Full length amino acid sequences of the heavy chain and light chain of codrituzumab were obtained according to U.S. Pat. No. 7,919,086B2 (incorporated herein by reference). Then, corresponding DNA sequences encoding these amino acid sequences were obtained using online tool DNAworks (helixweb.nih.gov/dnaworks/). Nucleic acid molecules encoding the light chain of codrituzumab (C-mab-LC) were then synthesized. The amino acid sequence of C-mab-LC is as set forth in SEQ ID NO:57, and the corresponding polynucleotide sequence encoding it is as set forth in SEQ ID NO:58. Then, point mutations (T366W and K409A) were introduced into the polynucleotide sequences encoding the Fc region of codrituzumab heavy chain gene, and nucleic acid molecules encoding the modified codrituzumab heavy chain were synthesized (referred to herein as C-mab-Fc9), the corresponding polypeptide encoding it was named as C-mab-Fc9. The amino acid sequences of C-mab-Fc9 is as set forth in SEQ ID NO: 59, and the polynucleotide sequence encoding it is as set forth in SEQ ID NO: 60.

1.7 Preparation of Anti-FAP(28H1)

Full length amino acid sequences of the heavy chain and light chain of 28H1 were obtained according to US20120128591A1 (incorporated herein by reference). Then, corresponding DNA sequences encoding these amino acid sequences were obtained using online tool DNAworks (helixweb.nih.gov/dnaworks/). Nucleic acid molecules encoding the light chain of 28H1 (28H1-LC) were then synthesized. The amino acid sequence of 28H1-LC is as set forth in SEQ ID NO: 61, and the corresponding polynucleotide sequence encoding it is as set forth in SEQ ID NO: 62. Then, point mutations (T366W and K409A) were introduced into the polynucleotide sequences encoding the Fc region of 28H1 heavy chain gene, and nucleic acid molecules encoding the modified 28H1 heavy chain were synthesized (referred to herein as 28H1-Fc9), the corresponding polypeptide encoding it was named as 28H1-Fc9. The amino acid sequences of 28H1-Fc9 is as set forth in SEQ ID NO:63, and the polynucleotide sequence encoding it is as set forth in SEQ ID NO:64.

1.8 Preparation of Anti-Muc1(5E5)

Full length amino acid sequences of the heavy chain and light chain of 5E5 were obtained according to U.S. Pat. No. 8,440,798B2 (incorporated herein by reference). Then, corresponding DNA sequences encoding these amino acid sequences were obtained using online tool DNAworks (helixweb.nih.gov/dnaworks/). Nucleic acid molecules encoding the light chain of 5E5 (5E5-LC) were then synthesized. The amino acid sequence of 5E5-LC is as set forth in SEQ ID NO: 65, and the corresponding polynucleotide sequence encoding it is as set forth in SEQ ID NO:66. Then, point mutations (T366W and K409A) were introduced into the polynucleotide sequences encoding the Fc region of 5E5 heavy chain gene, and nucleic acid molecules encoding the modified 5E5 heavy chain were synthesized (referred to herein as 5E5-Fc9), the corresponding polypeptide encoding it was named as 5E5-Fc9. The amino acid sequences of 5E5-Fc9 is as set forth in SEQ ID NO: 67, and the polynucleotide sequence encoding it is as set forth in SEQ ID NO: 68.

1.9 Preparation of Anti-MUCSAC(ensituximab)

Full length amino acid sequences of the heavy chain and light chain of ensituximab were obtained according to WO2006113546A2 (incorporated herein by reference). Then, corresponding DNA sequences encoding these amino acid sequences were obtained using online tool DNAworks (helixweb.nih.gov/dnaworks/). Nucleic acid molecules encoding the light chain of ensituximab(E-mab-LC) were then synthesized. The amino acid sequence of E-mab-LC is as set forth in SEQ ID NO: 69, and the corresponding polynucleotide sequence encoding it is as set forth in SEQ ID NO: 70. Then, point mutations (T366W and K409A) were introduced into the polynucleotide sequences encoding the Fc region of ensituximab heavy chain gene, and nucleic acid molecules encoding the modified ensituximab heavy chain were synthesized (referred to herein as E-mab-Fc9), the corresponding polypeptide encoding it was named as E-mab-Fc9. The amino acid sequences of E-mab-Fc9 is as set forth in SEQ ID NO: 71, and the polynucleotide sequence encoding it is as set forth in SEQ ID NO: 72.

1.10 Preparation of Anti-Mesothelin(Amatuximab)

Full length amino acid sequences of the heavy chain and light chain of amatuximab were obtained from http://www.imgt.org/mAb-DB/index. Then, corresponding DNA sequences encoding these amino acid sequences were obtained using online tool DNAworks (helixweb.nih.gov/dnaworks/). Nucleic acid molecules encoding the light chain of amatuximab(A-mab-LC) were then synthesized. The amino acid sequence of A-mab-LC is as set forth in SEQ ID NO: 73, and the corresponding polynucleotide sequence encoding it is as set forth in SEQ ID NO: 74. Then, point mutations (T366W and K409A) were introduced into the polynucleotide sequences encoding the Fc region of amatuximab heavy chain gene, and nucleic acid molecules encoding the modified amatuximab heavy chain were synthesized (referred to herein as A-mab-Fc9), the corresponding polypeptide encoding it was named as A-mab-Fc9. The amino acid sequences of A-mab-Fc9 is as set forth in SEQ ID NO: 75, and the polynucleotide sequence encoding it is as set forth in SEQ ID NO: 76.

1.11 Preparation of muIFNa4-Fc6

First of all, sequence information of mouse interferon α4(IFNα4) (NM 010504.2) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (T366S, L368G, Y407A and F405K) were introduced into the IgG1-Fc fragment, and the polypeptide obtained thereby is referred to as Fc6. Then, a linker sequence "GSGGG" (SEQ ID NO: 79) was added to the N-terminus of the Fc6, to obtain linker-Fc6. The corresponding DNA sequence encoding it was then designed using online tool DNAworks (helixweb.nih.gov/dnaworks/). Polynucleotide sequences encoding mouse IFNα4 were added to the 5' end of the polynucleotide sequences encoding the linker-Fc6, thereby obtaining and synthesizing a polynucleotide sequence encoding the fusion protein muIFNa4-Fc6. The amino acid sequence of muIFNa4-Fc6 is as set forth in SEQ ID NO: 77, and the polynucleotide sequence encoding it is as set forth in SEQ ID NO: 78.

1.12 Preparation of huIFNa2-Fc6

First of all, sequence information of human interferon α2 (IFNα2) (NM_000605.3) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (T366S, L368G, Y407A and F405K) were introduced into the IgG1-Fc fragment, and the polypeptide obtained thereby is referred to as Fc6. Then, a linker sequence "GSGGG" (SEQ ID NO: 79) was added to the N-terminus of the Fc6, to obtain linker-Fc6. The corresponding DNA sequence encoding it was then designed using online tool DNAworks (helixweb.nih.gov/dnaworks/). Polynucleotide sequences encoding humanIFNa2 were added to the 5' end of the polynucleotide sequences encoding the linker-Fc6, thereby obtaining and synthesizing a polynucleotide sequence encoding the fusion protein huIFNa2-Fc6. The amino acid sequence of huIFNa2-Fc6 is as set forth in SEQ ID NO: 80, and the polynucleotide sequence encoding it is as set forth in SEQ ID NO: 81.

1.13 Preparation of muIFNb-Fc6

First of all, sequence information of mouse interferon β (IFNβ) (NM_005018.2) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (T366S, L368G, Y407A and F405K) were introduced into the IgG1-Fc fragment, and the polypeptide obtained thereby is referred to as Fc6. Then, a linker sequence "GSGGG" (SEQ ID NO: 79) was added to the N-terminus of the Fc6, to obtain linker-Fc6. The corresponding DNA sequence encoding it was then designed using online tool DNAworks (helixweb.nih.gov/dnaworks/). Polynucleotide sequences encoding mouse IFNβ were added to the 5' end of the polynucleotide sequences encoding the linker-Fc6, thereby obtaining and synthesizing a polynucleotide sequence encoding the fusion protein muIFNb-Fc6. The amino acid sequence of muIFNb-Fc6 is as set forth in SEQ ID NO: 82, and the polynucleotide sequence encoding it is as set forth in SEQ ID NO: 83.

1.14 Preparation of huIFNb-Fc6

First of all, sequence information of human interferon β (IFNβ) (EF064725.1) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (T366S, L368G, Y407A and F405K) were introduced into the IgG1-Fc fragment, and the polypeptide obtained thereby is referred to as Fc6. Then, a linker sequence "GSGGG" (SEQ ID NO: 79) was added to the N-terminus of the Fc6, to obtain linker-Fc6. The corresponding DNA sequence encoding it was then designed using online tool DNAworks (helixweb.nih.gov/dnaworks/). Polynucleotide sequences encoding human IFNβ were added to the 5' end of the polynucleotide sequences encoding the linker-Fc6, thereby obtaining and synthesizing a polynucleotide sequence encoding the fusion protein huIFNb-Fc6. The amino acid sequence of huIFNb-Fc6 is as set forth in SEQ ID NO: 84, and the polynucleotide sequence encoding it is as set forth in SEQ ID NO: 85.

1.15 Preparation of huIFNL-Fc6

First of all, sequence information of human interferon λ, (IFNL) (BC117482.1) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1

(IgG1) constant region (P01857) from the protein database Uniprot. Afterwards, point mutations (T366S, L368G, Y407A and F405K) were introduced into the IgG1-Fc fragment, and the polypeptide obtained thereby is referred to as Fc6. Then, a linker sequence "GSGGG" (SEQ ID NO: 79) was added to the N-terminus of the Fc6, to obtain linker-Fc6. The corresponding DNA sequence encoding it was then designed using online tool DNAworks (helixweb.nih.gov/dnaworks/). Polynucleotide sequences encoding human IFNL were added to the 5' end of the polynucleotide sequences encoding the linker-Fc6, thereby obtaining and synthesizing a polynucleotide sequence encoding the fusion protein huIFNL-Fc6. The amino acid sequence of huIFNL-Fc6 is as set forth in SEQ ID NO: 86, and the polynucleotide sequence encoding it is as set forth in SEQ ID NO: 87.

1.16 Preparation of huIL10-Fc6

First of all, sequence information of human interleukin 10 (huIL10) (P22301) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (T366S, L368G, Y407A and F405K) were introduced into the IgG1-Fc fragment, and the polypeptide obtained thereby is referred to as Fc6. Then, a linker sequence "(GGGGS)3" (SEQ ID NO: 88) was added to the N-terminus of the Fc6, to obtain linker-Fc6. The corresponding DNA sequence encoding it was then designed using online tool DNAworks (helixweb.nih.gov/dnaworks/). Polynucleotide sequences encoding huIL10 were added to the 5' end of the polynucleotide sequences encoding the linker-Fc6, thereby obtaining and synthesizing a polynucleotide sequence encoding the fusion protein huIL10-Fc6. The amino acid sequence of huIL10-Fc6 is as set forth in SEQ ID NO: 89, and the polynucleotide sequence encoding it is as set forth in SEQ ID NO: 90.

1.17 Preparation of (huIL10)2-Fc6

First of all, sequence information of human interleukin 10 (huIL10) (P22301) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (T366S, L368G, Y407A and F405K) were introduced into the IgG1-Fc fragment, and the polypeptide obtained thereby is referred to as Fc6. Then, a linker sequence "(GGGGS)$_3$" (SEQ ID NO: 88) was added to the N-terminus of the Fc6, to obtain linker-Fc6. The corresponding DNA sequence encoding it was then designed using online tool DNAworks (helixweb.nih.gov/dnaworks/). Then, a linker sequence "(GGGGS)3" (SEQ ID NO: 88) was added between two copies of huIL10, to obtain (huIL10)2. Polynucleotide sequences encoding (huIL10)2 were then added to the 5' end of the polynucleotide sequences encoding the linker-Fc6, thereby obtaining and synthesizing a polynucleotide sequence encoding the fusion protein (huIL10)2-Fc6. The amino acid sequence of (huIL10)2-Fc6 is as set forth in SEQ ID NO: 91, and the polynucleotide sequence encoding it is as set forth in SEQ ID NO: 92.

1.18 Preparation of (huIL10)2-Fc9

First of all, sequence information of human interleukin 10 (huIL10) (P22301) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (T366W and K409A) were introduced into the IgG1-Fc fragment, and the polypeptide obtained thereby is referred to as Fc9. Then, a linker sequence "(GGGGS)3" (SEQ ID NO: 88) was added to the N-terminus of the Fc9, to obtain linker-Fc9. The corresponding DNA sequence encoding it was then designed using online tool DNAworks (helixweb.nih.gov/dnaworks/). Then, a linker sequence "(GGGGS)$_3$" (SEQ ID NO: 88) was added between two copies of huIL10, to obtain (huIL10)2. Polynucleotide sequences encoding (huIL10)2 were then added to the 5' end of the polynucleotide sequences encoding the linker-Fc9, thereby obtaining and synthesizing a polynucleotide sequence encoding the fusion protein (huIL10)2-Fc9. The amino acid sequence of (huIL10)2-Fc9 is as set forth in SEQ ID NO: 93, and the polynucleotide sequence encoding it is as set forth in SEQ ID NO: 94.

1.19 Preparation of (huIL10)2-Fc-hole

First of all, sequence information of human interleukin 10 (huIL10) (P22301) was obtained from the National Center for Biotechnology Information (NCBI), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (T366S, L368G, Y407A and F405K) were introduced into the IgG1-Fc fragment, and the polypeptide obtained thereby is referred to as Fc-hole. Then, a linker sequence "(GGGGS)$_3$" (SEQ ID NO: 88) was added to the N-terminus of the Fc-hole, to obtain linker-Fc-hole. The corresponding DNA sequence encoding it was then designed using online tool DNAworks (helixweb.nih.gov/dnaworks/). Then, a linker sequence "(GGGGS)3" (SEQ ID NO: 88) was added between two copies of huIL10, to obtain (huIL10)2. Polynucleotide sequences encoding (huIL10)2 were then added to the 5' end of the polynucleotide sequences encoding the linker-Fc-hole, thereby obtaining and synthesizing a polynucleotide sequence encoding the fusion protein (huIL10)2-Fc-hole. The amino acid sequence of (huIL10)2-Fc-hole is as set forth in SEQ ID NO: 95, and the polynucleotide sequence encoding it is as set forth in SEQ ID NO: 96.

1.20 Preparation of husIL2-Fc6

First of all, sequence information of human super interleukin 2 (husIL2) was obtained according to Nature 484, 529-533 (26 Apr. 2012) (incorporated herein by reference), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (T366S, L368G, Y407A and F405K) were introduced into the IgG1-Fc fragment, and the polypeptide obtained thereby is referred to as Fc6. Then, a linker sequence "GGGGS" (SEQ ID NO: 79) was added to the N-terminus of the Fc6, to obtain linker-Fc6. The corresponding DNA sequence encoding it was then designed using online tool DNAworks (helixweb.nih.gov/dnaworks/). Polynucleotide sequences encoding husIL2 were added to the 5' end of the polynucleotide sequences encoding the linker-Fc6, thereby obtaining and synthesizing a polynucleotide sequence encoding the fusion protein husIL2-Fc6. The amino acid sequence of husIL2-Fc6 is as set forth in SEQ ID NO: 97, and the polynucleotide sequence encoding it is as set forth in SEQ ID NO: 98. 1.21 Preparation of husIL2-hole First of all, sequence information of human super interleukin 2 (husIL2) was obtained according to *Nature* 484, 529-533 (26 Apr. 2012) (incorporated herein by reference), and the full length polynucleotide sequences encoding it were obtained. Then, amino acid sequences of human IgG1-Fc (i.e., residue 104 to residue 330 of P01857) were obtained according to the amino acid sequences of human immunoglobulin γ1 (IgG1) constant region (P01857) from the protein database Uniprot. Afterwards, point mutations (D356C, T366S, L368A and Y407V) were introduced into the IgG1-Fc fragment, and the polypeptide obtained thereby is referred to as Fc-hole. Then, a linker sequence "GGGGS" (SEQ ID NO: 79) was added to the N-terminus of the Fc-hole, to obtain linker-Fc-hole. The corresponding DNA sequence encoding it was then designed using online tool DNAworks (helixweb.nih.gov/dnaworks/). Polynucleotide sequences encoding husIL2 were added to the 5' end of the polynucleotide sequences encoding the linker-Fc-hole, thereby obtaining and synthesizing a polynucleotide sequence encoding the fusion protein husIL2-Fc-hole. The amino acid sequence of husIL2-Fc-hole is as set forth in SEQ ID NO: 99, and the polynucleotide sequence encoding it is as set forth in SEQ ID NO: 100.

Example 2 Construction of Recombinant Plasmids

The nucleic acid molecules (encoding Erb-Fc9, Erb-Fc6, Erb-Knob, T-Fc9, P-Fc9, Mab806-Fc9, C-mab-Fc9, 28H1-Fc9, 5E5-Fc9, E-mab-Fc9, A-mab-Fc9, T-LC (Trastuzumab light chain), P-LC (Pertuzumab light chain), Erb-LC (Cetuximab light chain), Mab806-LC (Mab806 light chain), C-mab-LC (codrituzumab light chain), 28H1-LC(28H1 light chain), 5E5-LC (5E5 light chain), E-mab-LC (ensituximab light chain), A-mab-LC (amatuximab light chain), muIFNa4-Fc6, huIFNa2-Fc6, muIFNb-Fc6, huIFNb-Fc6, huIFNL-Fc6, huIL10-Fc6, (huIL10)2-Fc6, (huIL10)2-Fc9, (huIL10)2-Fc-hole, husIL2-Fc6, and husIL2-hole, respectively) obtained according to Example 1 were digested with HindIII and EcoRI (Takara), and then sub-cloned into the vector pcDNA4/myc-HisA (Invitrogen, V863-20), respectively. The plasmids obtained were verified by sequencing, and the correct recombinant plasmids were named as: pcDNA4-Erb-Fc9, pcDNA4-Erb-Fc6, pcDNA4-Erb-Knob, pcDNA4-T-Fc9, pcDNA4-P-Fc9, pcDNA4-Mab806-Fc9, pcDNA4-C-mab-Fc9, pcDNA4-28H1-Fc9, pcDNA4-5E5-Fc9, pcDNA4-E-mab-Fc9, pcDNA4-A-mab-Fc9, pcDNA4-T-LC, pcDNA4-P-LC, pcDNA4-Erb-LC, pcDNA4-Mab806-LC, pcDNA4-C-mab-LC, pcDNA4-28H1-LC, pcDNA4-5E5-LC, pcDNA4-E-mab-LC, pcDNA4-A-mab-LC, pcDNA4-muIFNa4-Fc6, pcDNA4-huIFNa2-Fc6, pcDNA4-muIFNb-Fc6, pcDNA4-huIFNb-Fc6, pcDNA4-huIFNL-Fc6, pcDNA4-huIL10-Fc6, pcDNA4-(huIL10)2-Fc6, pcDNA4-(huIL10)2-Fc9, pcDNA4-(huIL10)2-Fc-hole, pcDNA4-husIL2-Fc6, and pcDNA4-husIL2-hole, respectively.

Example 3 Expression and Purification of Proteinaceous Heterodimers

Two days before transfection, 12×600 mL suspension domesticated HEK293 (ATCC, CRL-1573™) cells were prepared for transient transfection, the cells were seeded at a density of $0.8×10^6$ cells/ml. Two days later, three aliquots of cell suspension were centrifuged, and then resuspended in 600 mL Freestyle293 culture medium.

The recombinant expression vectors obtained from Example 2 were divided into the following groups:

Group1: pcDNA4-Erb-Knob (200 µg)+pcDNA4-Erb-LC (200 µg)+pcDNA4-(huIL10)2-Fc-hole (200 µg)

Group2: pcDNA4-Erb-Fc6 (200 µg)+pcDNA4-Erb-LC (200 µg)+pcDNA4-(huIL10)2-Fc9 (200 µg)

Group3: pcDNA4-Erb-Fc9 (200 µg)+pcDNA4-Erb-LC (200 µg)+pcDNA4-(huIL10)2-Fc6 (200 µg)

Group4: pcDNA4-Erb-Fc9 (200 µg)+pcDNA4-Erb-LC (200 µg)+pcDNA4-muIFNa4-Fc6 (200 µg)

Group5: pcDNA4-Erb-Fc9 (200 µg)+pcDNA4-Erb-LC (200 µg)+pcDNA4-huIFNa2-Fc6 (200 µg)

Group6: pcDNA4-Erb-Fc9 (200 µg)+pcDNA4-Erb-LC (200 µg)+pcDNA4-muIFNb-Fc6 (200 µg)

Group7: pcDNA4-Erb-Fc9 (200 µg)+pcDNA4-Erb-LC (200 µg)+pcDNA4-huIFNb-Fc6 (200 µg)

Group8: pcDNA4-Erb-Fc9 (200 µg)+pcDNA4-Erb-LC (200 µg)+pcDNA4-huIFNL-Fc6 (200 µg)

Group9: pcDNA4-Erb-Fc9 (200 µg)+pcDNA4-Erb-LC (200 µg)+pcDNA4-huIL10-Fc6 (200 µg)

Group10: pcDNA4-Erb-Knob (200 µg)+pcDNA4-Erb-LC (200 µg)+pcDNA4-husIL2-hole (200 µg)

Group11: pcDNA4-Erb-Fc9 (200 µg)+pcDNA4-Erb-LC (200 µg)+pcDNA4-husIL2-Fc6 (200 µg)

Group12: pcDNA4-Mab806-Fc9 (200 µg)+pcDNA4-Mab806-LC (200 µg)+pcDNA4-muIFNa4-Fc6 (200 µg)

Group13: pcDNA4-Mab806-Fc9 (200 µg)+pcDNA4-Mab806-LC (200 µg)+pcDNA4-huIFNa2-Fc6 (200 µg)

Group14: pcDNA4-Mab806-Fc9 (200 µg)+pcDNA4-Mab806-LC (200 µg)+pcDNA4-muIFNb-Fc6 (200 µg)

Group15: pcDNA4-Mab806-Fc9 (200 µg)+pcDNA4-Mab806-LC (200 µg)+pcDNA4-huIFNb-Fc6 (200 µg)

Group16: pcDNA4-Mab806-Fc9 (200 µg)+pcDNA4-Mab806-LC (200 µg)+pcDNA4-huIFNL-Fc6 (200 µg)

Group17: pcDNA4-Mab806-Fc9 (200 µg)+pcDNA4-Mab806-LC (200 µg)+pcDNA4-huIL10-Fc6 (200 µg)

Group18: pcDNA4-Mab806-Fc9 (200 µg)+pcDNA4-Mab806-LC (200 µg)+pcDNA4-(huIL10)2-Fc6 (200 µg)

Group19: pcDNA4-Mab806-Fc9 (200 µg)+pcDNA4-Mab806-LC (200 µg)+pcDNA4-husIL2-Fc6 (200 µg)

Group20: pcDNA4-T-Fc9 (200 µg)+pcDNA4-T-LC (200 µg)+pcDNA4-muIFNa4-Fc6 (200 µg)

Group21: pcDNA4-T-Fc9 (200 µg)+pcDNA4-T-LC (200 µg)+pcDNA4-huIFNa2-Fc6 (200 µg)

Group22: pcDNA4-T-Fc9 (200 µg)+pcDNA4-T-LC (200 µg)+pcDNA4-muIFNb-Fc6 (200 µg)

Group23: pcDNA4-T-Fc9 (200 µg)+pcDNA4-T-LC (200 µg)+pcDNA4-huIFNb-Fc6 (200 µg)

Group24: pcDNA4-T-Fc9 (200 µg)+pcDNA4-T-LC (200 µg)+pcDNA4-huIFNL-Fc6 (200 µg)

Group25: pcDNA4-T-Fc9 (200 µg)+pcDNA4-T-LC (200 µg)+pcDNA4-huIL10-Fc6 (200 µg)

Group26: pcDNA4-T-Fc9 (200m)+pcDNA4-T-LC (200m)+pcDNA4-(huIL10)2-Fc6 (200 µg)

Group27: pcDNA4-T-Fc9 (200 µg)+pcDNA4-T-LC (200 µg)+pcDNA4-husIL2-Fc6 (200 µg)

Group28: pcDNA4-P-Fc9 (200 µg)+pcDNA4-P-LC (200 µg)+pcDNA4-muIFNa4-Fc6 (200 µg)

Group29: pcDNA4-P-Fc9 (200 µg)+pcDNA4-P-LC (200 µg)+pcDNA4-huIFNa2-Fc6 (200 µg)

Group30: pcDNA4-P-Fc9 (200 µg)+pcDNA4-P-LC (200 µg)+pcDNA4-muIFNb-Fc6 (200 µg)

Group31: pcDNA4-P-Fc9 (200 µg)+pcDNA4-P-LC (200 µg)+pcDNA4-huIFNb-Fc6 (200 µg)

Group32: pcDNA4-P-Fc9 (200 µg)+pcDNA4-P-LC (200 µg)+pcDNA4-huIFNL-Fc6 (200 µg)

Group33: pcDNA4-P-Fc9 (200 µg)+pcDNA4-P-LC (200 µg)+pcDNA4-huIL10-Fc6 (200 µg)

Group34: pcDNA4-P-Fc9 (200 µg)+pcDNA4-P-LC (200 µg)+pcDNA4-(huIL10)2-Fc6 (200 µg)

Group35: pcDNA4-P-Fc9 (200 µg)+pcDNA4-P-LC (200 µg)+pcDNA4-husIL2-Fc6 (200 µg)

Group36: pcDNA4-C-mab-Fc9 (200 µg)+pcDNA4-C-mab-LC (200 µg)+pcDNA4-muIFNa4-Fc6 (200 µg)

Group37: pcDNA4-C-mab-Fc9 (200 µg)+pcDNA4-C-mab-LC (200 µg)+pcDNA4-huIFNa2-Fc6 (200 µg)

Group38: pcDNA4-C-mab-Fc9 (200 µg)+pcDNA4-C-mab-LC (200 µg)+pcDNA4-muIFNb-Fc6 (200 µg)

Group39: pcDNA4-C-mab-Fc9 (200 µg)+pcDNA4-C-mab-LC (200 µg)+pcDNA4-huIFNb-Fc6 (200 µg)

Group40: pcDNA4-C-mab-Fc9 (200 µg)+pcDNA4-C-mab-LC (200 µg)+pcDNA4-huIFNL-Fc6 (200 µg)

Group41: pcDNA4-C-mab-Fc9 (200 µg)+pcDNA4-C-mab-LC (200 µg)+pcDNA4-huIL10-Fc6 (200 µg)

Group42: pcDNA4-C-mab-Fc9 (200 µg)+pcDNA4-C-mab-LC (200 µg)+pcDNA4-(huIL10)2-Fc6 (200 µg)

Group43: pcDNA4-C-mab-Fc9 (200 µg)+pcDNA4-C-mab-LC (200 µg)+pcDNA4-husIL2-Fc6 (200 µg)

Group44: pcDNA4-28H1-Fc9 (200 µg)+pcDNA4-28H1-LC (200 µg)+pcDNA4-muIFNa4-Fc6 (200 µg)

Group45: pcDNA4-28H1-Fc9 (200 µg)+pcDNA4-28H1-LC (200 µg)+pcDNA4-huIFNa2-Fc6 (200 µg)

Group46: pcDNA4-28H1-Fc9 (200 µg)+pcDNA4-28H1-LC (200 µg)+pcDNA4-muIFNb-Fc6 (200 µg)

Group47: pcDNA4-28H1-Fc9 (200 µg)+pcDNA4-28H1-LC (200 µg)+pcDNA4-huIFNb-Fc6 (200 µg)

Group48: pcDNA4-28H1-Fc9 (200 µg)+pcDNA4-28H1-LC (200 µg)+pcDNA4-huIFNL-Fc6 (200 µg)

Group49: pcDNA4-28H1-Fc9 (200 µg)+pcDNA4-28H1-LC (200 µg)+pcDNA4-huIL10-Fc6 (200m)

Group50: pcDNA4-28H1-Fc9 (200 µg)+pcDNA4-28H1-LC (200 µg)+pcDNA4-(huIL10)2-Fc6 (200 µg)

Group51: pcDNA4-28H1-Fc9 (200 µg)+pcDNA4-28H1-LC (200 µg)+pcDNA4-husIL2-Fc6 (200 µg)

Group52: pcDNA4-5E5-Fc9 (200 µg)+pcDNA4-5E5-LC (200 µg)+pcDNA4-muIFNa4-Fc6 (200 µg)

Group53: pcDNA4-5E5-Fc9 (200 µg)+pcDNA4-5E5-LC (200 µg)+pcDNA4-huIFNa2-Fc6 (200 µg)

Group54: pcDNA4-5E5-Fc9 (200 µg)+pcDNA4-5E5-LC (200 µg)+pcDNA4-muIFNb-Fc6 (200m)

Group55: pcDNA4-5E5-Fc9 (200 µg)+pcDNA4-5E5-LC (200 µg)+pcDNA4-huIFNb-Fc6 (200 µg)

Group56: pcDNA4-5E5-Fc9 (200 µg)+pcDNA4-5E5-LC (200 µg)+pcDNA4-huIFNL-Fc6 (200 µg)

Group57: pcDNA4-5E5-Fc9 (200 µg)+pcDNA4-5E5-LC (200 µg)+pcDNA4-huIL10-Fc6 (200 µg)

Group58: pcDNA4-5E5-Fc9 (200 µg)+pcDNA4-5E5-LC (200 µg)+pcDNA4-(huIL10)2-Fc6 (200 µg)

Group59: pcDNA4-5E5-Fc9 (200 µg)+pcDNA4-5E5-LC (200 µg)+pcDNA4-husIL2-Fc6 (200 µg)

Group60: pcDNA4-E-mab-Fc9 (200 µg)+pcDNA4-E-mab-LC (200m)+pcDNA4-muIFNa4-Fc6 (200 µs)

Group61: pcDNA4-E-mab-Fc9 (200 µg)+pcDNA4-E-mab-LC (200 µg)+pcDNA4-huIFNa2-Fc6 (200 µg)

Group62: pcDNA4-E-mab-Fc9 (200 µg)+pcDNA4-E-mab-LC (200 µg)+pcDNA4-muIFNb-Fc6 (200 µg)

Group63: pcDNA4-E-mab-Fc9 (200 µg)+pcDNA4-E-mab-LC (200 µg)+pcDNA4-huIFNb-Fc6 (200 µg)

Group64: pcDNA4-E-mab-Fc9 (200 µg)+pcDNA4-E-mab-LC (200 µg)+pcDNA4-huIFNL-Fc6 (200 µg)

Group65: pcDNA4-E-mab-Fc9 (200 µg)+pcDNA4-E-mab-LC (200 µg)+pcDNA4-huIL10-Fc6 (200 µg)

Group66: pcDNA4-E-mab-Fc9 (200 µg)+pcDNA4-E-mab-LC (200 µg)+pcDNA4-(huIL10)2-Fc6 (200 µg)

Group67: pcDNA4-E-mab-Fc9 (200 µg)+pcDNA4-E-mab-LC (200 µg)+pcDNA4-husIL2-Fc6 (200 µg)

Group68: pcDNA4-A-mab-Fc9(200 µg)+pcDNA4-A-mab-LC (200 µg)+pcDNA4-muIFNa4-Fc6 (200 µg)

Group69: pcDNA4-A-mab-Fc9(200 µg)+pcDNA4-A-mab-LC (200 µg)+pcDNA4-huIFNa2-Fc6 (200 µg)

Group70: pcDNA4-A-mab-Fc9 (200 µg)+pcDNA4-A-mab-LC (200 µg)+pcDNA4-muIFNb-Fc6 (200 µg)

Group71: pcDNA4-A-mab-Fc9 (200 µg)+pcDNA4-A-mab-LC (200 µg)+pcDNA4-huIFNb-Fc6 (200 µg)

Group72: pcDNA4-A-mab-Fc9(200 µg)+pcDNA4-A-mab-LC (200 µg)+pcDNA4-huIFNL-Fc6 (200 µg)

Group73: pcDNA4-A-mab-Fc9 (200 µg)+pcDNA4-A-mab-LC (200 µg)+pcDNA4-huIL10-Fc6 (200 µg)

Group74: pcDNA4-A-mab-Fc9 (200 µg)+pcDNA4-A-mab-LC (200 µg)+pcDNA4-(huIL10)2-Fc6 (200 µg)

Group75: pcDNA4-A-mab-Fc9 (200 µg)+pcDNA4-A-mab-LC (200 µg)+pcDNA4-husIL2-Fc6 (200 µg)

Figure 2:
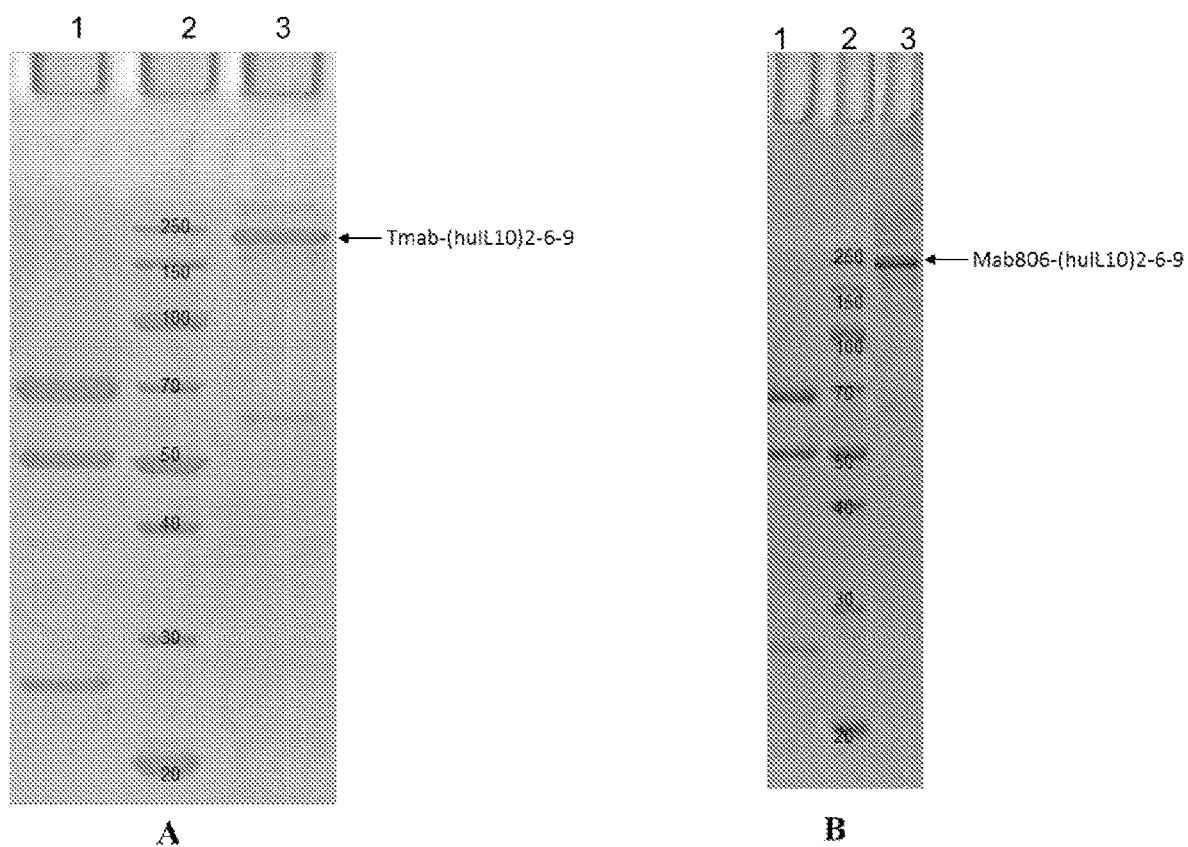
FIG. 2A-2G illustrates results of formation of the proteinaceous heterodimers according to the present application, as analyzed by SDS-PAGE.
Figure 2:
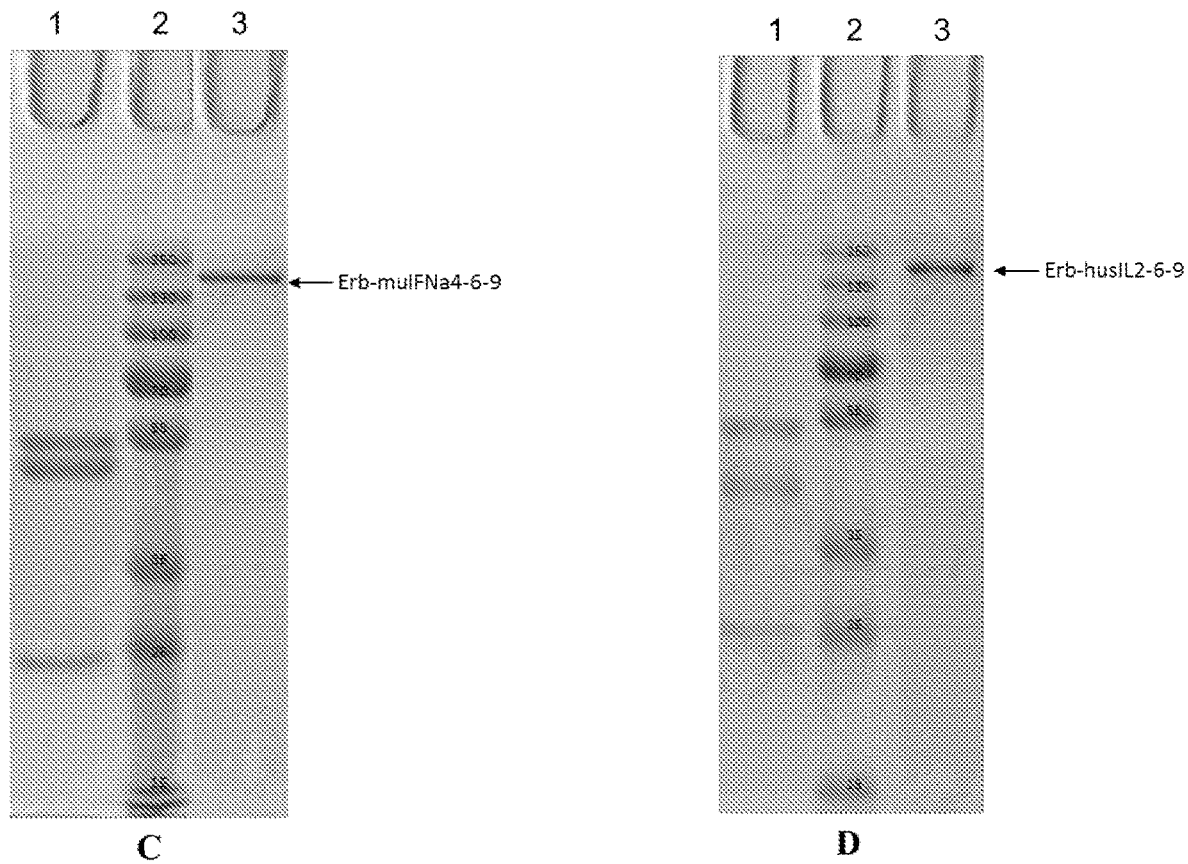
Figure 2:
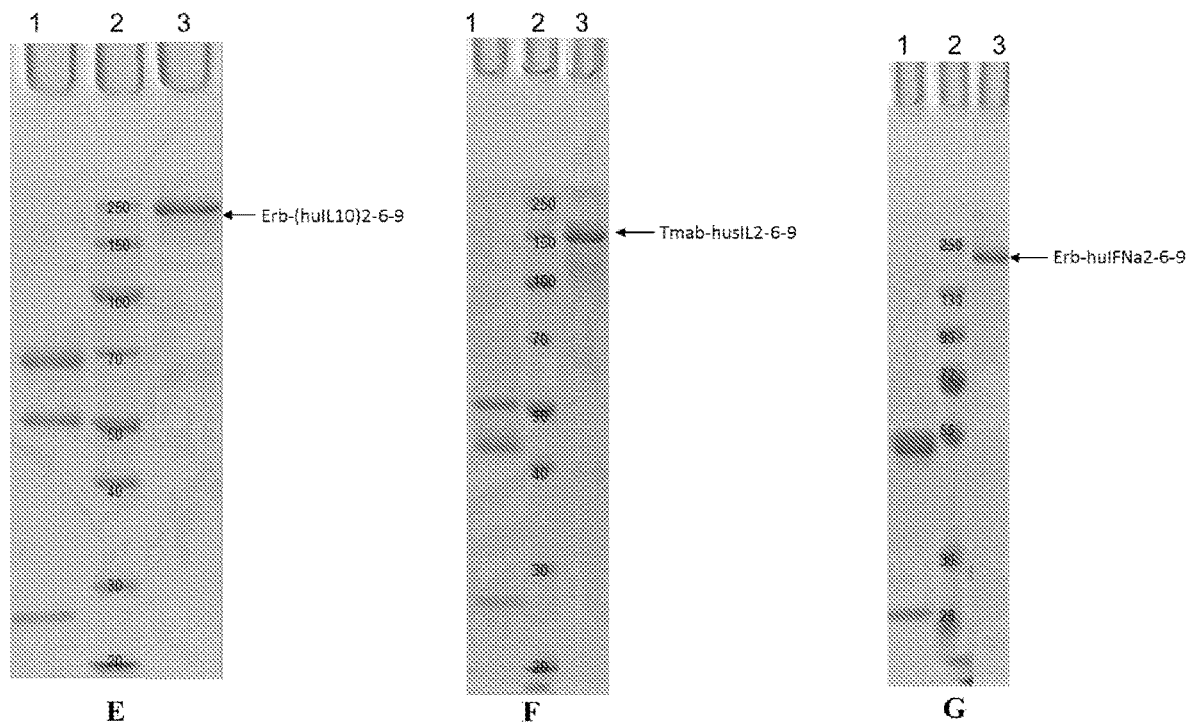

Each group of plasmid mixtures was diluted with 6 mL Freestyle293 medium and PEI (polyethylenimine) solution was added to perform transfection. Each group of plasmid/PEI mixtures was added into 600 mL cell suspension, respectively, which was then cultured at 37° C., 10% $CO_2$, 90 rpm, the medium was supplemented with 50 µg/L IGF-1 (insulin-like growth factor I). Four hours later, the culture was supplemented with 600 mL EX293 medium, 2 mM glutamine and 50 µg/L IGF-1, and cultured at 135 rpm. After 24 hours, 3.8 mM VPA was added. 5-6 days later, supernatant of 5×1200 mL cells was collected, and crude proteinaceous heterodimer samples were purified by Protein A affinity chromatography. The samples obtained were examined first with SDS-PAGE, and the target bands were clearly seen, examples are shown in FIG. 2.

FIG. 2A shows the SDS-PAGE assay result for Tmab-(huIL10)2-6-9, lane 2 was loaded with a protein marker (MW marker 26619), lane 1 was loaded with the reduced Tmab-(huIL10)2-6-9 heterodimer protein, and lane 3 was loaded with the non-reduced Tmab-(huIL10)2-6-9 heterodimer protein, T-LC has a MW of about 25 KD, T-Fc9 has a MW of about 50 KD, (huIL10)2-Fc6 has a MW of about 65 KD, and the Tmab-(huIL10)2-6-9 heterodimer Protein has a MW of about 140 KD.

FIG. 2B shows the SDS-PAGE assay result for Mab806-(huIL10)2-6-9, lane 2 was loaded with a protein marker (MW marker 26619), lane 1 was loaded with the reduced Mab806-(huIL10)2-6-9 heterodimer protein, and lane 3 was loaded with the non-reduced Mab806-(huIL10)2-6-9 heterodimer protein, Mab806-LC has a MW of about 25 KD, Mab806-Fc9 has a MW of about 50 KD, (huIL10)2-Fc6 has a MW of about 65 KD, and the Mab806-(huIL10)2-6-9 heterodimer protein has a MW of about 140 KD.

FIG. 2C shows the SDS-PAGE assay result for Erb-muIFNa4-6-9, lane 2 was loaded with a protein marker (MW marker 26619), lane 1 was loaded with the reduced Erb-muIFNa4-6-9 heterodimer protein, and lane 3 was loaded with the non-reduced Erb-muIFNa4-6-9 heterodimer protein, Erb-LC has a MW of about 25 KD, Erb-Fc9 has a MW of about 50 KD, muIFNa4-Fc6 has a MW of about 45 KD, and the Erb-muIFNa4-6-9 heterodimer protein has a MW of about 120 KD.

FIG. 2D shows the SDS-PAGE assay result for Erb-husIL2-6-9, lane 2 was loaded with a protein marker (MW marker 26619), lane 1 was loaded with the reduced ErbhusIL2-6-9 heterodimer protein, and lane 3 was loaded with the non-reduced Erb-husIL2-6-9 heterodimer protein, Erb-LC has a MW of about 25 KD, Erb-Fc9 has a MW of about 50 KD, husIL2-Fc6 has a MW of about 41 KD, and the Erb-husIL2-6-9 heterodimer protein has a MW of about 120 KD.

FIG. 2E shows the SDS-PAGE assay result for Erb-(huIL10)2-6-9, lane 2 was loaded with a protein marker (MW marker 26619), lane 1 was loaded with the reduced Erb-(huIL10)2-6-9 heterodimer protein, and lane 3 was loaded with the non-reduced Erb-(huIL10)2-6-9 heterodimer protein, Erb-LC has a MW of about 25 KD, Erb-Fc9 has a MW of about 50 KD, (huIL10)2-Fc6 has a MW of about 65 KD, and the Erb-(huIL10)2-6-9 heterodimer protein has a MW of about 140 KD.

FIG. 2F shows the SDS-PAGE assay result for Tmab-husIL2-6-9, lane 2 was loaded with a protein marker (MW marker 26619), lane 1 was loaded with the reduced Tmab-husIL2-6-9 heterodimer protein, and lane 3 was loaded with the non-reduced Tmab-husIL2-6-9 heterodimer protein, T-LC has a MW of about 25 KD, T-Fc9 has a MW of about 50 KD, husIL2-Fc6 has a MW of about 41 KD, and the Tmab-husIL2-6-9 heterodimer protein has a MW of about 116 KD.

FIG. 2G shows the SDS-PAGE assay result for Erb-huIFNa2-6-9, lane 2 was loaded with a protein marker (MW marker 26619), lane 1 was loaded with the reduced Erb-huIFNa2-6-9 heterodimer protein, and lane 3 was loaded with the non-reduced Erb-huIFNa2-6-9 heterodimer protein, Erb-LC has a MW of about 25 KD, Erb-Fc9 has a MW of about 50 KD, huIFNa2-Fc6 has a MW of about 45 KD, and the Erb-huIFNa2-6-9 heterodimer protein has a MW of about 120 KD.

Similarly, the expression and purification results of the other proteinaceous heterodimers of the present application were verified and confirmed with SDS-PAGE.

The proteinaceous heterodimers thus obtained are named as (from Group 1 to Group 75, respectively): Erb-(huIL10)2-KH, Erb-(huIL10)2-6-9, Erb-(huIL10)2-9-6, Erb-muIFNa4-6-9, Erb-huIFNa2-6-9, Erb-muIFNb-6-9, Erb-huIFNb-6-9, Erb-huIFNL-6-9, Erb-huIL10-6-9, Erb-husIL2-6-9, Erb-husIL2-KH, Mab806-muIFNa4-6-9, Mab806-huIFNa2-6-9, Mab806-muIFNb-6-9, Mab806-huIFNb-6-9, Mab806-huIFNL-6-9, Mab806-huIL10-6-9, Mab806-husIL2-6-9, Mab806-(huIL10)2-6-9, Tmab-muIFNa4-6-9, Tmab-huIFNa2-6-9, Tmab-muIFNb-6-9, Tmab-huIFNb-6-9, Tmab-huIFNL-6-9, Tmab-huIL10-6-9, Tmab-husIL2-6-9, Tmab-(huIL10)2-6-9, Pmab-muIFNa4-6-9, Pmab-huIFNa2-6-9, Pmab-muIFNb-6-9, Pmab-huIFNb-6-9, Pmab-huIFNL-6-9, Pmab-huIL10-6-9, Pmab-husIL2-6-9, Pmab-(huIL10)2-6-9, C-mab-muIFNa4-6-9, C-mab-huIFNa2-6-9, C-mab-muIFNb-6-9, C-mab-huIFNb-6-9, C-mab-huIFNL-6-9, C-mab-huIL10-6-9, C-mab-husIL2-6-9, C-mab-(huIL10)2-6-9, 28H1-muIFNa4-6-9, 28H1-huIFNa2-6-9, 28H1-muIFNb-6-9, 28H1-huIFNb-6-9, 28H1-huIFNL-6-9, 28H1-huIL10-6-9, 28H1-husIL2-6-9, 28H1-(huIL10)2-6-9, 5E5-muIFNa4-6-9, 5E5-huIFNa2-6-9, 5E5-muIFNb-6-9, 5E5-huIFNb-6-9, 5E5-huIFNL-6-9, 5E5-huIL10-6-9, 5E5-husIL2-6-9, 5E5-(huIL10)2-6-9, E-mab-muIFNa4-6-9, E-mab-huIFNa2-6-9, E-mab-muIFNb-6-9, E-mab-huIFNb-6-9, E-mab-huIFNL-6-9, E-mab-huIL10-6-9, E-mab-husIL2-6-9, E-mab-(huIL10)2-6-9, A-mab-muIFNa4-6-9, A-mab-huIFNa2-6-9, A-mab-muIFNb-6-9, A-mab-huIFNb-6-9, A-mab-huIFNL-6-9, A-mab-huIL10-6-9, A-mab-husIL2-6-9, and A-mab-(huIL10)2-6-9, respectively.

Figure 3:
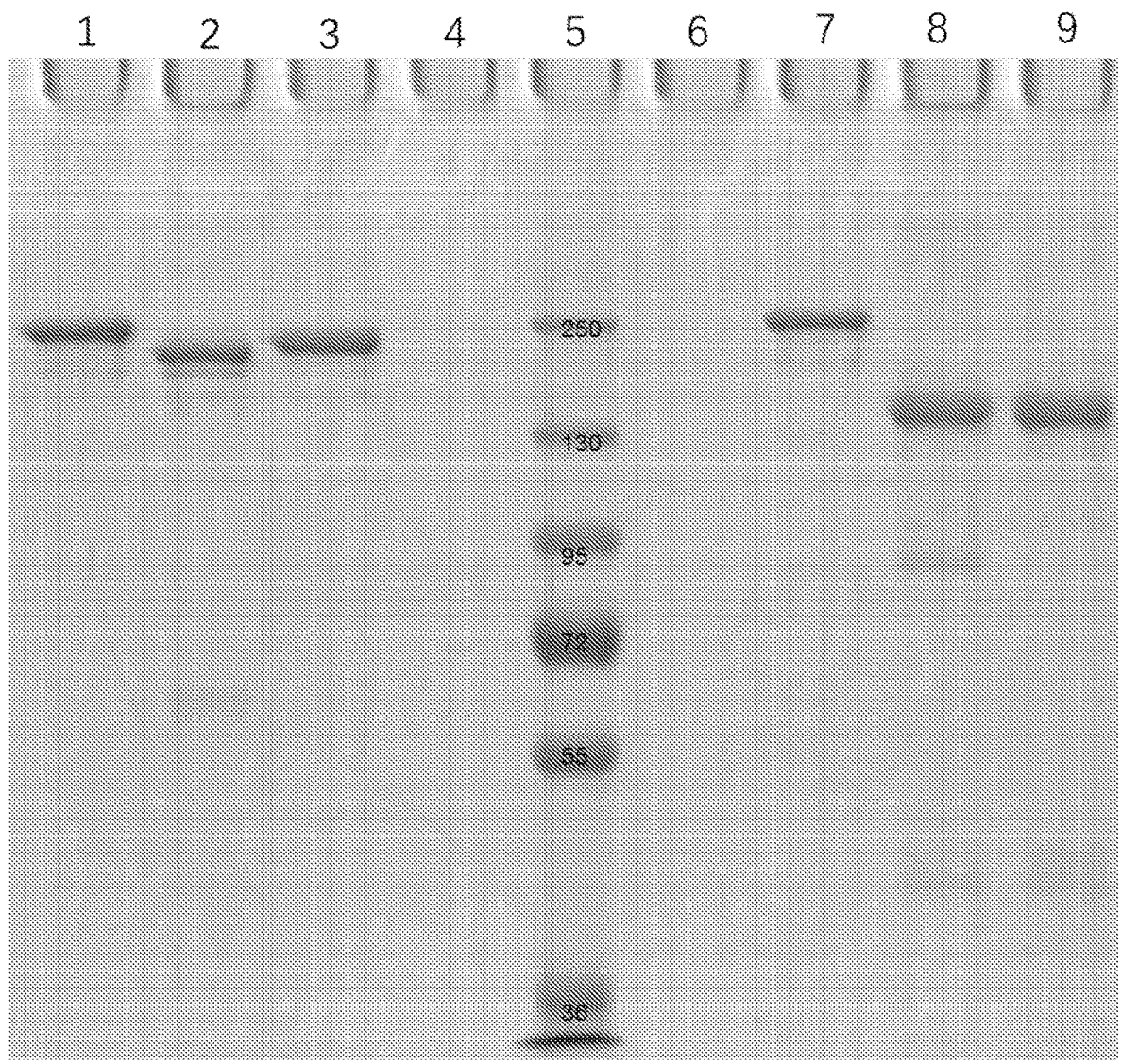
FIG. 3 illustrates a comparison result of the formation of different proteinaceous heterodimers.

Example 4 Formation of the Proteinaceous Heterodimers 4.1 Comparison of Heterodimer Formation of the Heterodimer Erb-(huIL10)2-6-9 with the Reference Protein Erb-(huIL10)2-KH Two days before transfection, 2×100 mL suspension domesticated HEK293 (ATCC, CRL-1573™) cells were prepared for transient transfection, the cells were seeded at a density of $0.8 \times 10^6$ cells/mL. Two days later, cell suspension was centrifuged, and then resuspended in 100 mL Freestyle293 culture medium. The expression plasmids were divided into "Erb-(huIL10)2-6-9 group" and "Erb-(huIL10)2-KH group," wherein the Erb-(huIL10)2-6-9 group comprised: pcDNA4-Erb-Fc9 (33m)+pcDNA4-Erb-LC (33m)+pcDNA4-(huIL10)2-Fc6 (33 μg); and the Erb-(huIL10)2-KH group comprised: pcDNA4-Erb-Knob (33m)+pcDNA4-Erb-LC (33 μg)+pcDNA4-(huIL10)2-Fc-hole (33 μg). Each group of plasmids mixture was diluted with 1 mL Freestyle293 medium and PEI (polyethylenimine) solution was added to perform transfection. Each group of plasmids/PEI mixture was added into 100 mL cell suspension, respectively, and it was then cultured at 37° C., 10% $CO_2$, 90 rpm, the medium was supplemented with 50 μg/L IGF-1. Four hours later, the culture was supplemented with 100 mL EX293 medium, 2 mM glutamine and 50 μg/L IGF-1, and cultured at 135 rpm. After 24 hours, 3.8 mM VPA was added. 5-6 days later, culture supernatant from the transient expression was collected, and the expression products comprising corresponding protein heterodimers were preliminarily purified using Protein A affinity chromatography. The preliminarily purified expression products from the Erb-(huIL10)2-6-9 group comprise the homodimer protein Erb-Fc9/Erb-Fc9, the homodimer protein (huIL10)2-Fc6/(huIL10)2-Fc6, and the heterodimer protein Erb-Fc9/(huIL10)2-Fc6, present in various percentages respectively. The preliminarily purified expression products from the Erb-(huIL10)2-KH group comprise the homodimer protein Erb-Knob/Erb-Knob, the homodimer protein (huIL10)2-Hole/(huIL10)2-Hole, and the heterodimer protein Erb-Knob/(huIL10)2-Hole, present in various percentages respectively. Since the molecular weight of these proteins (i.e., the homodimers and the heterodimers) are different, their corresponding percentage could be determined according to corresponding band intensities reflected on non-reduced SDS-PAGE gels, as shown in FIG. 3. In FIG. 3, lane 1 was loaded with the antibody control (Erbitux), lane 2 was loaded with the expression products from the Erb-(huIL10)2-KH group, and lane 3 was loaded with the expression products from the Erb-(huIL10)2-6-9 group. Lane 4 and lane 6 were blank, lane 5 was loaded with a standard protein marker. The relative band intensities were quantified and the results are summarized in table 7 below, and the intensity of the Erbitux control was 90.9%.

TABLE 7

| Percentage of protein homodimers and heterodimers | | |
|---|---|---|
| Group | Heterodimer (%) | Homodimer (%) |
| Erb-(huIL10)2-KH | 73.7 | 7.6 |
| Erb-(huIL10)2-6-9 | 96.7 | N.A. |

Accordingly, comparing to a corresponding proteinaceous heterodimer comprising the knob-and-hole modifications, the modifications comprised by the proteinaceous heterodimers of the present disclosure more effectively promote heterodimer formation.

4.2 Comparison of Heterodimer Formation of the Heterodimer Erb-husIL2-6-9 with the Reference Protein Erb-husIL2-KH Two days before transfection, 2×100 mL suspension domesticated HEK293 (ATCC CRL-1573™) cells were prepared for transient transfection, the cells were seeded at a density of $0.8 \times 10^6$ cells/mL. Two days later, cell suspension was centrifuged, and then resuspended in 100 mL Freestyle293 culture medium. The expression plasmids were divided into "Erb-husIL2-6-9 group" and "Erb-husIL2-KH group," wherein the Erb-husIL2-6-9 group comprised: pcDNA4-Erb-Fc9 (33 μg)+pcDNA4-Erb-LC (33 μg)+pcDNA4-husIL2-Fc6 (33 μg); and the Erb-husIL2-KH group comprised: pcDNA4-Erb-Knob (33 μg)+pcDNA4-Erb-LC (33 μg)+pcDNA4-husIL2-Fc-hole (33 μg). Each group of plasmids mixture was diluted with 1 mL Freestyle293 medium and PEI (polyethylenimine) solution was added to perform transfection. Each group of plasmids/PEI mixture was added into 100 mL cell suspension, respectively, and it was then cultured at 37° C., 10% $CO_2$, 90 rpm, the medium was supplemented with 50 μg/L IGF-1. Four hours later, the culture was supplemented with 100 mL EX293 medium, 2 mM glutamine and 50 μg/L IGF-1, and cultured at 135 rpm. After 24 hours, 3.8 mM VPA was added. 5-6 days later, culture supernatant from the transient expression was collected, and the expression products comprising corresponding protein heterodimers were preliminarily purified using Protein A affinity chromatography. The preliminarily purified expression products from the Erb-husIL2-6-9 group comprise the homodimer protein Erb-Fc9/Erb-Fc9, the homodimer protein husIL2-Fc6/husIL2-Fc6, and the heterodimer protein Erb-Fc9/husIL2-Fc6, present in various percentages respectively. The preliminarily purified expression products from the Erb-husIL2-KH group comprise the homodimer protein Erb-Knob/Erb-Knob, the homodimer protein husIL2-Hole/husIL2-Hole, and the heterodimer protein Erb-Knob/husIL2-Hole, present in various percentages respectively. Since the molecular weight of these proteins (i.e., the homodimers and the heterodimers) are different, their corresponding percentage could be determined according to corresponding band intensities reflected on non-reduced SDS-PAGE gels, as shown in FIG. 3. In FIG. 3, lane 7 was loaded with the antibody control (Erbitux), lane 8 was loaded with the expression products from the Erb-husIL2-KH group, and lane 9 was loaded with the expression products from the Erb-husIL2-6-9 group. Lane 4 and lane 6 were blank, lane 5 was loaded with a standard protein marker. The relative band intensities were quantified and the results are summarized in table 8 below, and the intensity of the Erbitux control was 90.3%.

TABLE 8

Percentage of protein homodimers and heterodimers

| Group | Heterodimer (%) | Homodimer (%) |
|---|---|---|
| Erb-husIL2-KH | 69.0 | 12.5 |
| Erb-husIL2-6-9 | 97.5 | N.A. |

Accordingly, comparing to a corresponding proteinaceous heterodimer comprising the knob-and-hole modifications, the modifications comprised by the proteinaceous heterodimers of the present disclosure more effectively promote heterodimer formation.

Example 5 Comparison of Expression Products with Different Modifications

As shown in Example 4, comparing to a corresponding proteinaceous heterodimer comprising the knob-and-hole modifications, the modifications comprised by the proteinaceous heterodimers of the present disclosure more effectively promote heterodimer formation.

To further examine the effects of the first modification and that of the second modification, we compared the expression products of:

Group2: pcDNA4-Erb-Fc6+pcDNA4-Erb-LC+pcDNA4-(huIL10)2-Fc9; and
Group3: pcDNA4-Erb-Fc9+pcDNA4-Erb-LC+pcDNA4-(huIL10)2-Fc6 as described above in Example 3.

Figure 4:
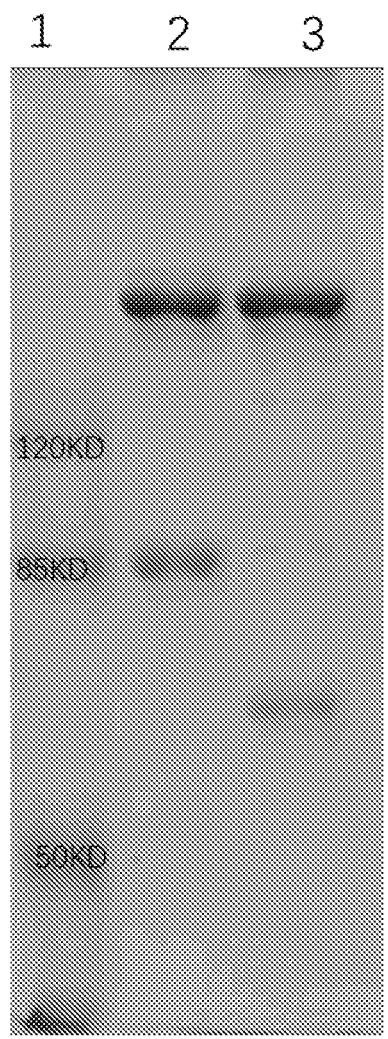
FIG. 4 illustrates a comparison of protein expression results with the immunoregulator fused to different Fc regions.

Briefly, two days before transfection, 2×100 mL suspension domesticated HEK293 (ATCC, CRL-1573™) cells were prepared for transient transfection, the cells were seeded at a density of $0.8 \times 10^6$ cells/mL. Two days later, cell suspension was centrifuged, and then resuspended in 100 mL Freestyle293 culture medium. The expression plasmids were divided into "Erb-(huIL10)2-6-9 group" and "Erb-(huIL10)2-9-6 group," wherein the Erb-(huIL10)2-6-9 group comprised: pcDNA4-Erb-Fc9(33 μg)+pcDNA4-Erb-LC (33 μg)+pcDNA4-(huIL10)2-Fc6 (33 μg); and the Erb-(huIL10)2-9-6 group comprised: pcDNA4-Erb-Fc6(33 μg)+pcDNA4-Erb-LC (33 μg)+pcDNA4-(huIL10)2-Fc9(33 μg). Each group of plasmids mixture was diluted with 1 mL Freestyle293 medium and PEI (polyethylenimine) solution was added to perform transfection. Each group of plasmids/PEI mixture was added into 100 mL cell suspension, respectively, and it was then cultured at 37° C., 10% $CO_2$, 90 rpm, the medium was supplemented with 50 μg/L IGF-1. Four hours later, the culture was supplemented with 100 mL EX293 medium, 2 mM glutamine and 50 μg/L IGF-1, and cultured at 135 rpm. After 24 hours, 3.8 mM VPA was added. 5-6 days later, culture supernatant from the transient expression was collected, and the expression products comprising corresponding protein heterodimers were preliminarily purified using Protein A affinity chromatography. The preliminarily purified expression products from the Erb-(huIL10)2-6-9 group comprise the homodimer protein Erb-Fc9/Erb-Fc9 (i.e. Fc9 homodimer), the homodimer protein (huIL10)2-Fc6/(huIL10)2-Fc6 (i.e. Fc6 homodimer), and the heterodimer protein Erb-Fc9/(huIL10)2-Fc6, present in various percentages respectively. The preliminarily purified expression products from the Erb-(huIL10)2-9-6 group comprise the homodimer protein Erb-Fc6/Erb-Fc6 (i.e. Fc6 homodimer), the homodimer protein (huIL10)2-Fc9/(huIL10)2-Fc9 (i.e. Fc9 homodimer), and the heterodimer protein Erb-Fc6/(huIL10)2-Fc9, present in various percentages respectively. Since the molecular weight of these proteins (i.e., the homodimers and the heterodimers) are different, their corresponding percentage could be determined according to corresponding band intensities reflected on non-reduced SDS-PAGE gels, as shown in FIG. 4. In FIG. 4, lane 1 was loaded with a standard protein marker, lane 2 was loaded with the expression products from the Erb-(huIL10)2-6-9 group, and lane 3 was loaded with the expression products from the Erb-(huIL10)2-9-6 group. As can be seen from FIG. 4, in lane 2, most of the homodimers (i.e., undesired impurities in the protein mixture) formed were the Erb-Fc9/Erb-Fc9 homodimers (i.e. Fc9 homodimer), as indicated by the band around 85 KD (the Erb-Fc9/Erb-Fc9 homodimers were very unstable and easily dissociated into monomers with a molecular weight of about 85

KD). Interestingly and surprisingly, in lane 3, most of the homodimers (i.e., undesired impurities in the protein mixture) formed were the (huIL10)2-Fc9/(huIL10)2-Fc9 homodimers (i.e. Fc9 homodimer), as indicated by the band between 50 KD and 85 KD (the (huIL10)2-Fc9/(huIL10)2-Fc9 homodimers were very unstable and easily dissociated into monomers with a molecular weight between 50 KD and 85 KD). Thus, the tendency for forming Erb-Fc9/Erb-Fc9 homodimers was not due to the Erb portions but the Fc9 portions.

Accordingly, the member of the proteinaceous heterodimers comprising the Fc9 region intends to cause formation of undesired homodimer impurities. Thus, in the proteinaceous heterodimers of the present disclosure, it is more advantageous to fuse the immunoregulators (such as the cytokines) to the Fc6 domain (i.e., the second Fc region), instead of the Fc9 domain (i.e., the first Fc region).

Figures 5, 6:
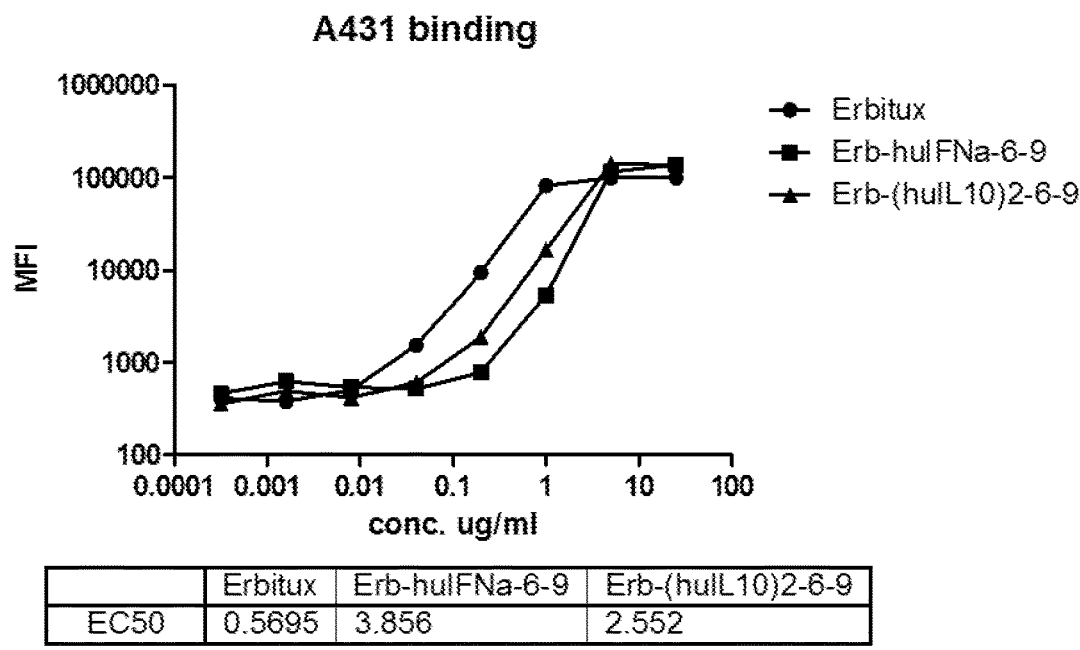
FIG. 5 illustrates specific target binding affinity of the proteinaceous heterodimers according to the present application.
FIG. 6 illustrates the target binding affinity of the proteinaceous heterodimers according to the present application.

Example 6 Binding of the Proteinaceous Heterodimers to Corresponding Targets 6.1 Binding of Erb-Interferon Proteinaceous Heterodimers to EGFR Human squamous cell carcinoma A431 cell line was used to examine binding of the Erb-interferon proteinaceous heterodimers to EGFR. Flow cytometry analysis was used, wherein series diluted Erb-interferon proteinaceous heterodimers of the present disclosure (or control Erb antibody (Merck Erbitux)) and anti-human IgG Fc specific PE (eBioscience:12-4998-82) secondary antibody were added sequentially into the cells. Then, flow cytometry analysis was performed, and dosage-effect curve was made with protein concentration and medium fluorescence intensity (MFI) from the PE channel. As demonstrated in FIG. 5, the proteinaceous heterodimer Erb-huIFNa2-6-9 specifically binds to the target EGFR, in a manner similar to the control antibody Cetuximab (Erbitux). Since the proteinaceous heterodimer comprises only one EGFR binding moiety, the EC50 thereof is higher than that of the control antibody Cetuximab, which comprises two EGFR binding moieties.

The binding affinity of Erb-huIFNa2-6-9 to its target EGFR was also examinedwith Bio-Layer Interferometry (BLI), in comparison to the control antibody Cetuximab. The experiments were conducted using Octect K2. Protein A biosensors and EGFR-His protein were used. The respective binding affinities of Erb-huIFNa2-6-9 and Cetuximab to EGFR-His were shown in FIG. 6. The results demonstrate that the binding affinity of Erb-huIFNa2-6-9 to EGFR-His was not significantly different from that of the control antibody Cetuximab.

6.2 Binding of Erb-Interleukin Proteinaceous Heterodimers to EGFR

Human squamous cell carcinoma A431 cell line was used to examine binding of the Erb-interleukin proteinaceous heterodimers to EGFR. Flow cytometry analysis was used, wherein series diluted Erb-interleukin proteinaceous heterodimers of the present disclosure (or control Erb antibody (Merck Erbitux)) and anti-human IgG Fc specific PE (eBioscience:12-4998-82) secondary antibody were added sequentially into the cells. Then, flow cytometry analysis was performed, and dosage-effect curve was made with protein concentration and medium fluorescence intensity (MFI) from the PE channel. As demonstrated in FIG. 5, the proteinaceous heterodimer Erb-(huIL10)2-6-9 specifically bound to the target EGFR, in a manner similar to the control antibody Cetuximab. Since the proteinaceous heterodimer comprises only one EGFR binding moiety, the EC50 thereof is higher than that of the control antibody Cetuximab, which comprises two EGFR binding moieties.

The binding affinity of Erb-(huIL10)2-6-9 to its target EGFR was also examined with Bio-Layer Interferometry (BLI), in comparison to the control antibody Cetuximab. The experiments were conducted using Octect K2. Protein A biosensors and EGFR-His protein were used. The respective binding affinities of Erb-(huIL10)2-6-9 and Cetuximab to EGFR-His were shown in FIG. 6. The results demonstrate that the binding affinity of Erb-(huIL10)2-6-9 to EGFR-His was not significantly different from that of the control antibody Cetuximab.

Figure 7:
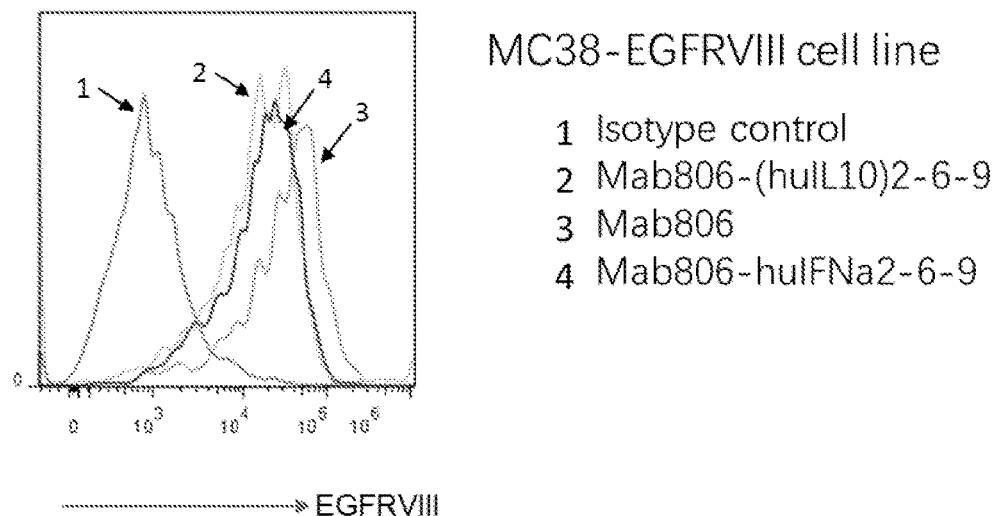
FIG. 7 illustrates specific target binding affinity of the proteinaceous heterodimers according to the present application.

6.3 Binding of Mab806-Interferon and Mab806-Interleukin Proteinaceous Heterodimers to EGFR The binding of Mab806-huIFNa2-6-9 and Mab806-(huIL10)2-6-9 to EGFRVIII were examined using a mouse colon cancer cell line (i.e., the MC38 cell line) stably expressing human EGFRvIII. Mab806 is an antibody binding to the EGFRvIII mutant, however, it may also bind to wild-type EGFR with low affinity. Flow cytometry was performed, and the results are shown in FIG. 7. As can be seen from FIG. 7, Mab806-huIFNa2-6-9 and Mab806-(huIL10)2-6-9 bind to the EGFRvIII expressed on MC38 cells.

6.4 Binding of Tmab-Interleukin Proteinaceous Heterodimers to Her2

Figure 8:
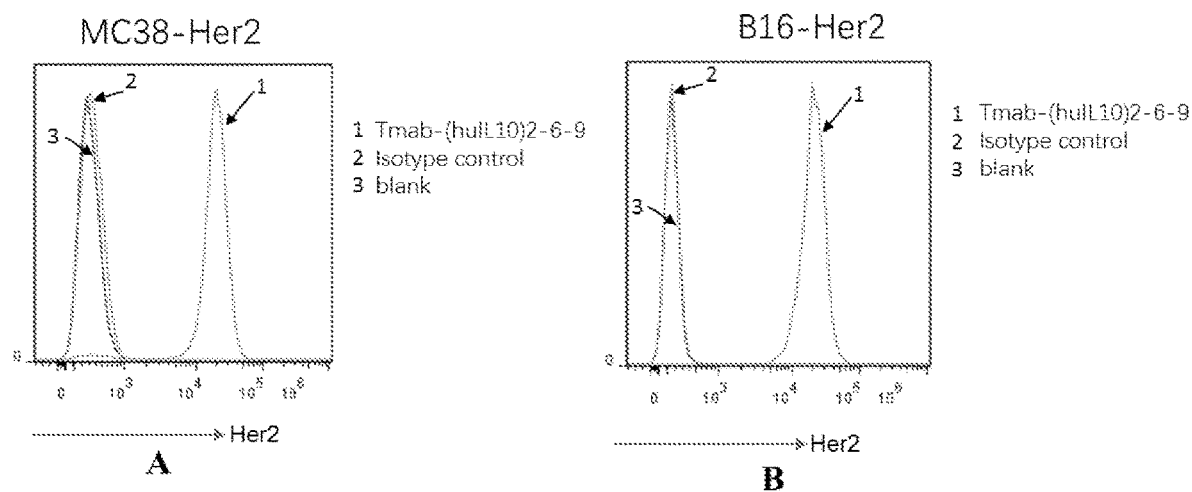
FIG. 8 illustrates specific target binding affinity of the proteinaceous heterodimers according to the present application.

Similarly, binding of Tmab-(huIL10)2-6-9 heterodimers to Her2 was also examined, the experiments were conducted using a mouse colon cancer cell line (i.e., the MC38 cell line) stably expressing human Her2 and a melanoma cell line (i.e., the B16 cell line) stably expressing human Her2. The results are shown in panel (A) (MC38 cells) and panel (B) (B16 cells) of FIG. 8, respectively. As can be seen from FIG. 8, Tmab-(huIL10)2-6-9 binds to Her2 expressed on MC38 or B16 cells. Similar results were obtained for the Pmab-interleukin proteinaceous heterodimers (e.g., Pmab-(huIL10)2-6-9).

6.5 Binding of C-Mab-Interferon and C-Mab-Interleukin Proteinaceous Heterodimers to GPC3

Figure 9:
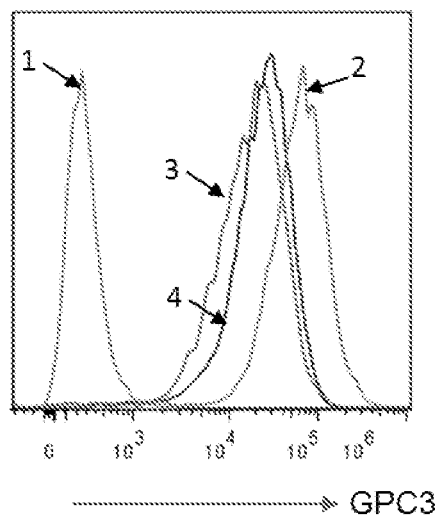
FIG. 9 illustrates specific target binding affinity of the proteinaceous heterodimers according to the present application.

The binding of C-mab-huIFNa2-6-9 and C-mab-(huIL10)2-6-9 to GPC3 was examined using a mouse colon cancer cell line (the MC38 cell line) stably expressing human GPC3. Flow cytometry was performed, and the result is shown in FIG. 9. As can be seen from FIG. 9, C-mab-huIFNa2-6-9 and C-mab-(huIL10)2-6-9 bind to GPC3 expressed on MC38 cells.

Figure 10:
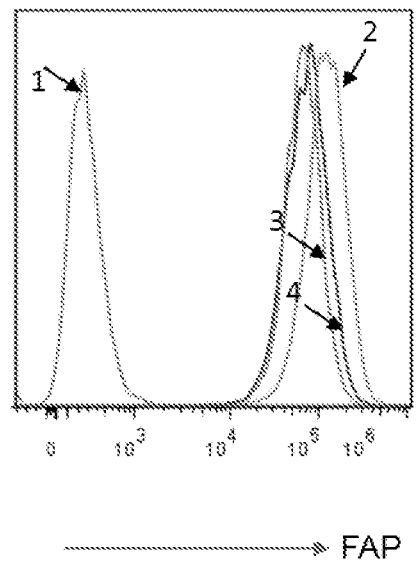
FIG. 10 illustrates specific target binding affinity of the proteinaceous heterodimers according to the present application.

6.6 Binding of 28H1-Interferon and 28H1-Interleukin Proteinaceous Heterodimers to FAP The binding of 28H1-huIFNa2-6-9 and 28H1-(huIL10)2-6-9 to FAP were examined using mouse colon cancer cell line (MC38 cell line) expressing human FAP. Flow cytometry was performed, and the result is shown in FIG. 10. As can be seen from FIG. 10, 28H1-huIFNa2-6-9 and 28H1-(huIL10)2-6-9 bind to FAP expressed on MC38 cells.

6.7 Binding of 5E5-Interferon and 5E5-Interleukin Proteinaceous Heterodimers to MUC1

Figure 21:
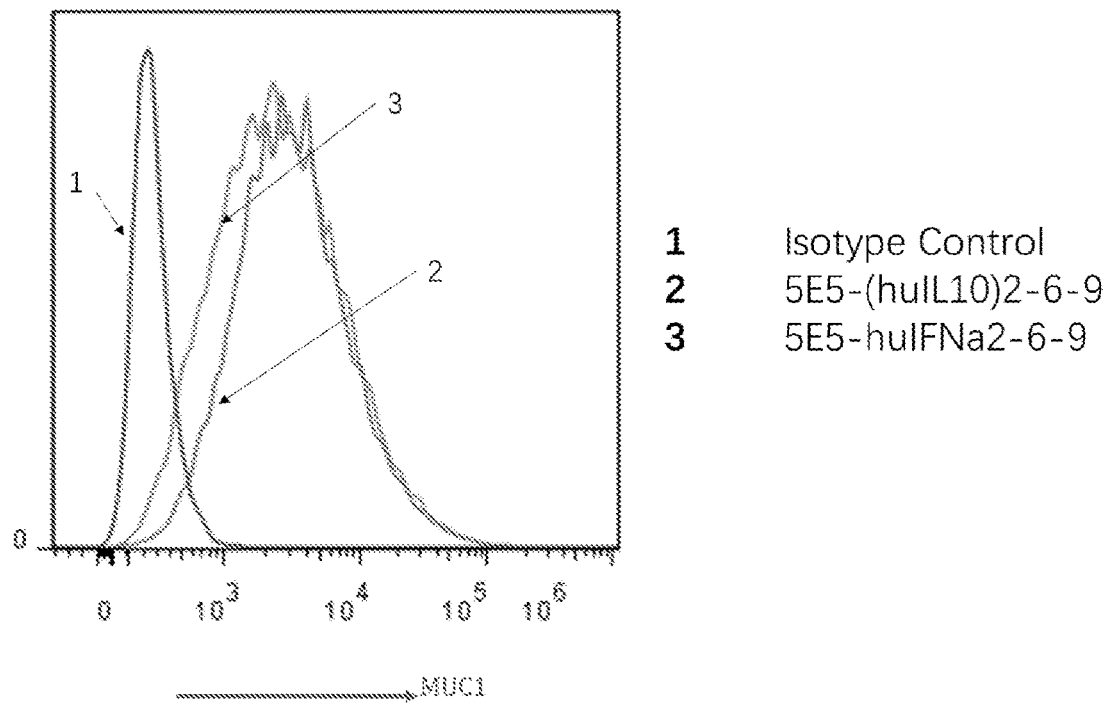
FIG. 21 illustrates specific target binding affinity of the proteinaceous heterodimers according to the present application.

The binding of 5E5-huIFNa2-6-9 and 5E5-(huIL10)2-6-9 to MUC1 were examined using human breast cancer cell line (T-47D cell line) expressing human MUC1. Flow cytometry was performed, and the result is shown in FIG. 21. As can be seen from FIG. 21, 5E5-huIFNa2-6-9 and 5E5-(huIL10)2-6-9 bind to MUC1 expressed on T-47D cells.

Figure 22:
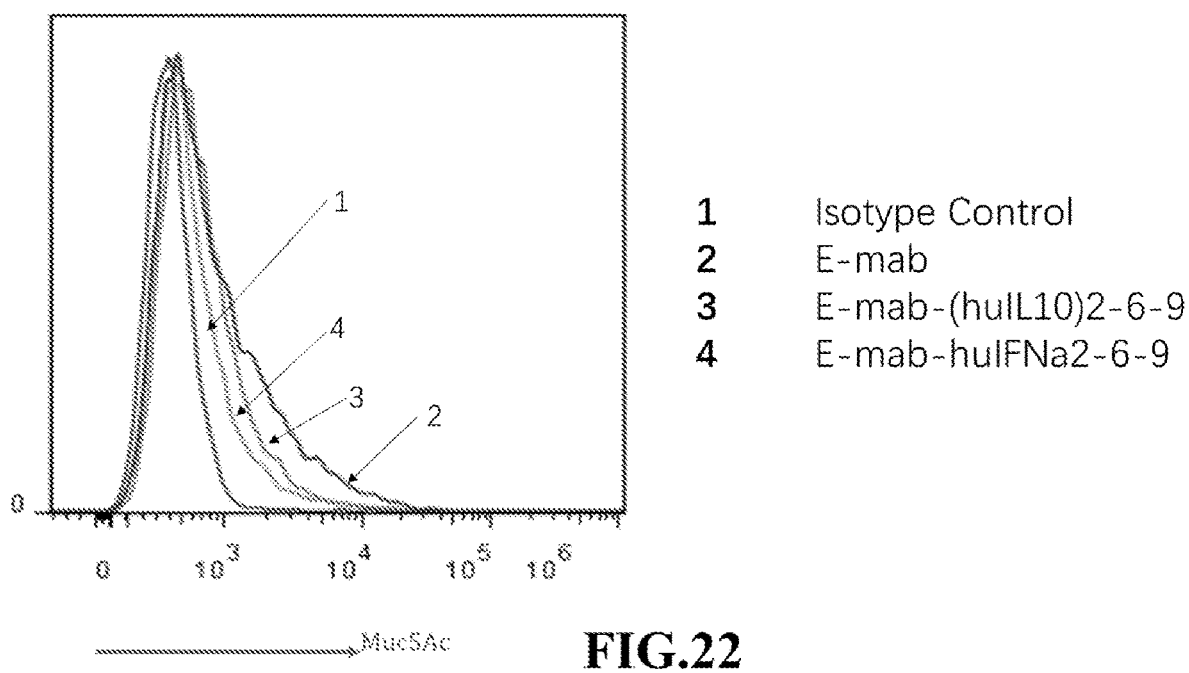
FIG. 22 illustrates specific target binding affinity of the proteinaceous heterodimers according to the present application.

6.8 Binding of Ensituximab-Interferon and Ensituximab-Interleukin Proteinaceous Heterodimers to MUCSAC The binding of E-mab-huIFNa2-6-9 and E-mab-(huIL10)2-6-9 to MUC5AC were examined using human pancreatic cancer cell line (CFPAC-1 cell line) expressing human MUC5AC. Flow cytometry was performed, and the result is shown in FIG. 22. As can be seen from FIG. 22, the binding of E-mab-huIFNa2-6-9 and E-mab-(huIL10)2-6-9 to the MUC5AC expressed on CFPAC-1 cells was not very strong. This may be due to a potential inadequate expression of the specific protein glycotype found in situ in tumor tissues, and it was known that E-mab binds strongly to the specific protein glycotype.

Figure 23:
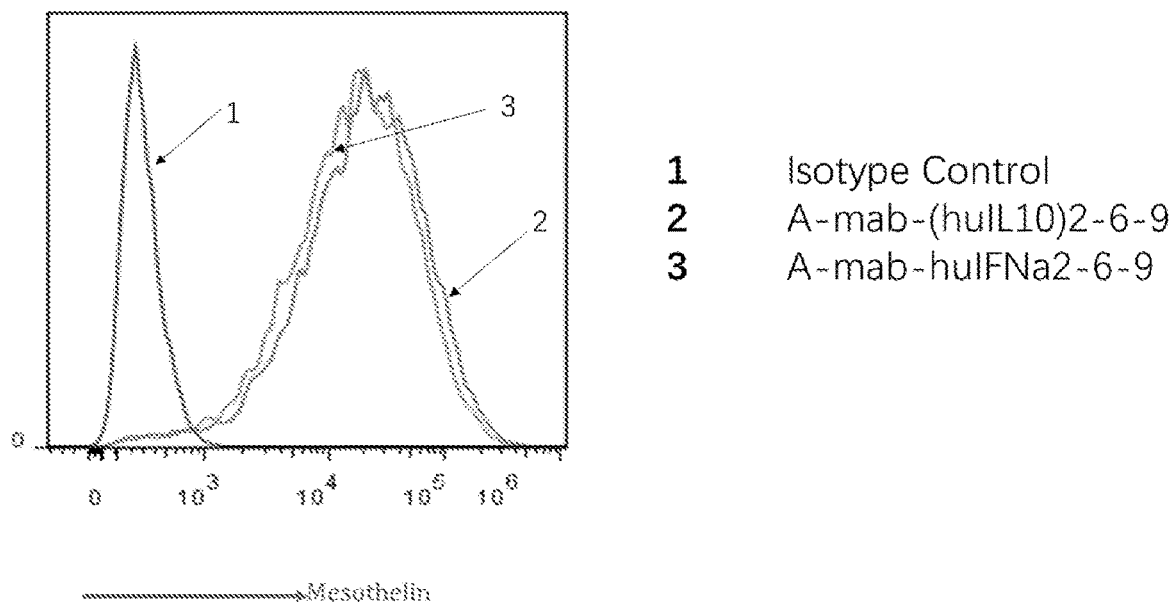
FIG. 23 illustrates specific target binding affinity of the proteinaceous heterodimers according to the present application.

6.9 Binding of Amatuximab-Interferon and Amatuximab-Interleukin Proteinaceous Heterodimers to Mesothelin The binding of A-mab-huIFNa2-6-9 and A-mab-(huIL10) 2-6-9 to Mesothelin were examined using human stomach cancer cell line (NCI-N87 cell line) expressing human Mesothelin. Flow cytometry was performed, and the result is shown in FIG. 23. As can be seen from FIG. 23, A-mab-huIFNa2-6-9 and A-mab-(huIL10)2-6-9 bind to Mesothelin expressed on NCI-N87 cells.

Figure 11:
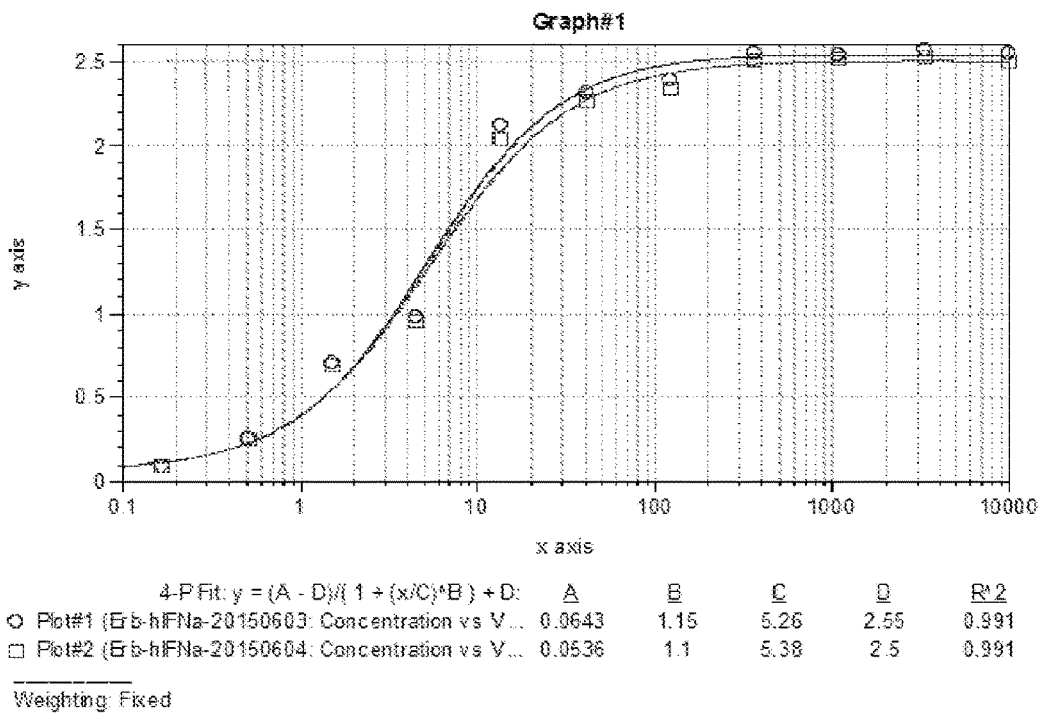
FIG. 11 illustrates the presence of immunoregulators in the proteinaceous heterodimers according to the present application.

Example 7 the Presence and the Biological Activity of the Immunoregulators Comprised in the Proteinaceous Heterodimers 7.1 the Presence and the Biological Activity of Interferons in the Proteinaceous Heterodimers of the Present Disclosure The presence of huIFNa2 in the heterodimer Erb-huIFNa2-6-9 was confirmed with ELISA, as shown in FIG. 11. Briefly, ELISA plates were coated with EGFR-huFc at 2 µg/ml dissolved in buffer (50 mM $Na_2CO_3/NaHCO_3$; pH9.6), overnight at 4° C. The plates were washed for three times with PBST (PH7.4) containing 0.05% (V/V) Tween-20 and blocked with 3% BSA in PBS for 1 h, then, serial diluted Erb-huIFNa2-6-9 was added and incubated for 2 h at 37° C. Then 1 µg/ml anti-huIFNa-biotin was added and incubated for 1 h at 37° C. Subsequently, 1:1000 diluted SA-HRP was added and incubated for 40 min at 37° C. The binding was examined with the (TMB, TIANGEN Cat #PA107-01; Lot #1614) substrate, stopped with 2M $H_2SO_4$. The absorbance at 450 nm-650 nm was examined in a Molecular Devices SpectraMax Plus-384 microplate reader. The concentration was determined using the computer program SoftMax Pro 5.4.

Figure 13:
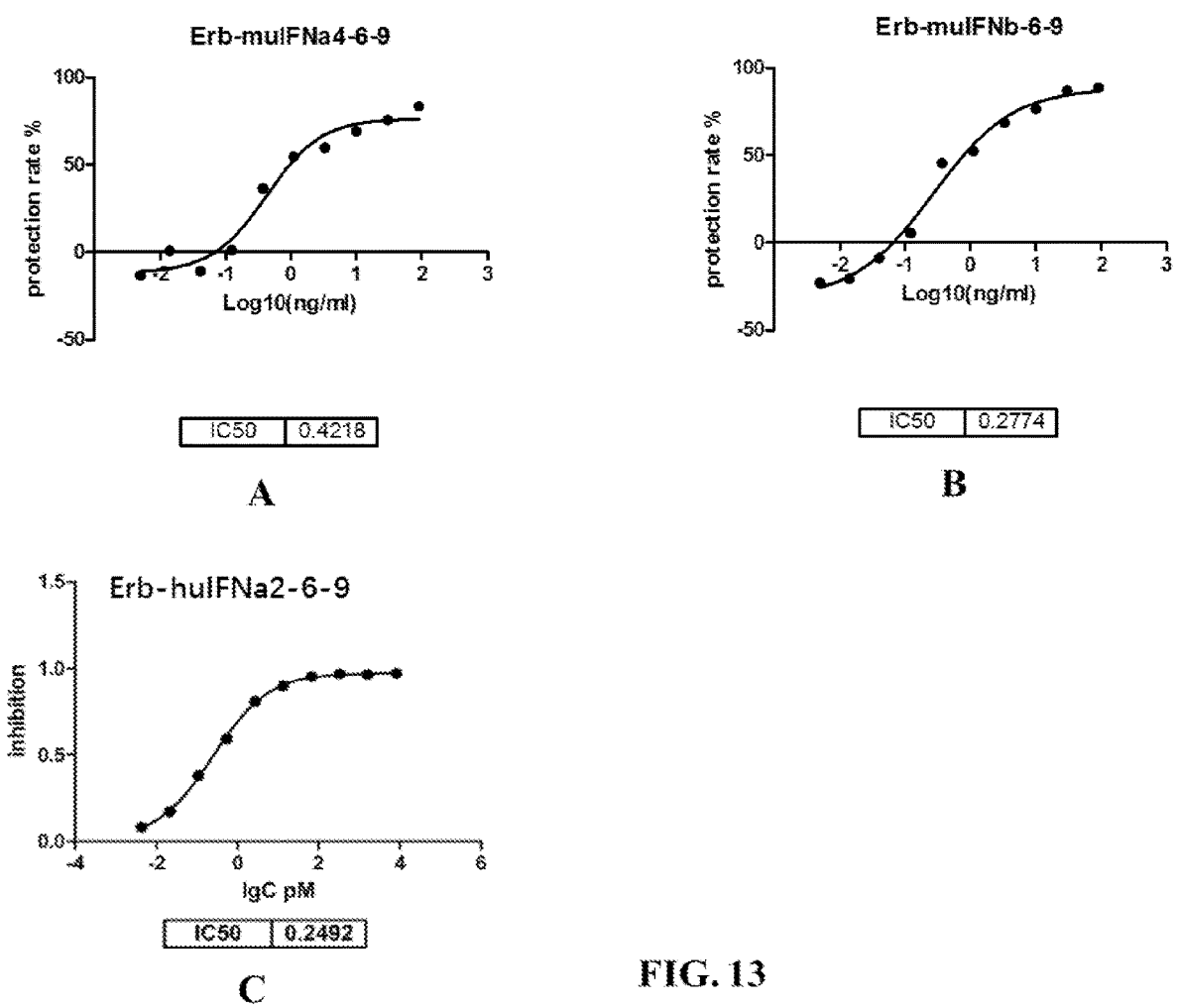
FIG. 13 illustrates anti-virus activities of the proteinaceous heterodimers according to the present application.

Mouse fibroblast cell line L929 or human hepatoma cell line HepG2 was infected with EGFP (Enhanced Green Fluorescent Protein) labeled Vesicular stomatitis viruses (VSV), to examine the activity of interferons in increasing anti-virus ability of the cells. The activity of muIFNa4, muIFNb, and huIFNa2 was examined, respectively. Briefly, cells were cultured for 8 hours in the presence of series diluted proteinaceous heterodimers of the present disclosure, then, appropriate number of cells infected with VSV-EGFP was added. 24 hours later, the percentage of infected cells was determined with flow cytometry analysis, and protection rate of the proteinaceous heterodimers for virus infection was calculated. $EC_{50}$ was then obtained according to the dosage-effect curve of protection rate and concentration of the proteinaceous heterodimers. As shown in FIG. 13, the heterodimers Erb-muIFNa4-6-9 (A), Erb-muIFNb-6-9 (B), and Erb-huIFNa2-6-9 (C) protected the cells from virus infection.

Figure 12:
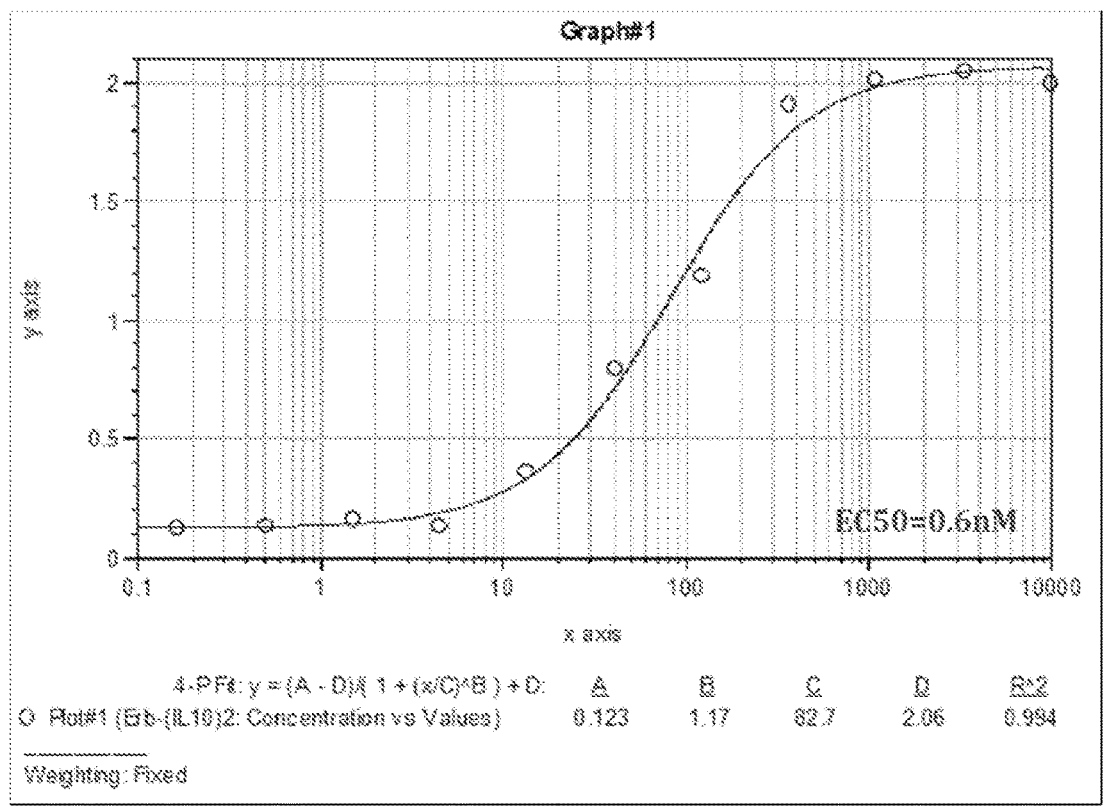
FIG. 12 illustrates the presence of immunoregulators in the proteinaceous heterodimers according to the present application.

7.2 the Presence and the Biological Activity of Interleukins in the Proteinaceous Heterodimers of the Present Disclosure The presence of huIL10 in the heterodimer Erb-(huIL10) 2-6-9 was confirmed with the ELISA, as shown in FIG. 12. Briefly, ELISA plates were coated with anti-human IL10 (BioLegend, Lot.NO:B179948) at 5 µg/ml dissolved in buffer (50 mM $Na_2CO_3/NaHCO_3$; pH9.6), overnight at 4° C. The plates were washed for three times with PBST (PH7.4) containing 0.05% (V/V) Tween-20 and blocked with 3% BSA in PBS for 1 h, then, Erb-(huIL10)2-6-9 that was 2-fold serial diluted from 2000 ng/ml was added and incubated for 2 h at 37° C. Then 2 µg/ml EGFR-Fc-biotin was added and incubated for 1 h at 37° C. After that, 1:1000 diluted SA-HRP was added and incubated for 40 min at 37° C. The binding was examined with the (TMB, TIANGEN Cat #PA107-01; Lot #1614) substrate, stopped with 2M $H_2SO_4$. The absorbance at 450 nm-650 nm was detected in a Molecular Devices SpectraMax Plus-384 microplate reader. The concentration was determined using computer program SoftMax Pro 5.4.

Figure 14:
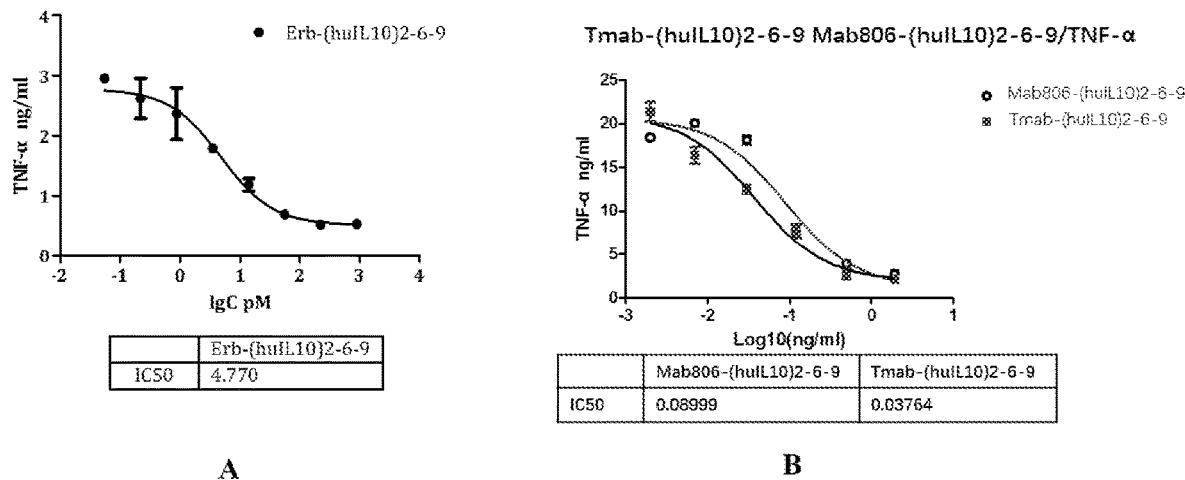
FIG. 14 illustrates interleukin activities of the proteinaceous heterodimers according to the present application.

Interleukins can inhibit lipopolysaccharide (LPS) stimulated release of TNF-α from macrophages (David F. et al., 1991, The Journal of Immunology. Vol. 147.3815-3822). To test this activity of interleukins in the proteinaceous heterodimers of the present disclosure, human peripheral blood mononuclear cells (PBMC) were seeded in a 96-well plate, suspended cells were washed away after 3-4 hours. Then, various concentrations of Erb-(huIL10)2-6-9, Mab806-(huIL10)2-6-9 and Tmab-(huIL10)2-6-9 of the present disclosure were added, and 2 hrs later, 2 µg/ml LPS was added for stimulation of 24 hours. Supernatant was collected, and release of TNF-α was examined using ELISA. The ELISA was conducted according to the instructions included in the TNF-α Kit (eBioscience, 88-7346). Briefly, capture antibody was diluted with coating buffer, then, Costar 9018 ELISA plate was coated; then, a standard and some appropriately diluted samples were added. Afterwards, reaction was detected using detection antibody, and developed with TMB. The results are shown in FIG. 14. As demonstrated in FIG. 14A, Erb-(huIL10)2-6-9 inhibits release of TNF-α in a dosage dependent manner. FIG. 14B also shows that Mab806-(huIL10)2-6-9 and Tmab-(huIL10)2-6-9 of the present disclosure also effectively inhibit release of TNF-α in a dosage dependent manner.

Figure 15:
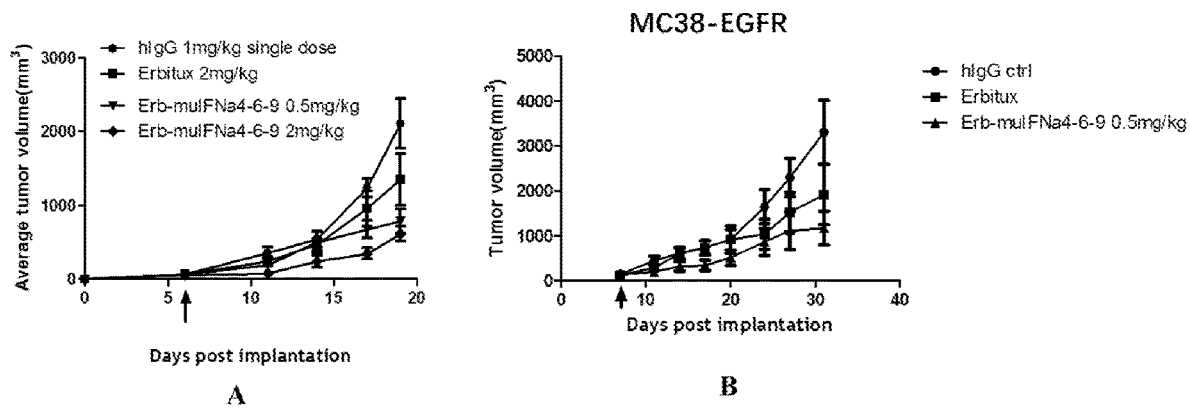
FIG. 15 illustrates the in vivo anti-tumor activity of the proteinaceous heterodimers according to the present application.

Example 8 Anti-Tumor Activity of the Proteinaceous Heterodimers 8.1 Anti-Tumor Activity of Erb-Interferon Heterodimers of the Present Disclosure The in vivo anti-tumor activity of the Erb-muIFNa4-6-9 heterodimer was tested using C57 BL/6 wide type mouse model. Briefly, 8-week old female C57 BL/6 mice were subcutaneously injected with $7 \times 10^5$ B16-EGFR (FIG. 15A) or $1 \times 10^6$ MC38-EGFR (FIG. 15B) cells. After 7 days, the tumor volume was measured to be around 70 $mm^3$. Erb-muIFNa4-6-9 heterodimer or control antibody Cetuximab (Erbitux, Merck) was injected intra-peritoneally (i.p.). The Erb-muIFNa4-6-9 heterodimer was injected at 2 mg/kg and 0.5 mg/kg, respectively, and the dosage of Cetuximab was 2 mg/kg. Tumor size was measured twice per week, and the volume of the tumors was calculated to obtain a curve of tumor growth. The results are demonstrated in FIG. 15, for each dosage administered, the Erb-muIFNa4-6-9 heterodimer effectively reduced tumor volume in vivo.

Figure 16:
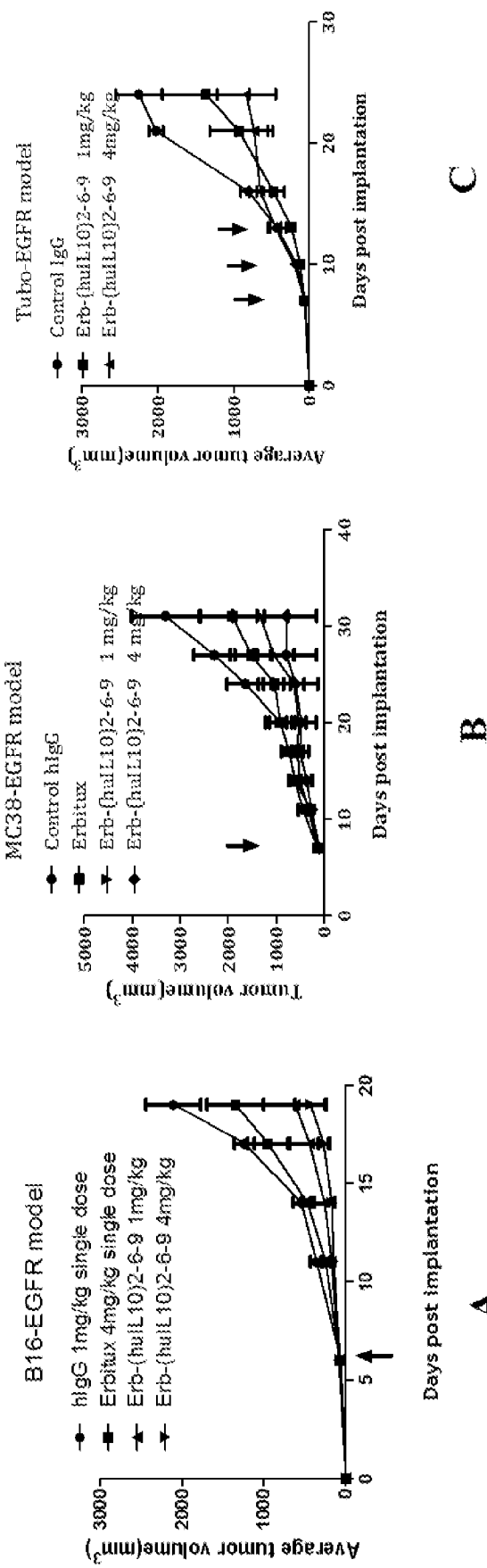
FIG. 16 illustrates the in vivo anti-tumor activity of the proteinaceous heterodimers according to the present application.

8.2 Anti-Tumor Activity of Erb-Interleukin Heterodimers of the Present Disclosure Similar to Example 8.1, in vivo anti-tumor activity of Erb-(huIL10)2-6-9 was tested using C57BL/6 mouse model. Briefly, 8-week old female C57 BL/6 mice were subcutaneously injected with $7 \times 10^5$ B16-EGFR cells (FIG. 16A) or $1 \times 10^6$ MC38-EGFR cells (FIG. 16B). After 7 days, the tumor volume was measured to be around 70 $mm^3$. Erb-(huIL10) 2-6-9 heterodimer or control antibody Cetuximab (Erbitux, Merck) was injected once intra-peritoneally (i.p.). The Erb-(huIL10)2-6-9 heterodimer was injected at two different doses (1 mg/kg and 4 mg/kg, respectively), and the dosage of Cetuximab was 4 mg/kg. Tumor size was measured twice per week, the volume of the tumors was calculated to obtain a curve of tumor growth. The results are demonstrated in FIGS. 16A and 16B.

Similarly, Balb/c mice were inoculated subcutaneously with $5\times10^5$ Tubo-EGFR on the right flank. The mice were treated three times with Erb-(huIL10)2-6-9 heterodimer i.p. at two different doses (1 mg/kg and 4 mg/kg respectively) on day7, day10, day14. Erb-(huIL10)2-6-9 effectively reduced tumor volume in vivo in a dosage dependent manner, as shown in FIG. 16C.

Figure 17:
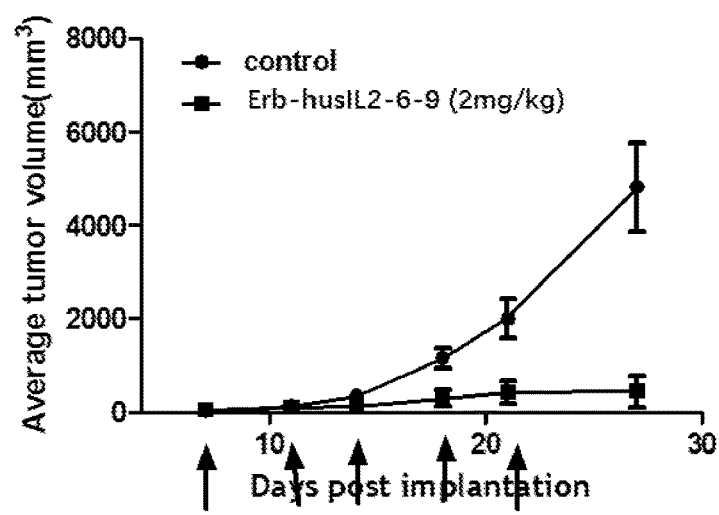
FIG. 17 illustrates the in vivo anti-tumor activity of the proteinaceous heterodimers according to the present application.

8.3 Anti-Tumor Activity of Other Proteinaceous Heterodimers of the Present Disclosure Similar to Example 8.1, in vivo anti-tumor activity of Erb-husIL2-6-9 was tested using C57 BL/6 mouse model. Briefly, 8-week old female C57 BL/6 mice were subcutaneously injected with $7\times10^5$ B16-EGFR. After 7 days, the tumor volume was measured to be around 70 mm$^3$. The Erb-husIL2-6-9 heterodimer at 2 mg/kg or PBS was injected intra-peritoneally (i.p.) every three days and for a total of five doses. Tumor size was measured twice per week, the volume of the tumors was calculated to obtain a curve of tumor growth. The results are demonstrated in FIG. 17, it can be seen that the Erb-husIL2-6-9 heterodimer effectively reduced tumor volume in vivo.

Figure 18:
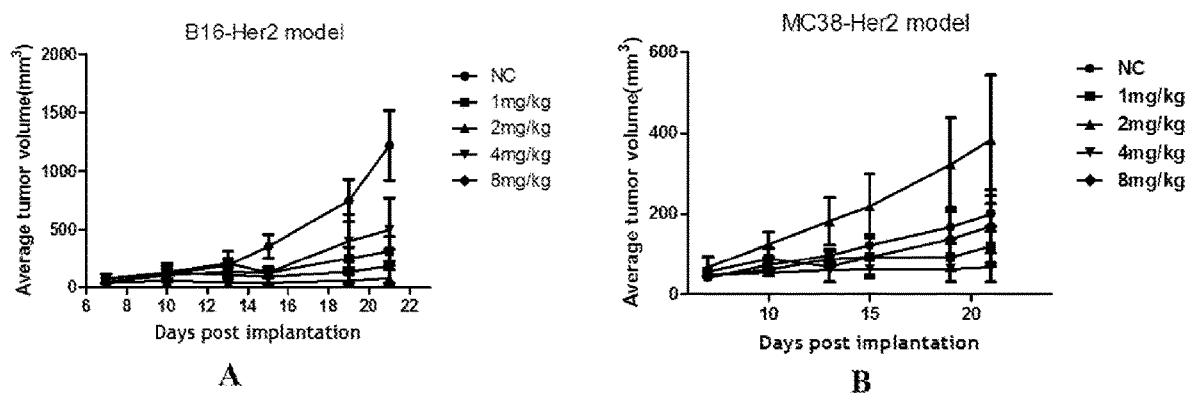
FIG. 18 illustrates the in vivo anti-tumor activity of the proteinaceous heterodimers according to the present application.

The in vivo anti-tumor activity of the Tmab-(huIL10)2-6-9 heterodimer was also tested using C57 BL/6 mouse model. Briefly, 8-week old female C57 BL/6 mice were subcutaneously injected with $5\times10^5$ B16-Her2 (FIG. 18A) or $5\times10^5$MC38-Her2 cells (FIG. 18B). After 7 days, the tumor volume was measured to be around 70 mm$^3$. The Tmab-(huIL10)2-6-9 heterodimer protein or PBS was injected intra-peritoneally (i.p.) at different doses (8 mg/kg, 4 mg/kg, 2 mg/kg, and 1 mg/kg respectively) on day 7, 10, and 14. Tumor size was measured twice per week, and the volume of the tumors was calculated to obtain a curve of tumor growth. The results are demonstrated in FIGS. 18A and 18B, for each dosage administered, the Tmab-(huIL10)2-6-9 heterodimer effectively reduced tumor volume in vivo.

Similarly, the anti-tumor activity of C-mab-(huIL10)2-6-9, 28H1-(huIL10)2-6-9, and 28H1-huIFNa2-6-9 heterodimers was also tested in MC38-GPC3, MC38-FAP, B16-GPC3, and B16-FAP syngeneic tumor models, and significant anti-tumor effects were observed.

Specifically, the anti-tumor activity of 28H1-huIFNa2-6-9 was tested in a pancreatic cancer model (an in vitro micro-organ culture system), and inhibition of tumor growth was observed.

Figure 24:
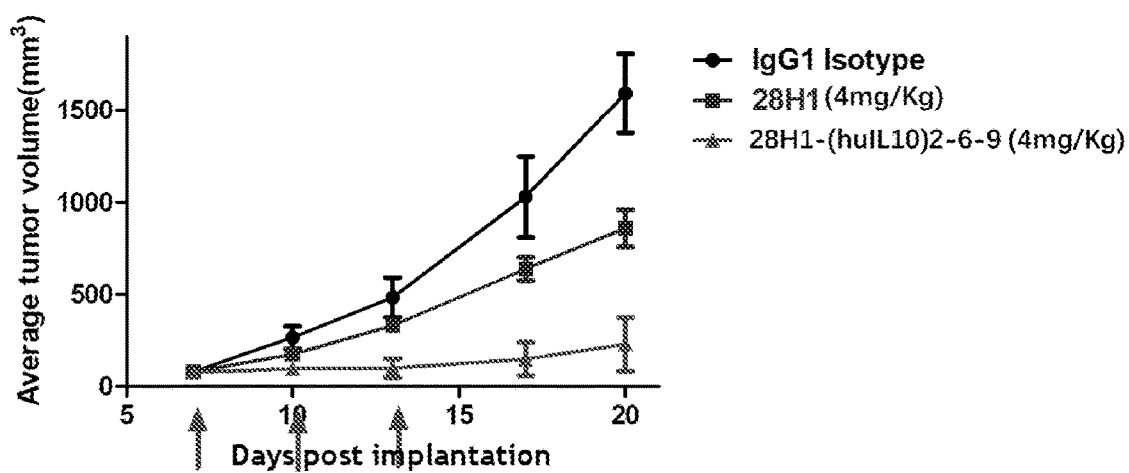
FIG. 24 illustrates the in vivo anti-tumor activity of the proteinaceous heterodimers according to the present application.

The in vivo anti-tumor activity of the 28H1-(huIL10)2-6-9 heterodimer was also examined using a B16-FAP syngeneic tumor model. Briefly, 8-week old female C57 BL/6 mice were subcutaneously injected with $7\times10^5$ B16-FAP-5 cells. After 7 days, the tumor volume was measured to be around 70-100 mm$^3$. The 28H1-(huIL10)2-6-9 heterodimer protein, 28H1 antibody control, or IgG1 isotype control was injected intra-peritoneally (i.p.) at 4 mg/kg on day 7, 10, and 13. Tumor size was measured every five days, and the volume of the tumors was calculated to obtain a tumor growth curve. The results are demonstrated in FIG. 24, it can be seen that the 28H1-(huIL10)2-6-9 heterodimer effectively reduced tumor volume in vivo, and it was more effective than the IgG1 isotype control, or the 28H1 antibody control.

In addition, the in vivo anti-tumor activity of Erb-(huIL10)2-6-9, Erb-muIFNa4-6-9, C-mab-(huIL10)2-6-9, 28H1-(huIL10)2-6-9, 28H1-huIFNa2-6-9, and E-mab-(huIL10)2-6-9 were also tested in corresponding humanized PDX mouse models, and in vivo anti-tumor effects were observed.

Figure 25:
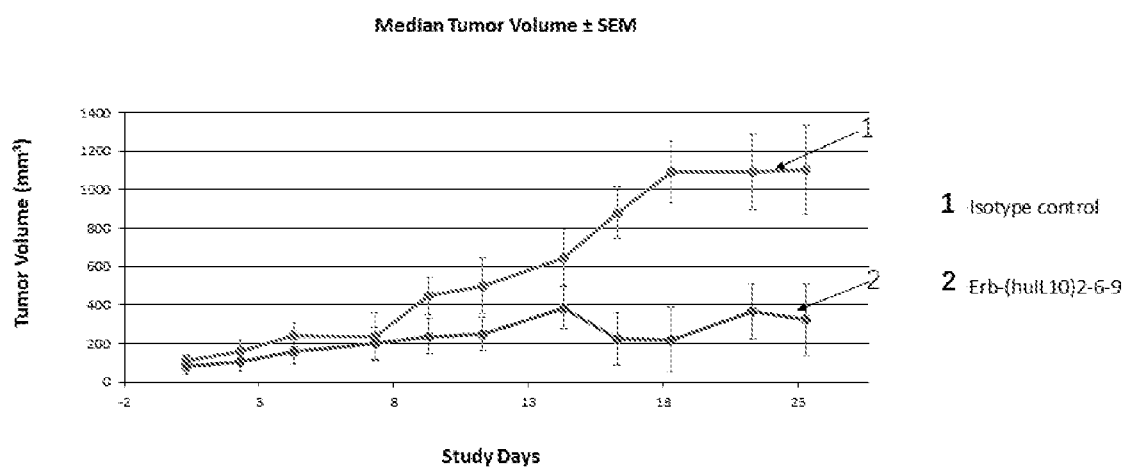
FIG. 25 illustrates the in vivo anti-tumor activity of the proteinaceous heterodimers according to the present application.

Specifically, the in vivo anti-tumor activity of the Erb-(huIL10)2-6-9 heterodimer was also tested using a PDX mouse model. Briefly, 8-week old female Hu-CD34 NSG mice were implanted with pancreatic cancer A15668 P4 PDX tumor cells. When the tumor volume was measured to be around 100 mm$^3$, the Erb-(huIL10)2-6-9 heterodimer protein (0.2 mpk) or Isotype control (Lot #20170816, Crownbio, 1 mpk) was injected intra-peritoneally (i.p.) on day 0 (the date of administration for the first time), day 3, day 6, day 9, day 12 and day 15. Tumor size was measured every two days, and the volume of the tumors was calculated to obtain a tumor growth curve. The results are demonstrated in FIG. 25, it can be seen that the Erb-(huIL10)2-6-9 heterodimer effectively reduced tumor volume in vivo in the PDX mouse model.

Example 9 Targeting Behavior of the Proteinaceous Heterodimers In Vivo

Figure 19:
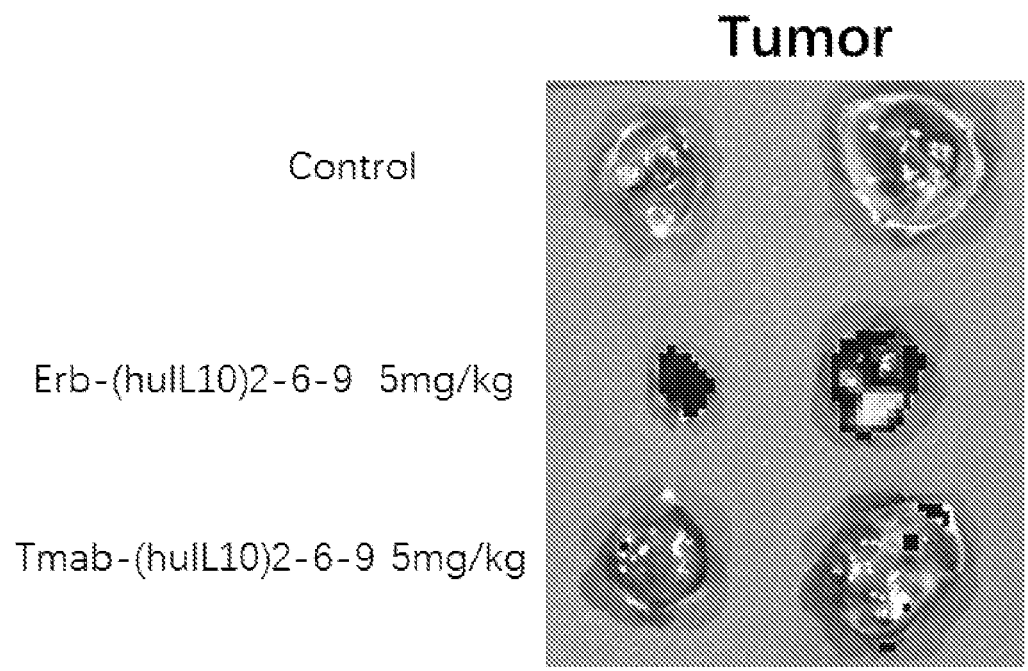
FIG. 19 illustrates the in vivo targeting activity of the proteinaceous heterodimers according to the present application.

Similar to the procedures shown in Example 8.1, in vivo distribution of Erb-(huIL10)2-6-9 was examined using C57BL/6 B16-EGFR mouse model. Briefly, 8-week old female C57 BL/6 mice were subcutaneously injected with $7\times10^5$ B16-EGFR-SIY cells. After 7 days, tumor volume was measured to be around 45 mm$^3$. Alexa Fluor 750 (AF750) labelled Erb-(huIL10)2-6-9 heterodimer or control heterodimer Tmab-(huIL10)2-6-9 was injected intra-peritoneally (i.p). 24 hrs after injection, the AF750 immunofluorescence signal was screened for in vivo with IVIS spectrum in vivo imaging system (Perkin Elmer) or in vitro after removing the tumors. The results (as shown in FIG. 19) demonstrated that the concentration of Erb-(huIL10)2-6-9 is much higher than that of Tmab-(huIL10)2-6-9 in EGFR positive tumors. Thus, proteinaceous heterodimers of the present disclosure could be effectively directed to the targeting tissues (e.g., tumors) in vivo.

Example 10 ADCC Effects of the Proteinaceous Heterodimers

The Antibody-dependent cell-mediated cytotoxicity (ADCC) was also tested for the proteinaceous heterodimers of the present application. LDH release was used to test the ADCC effects of the proteinaceous heterodimers of the present application (e.g., Erb-huIFNa2-6-9, and Erb-(huIL10)2-6-9). Briefly, PBMCs were obtained by Ficoll-Hypaque density gradient centrifuge from heparinized peripheral blood samples of healthy donors and then cultured 24h at 37° C. in 1*10E7 cells/dish with 1640 medium which contain 30 ng/ml IL-2 and 10% FBS. 96-well plates were seeded with PBMC cells and A431 cells at a density of $2.25*10^5$/well and $1.5*10^4$/well with 1640 medium which contain 15 ng/ml IL-2 and 2% FBS. Starting from 9 nM (final concentration was 3 nM), Erbitux, Erb-huIFNa2-6-9 and Erb-(huIL10)2-6-9 were diluted by 5-fold to get 8 different doses and then were added to 96-well plates. 5h later, the LDH in each well was detected.

Figure 20:
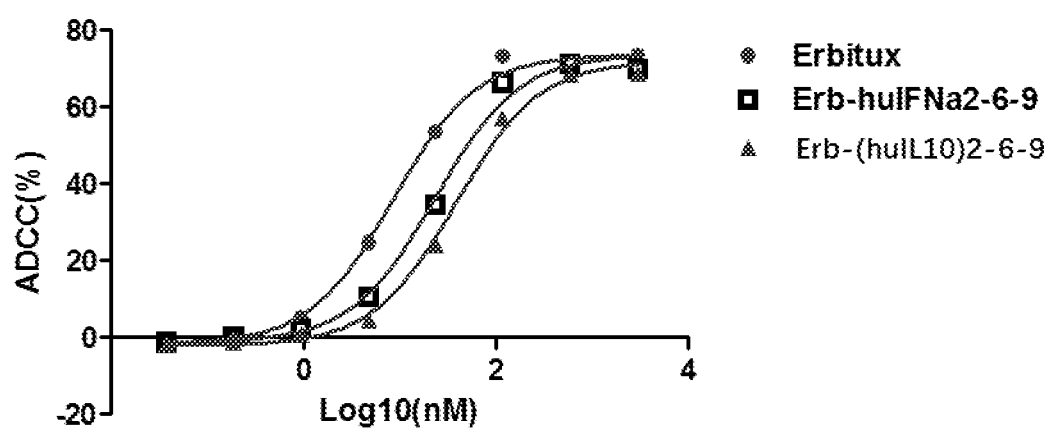
FIG. 20 illustrates the ADCC activity of the proteinaceous heterodimers according to the present application.

As shown in FIG. 20, the proteinaceous heterodimers showed ADCC activities comparable to that of the control Erbitux, though slightly lower, indicating that the modifications (i.e., the first modification and/or the second modification of proteinaceous heterodimer of the present application) in the Fc regions do not destroy the ADCC activities.

What is claimed is:

1. A proteinaceous heterodimer comprising a first member and a second member different from said first member, wherein:

said first member comprises a light chain and a heavy chain comprising a first Fc region, the light chain is complexed with the heavy chain to form a targeting moiety exhibiting binding specificity to a tumor antigen;

said second member comprises a polypeptide comprising an immunoregulator fused to a second Fc region;

the polypeptide comprised in the second member is a fusion protein, and a C-terminus of the immunoregulator is fused to a N-terminus of the second Fc region to form the fusion protein, optionally via a linker, wherein the immunoregulator is a cytokine selected from the group consisting of an interferon, an interleukin, a chemokine, a lymphokine, and a tumor necrosis factor;

said first member associates with said second member to form said heterodimer through complexation of said first Fc region with said second Fc region; and wherein the amino acid sequence of the light chain comprised in the first member is selected from SEQ ID NO: 37, 45, 49, 53, 57, 61, 69, and 73, the amino acid sequence of the heavy chain comprised in the first member is selected from SEQ 11) NO: 39, 47, 51, 55, 59, 63, 67, 71, and 75, and the amino acid sequence of the polypeptide comprised in the second member is selected from SEQ ID NO: 77, 80, 82, 84, 86, 89, 91, and 97.

2. The proteinaceous heterodimer according to claim 1, wherein the amino acid sequence of the light chain comprised in the first member is SEQ NO: 37, and the amino acid sequence of the heavy chain comprised in the first member is SEQ ID NO: 39; and the amino acid sequence of the polypeptide comprised in the second member is selected from SEQ ID NO: 77, 80, 82, 84, 86, 89, 91, and 97;

the amino acid sequence of the light chain comprised in the first member is SEQ NO: 45, and the amino acid sequence of the heavy chain comprised in the first member is SEQ ID NO: 47, and the amino acid sequence of the polypeptide comprised in the second member is selected from SEQ ID NO: 77, 80, 82, 84, 86, 89, 91, and 97;

the amino acid sequence of the light chain comprised in the first member is SEQ ID NO: 49, and the amino acid sequence of the heavy chain comprised in the first member is SEQ ID NO: 51, and the amino acid sequence of the polypeptide comprised in the second member is selected from SEQ ID NO: 77, 80, 82, 84, 86, 89, 91, and 97;

the amino acid sequence of the light chain comprised in the first member is SEQ ID NO: 53, and the amino acid sequence of the heavy chain comprised in the first member is SEQ ID NO: 55, and the amino acid sequence of the polypeptide comprised in the second member is selected from SEQ ID NO: 77, 80, 82, 84, 86, 89, 91, and 97;

the amino acid sequence of the light chain comprised in the first member is SEQ LTA NO: 57, and the amino acid sequence of the heavy chain comprised in the first member is SEQ ID NO: 59, and the amino acid sequence of the polypeptide comprised in the second member is selected from SEQ ID NO: 77, 80, 82, 84, 86, 89, 91, and 97;

the amino acid sequence of the light chain comprised in the first member is SEQ ID NO: 61, and the amino acid sequence of the heavy chain comprised in the first member is SEQ ID NO: 63, and the amino acid sequence of the polypeptide comprised in the second member is selected from SEQ ID NO: 77, 80, 82, 84, 86, 89, 91, and 97;

the amino acid sequence of the light chain comprised in the first member is SEQ NO: 65, and the amino acid sequence of the heavy chain comprised in the first member is SEQ ID NO: 67, and the amino acid sequence of the polypeptide comprised in the second member is selected from SEQ ID NO: 77, 80, 82, 84, 86, 89, 91, and 97;

the amino acid sequence of the light chain comprised in the first member is SEQ LTA NO: 69, and the amino acid sequence of the heavy chain comprised in the first member is SEQ ID NO: 71, and the amino acid sequence of the polypeptide comprised in the second member is selected from SEQ ID NO: 77, 80, 82, 84, 86, 89, 91, and 97; or, the amino acid sequence of the light chain comprised in the first member is SEQ ID NO: 73, and the amino acid sequence of the heavy chain comprised in the first member is SEQ ID NO: 75, and the amino acid sequence of the polypeptide comprised in the second member is selected from SEQ ID NO: 77, 80, 82, 84, 86, 89, 91, and 97.

3. A protein mixture, comprising:
1) the proteinaceous heterodimer according to claim 1;
2) a first homodimer formed by two of said first member of said proteinaceous heterodimer; and
3) a second homodimer formed by two of said second member of said proteinaceous heterodimer;

wherein a percentage of said proteinaceous heterodimer in said protein mixture is at least 50%.

4. A pharmaceutical composition, comprising: the proteinaceous heterodimer according to claim 1, and optionally a pharmaceutically acceptable excipient.

5. A method of inhibiting growth of a tumor or a tumor cell, the method comprising: administrating an effective amount of the proteinaceous heterodimer according to claim 1 to a subject in need thereof.

6. An isolated polynucleotide encoding the proteinaceous heterodimer according to claim 1.

* * * * *